(12) United States Patent
Stone et al.

(10) Patent No.: US 12,727,871 B2
(45) **Date of Patent: *Sep. 8, 2026**

(54) METHOD FOR TISSUE FIXATION

(71) Applicant: Biomet Sports Medicine, LLC, Warsaw, IN (US)

(72) Inventors: Kevin T. Stone, Winona Lake, IN (US); Gregory J. Denham, Warsaw, IN (US); Ryan Harper, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1249 days.

This patent is subject to a terminal disclaimer.

(21) Appl. No.: 17/577,188

(22) Filed: Jan. 17, 2022

(65) Prior Publication Data

US 2022/0133296 A1 May 5, 2022

Related U.S. Application Data

(60) Continuation of application No. 16/380,742, filed on Apr. 10, 2019, now Pat. No. 11,311,287, which is a (Continued)

(51) Int. Cl.
*A61B 17/04* (2006.01)

(52) U.S. Cl.
CPC .. *A61B 17/0401* (2013.01); *A61B 2017/0409* (2013.01); *A61B 2017/0414* (2013.01); (Continued)

(58) Field of Classification Search
CPC ............ A61B 17/0401; A61B 17/0487; A61B 2017/0496; A61B 2017/0446; (Continued)

(56) References Cited

U.S. PATENT DOCUMENTS

| | | | |
|---|---|---|---|
| 26,501 | A | 12/1859 | Kendrick et al. |
| 64,499 | A | 5/1867 | Daubert |

(Continued)

FOREIGN PATENT DOCUMENTS

| | | | |
|---|---|---|---|
| AU | 4957264 | A | 3/1966 |
| AU | 440266 | A1 | 10/1967 |

(Continued)

OTHER PUBLICATIONS

US 6,238,418 B1, 05/2001, Schwartz (withdrawn)

(Continued)

*Primary Examiner* — Dianne Dornbusch
(74) *Attorney, Agent, or Firm* — SCHWEGMAN LUNDBERG & WOESSNER, P.A.

(57) ABSTRACT

A method for securing a strand to a fixation member for arthroscopic fixation, wherein the fixation member includes a channel on an exterior surface and an aperture therethrough. The method includes passing a strand having first and second ends through a flexible sleeve, passing the sleeve through the aperture of the fixation member in a first direction, tensioning the strand, and pulling the sleeve in a second direction different than the first direction to secure the sleeve to the fixation member without tying the strand on the fixation member.

20 Claims, 20 Drawing Sheets

Related U.S. Application Data continuation of application No. 15/945,425, filed on Apr. 4, 2018, now Pat. No. 10,987,099, which is a continuation of application No. 14/983,108, filed on Dec. 29, 2015, now Pat. No. 10,321,906, which is a continuation of application No. 13/625,413, filed on Sep. 24, 2012, now Pat. No. 9,402,621, which is a division of application No. 13/412,116, filed on Mar. 5, 2012, now Pat. No. 8,771,316, and a division of application No. 12/489,181, filed on Jun. 22, 2009, now Pat. No. 8,298,262, which is a continuation-in-part of application No. 12/474,802, filed on May 29, 2009, now Pat. No. 8,088,130, said application No. 13/412,116 is a continuation-in-part of application No. 12/196,410, filed on Aug. 22, 2008, now Pat. No. 8,118,836, and a continuation-in-part of application No. 12/196,407, filed on Aug. 22, 2008, now Pat. No. 8,137,382, and a continuation-in-part of application No. 12/196,405, filed on Aug. 22, 2008, now Pat. No. 8,128,658, said application No. 12/489,181 is a continuation-in-part of application No. 12/014,340, filed on Jan. 15, 2008, now Pat. No. 7,905,904, and a continuation-in-part of application No. 12/014,399, filed on Jan. 15, 2008, now Pat. No. 7,909,851, and a continuation-in-part of application No. 11/935,681, filed on Nov. 6, 2007, now Pat. No. 7,905,903.

(52) U.S. Cl.
CPC . *A61B 2017/0432* (2013.01); *A61B 2017/044* (2013.01); *A61B 2017/0445* (2013.01); *A61B 2017/0448* (2013.01)

(58) Field of Classification Search
CPC .... A61B 2017/0404; A61B 2017/0414; A61B 2017/0432; A61B 2017/0448; A61B 2017/044; A61B 2017/0458; A61B 2017/0409; A61B 2017/0427; A61F 2/0811; A61F 2002/0817; A61F 2002/0852; A61F 2002/0882; A61F 2002/0888
See application file for complete search history.

(56) References Cited

U.S. PATENT DOCUMENTS 65,499 A 6/1867 Miller
126,366 A 4/1872 Wills
233,475 A 10/1880 Cook et al.
261,501 A 7/1882 Vandermark
268,407 A 12/1882 Hughes
330,087 A 11/1885 Binns
394,739 A 12/1888 Toulmin
401,677 A 4/1889 Autenrieth
417,805 A 12/1889 Beaman
445,875 A 2/1891 Brickell
487,304 A 12/1892 Todd
687,221 A 11/1901 Gaff et al.
762,710 A 6/1904 Hall
837,767 A 12/1906 Aims
838,203 A 12/1906 Neil
1,059,631 A 4/1913 Popovics
1,131,155 A 3/1915 Murphy
1,153,450 A 9/1915 Schaff
1,346,940 A 7/1920 Collins
1,505,470 A 8/1924 Kelm
1,635,066 A 7/1927 Wells
1,950,799 A 3/1934 Jones
2,042,403 A 5/1936 Andrew
2,065,659 A 12/1936 Cullen
2,108,206 A 2/1938 Meeker
2,121,193 A 6/1938 Erich
2,242,003 A 5/1941 Lorenzo
2,267,925 A 12/1941 Johnston
2,302,986 A 11/1942 Vollrath
2,329,398 A 9/1943 Duffy
2,379,629 A 7/1945 Eweson
2,397,216 A 3/1946 Stellin
RE22,857 E 3/1947 Ogburn
2,526,959 A 10/1950 Lorenzo
2,528,456 A 10/1950 Thomas
2,549,382 A 4/1951 Mitterway
2,562,419 A 7/1951 Ferris
2,581,564 A 1/1952 Jaime
2,600,395 A 6/1952 Joseph et al.
2,610,631 A 9/1952 Calicchio
2,665,597 A 1/1954 Hill
2,669,774 A 2/1954 Mitchell
2,698,986 A 1/1955 Brown
2,760,488 A 8/1956 Pierce
2,833,284 A 5/1958 Springer
2,846,712 A 8/1958 Moe
2,860,393 A 11/1958 Brock
2,880,728 A 4/1959 Rights
2,881,762 A 4/1959 Lowrie
2,883,096 A 4/1959 Horace
2,913,042 A 11/1959 John
2,947,504 A 8/1960 Ruhlman
3,000,009 A 9/1961 Selstad
3,003,155 A 10/1961 Mielzynski
3,013,559 A 12/1961 Thomas
3,037,619 A 6/1962 Ernest
3,039,460 A 6/1962 Chandler
3,081,781 A 3/1963 Stermer
3,090,386 A 5/1963 William
3,103,666 A 9/1963 Bone
3,123,077 A 3/1964 Alcamo
3,125,095 A 3/1964 Kaufman et al.
3,209,422 A 10/1965 Arthur
3,223,083 A 12/1965 Cobey
3,234,938 A 2/1966 Robinson
3,240,379 A 3/1966 Bremer et al.
3,250,271 A 5/1966 Jack
3,399,432 A 9/1968 Merser
3,409,014 A 11/1968 Grant
RE26,501 E 12/1968 Himmelstein et al.
3,435,475 A 4/1969 Bisk
3,467,089 A 9/1969 Hasson
3,470,834 A 10/1969 Bone
3,470,875 A 10/1969 Johnson
3,500,820 A 3/1970 Almen
3,507,274 A 4/1970 Soichet
3,513,484 A 5/1970 Hausner
3,515,132 A 6/1970 Mcknight
3,522,803 A 8/1970 Majzlin
3,527,223 A 9/1970 Shein
3,533,406 A 10/1970 Tatum
3,541,591 A 11/1970 Hoegerman
3,545,008 A 12/1970 Bader, Jr.
3,547,389 A 12/1970 Mitchell
3,579,831 A 5/1971 Stevens et al.
3,590,616 A 7/1971 Schussler
3,608,095 A 9/1971 Barry
3,618,447 A 11/1971 Goins
3,628,530 A 12/1971 Schwartz
3,643,649 A 2/1972 Amato
3,648,705 A 3/1972 Lary
3,650,274 A 3/1972 Edwards et al.
3,656,483 A 4/1972 Rudel
3,659,597 A 5/1972 Wolfers
3,664,345 A 5/1972 Dabbs et al.
3,665,560 A 5/1972 Bennett et al.
3,675,639 A 7/1972 Cimber
3,683,422 A 8/1972 Stemmer et al.
3,692,022 A 9/1972 Ewing
3,695,271 A 10/1972 Chodorow
3,699,969 A 10/1972 Allen
3,716,058 A 2/1973 Tanner
3,744,488 A 7/1973 Cox

(56) References Cited

U.S. PATENT DOCUMENTS 3,752,516 A 8/1973 Mumma
3,757,629 A 9/1973 Schneider
3,763,856 A 10/1973 Blomberg
3,771,520 A 11/1973 Lerner
3,777,748 A 12/1973 Abramson
3,786,801 A 1/1974 Sartorius
3,802,438 A 4/1974 Wolvek
3,807,407 A 4/1974 Schweizer
3,810,456 A 5/1974 Karman
3,825,010 A 7/1974 Mc Donald
3,840,017 A 10/1974 Violante
3,842,824 A 10/1974 Neufeld
3,842,840 A 10/1974 Schweizer
3,845,772 A 11/1974 Smith
3,867,933 A 2/1975 Kitrilakis
3,867,944 A 2/1975 Samuels
3,871,368 A 3/1975 Johnson et al.
3,871,379 A 3/1975 Clarke
3,874,388 A 4/1975 King et al.
3,875,648 A 4/1975 Bone
3,877,570 A 4/1975 Barry
3,880,156 A 4/1975 Hoff
3,881,475 A 5/1975 Gordon et al.
3,889,666 A 6/1975 Lerner
3,892,240 A 7/1975 Park
3,896,500 A 7/1975 Rambert et al.
3,896,810 A 7/1975 Akiyama
3,907,442 A 9/1975 Reid
3,910,281 A 10/1975 Kletschka
3,918,444 A 11/1975 Hoff et al.
3,918,455 A 11/1975 Coplan
3,927,666 A 12/1975 Hoff
3,931,667 A 1/1976 Merser et al.
3,933,153 A 1/1976 Csatary et al.
3,937,217 A 2/1976 Kosonen
3,943,932 A 3/1976 Woo
3,946,446 A 3/1976 Schofield
3,946,728 A 3/1976 Bettex
3,946,740 A 3/1976 Bassett
3,949,755 A 4/1976 Vauquois
3,953,896 A 5/1976 Treace
3,954,103 A 5/1976 Garcia-roel et al.
3,961,632 A 6/1976 Moossun
3,973,560 A 8/1976 Emmett
3,976,079 A 8/1976 Samuels et al.
3,977,050 A 8/1976 Perez
3,979,799 A 9/1976 Merser et al.
3,985,138 A 10/1976 Jarvik
3,990,619 A 11/1976 Russell
4,005,707 A 2/1977 Moulding, Jr.
4,006,747 A 2/1977 Kronenthal et al.
4,007,743 A 2/1977 Blake
4,013,071 A 3/1977 Rosenberg
4,026,281 A 5/1977 Mayberry et al.
4,036,101 A 7/1977 Burnett
4,050,100 A 9/1977 Barry
4,054,954 A 10/1977 Nakayama et al.
4,084,478 A 4/1978 Simmons
4,085,466 A 4/1978 Goodfellow et al.
4,094,313 A 6/1978 Komamura et al.
4,099,750 A 7/1978 Mcgrew
4,103,690 A 8/1978 Harris
RE29,819 E 10/1978 Bone
4,121,487 A 10/1978 Bone
4,143,656 A 3/1979 Holmes
4,144,876 A 3/1979 Deleo
4,146,022 A 3/1979 Johnson et al.
4,149,277 A 4/1979 Bokros
4,157,714 A 6/1979 Foltz et al.
4,158,250 A 6/1979 Ringwald
4,160,453 A 7/1979 Miller
4,164,225 A 8/1979 Johnson et al.
4,172,458 A 10/1979 Pereyra
4,175,555 A 11/1979 Herbert
4,185,636 A 1/1980 Gabbay et al.
4,196,883 A 4/1980 Einhorn et al.
4,207,627 A 6/1980 Cloutier
4,210,148 A 7/1980 Stivala
4,235,161 A 11/1980 Kunreuther
4,235,238 A 11/1980 Ogiu et al.
4,237,779 A 12/1980 Kunreuther
4,243,037 A 1/1981 Smith
4,249,525 A 2/1981 Krzeminski
4,263,913 A 4/1981 Malmin
4,265,246 A 5/1981 Barry
4,273,117 A 6/1981 Neuhauser
4,275,490 A 6/1981 Bivins
4,275,717 A 6/1981 Bolesky
4,287,807 A 9/1981 Pacharis et al.
4,291,698 A 9/1981 Fuchs et al.
4,301,551 A 11/1981 Dore et al.
4,302,397 A 11/1981 Frainier et al.
4,307,723 A 12/1981 Finney
4,312,337 A 1/1982 Donohue
4,316,469 A 2/1982 Kapitanov
4,319,428 A 3/1982 Fox
4,326,531 A 4/1982 Shimonaka
4,344,193 A 8/1982 Kenny
4,345,601 A 8/1982 Fukuda
4,349,027 A 9/1982 Difrancesco
4,388,921 A 6/1983 Sutter et al.
4,400,833 A 8/1983 Kurland
4,402,445 A 9/1983 Green
4,409,974 A 10/1983 Freedland et al.
4,438,769 A 3/1984 Pratt et al.
4,441,489 A 4/1984 Evans et al.
4,454,875 A 6/1984 Pratt et al.
4,462,395 A 7/1984 Johnson
4,463,753 A 8/1984 Gustilo
4,473,102 A 9/1984 Ohman et al.
4,484,570 A 11/1984 Sutter et al.
4,489,446 A 12/1984 Reed
4,489,464 A 12/1984 Massari et al.
4,493,323 A 1/1985 Albright et al.
4,496,468 A 1/1985 House et al.
4,505,274 A 3/1985 Speelman
4,509,516 A 4/1985 Richmond
4,531,522 A 7/1985 Bedi et al.
4,532,926 A 8/1985 O'holla
4,534,350 A 8/1985 Golden et al.
4,535,764 A 8/1985 Ebert
4,537,185 A 8/1985 Stednitz
4,549,545 A 10/1985 Levy
4,549,652 A 10/1985 Free
4,561,432 A 12/1985 Mazor
4,564,007 A 1/1986 Coombs
4,570,623 A 2/1986 Ellison et al.
4,573,844 A 3/1986 Smith
4,576,608 A 3/1986 Homsy
4,584,722 A 4/1986 Levy et al.
4,587,963 A 5/1986 Leibinger et al.
4,590,928 A 5/1986 Hunt et al.
4,595,007 A 6/1986 Mericle
4,596,249 A 6/1986 Freda et al.
4,597,766 A 7/1986 Hilal et al.
4,602,635 A 7/1986 Mulhollan et al.
4,602,636 A 7/1986 Noiles
4,604,997 A 8/1986 De Bastiani et al.
4,605,414 A 8/1986 Czajka
4,616,650 A 10/1986 Green et al.
4,621,640 A 11/1986 Mulhollan et al.
4,624,254 A 11/1986 Mcgarry et al.
4,632,100 A 12/1986 Somers et al.
4,635,637 A 1/1987 Schreiber
4,636,121 A 1/1987 Miller
4,640,271 A 2/1987 Lower
4,641,652 A 2/1987 Hutterer et al.
4,649,916 A 3/1987 Frimberger
4,649,952 A 3/1987 Jobe
4,653,486 A 3/1987 Coker
4,653,487 A 3/1987 Maale
4,653,489 A 3/1987 Tronzo
4,655,771 A 4/1987 Wallsten
4,655,777 A 4/1987 Dunn

(56) References Cited

U.S. PATENT DOCUMENTS 4,662,068 A 5/1987 Polonsky
4,667,662 A 5/1987 Titone et al.
4,667,675 A 5/1987 Davis
4,669,473 A 6/1987 Richards et al.
4,683,895 A 8/1987 Pohndorf
4,688,561 A 8/1987 Reese
4,690,169 A 9/1987 Jobe
4,696,300 A 9/1987 Anderson
4,705,040 A 11/1987 Mueller et al.
4,708,132 A 11/1987 Silvestrini
4,711,639 A 12/1987 Grundei
4,714,474 A 12/1987 Brooks, Jr. et al.
4,714,475 A 12/1987 Grundei et al.
4,716,893 A 1/1988 Fischer et al.
4,719,671 A 1/1988 Ito et al.
4,719,917 A 1/1988 Barrows et al.
4,723,540 A 2/1988 Gilmer, Jr.
4,724,839 A 2/1988 Bedi et al.
4,728,329 A 3/1988 Mansat
4,728,332 A 3/1988 Albrektsson
4,730,615 A 3/1988 Sutherland et al.
4,736,746 A 4/1988 Anderson
4,738,255 A 4/1988 Goble et al.
4,739,751 A 4/1988 Sapega et al.
4,741,330 A 5/1988 Hayhurst
4,741,336 A 5/1988 Failla et al.
4,744,353 A 5/1988 Mcfarland
4,744,793 A 5/1988 Parr et al.
4,750,492 A 6/1988 Jacobs
4,751,922 A 6/1988 Dipietropolo
4,754,685 A 7/1988 Kite et al.
4,760,843 A 8/1988 Fischer et al.
4,760,844 A 8/1988 Kyle
4,760,848 A 8/1988 Hasson
4,770,663 A 9/1988 Hanslik et al.
4,772,261 A 9/1988 Von Hoff et al.
4,772,286 A 9/1988 Goble et al.
4,773,910 A 9/1988 Chen et al.
4,775,380 A 10/1988 Seedhom et al.
4,776,328 A 10/1988 Frey et al.
4,779,372 A 10/1988 Pozo Obeso
4,781,190 A 11/1988 Lee
4,784,126 A 11/1988 Hourahane
4,787,882 A 11/1988 Claren
4,790,297 A 12/1988 Luque
4,790,850 A 12/1988 Dunn et al.
4,793,363 A 12/1988 Ausherman et al.
4,795,468 A 1/1989 Hodorek et al.
4,809,695 A 3/1989 Gwathmey et al.
4,813,406 A 3/1989 Ogle, II
4,813,416 A 3/1989 Pollak et al.
4,823,780 A 4/1989 Odensten et al.
4,823,794 A 4/1989 Pierce
4,828,562 A 5/1989 Kenna
4,832,026 A 5/1989 Jones
4,834,098 A 5/1989 Jones
4,836,080 A 6/1989 Kite, III et al.
4,838,282 A 6/1989 Strasser et al.
4,841,960 A 6/1989 Garner
4,846,835 A 7/1989 Grande
4,851,005 A 7/1989 Hunt et al.
4,858,601 A 8/1989 Glisson
4,858,603 A 8/1989 Clemow et al.
4,858,608 A 8/1989 Mcquilkin
4,860,513 A 8/1989 Whitman
4,863,383 A 9/1989 Grafelmann
4,863,471 A 9/1989 Mansat
4,870,957 A 10/1989 Goble et al.
4,872,450 A 10/1989 Austad
4,873,976 A 10/1989 Schreiber
4,884,572 A 12/1989 Bays et al.
4,887,601 A 12/1989 Richards
4,889,110 A 12/1989 Galline et al.
4,890,615 A 1/1990 Caspari et al.
4,893,619 A 1/1990 Dale et al.
4,893,974 A 1/1990 Fischer et al.
4,895,148 A 1/1990 Bays et al.
4,896,668 A 1/1990 Popoff et al.
4,898,156 A 2/1990 Gatturna et al.
4,899,743 A 2/1990 Nicholson et al.
4,901,721 A 2/1990 Hakki
4,917,700 A 4/1990 Aikins
4,919,667 A 4/1990 Richmond
4,922,897 A 5/1990 Sapega et al.
4,923,461 A 5/1990 Caspari et al.
4,927,421 A 5/1990 Goble et al.
4,946,377 A 8/1990 Kovach
4,946,467 A 8/1990 Ohi et al.
4,946,468 A 8/1990 Li
4,950,270 A 8/1990 Bowman et al.
4,950,285 A 8/1990 Wilk
4,959,069 A 9/1990 Brennan et al.
4,960,381 A 10/1990 Niznick
4,961,741 A 10/1990 Hayhurst
4,962,929 A 10/1990 Melton, Jr.
4,968,315 A 11/1990 Gatturna
4,968,317 A 11/1990 Tormala et al.
4,969,886 A 11/1990 Cziffer et al.
4,974,488 A 12/1990 Spralja
4,974,656 A 12/1990 Judkins
4,976,736 A 12/1990 White et al.
4,978,350 A 12/1990 Wagenknecht
4,979,956 A 12/1990 Silvestrini
4,983,176 A 1/1991 Cushman et al.
4,983,184 A 1/1991 Steinemann
4,983,240 A 1/1991 Orkin et al.
4,988,351 A 1/1991 Paulos et al.
4,994,074 A 2/1991 Bezwada et al.
4,997,433 A 3/1991 Goble et al.
5,002,545 A 3/1991 Whiteside et al.
5,002,550 A 3/1991 Li
5,002,562 A 3/1991 Oberlander
5,002,574 A 3/1991 May et al.
5,007,921 A 4/1991 Brown
5,019,093 A 5/1991 Kaplan et al.
5,020,713 A 6/1991 Kunreuther
5,026,398 A 6/1991 May et al.
5,028,569 A 7/1991 Cihon
5,030,224 A 7/1991 Wright
5,030,235 A 7/1991 Campbell, Jr.
5,035,701 A 7/1991 Kabbara
5,037,422 A 8/1991 Hayhurst et al.
5,037,426 A 8/1991 Goble et al.
5,041,129 A 8/1991 Hayhurst et al.
5,046,513 A 9/1991 Gatturna et al.
5,047,030 A 9/1991 Draenert
5,053,046 A 10/1991 Janese
5,053,047 A 10/1991 Yoon
5,059,201 A 10/1991 Asnis
5,059,206 A 10/1991 Winters
5,061,277 A 10/1991 Carpentier et al.
5,062,344 A 11/1991 Gerker
5,062,843 A 11/1991 Mahony, III
5,064,431 A 11/1991 Gilbertson et al.
5,067,962 A 11/1991 Campbell et al.
5,071,420 A 12/1991 Paulos et al.
5,074,874 A 12/1991 Yoon, Inbae et al.
5,078,731 A 1/1992 Hayhurst
5,078,843 A 1/1992 Pratt
5,080,050 A 1/1992 Dale
5,080,675 A 1/1992 Lawes et al.
5,084,050 A 1/1992 Draenert
5,084,058 A 1/1992 Li
5,085,661 A 2/1992 Moss
5,087,263 A 2/1992 Li
5,087,309 A 2/1992 Melton, Jr.
5,089,012 A 2/1992 Prou
5,092,727 A 3/1992 Moghe
5,092,866 A 3/1992 Breard et al.
5,098,433 A 3/1992 Freedland
5,098,435 A 3/1992 Stednitz et al.
5,100,415 A 3/1992 Hayhurst
5,100,417 A 3/1992 Cerier
5,108,433 A 4/1992 May et al.

(56) References Cited

U.S. PATENT DOCUMENTS 5,112,335 A 5/1992 Laboureau et al.
5,116,337 A 5/1992 Johnson
5,116,373 A 5/1992 Jakob et al.
5,116,375 A 5/1992 Hofmann
5,123,913 A 6/1992 Wilk et al.
5,123,914 A 6/1992 Cope
5,127,783 A 7/1992 Moghe et al.
5,127,785 A 7/1992 Faucher
5,129,901 A 7/1992 Decoste
5,129,902 A 7/1992 Goble et al.
5,129,904 A 7/1992 Illi
5,129,906 A 7/1992 Ross et al.
5,139,498 A 8/1992 Astudillo Ley
5,139,499 A 8/1992 Small et al.
5,139,520 A 8/1992 Rosenberg
5,143,498 A 9/1992 Whitman
5,147,362 A 9/1992 Goble
5,149,329 A 9/1992 Richardson
5,151,104 A 9/1992 Kenna
5,152,790 A 10/1992 Rosenberg et al.
5,154,189 A 10/1992 Oberlander
5,156,616 A 10/1992 Meadows et al.
5,163,960 A 11/1992 Bonutti
D331,626 S 12/1992 Hayhurst et al.
5,169,400 A 12/1992 Muhling et al.
5,171,274 A 12/1992 Fluckiger et al.
5,176,682 A 1/1993 Chow
5,178,629 A 1/1993 Kammerer
5,183,458 A 2/1993 Marx
5,190,545 A 3/1993 Corsi et al.
5,192,282 A 3/1993 Draenert
5,197,987 A 3/1993 Koch et al.
5,199,135 A 4/1993 Gold
5,203,784 A 4/1993 Ross et al.
5,203,787 A 4/1993 Noblitt et al.
5,207,679 A 5/1993 Li
5,209,753 A 5/1993 Biedermann et al.
5,209,805 A 5/1993 Spraggins
5,211,647 A 5/1993 Schmieding
5,211,650 A 5/1993 Noda
5,214,987 A 6/1993 Fenton, Sr.
5,217,495 A 6/1993 Kaplan et al.
5,219,359 A 6/1993 McQuilkin et al.
5,222,976 A 6/1993 Yoon
5,224,940 A 7/1993 Dann et al.
5,224,946 A 7/1993 Hayhurst et al.
5,226,914 A 7/1993 Caplan et al.
5,230,699 A 7/1993 Grasinger
5,232,436 A 8/1993 Janevski
5,234,435 A 8/1993 Seagrave, Jr.
5,235,238 A 8/1993 Nomura et al.
5,236,445 A 8/1993 Hayhurst et al.
5,236,461 A 8/1993 Forte
5,242,447 A 9/1993 Borzone
5,246,441 A 9/1993 Ross et al.
5,249,899 A 10/1993 Wilson
5,250,053 A 10/1993 Snyder
5,258,015 A 11/1993 Li et al.
5,258,016 A 11/1993 Dipoto et al.
5,258,040 A 11/1993 Bruchman et al.
5,261,908 A 11/1993 Campbell, Jr.
5,268,001 A 12/1993 Nicholson et al.
5,269,160 A 12/1993 Wood
5,269,783 A 12/1993 Sander
5,269,806 A 12/1993 Sardelis et al.
5,269,809 A 12/1993 Hayhurst et al.
5,279,311 A 1/1994 Snyder
5,281,422 A 1/1994 Badylak et al.
5,282,809 A 2/1994 Kammerer et al.
5,282,832 A 2/1994 Toso et al.
5,282,867 A 2/1994 Mikhail
5,282,868 A 2/1994 Bahler
5,285,040 A 2/1994 Brandberg et al.
5,290,217 A 3/1994 Campos
5,290,243 A 3/1994 Chodorow et al.
5,306,301 A 4/1994 Graf et al.
5,312,410 A 5/1994 Miller et al.
5,312,422 A 5/1994 Trott
5,312,438 A 5/1994 Johnson
5,314,429 A 5/1994 Goble
5,318,566 A 6/1994 Miller
5,318,575 A 6/1994 Chesterfield et al.
5,318,577 A 6/1994 Li
5,318,578 A 6/1994 Hasson
5,320,115 A 6/1994 Kenna
5,320,626 A 6/1994 Schmieding
5,320,633 A 6/1994 Allen et al.
5,324,308 A 6/1994 Pierce
5,330,489 A 7/1994 Green et al.
5,330,534 A 7/1994 Herrington et al.
5,333,625 A 8/1994 Klein
5,334,204 A 8/1994 Clewett et al.
5,336,229 A 8/1994 Noda
5,336,231 A 8/1994 Adair
5,336,240 A 8/1994 Metzler et al.
5,339,870 A 8/1994 Green et al.
5,342,369 A 8/1994 Harryman, II
5,344,460 A 9/1994 Turanyi et al.
5,346,462 A 9/1994 Barber
5,350,380 A 9/1994 Goble et al.
RE34,762 E 10/1994 Goble et al.
5,354,292 A 10/1994 Braeuer et al.
5,354,298 A 10/1994 Lee et al.
5,354,299 A 10/1994 Coleman
5,356,412 A 10/1994 Golds et al.
5,356,413 A 10/1994 Martins et al.
5,356,417 A 10/1994 Golds
5,358,511 A 10/1994 Gatturna et al.
5,358,530 A 10/1994 Hodorek
5,358,531 A 10/1994 Goodfellow et al.
5,360,431 A 11/1994 Puno et al.
5,362,294 A 11/1994 Seitzinger
5,362,911 A 11/1994 Cevasco et al.
5,364,400 A 11/1994 Rego, Jr. et al.
5,366,461 A 11/1994 Blasnik
5,368,599 A 11/1994 Hirsch et al.
5,370,646 A 12/1994 Reese et al.
5,370,661 A 12/1994 Branch
5,370,662 A 12/1994 Stone et al.
5,372,146 A 12/1994 Branch
5,372,604 A 12/1994 Trott
5,372,821 A 12/1994 Badylak et al.
5,374,268 A 12/1994 Sander
5,374,269 A 12/1994 Rosenberg
5,376,118 A 12/1994 Kaplan et al.
5,379,492 A 1/1995 Glesser
5,383,878 A 1/1995 Roger et al.
5,383,904 A 1/1995 Totakura et al.
5,385,567 A 1/1995 Goble
5,391,171 A 2/1995 Schmieding
5,391,176 A 2/1995 De La Torre
5,391,182 A 2/1995 Chin
5,393,302 A 2/1995 Clark et al.
RE34,871 E 3/1995 Mcguire et al.
5,395,374 A 3/1995 Miller et al.
5,395,401 A 3/1995 Bahler
5,397,356 A 3/1995 Goble et al.
5,403,328 A 4/1995 Shallman
5,403,329 A 4/1995 Hinchcliffe
5,403,348 A 4/1995 Bonutti
5,405,359 A 4/1995 Pierce
5,411,550 A 5/1995 Herweck et al.
5,415,658 A 5/1995 Kilpela et al.
5,417,690 A 5/1995 Sennett et al.
5,417,691 A 5/1995 Hayhurst
5,417,698 A 5/1995 Green et al.
5,417,712 A 5/1995 Whittaker et al.
5,423,819 A 6/1995 Small et al.
5,423,821 A 6/1995 Pasque
5,423,823 A 6/1995 Schmieding
5,423,824 A 6/1995 Akerfeldt et al.
5,423,860 A 6/1995 Lizardi et al.
5,425,733 A 6/1995 Schmieding
5,425,766 A 6/1995 Bowald

(56) References Cited

U.S. PATENT DOCUMENTS 5,433,751 A 7/1995 Christel et al.
5,437,680 A 8/1995 Yoon
5,437,685 A 8/1995 Blasnik
5,439,684 A 8/1995 Prewett et al.
5,441,508 A 8/1995 Gazielly et al.
5,443,468 A 8/1995 Johnson
5,443,482 A 8/1995 Stone et al.
5,443,483 A 8/1995 Kirsch
5,443,509 A 8/1995 Boucher et al.
5,445,833 A 8/1995 Badylak et al.
5,447,512 A 9/1995 Wilson et al.
5,449,361 A 9/1995 Preissman
5,451,203 A 9/1995 Lamb
5,454,811 A 10/1995 Huebner
5,454,821 A 10/1995 Harm et al.
5,456,685 A 10/1995 Huebner
5,456,721 A 10/1995 Legrand
5,456,722 A 10/1995 Mcleod et al.
5,458,601 A 10/1995 Young, Jr. et al.
5,458,604 A 10/1995 Schmieding
5,462,542 A 10/1995 Alesi, Jr.
5,462,560 A 10/1995 Stevens
5,464,426 A 11/1995 Bonutti
5,464,427 A 11/1995 Curtis et al.
5,464,440 A 11/1995 Johansson
5,466,237 A 11/1995 Byrd, III et al.
5,467,786 A 11/1995 Allen et al.
5,470,334 A 11/1995 Ross et al.
5,470,337 A 11/1995 Moss
5,470,338 A 11/1995 Whitfield et al.
5,470,354 A 11/1995 Hershberger et al.
5,472,452 A 12/1995 Trott
5,474,565 A 12/1995 Trott
5,474,568 A 12/1995 Scott et al.
5,474,572 A 12/1995 Hayhurst
5,476,465 A 12/1995 Preissman
5,478,344 A 12/1995 Stone et al.
5,478,345 A 12/1995 Stone et al.
5,480,403 A 1/1996 Lee et al.
5,480,406 A 1/1996 Nolan et al.
5,480,446 A 1/1996 Goodfellow et al.
5,484,442 A 1/1996 Melker et al.
5,486,197 A 1/1996 Le et al.
5,486,359 A 1/1996 Caplan et al.
5,489,210 A 2/1996 Hanosh
5,490,750 A 2/1996 Gundy
5,495,974 A 3/1996 Deschenes et al.
5,496,290 A 3/1996 Ackerman
5,496,331 A 3/1996 Xu et al.
5,496,348 A 3/1996 Bonutti
5,498,302 A 3/1996 Davidson
5,500,000 A 3/1996 Feagin et al.
5,505,735 A 4/1996 Li
5,505,736 A 4/1996 Reimels et al.
5,507,754 A 4/1996 Green et al.
5,514,059 A 5/1996 Romney
5,520,691 A 5/1996 Branch
5,520,694 A 5/1996 Dance et al.
5,520,700 A 5/1996 Beyar et al.
5,520,702 A 5/1996 Sauer et al.
5,522,817 A 6/1996 Sander et al.
5,522,820 A 6/1996 Caspari et al.
5,522,843 A 6/1996 Zang
5,522,844 A 6/1996 Johnson
5,522,845 A 6/1996 Wenstrom, Jr.
5,522,846 A 6/1996 Bonutti
5,524,946 A 6/1996 Thompson
5,527,321 A 6/1996 Hinchliffe
5,527,342 A 6/1996 Pietrzak et al.
5,527,343 A 6/1996 Bonutti
5,531,759 A 7/1996 Kensey et al.
5,534,011 A 7/1996 Greene, Jr. et al.
5,534,012 A 7/1996 Bonutti
5,534,033 A 7/1996 Simpson
5,536,270 A 7/1996 Songer et al.
5,540,698 A 7/1996 Preissman
5,540,703 A 7/1996 Barker, Jr. et al.
5,540,718 A 7/1996 Bartlett
5,545,168 A 8/1996 Burke
5,545,178 A 8/1996 Kensey et al.
5,545,180 A 8/1996 Le et al.
5,545,228 A 8/1996 Kambin
5,549,613 A 8/1996 Goble et al.
5,549,617 A 8/1996 Green et al.
5,549,619 A 8/1996 Peters et al.
5,549,630 A 8/1996 Bonutti
5,549,631 A 8/1996 Bonutti
5,562,664 A 10/1996 Durlacher et al.
5,562,668 A 10/1996 Johnson
5,562,669 A 10/1996 Mcguire
5,562,683 A 10/1996 Chan
5,562,685 A 10/1996 Mollenauer et al.
5,562,686 A 10/1996 Sauer et al.
5,569,252 A 10/1996 Justin et al.
5,569,269 A 10/1996 Hart et al.
5,569,305 A 10/1996 Bonutti
5,569,306 A 10/1996 Thal
5,570,706 A 11/1996 Howell
5,571,090 A 11/1996 Sherts
5,571,104 A 11/1996 Li
5,571,139 A 11/1996 Jenkins, Jr.
5,572,655 A 11/1996 Tuljapurkar et al.
5,573,286 A 11/1996 Rogozinski
5,573,542 A 11/1996 Stevens
5,573,547 A 11/1996 LeVeen et al.
5,573,548 A 11/1996 Nazre et al.
5,577,299 A 11/1996 Thompson et al.
5,578,057 A 11/1996 Wenstrom, Jr.
5,584,695 A 12/1996 Sachdeva et al.
5,584,835 A 12/1996 Greenfield
5,584,836 A 12/1996 Ballintyn et al.
5,584,862 A 12/1996 Bonutti
5,586,986 A 12/1996 Hinchliffe
5,588,575 A 12/1996 Davignon
5,591,180 A 1/1997 Hinchliffe
5,591,181 A 1/1997 Stone et al.
5,591,207 A 1/1997 Coleman
5,593,407 A 1/1997 Reis
5,593,425 A 1/1997 Bonutti et al.
5,601,557 A 2/1997 Hayhurst
5,601,559 A 2/1997 Melker et al.
5,601,571 A 2/1997 Moss
5,603,716 A 2/1997 Morgan et al.
5,607,429 A 3/1997 Hayano et al.
5,607,430 A 3/1997 Bailey
5,613,971 A 3/1997 Lower et al.
5,618,290 A 4/1997 Toy et al.
5,626,611 A 5/1997 Liu et al.
5,626,614 A 5/1997 Hart
5,628,756 A 5/1997 Barker, Jr. et al.
5,628,766 A 5/1997 Johnson
5,630,824 A 5/1997 Hart
5,632,745 A 5/1997 Schwartz
5,632,748 A 5/1997 Beck, Jr. et al.
5,641,256 A 6/1997 Gundy
5,643,266 A 7/1997 Li
5,643,269 A 7/1997 Harle
5,643,273 A 7/1997 Clark
5,643,295 A 7/1997 Yoon
5,643,319 A 7/1997 Green et al.
5,643,320 A 7/1997 Lower et al.
5,643,321 A 7/1997 Mcdevitt
5,645,546 A 7/1997 Fard
5,645,547 A 7/1997 Coleman
5,645,568 A 7/1997 Chervitz et al.
5,645,588 A 7/1997 Graf et al.
5,647,874 A 7/1997 Hayhurst
5,649,959 A 7/1997 Hannam et al.
5,649,960 A 7/1997 Pavletic
5,649,963 A 7/1997 Mcdevitt
5,658,289 A 8/1997 Boucher et al.
5,658,299 A 8/1997 Hart
5,658,313 A 8/1997 Thal
5,662,658 A 9/1997 Wenstrom, Jr.

(56) References Cited

U.S. PATENT DOCUMENTS 5,662,663 A 9/1997 Shallman
5,662,677 A 9/1997 Wimmer
5,662,681 A 9/1997 Nash et al.
5,665,112 A 9/1997 Thal
5,667,513 A 9/1997 Torrie et al.
5,671,695 A 9/1997 Schroeder
5,673,546 A 10/1997 Abraham et al.
5,674,224 A 10/1997 Howell et al.
5,679,723 A 10/1997 Cooper
5,681,334 A 10/1997 Evans et al.
5,681,352 A 10/1997 Clancy, III et al.
5,683,404 A 11/1997 Johnson
5,683,419 A 11/1997 Thal
5,688,284 A 11/1997 Chervitz et al.
5,688,285 A 11/1997 Yamada
5,690,655 A 11/1997 Hart et al.
5,690,676 A 11/1997 Dipoto et al.
5,690,678 A 11/1997 Johnson
5,693,046 A 12/1997 Songer et al.
5,695,497 A 12/1997 Stahelin
5,697,929 A 12/1997 Mellinger
5,697,969 A 12/1997 Schmitt et al.
5,699,657 A 12/1997 Paulson
5,700,277 A 12/1997 Nash et al.
5,702,397 A 12/1997 Goble et al.
5,702,422 A 12/1997 Stone
5,702,462 A 12/1997 Oberlander
5,702,464 A 12/1997 Lackey et al.
5,707,373 A 1/1998 Sevrain et al.
5,709,708 A 1/1998 Thal et al.
5,711,969 A 1/1998 Patel et al.
5,713,005 A 1/1998 Proebsting
5,713,897 A 2/1998 Goble et al.
5,713,904 A 2/1998 Errico et al.
5,713,905 A 2/1998 Goble et al.
5,713,921 A 2/1998 Bonutti
5,715,578 A 2/1998 Knudson
5,716,359 A 2/1998 Ojima et al.
5,716,397 A 2/1998 Myers
5,716,616 A 2/1998 Prockop et al.
5,718,717 A 2/1998 Bonutti
5,720,747 A 2/1998 Burke
5,720,765 A 2/1998 Thal
5,720,766 A 2/1998 Zang et al.
5,722,976 A 3/1998 Brown
5,723,331 A 3/1998 Tubo et al.
5,725,529 A 3/1998 Nicholson et al.
5,725,549 A 3/1998 Lam
5,725,556 A 3/1998 Moser et al.
5,725,557 A 3/1998 Gatturna et al.
5,725,581 A 3/1998 Branemark
5,725,582 A 3/1998 Bevan et al.
5,726,722 A 3/1998 Uehara et al.
5,728,107 A 3/1998 Zlock et al.
5,728,109 A 3/1998 Schulze et al.
5,728,136 A 3/1998 Thal
5,733,293 A 3/1998 Scirica et al.
5,733,306 A 3/1998 Bonutti
5,733,307 A 3/1998 Dinsdale
5,735,875 A 4/1998 Bonutti et al.
5,741,259 A 4/1998 Chan
5,741,260 A 4/1998 Songer et al.
5,741,281 A 4/1998 Martin
5,743,912 A 4/1998 Lahille et al.
5,746,751 A 5/1998 Sherts
5,746,752 A 5/1998 Burkhart
5,746,754 A 5/1998 Chan
5,749,898 A 5/1998 Schulze et al.
5,755,729 A 5/1998 De La Torre et al.
5,755,791 A 5/1998 Whitson et al.
5,766,176 A 6/1998 Duncan
5,766,218 A 6/1998 Arnott
5,766,250 A 6/1998 Chervitz et al.
5,769,894 A 6/1998 Ferragamo
5,769,899 A 6/1998 Schwartz et al.
5,772,673 A 6/1998 Cuny et al.
5,776,196 A 7/1998 Matsuzaki et al.
5,776,200 A 7/1998 Johnson et al.
5,782,845 A 7/1998 Shewchuk
5,782,862 A 7/1998 Bonutti
5,782,864 A 7/1998 Lizardi
5,782,866 A 7/1998 Wenstrom, Jr.
5,782,925 A 7/1998 Collazo et al.
5,785,714 A 7/1998 Morgan et al.
5,786,217 A 7/1998 Tubo et al.
5,792,142 A 8/1998 Galitzer
5,792,149 A 8/1998 Sherts et al.
5,796,127 A 8/1998 Hayafuji et al.
5,797,913 A 8/1998 Dambreville et al.
5,797,915 A 8/1998 Pierson, III et al.
5,797,916 A 8/1998 McDowell
5,797,928 A 8/1998 Kogasaka
5,800,407 A 9/1998 Eldor
5,800,447 A 9/1998 Wenstrom, Jr.
5,800,543 A 9/1998 Mcleod et al.
5,810,824 A 9/1998 Chan
5,810,848 A 9/1998 Hayhurst
5,811,094 A 9/1998 Caplan et al.
5,814,056 A 9/1998 Prosst et al.
5,814,069 A 9/1998 Schulze et al.
5,814,070 A 9/1998 Borzone et al.
5,814,071 A 9/1998 Mcdevitt et al.
5,814,072 A 9/1998 Bonutti
5,814,073 A 9/1998 Bonutti
5,817,095 A 10/1998 Smith
5,823,980 A 10/1998 Kopfer
5,824,011 A 10/1998 Stone et al.
5,824,066 A 10/1998 Gross
5,827,285 A 10/1998 Bramlet
5,830,234 A 11/1998 Wojciechowicz et al.
5,836,955 A 11/1998 Buelna et al.
5,843,084 A 12/1998 Hart et al.
5,845,645 A 12/1998 Bonutti
5,846,254 A 12/1998 Schulze et al.
5,848,983 A 12/1998 Basaj et al.
5,849,012 A 12/1998 Abboudi
5,860,947 A 1/1999 Stamler
5,860,973 A 1/1999 Michelson
5,860,978 A 1/1999 Mcdevitt et al.
5,868,740 A 2/1999 LaVeen et al.
5,868,748 A 2/1999 Burke
5,868,789 A 2/1999 Huebner
5,871,456 A 2/1999 Armstrong et al.
5,871,484 A 2/1999 Spievack et al.
5,871,486 A 2/1999 Huebner
5,871,490 A 2/1999 Schulze et al.
5,871,542 A 2/1999 Goodfellow et al.
5,871,543 A 2/1999 Hofmann
5,885,294 A 3/1999 Pedlick et al.
5,891,168 A 4/1999 Thal
5,893,592 A 4/1999 Schulze et al.
5,895,395 A 4/1999 Yeung
5,897,564 A 4/1999 Schulze et al.
5,897,574 A 4/1999 Bonutti
5,899,902 A 5/1999 Brown et al.
5,899,920 A 5/1999 Desatnick et al.
5,899,938 A 5/1999 Sklar et al.
5,906,934 A 5/1999 Grande et al.
5,908,421 A 6/1999 Beger
5,908,436 A 6/1999 Cuschieri et al.
5,910,148 A 6/1999 Reimels et al.
5,911,721 A 6/1999 Nicholson et al.
5,916,557 A 6/1999 Berlowitz-tarrant et al.
5,918,604 A 7/1999 Whelan
5,919,232 A 7/1999 Chaffringeon et al.
5,921,986 A 7/1999 Bonutti
5,925,008 A 7/1999 Douglas
5,928,231 A 7/1999 Klein et al.
5,928,267 A 7/1999 Bonutti et al.
5,928,286 A 7/1999 Ashby et al.
RE36,289 E 8/1999 Le et al.
5,931,838 A 8/1999 Vito
5,931,844 A 8/1999 Thompson et al.
5,931,869 A 8/1999 Boucher et al.

(56) References Cited

U.S. PATENT DOCUMENTS 5,935,119 A 8/1999 Guy et al.
5,935,129 A 8/1999 Mcdevitt et al.
5,935,133 A 8/1999 Wagner et al.
5,935,134 A 8/1999 Pedlick et al.
5,935,149 A 8/1999 Ek
5,938,668 A 8/1999 Scirica et al.
5,941,439 A 8/1999 Kammerer et al.
5,941,900 A 8/1999 Bonutti
5,944,739 A 8/1999 Zlock et al.
5,946,783 A 9/1999 Plociennik et al.
5,947,915 A 9/1999 Thibodo, Jr.
5,947,982 A 9/1999 Duran
5,947,999 A 9/1999 Groiso
5,948,002 A 9/1999 Bonutti
5,951,559 A 9/1999 Burkhart
5,951,560 A 9/1999 Simon et al.
5,954,747 A 9/1999 Clark
5,957,953 A 9/1999 Dipoto et al.
5,961,520 A 10/1999 Beck, Jr. et al.
5,961,521 A 10/1999 Roger
5,961,524 A 10/1999 Crombie
5,963,869 A 10/1999 Fehnel
5,964,764 A 10/1999 West, Jr. et al.
5,964,767 A 10/1999 Tapia et al.
5,964,769 A 10/1999 Wagner et al.
5,964,783 A 10/1999 Grafton et al.
5,964,808 A 10/1999 Blaha et al.
5,968,045 A 10/1999 Frazier
5,968,047 A 10/1999 Reed
5,968,077 A 10/1999 Wojciechowicz et al.
5,968,078 A 10/1999 Grotz
5,968,099 A 10/1999 Badorf et al.
5,970,697 A 10/1999 Jacobs et al.
5,972,006 A 10/1999 Sciaino, Jr.
5,976,125 A 11/1999 Graham
5,976,127 A 11/1999 Lax
5,980,473 A 11/1999 Korakianitis et al.
5,980,524 A 11/1999 Justin et al.
5,980,539 A 11/1999 Kontos
5,980,548 A 11/1999 Evans et al.
5,980,558 A 11/1999 Wiley
5,980,559 A 11/1999 Bonutti
5,989,252 A 11/1999 Fumex
5,989,256 A 11/1999 Kuslich et al.
5,989,282 A 11/1999 Bonutti
5,989,294 A 11/1999 Marlow
5,993,452 A 11/1999 Vandewalle
5,993,476 A 11/1999 Groiso
5,997,542 A 12/1999 Burke
5,997,552 A 12/1999 Person et al.
5,997,575 A 12/1999 Whitson et al.
6,001,100 A 12/1999 Sherman et al.
6,001,106 A 12/1999 Ryan et al.
6,004,351 A 12/1999 Tomita et al.
6,004,352 A 12/1999 Buni
6,007,538 A 12/1999 Levin
6,007,567 A 12/1999 Bonutti
6,010,525 A 1/2000 Bonutti et al.
6,013,103 A 1/2000 Kaufman et al.
6,016,727 A 1/2000 Morgan
6,019,767 A 2/2000 Howell
6,022,352 A 2/2000 Vandewalle
6,022,373 A 2/2000 Li
6,023,661 A 2/2000 Sottery
6,024,758 A 2/2000 Thal
6,027,523 A 2/2000 Schmieding
6,030,410 A 2/2000 Zurbrugg
6,033,429 A 3/2000 Magovern
6,033,430 A 3/2000 Bonutti
6,036,695 A 3/2000 Smith
6,039,753 A 3/2000 Meislin
6,041,485 A 3/2000 Pedlick et al.
6,042,601 A 3/2000 Smith
6,042,609 A 3/2000 Giordano et al.
6,045,551 A 4/2000 Bonutti
6,045,571 A 4/2000 Hill et al.
6,045,572 A 4/2000 Johnson et al.
6,045,573 A 4/2000 Wenstrom, Jr. et al.
6,045,574 A 4/2000 Thal
6,047,826 A 4/2000 Kalinski et al.
6,048,343 A 4/2000 Mathis et al.
6,051,006 A 4/2000 Shluzas et al.
6,051,007 A 4/2000 Hogendijk et al.
6,053,916 A 4/2000 Moore
6,053,921 A 4/2000 Wagner et al.
6,056,752 A 5/2000 Roger
6,056,772 A 5/2000 Bonutti
6,056,773 A 5/2000 Bonutti
6,059,817 A 5/2000 Bonutti et al.
6,059,818 A 5/2000 Johnson et al.
6,062,344 A 5/2000 Okabe et al.
6,066,146 A 5/2000 Carroll et al.
6,066,173 A 5/2000 Mckernan et al.
6,068,648 A 5/2000 Cole et al.
6,071,305 A 6/2000 Brown et al.
6,074,403 A 6/2000 Nord
6,077,277 A 6/2000 Mollenauer et al.
6,077,292 A 6/2000 Bonutti
6,080,185 A 6/2000 Johnson et al.
6,083,257 A 7/2000 Taylor et al.
6,086,591 A 7/2000 Bojarski
6,086,592 A 7/2000 Rosenberg et al.
6,086,608 A 7/2000 Ek et al.
6,093,200 A 7/2000 Liu et al.
6,096,060 A 8/2000 Fitts et al.
6,099,527 A 8/2000 Hochschuler et al.
6,099,530 A 8/2000 Simonian et al.
6,099,568 A 8/2000 Simonian et al.
6,102,934 A 8/2000 Li
6,106,545 A 8/2000 Egan et al.
6,110,128 A 8/2000 Andelin et al.
6,110,207 A 8/2000 Eichhorn et al.
6,113,604 A 9/2000 Whittaker et al.
6,117,160 A 9/2000 Bonutti
6,117,162 A 9/2000 Schmieding et al.
6,123,710 A 9/2000 Pinczewski et al.
6,127,596 A 10/2000 Brown et al.
6,132,433 A 10/2000 Whelan
6,132,437 A 10/2000 Omurtag
6,136,010 A 10/2000 Modesitt et al.
6,139,565 A 10/2000 Stone et al.
RE36,974 E 11/2000 Bonutti
6,143,017 A 11/2000 Thal
6,146,406 A 11/2000 Shluzas et al.
6,146,408 A 11/2000 Bartlett
6,149,653 A 11/2000 Deslauriers
6,149,669 A 11/2000 Li
6,150,163 A 11/2000 McPherson et al.
6,152,928 A 11/2000 Wenstrom, Jr.
6,152,934 A 11/2000 Harper et al.
6,152,936 A 11/2000 Christy et al.
6,152,949 A 11/2000 Bonutti
6,156,039 A 12/2000 Thal
6,156,056 A 12/2000 Kearns et al.
6,159,234 A 12/2000 Bonutti et al.
6,165,203 A 12/2000 Krebs
6,168,598 B1 1/2001 Martello
6,168,628 B1 1/2001 Huebner
6,171,310 B1 1/2001 Giordano et al.
6,174,324 B1 1/2001 Egan et al.
6,179,840 B1 1/2001 Bowman
6,183,461 B1 2/2001 Matsuura et al.
6,183,737 B1 2/2001 Zaleske et al.
6,187,025 B1 2/2001 Machek
6,190,348 B1 2/2001 Tiemann
6,190,401 B1 2/2001 Green et al.
6,190,411 B1 2/2001 Lo
6,190,415 B1 2/2001 Cooke et al.
6,193,754 B1 2/2001 Seedhom
6,200,318 B1 3/2001 Har-shai et al.
6,200,329 B1 3/2001 Fung et al.
6,200,330 B1 3/2001 Benderev et al.
6,200,606 B1 3/2001 Peterson et al.
6,200,685 B1 3/2001 Davidson

(56) References Cited

U.S. PATENT DOCUMENTS 6,203,556 B1 3/2001 Evans et al.
6,203,563 B1 3/2001 Fernandez
6,203,565 B1 3/2001 Bonutti et al.
6,203,572 B1 3/2001 Johnson et al.
6,203,576 B1 3/2001 Afriat et al.
6,206,883 B1 3/2001 Tunc
6,210,376 B1 4/2001 Grayson
6,210,381 B1 4/2001 Morse
6,210,445 B1 4/2001 Zawadzki
6,214,007 B1 4/2001 Anderson
6,214,012 B1 4/2001 Karpman et al.
6,217,580 B1 4/2001 Levin
6,221,107 B1 4/2001 Steiner
6,228,096 B1 5/2001 Marchand
6,231,592 B1 5/2001 Bonutti et al.
6,234,980 B1 5/2001 Bell
6,235,057 B1 5/2001 Roger et al.
6,235,058 B1 5/2001 Huene
6,238,395 B1 5/2001 Bonutti
6,241,734 B1 6/2001 Scribner et al.
6,241,747 B1 6/2001 Ruff
6,241,771 B1 6/2001 Gresser et al.
6,245,024 B1 6/2001 Montagnino et al.
6,245,081 B1 6/2001 Bowman
6,254,604 B1 7/2001 Howell
6,258,091 B1 7/2001 Sevrain et al.
6,267,766 B1 7/2001 Burkhart
6,269,716 B1 8/2001 Amis
6,270,518 B1 8/2001 Pedlick et al.
6,273,890 B1 8/2001 Frazier
6,280,474 B1 8/2001 Cassidy et al.
6,283,973 B1 9/2001 Hubbard et al.
6,283,996 B1 9/2001 Chervitz et al.
6,287,307 B1 9/2001 Abboudi
6,287,325 B1 9/2001 Bonutti
6,293,929 B1 9/2001 Smith et al.
6,293,961 B2 9/2001 Schwartz et al.
6,296,659 B1 10/2001 Foerster
6,299,615 B1 10/2001 Huebner
6,302,888 B1 10/2001 Mellinger et al.
6,302,899 B1 10/2001 Johnson et al.
6,302,915 B1 10/2001 Cooney, III et al.
6,303,158 B1 10/2001 Odgaard et al.
6,306,156 B1 10/2001 Clark
6,306,158 B1 10/2001 Bartlett
6,306,159 B1 10/2001 Schwartz et al.
6,309,124 B1 10/2001 Gueret
6,309,405 B1 10/2001 Bonutti
6,312,448 B1 11/2001 Bonutti
6,315,788 B1 11/2001 Roby
6,319,224 B1 11/2001 Stout et al.
6,319,271 B1 11/2001 Schwartz et al.
6,328,758 B1 12/2001 Tornier et al.
6,334,064 B1 12/2001 Fiddian-green
6,342,060 B1 1/2002 Adams
6,343,531 B2 2/2002 Amis
6,355,066 B1 3/2002 Kim et al.
6,358,270 B1 3/2002 Lemer
6,364,897 B1 4/2002 Bonutti
6,368,322 B1 4/2002 Luks et al.
6,368,326 B1 4/2002 Dakin et al.
6,368,343 B1 4/2002 Bonutti et al.
6,371,124 B1 4/2002 Whelan
6,379,361 B1 4/2002 Beck, Jr. et al.
6,383,190 B1 5/2002 Preissman
6,383,199 B2 5/2002 Carter et al.
6,387,111 B1 5/2002 Barber
6,387,113 B1 5/2002 Hawkins et al.
6,387,129 B2 5/2002 Rieser et al.
6,391,030 B1 5/2002 Wagner et al.
6,398,785 B2 6/2002 Carchidi et al.
6,406,456 B1 6/2002 Slate et al.
6,406,479 B1 6/2002 Justin et al.
6,409,743 B1 6/2002 Fenton, Jr.
6,413,260 B1 7/2002 Berrevoets et al.
6,423,073 B2 7/2002 Bowman
6,423,088 B1 7/2002 Fenton, Jr.
6,425,924 B1 7/2002 Rousseau
6,428,562 B2 8/2002 Bonutti
6,432,123 B2 8/2002 Schwartz et al.
6,436,123 B1 8/2002 Magovern
6,436,124 B1 8/2002 Anderson et al.
6,440,134 B1 8/2002 Zaccherotti et al.
6,440,136 B1 8/2002 Gambale et al.
6,447,516 B1 9/2002 Bonutti
6,451,030 B2 9/2002 Li et al.
6,454,768 B1 9/2002 Jackson
6,458,134 B1 10/2002 Songer et al.
6,458,161 B1 10/2002 Gibbs et al.
6,461,373 B2 10/2002 Wyman et al.
6,464,690 B1 10/2002 Castaneda et al.
6,464,713 B2 10/2002 Bonutti
6,468,293 B2 10/2002 Bonutti et al.
6,471,707 B1 10/2002 Miller et al.
6,475,230 B1 11/2002 Bonutti et al.
6,478,753 B2 11/2002 Reay-young
6,482,210 B1 11/2002 Skiba et al.
6,485,504 B1 11/2002 Johnson et al.
6,491,714 B1 12/2002 Bennett
6,497,901 B1 12/2002 Royer
6,500,184 B1 12/2002 Chan et al.
6,500,195 B2 12/2002 Bonutti
6,500,208 B1 12/2002 Metzger et al.
RE37,963 E 1/2003 Thal
6,503,267 B2 1/2003 Bonutti et al.
6,506,190 B1 1/2003 Walshe
6,508,820 B2 1/2003 Bales
6,508,821 B1 1/2003 Schwartz et al.
6,508,830 B2 1/2003 Steiner
6,511,498 B1 1/2003 Fumex
6,511,499 B2 1/2003 Schmieding et al.
6,514,274 B1 2/2003 Boucher et al.
6,517,542 B1 2/2003 Papay et al.
6,517,552 B1 2/2003 Nord et al.
6,517,564 B1 2/2003 Grafton et al.
6,517,578 B2 2/2003 Hein
6,517,579 B1 2/2003 Paulos et al.
6,520,964 B2 2/2003 Tallarida et al.
6,520,980 B1 2/2003 Foerster
6,524,317 B1 2/2003 Ritchart et al.
6,527,777 B2 3/2003 Justin
6,527,794 B1 3/2003 Mcdevitt et al.
6,527,795 B1 3/2003 Lizardi
6,533,795 B1 3/2003 Tran et al.
6,533,802 B2 3/2003 Bojarski et al.
6,537,319 B2 3/2003 Whelan
6,540,750 B2 4/2003 Burkhart
6,540,769 B1 4/2003 Miller, III
6,540,770 B1 4/2003 Tornier et al.
6,540,783 B1 4/2003 Whittaker et al.
6,543,094 B2 4/2003 D'addario
6,544,281 B2 4/2003 Elattrache et al.
6,547,564 B1 4/2003 Hansson
6,547,778 B1 4/2003 Sklar et al.
6,547,800 B2 4/2003 Foerster et al.
6,551,330 B1 4/2003 Bain et al.
6,551,343 B1 4/2003 Tormala et al.
6,551,353 B1 4/2003 Baker et al.
6,553,802 B1 4/2003 Jacob
6,554,830 B1 4/2003 Chappius
6,554,852 B1 4/2003 Oberlander
6,554,862 B2 4/2003 Hays et al.
6,558,389 B2 5/2003 Clark et al.
6,562,071 B2 5/2003 Järvinen
6,565,572 B2 5/2003 Chappius
6,565,573 B1 5/2003 Ferrante
6,569,167 B1 5/2003 Bobechko et al.
6,569,186 B1 5/2003 Winters et al.
6,569,187 B1 5/2003 Bonutti et al.
6,572,635 B1 6/2003 Bonutti
6,572,655 B1 6/2003 Johnson
6,575,925 B1 6/2003 Noble
6,579,295 B1 6/2003 Supinski
6,582,453 B1 6/2003 Tran et al.

(56) References Cited

U.S. PATENT DOCUMENTS 6,585,730 B1 7/2003 Foerster
6,585,740 B2 7/2003 Schlapfer et al.
6,585,750 B2 7/2003 Bonutti et al.
6,589,245 B1 7/2003 Weiler et al.
6,589,246 B1 7/2003 Hack et al.
6,592,609 B1 7/2003 Bonutti
6,592,622 B1 7/2003 Ferguson
6,595,911 B2 7/2003 Lovuolo
6,599,289 B1 7/2003 Bojarski et al.
6,599,319 B2 7/2003 Knudsen et al.
6,605,096 B1 8/2003 Ritchart
6,607,548 B2 8/2003 Pohjonen et al.
6,610,064 B1 8/2003 Goble et al.
6,610,079 B1 8/2003 Li et al.
6,613,018 B2 9/2003 Bagga et al.
6,616,694 B1 9/2003 Hart
6,620,166 B1 9/2003 Wenstrom, Jr. et al.
6,620,185 B1 9/2003 Harvie et al.
6,620,195 B2 9/2003 Goble et al.
6,620,329 B2 9/2003 Rosen et al.
6,620,349 B1 9/2003 Lopez
6,623,492 B1 9/2003 Berube et al.
6,623,524 B2 9/2003 Schmieding
6,626,910 B1 9/2003 Hugues
6,626,919 B1 9/2003 Swanstrom
6,626,930 B1 9/2003 Allen et al.
6,629,977 B1 10/2003 Wolf
6,629,997 B2 10/2003 Mansmann
6,632,245 B2 10/2003 Kim
6,635,073 B2 10/2003 Bonutti
6,638,279 B2 10/2003 Bonutti
6,638,286 B1 10/2003 Burbank et al.
6,638,312 B2 10/2003 Plouhar et al.
6,641,596 B1 11/2003 Lizardi
6,641,597 B2 11/2003 Burkhart et al.
6,645,169 B1 11/2003 Slate et al.
6,645,211 B2 11/2003 Magana
6,645,227 B2 11/2003 Fallin et al.
6,648,903 B1 11/2003 Pierson, III
6,648,921 B2 11/2003 Anderson et al.
6,652,450 B2 11/2003 Neisz et al.
6,652,533 B2 11/2003 O'neil
6,652,560 B1 11/2003 Gerke et al.
6,652,562 B2 11/2003 Collier et al.
6,652,563 B2 11/2003 Dreyfuss
6,656,182 B1 12/2003 Hayhurst
6,656,183 B2 12/2003 Colleran et al.
6,658,182 B1 12/2003 Gonthier
6,660,008 B1 12/2003 Foerster et al.
6,660,022 B1 12/2003 Li et al.
6,663,634 B2 12/2003 Ahrens et al.
6,663,656 B2 12/2003 Schmieding et al.
6,666,868 B2 12/2003 Fallin
6,666,877 B2 12/2003 Morgan et al.
6,669,707 B1 12/2003 Swanstrom et al.
6,679,889 B1 1/2004 West, Jr. et al.
6,682,533 B1 1/2004 Dinsdale et al.
6,682,549 B2 1/2004 Bartlett
6,685,728 B2 2/2004 Sinnott et al.
6,689,137 B2 2/2004 Reed
6,689,153 B1 2/2004 Skiba
6,689,154 B2 2/2004 Bartlett
6,692,499 B2 2/2004 Tormala et al.
6,692,516 B2 2/2004 West, Jr. et al.
6,695,852 B2 2/2004 Gleason
6,712,849 B2 3/2004 Re et al.
6,712,859 B2 3/2004 Rousseau
6,716,190 B1 4/2004 Glines et al.
6,716,224 B2 4/2004 Singhatat
6,716,234 B2 4/2004 Grafton et al.
6,716,957 B2 4/2004 Tunc
6,730,092 B2 5/2004 Songer
6,730,124 B2 5/2004 Steiner
6,736,799 B1 5/2004 Erbe et al.
6,737,053 B1 5/2004 Goh et al.
6,746,483 B1 6/2004 Bojarski et al.
6,752,780 B2 6/2004 Stout et al.
6,752,810 B1 6/2004 Gao et al.
6,752,831 B2 6/2004 Sybert et al.
6,755,836 B1 6/2004 Lewis
6,755,868 B2 6/2004 Rousseau
6,761,722 B2 7/2004 Cole et al.
6,761,739 B2 7/2004 Shepard
6,767,037 B2 7/2004 Wenstrom, Jr.
6,770,076 B2 8/2004 Foerster
6,770,084 B1 8/2004 Bain et al.
6,773,450 B2 8/2004 Leung et al.
6,779,701 B2 8/2004 Bailly et al.
6,780,190 B2 8/2004 Maroney
6,780,198 B1 8/2004 Gregoire et al.
6,790,210 B1 9/2004 Cragg et al.
6,793,595 B1 9/2004 Monnet
6,802,862 B1 10/2004 Roger et al.
6,808,502 B2 10/2004 Nguyen
6,808,526 B1 10/2004 Magerl et al.
6,814,741 B2 11/2004 Bowman et al.
6,830,572 B2 12/2004 Mcdevitt et al.
6,833,005 B1 12/2004 Mantas
6,835,377 B2 12/2004 Goldberg et al.
6,840,953 B2 1/2005 Martinek
6,860,885 B2 3/2005 Bonutti
6,860,895 B1 3/2005 Akerfeldt et al.
6,863,671 B1 3/2005 Strobel et al.
6,872,040 B2 3/2005 Deeg et al.
6,872,210 B2 3/2005 Hearn
6,875,216 B2 4/2005 Wolf
6,884,249 B2 4/2005 May et al.
6,887,243 B2 5/2005 Culbert
6,887,259 B2 5/2005 Lizardi
6,887,271 B2 5/2005 Justin et al.
6,890,354 B2 5/2005 Steiner et al.
6,893,448 B2 5/2005 O'quinn et al.
6,896,686 B2 5/2005 Weber
6,899,722 B2 5/2005 Bonutti
6,902,573 B2 6/2005 Strobel et al.
6,905,513 B1 6/2005 Metzger
6,908,466 B1 6/2005 Bonutti et al.
6,911,202 B2 6/2005 Amir et al.
6,916,292 B2 7/2005 Morawski et al.
6,916,321 B2 7/2005 Tenhuisen et al.
6,921,402 B2 7/2005 Contiliano et al.
6,923,823 B1 8/2005 Bartlett et al.
6,923,824 B2 8/2005 Morgan et al.
6,923,832 B1 8/2005 Sharkey et al.
6,939,379 B2 9/2005 Sklar
6,946,001 B2 9/2005 Sanford et al.
6,949,102 B2 9/2005 Andrews
6,951,565 B2 10/2005 Keane et al.
6,960,214 B2 11/2005 Burkinshaw
6,966,887 B1 11/2005 Chin
6,966,916 B2 11/2005 Kumar
6,969,391 B1 11/2005 Gazzani
6,969,398 B2 11/2005 Stevens et al.
6,972,027 B2 12/2005 Fallin et al.
6,980,903 B2 12/2005 Daniels et al.
6,984,237 B2 1/2006 Hatch et al.
6,986,781 B2 1/2006 Smith
6,989,034 B2 1/2006 Hammer et al.
6,994,719 B2 2/2006 Grafton
6,994,725 B1 2/2006 Goble
7,001,429 B2 2/2006 Ferguson
7,004,959 B2 2/2006 Bonutti
7,008,451 B2 3/2006 Justin et al.
7,011,682 B2 3/2006 Lashinski et al.
7,033,397 B2 4/2006 Webster et al.
7,048,754 B2 5/2006 Martin et al.
7,052,499 B2 5/2006 Steger et al.
7,060,101 B2 6/2006 O'Connor et al.
7,066,942 B2 6/2006 Treace
7,066,944 B2 6/2006 Laufer et al.
7,081,126 B2 7/2006 Mcdevitt et al.
7,083,638 B2 8/2006 Foerster
7,087,064 B1 8/2006 Hyde
7,087,073 B2 8/2006 Bonutti

(56) References Cited

U.S. PATENT DOCUMENTS 7,090,690 B2 8/2006 Foerster et al.
7,097,654 B1 8/2006 Freedland
7,101,395 B2 9/2006 Tremulis et al.
7,105,010 B2 9/2006 Hart et al.
7,105,026 B2 9/2006 Johnson et al.
7,112,221 B2 9/2006 Harris
7,118,578 B2 10/2006 West, Jr. et al.
7,118,583 B2 10/2006 O'quinn et al.
7,125,421 B2 10/2006 Tremulis et al.
7,131,467 B2 11/2006 Gao et al.
7,137,996 B2 11/2006 Steiner et al.
7,141,066 B2 11/2006 Steiner et al.
7,144,414 B2 12/2006 Harvie et al.
7,148,209 B2 12/2006 Hoemann et al.
7,153,127 B2 12/2006 Struble et al.
7,153,307 B2 12/2006 Scribner
7,153,312 B1 12/2006 Torrie et al.
7,153,327 B1 12/2006 Metzger
7,160,285 B2 1/2007 Sklar et al.
7,160,333 B2 1/2007 Plouhar et al.
7,172,626 B1 2/2007 Andrews
7,179,259 B1 2/2007 Gibbs
7,201,722 B2 4/2007 Krueger
7,207,993 B1 4/2007 Baldwin et al.
7,229,441 B2 6/2007 Trieu et al.
7,235,091 B2 6/2007 Thornes
7,255,675 B2 8/2007 Gertner et al.
7,255,700 B2 8/2007 Kaiser et al.
7,255,715 B2 8/2007 Metzger
7,261,716 B2 8/2007 Strobel et al.
7,264,634 B2 9/2007 Schmieding
7,279,008 B2 10/2007 Brown et al.
7,285,124 B2 10/2007 Foerster
7,291,177 B2 11/2007 Gibbs
7,303,577 B1 12/2007 Dean
7,306,417 B2 12/2007 Dorstewitz
7,309,355 B2 12/2007 Donnelly et al.
7,326,222 B2 2/2008 Dreyfuss et al.
7,329,272 B2 2/2008 Burkhart et al.
7,354,354 B2 4/2008 Palumbo et al.
7,361,179 B2 4/2008 Rousseau et al.
7,377,845 B2 5/2008 Stewart et al.
7,390,329 B2 6/2008 Westra et al.
7,390,332 B2 6/2008 Selvitelli et al.
7,399,018 B1 7/2008 Khachaturian
7,442,210 B2 10/2008 Segal et al.
7,462,198 B2 12/2008 Webster et al.
7,463,198 B2 12/2008 Deaett et al.
7,465,308 B2 12/2008 Sikora et al.
7,468,074 B2 12/2008 Caborn
7,481,814 B1 1/2009 Metzger
7,484,539 B1 2/2009 Huang
7,485,149 B1 2/2009 White
7,494,496 B2 2/2009 Swain et al.
7,494,506 B2 2/2009 Brulez et al.
D587,807 S 3/2009 Wolf et al.
7,500,983 B1 3/2009 Kaiser et al.
7,513,910 B2 4/2009 Buskirk et al.
7,517,357 B2 4/2009 Abrams et al.
7,572,275 B2 8/2009 Fallin et al.
7,572,298 B2 8/2009 Roller et al.
7,578,825 B2 8/2009 Huebner
7,585,311 B2 9/2009 Green et al.
7,588,587 B2 9/2009 Barbieri et al.
7,591,823 B2 9/2009 Tipirneni
7,597,705 B2 10/2009 Forsberg et al.
7,601,165 B2 10/2009 Stone
7,604,636 B1 10/2009 Walters et al.
7,608,092 B1 10/2009 Schaffhasen
7,608,098 B1 10/2009 Stone et al.
7,615,076 B2 11/2009 Cauthen, III et al.
7,621,937 B2 11/2009 Pipenhagen et al.
7,632,287 B2 12/2009 Baker et al.
7,651,509 B2 1/2010 Bojarski et al.
7,658,750 B2 2/2010 Li
7,658,751 B2 2/2010 Stone et al.
7,670,279 B2 3/2010 Gertner
7,678,123 B2 3/2010 Chanduszko
7,686,810 B2 3/2010 West, Jr. et al.
7,691,112 B2 4/2010 Chanduszko et al.
7,695,493 B2 4/2010 Saadat et al.
7,695,503 B1 4/2010 Kaiser
7,703,372 B1 4/2010 Shakespeare
7,713,188 B2 5/2010 Bouffier
7,713,285 B1 5/2010 Stone et al.
7,717,929 B2 5/2010 Fallman
7,731,732 B2 6/2010 Ken
7,736,364 B2 6/2010 Stone
7,736,379 B2 6/2010 Ewers et al.
7,749,250 B2 7/2010 Stone et al.
7,758,594 B2 7/2010 Lamson et al.
7,758,611 B2 7/2010 Kato
7,762,942 B2 7/2010 Neisz et al.
7,771,482 B1 8/2010 Karmon
7,776,041 B1 8/2010 Walters
7,780,701 B1 8/2010 Meridew et al.
7,790,945 B1 9/2010 Watson, Jr.
7,803,173 B2 9/2010 Burkhart et al.
7,819,895 B2 10/2010 Ginn et al.
7,828,820 B2 11/2010 Stone et al.
7,828,850 B2 11/2010 Cauthen, III et al.
7,856,698 B2 12/2010 Hays
7,857,830 B2 12/2010 Stone et al.
7,867,252 B2 1/2011 Criscuolo et al.
7,867,264 B2 1/2011 Mcdevitt et al.
7,875,058 B2 1/2011 Holmes, Jr.
7,878,058 B2 2/2011 Blendinger et al.
7,887,586 B2 2/2011 Linares
7,896,907 B2 3/2011 Mcdevitt et al.
7,905,903 B2 3/2011 Stone et al.
7,905,904 B2 3/2011 Stone et al.
7,909,851 B2 3/2011 Stone et al.
7,914,539 B2 3/2011 Stone et al.
7,938,847 B2 5/2011 Fanton et al.
7,951,198 B2 5/2011 Sucec et al.
7,955,388 B2 6/2011 Jensen et al.
7,959,650 B2 6/2011 Kaiser et al.
7,976,565 B1 7/2011 Meridew
7,981,140 B2 7/2011 Burkhart
7,998,203 B2 8/2011 Blum
8,034,090 B2 10/2011 Stone et al.
8,062,334 B2 11/2011 Green et al.
8,066,776 B2 11/2011 O'Connor et al.
8,075,574 B2 12/2011 May et al.
8,075,626 B2 12/2011 Dun
8,088,108 B2 1/2012 Kraft
8,088,130 B2 1/2012 Kaiser et al.
8,109,867 B2 2/2012 Rosenblatt
8,114,127 B2 2/2012 West, Jr.
8,114,128 B2 2/2012 Cauldwell et al.
8,118,835 B2 2/2012 Weisel et al.
8,118,836 B2 2/2012 Denham et al.
8,118,868 B2 2/2012 May et al.
8,128,658 B2 3/2012 Kaiser et al.
8,137,354 B2 3/2012 Stone
8,137,382 B2 3/2012 Denham et al.
8,137,407 B2 3/2012 Todd et al.
8,142,510 B2 3/2012 Lee et al.
8,147,557 B2 4/2012 Lee et al.
8,147,558 B2 4/2012 Lee et al.
8,162,997 B2 4/2012 Struhl
8,167,906 B2 5/2012 Cauldwell et al.
8,177,810 B2 5/2012 Ferree
8,202,295 B2 6/2012 Kaplan
8,202,318 B2 6/2012 Willobee
8,221,454 B2 7/2012 Schaffhasen
8,231,654 B2 7/2012 Kaiser et al.
8,251,998 B2 8/2012 Hoeppner et al.
8,252,022 B2 8/2012 Holman et al.
8,273,106 B2 9/2012 Stone et al.
8,292,921 B2 10/2012 Stone et al.
8,298,262 B2 10/2012 Stone et al.
8,298,284 B2 10/2012 Cassani
8,303,589 B2 11/2012 Tyber et al.

(56) References Cited

U.S. PATENT DOCUMENTS 8,303,604 B2 11/2012 Stone et al.
8,317,825 B2 11/2012 Stone
8,328,806 B2 12/2012 Tyber et al.
8,333,788 B2 12/2012 Maiorino
8,337,525 B2 12/2012 Stone et al.
8,343,155 B2 1/2013 Fisher et al.
8,343,227 B2 1/2013 Metzger et al.
8,361,054 B2 1/2013 Ducharme et al.
8,361,113 B2 1/2013 Stone et al.
8,409,253 B2 4/2013 Stone et al.
8,454,635 B2 6/2013 Paolitto et al.
8,486,114 B2 7/2013 Gillard et al.
8,500,818 B2 8/2013 Metzger et al.
8,506,597 B2 8/2013 Kaiser et al.
8,545,535 B2 10/2013 Hirotsuka et al.
8,551,140 B2 10/2013 Denham et al.
8,562,645 B2 10/2013 Stone et al.
8,562,647 B2 10/2013 Kaiser et al.
8,574,235 B2 11/2013 Stone
8,579,901 B1 11/2013 Foerster
8,579,944 B2 11/2013 Holloway et al.
8,591,544 B2 11/2013 Jolly et al.
8,597,327 B2 12/2013 Stone et al.
8,608,777 B2 12/2013 Kaiser et al.
8,632,566 B2 1/2014 Olson
8,632,569 B2 1/2014 Stone et al.
8,652,171 B2 2/2014 Stone et al.
8,652,172 B2 2/2014 Denham et al.
8,672,904 B1 3/2014 Schultz
8,672,968 B2 3/2014 Stone et al.
8,672,969 B2 3/2014 Stone et al.
8,702,718 B2 4/2014 Bhatnagar et al.
8,715,297 B1 5/2014 Foerster et al.
8,721,650 B2 5/2014 Fanton et al.
8,721,684 B2 5/2014 Denham et al.
8,771,316 B2 7/2014 Denham et al.
8,771,352 B2 7/2014 Conner et al.
8,777,956 B2 7/2014 Hoeppner et al.
8,801,783 B2 8/2014 Stone et al.
8,808,374 B2 8/2014 Eggli
8,814,903 B2 8/2014 Sengun et al.
8,828,067 B2 9/2014 Tipirneni et al.
8,840,645 B2 9/2014 Denham et al.
8,858,642 B2 10/2014 Metzger et al.
8,894,715 B2 11/2014 Metzger et al.
8,900,314 B2 12/2014 Metzger et al.
8,926,613 B2 1/2015 Kaiser et al.
8,932,331 B2 1/2015 Kaiser et al.
8,936,621 B2 1/2015 Denham et al.
8,961,548 B2 2/2015 Buser
8,968,364 B2 3/2015 Berelsman
8,998,949 B2 4/2015 Stone et al.
9,005,287 B2 4/2015 Stone
9,017,381 B2 4/2015 Kaiser et al.
9,023,058 B2 5/2015 Jaramillo et al.
9,028,509 B2 5/2015 Chu et al.
9,078,644 B2 7/2015 Stone
9,149,267 B2 10/2015 Norton et al.
9,173,651 B2 11/2015 Stone et al.
9,179,950 B2 11/2015 Zajac et al.
9,198,673 B2 12/2015 Stone
9,216,078 B2 12/2015 Conner et al.
9,271,713 B2 3/2016 Denham et al.
9,271,826 B2 3/2016 Eggli et al.
9,289,285 B2 3/2016 Eggli
9,314,235 B2 4/2016 Bojarski et al.
9,314,241 B2 4/2016 Stone et al.
9,357,991 B2 6/2016 Denham et al.
9,357,992 B2 6/2016 Stone et al.
9,370,350 B2 6/2016 Norton
9,381,013 B2 7/2016 Norton
9,402,621 B2 8/2016 Stone et al.
9,408,599 B2 8/2016 Kaiser et al.
9,414,833 B2 8/2016 Stone et al.
9,414,925 B2 8/2016 Metzger et al.
9,468,433 B2 10/2016 Denham et al.
9,486,211 B2 11/2016 Stone et al.
9,492,158 B2 11/2016 Stone et al.
9,498,204 B2 11/2016 Denham et al.
9,504,460 B2 11/2016 Stone et al.
9,510,819 B2 12/2016 Stone et al.
9,510,821 B2 12/2016 Denham et al.
9,532,777 B2 1/2017 Kaiser et al.
9,538,998 B2 1/2017 Stone et al.
9,539,003 B2 1/2017 Stone et al.
9,561,025 B2 2/2017 Stone et al.
9,572,655 B2 2/2017 Denham
9,585,651 B2 3/2017 Lam et al.
9,603,591 B2 3/2017 Denham et al.
9,622,736 B2 4/2017 Stone et al.
9,642,661 B2 5/2017 Stone et al.
9,681,940 B2 6/2017 Stone et al.
9,724,090 B2 8/2017 Kaiser et al.
9,743,919 B2 8/2017 Manos et al.
9,757,119 B2 9/2017 Norton et al.
9,763,656 B2 9/2017 Stone et al.
9,782,245 B2 10/2017 Mujwid et al.
9,788,876 B2 10/2017 Stone
9,801,620 B2 10/2017 Kaiser et al.
9,801,708 B2 10/2017 Denham et al.
9,833,230 B2 12/2017 Stone
9,861,351 B2 1/2018 Kaiser et al.
9,918,826 B2 3/2018 Berelsman et al.
9,918,827 B2 3/2018 Berelsman et al.
9,993,241 B2 6/2018 Denham et al.
10,004,489 B2 6/2018 Kaiser et al.
10,004,493 B2 6/2018 Stone et al.
10,004,588 B2 6/2018 Berelsman et al.
10,022,118 B2 7/2018 Norton et al.
10,092,288 B2 10/2018 Denham et al.
10,098,629 B2 10/2018 Kaiser et al.
10,154,837 B2 12/2018 Stone et al.
10,167,582 B1 1/2019 Pilgeram et al.
10,251,637 B2 4/2019 Stone et al.
10,265,064 B2 4/2019 Stone et al.
10,265,159 B2 4/2019 Denham et al.
10,321,906 B2 6/2019 Stone et al.
10,349,931 B2 7/2019 Stone
10,363,028 B2 7/2019 Norton
10,368,856 B2 8/2019 Stone et al.
10,398,428 B2 9/2019 Denham et al.
10,398,430 B2 9/2019 Stone et al.
10,441,264 B2 10/2019 Stone et al.
10,517,587 B2 12/2019 Denham et al.
10,517,714 B2 12/2019 Stone et al.
10,542,967 B2 1/2020 Kaiser et al.
10,595,851 B2 3/2020 Kaiser et al.
10,603,029 B2 3/2020 Kaiser et al.
10,610,217 B2 4/2020 Stone et al.
10,675,073 B2 6/2020 Stone et al.
10,687,803 B2 6/2020 Denham et al.
10,695,045 B2 6/2020 Kaiser et al.
10,695,052 B2 6/2020 Denham et al.
10,702,259 B2 7/2020 Stone et al.
10,716,557 B2 7/2020 Denham et al.
10,729,421 B2 8/2020 Stone et al.
10,729,423 B2 8/2020 Kaiser et al.
10,729,430 B2 8/2020 Denham et al.
10,743,925 B2 8/2020 Stone et al.
10,758,221 B2 9/2020 Berelsman et al.
10,835,232 B2 11/2020 Stone et al.
10,932,770 B2 3/2021 Stone et al.
10,973,507 B2 4/2021 Stone et al.
10,987,099 B2 4/2021 Stone et al.
11,039,826 B2 6/2021 Denham et al.
11,065,103 B2 7/2021 Berelsman et al.
11,096,684 B2 8/2021 Stone et al.
11,109,857 B2 9/2021 Stone et al.
11,116,495 B2 9/2021 Stone et al.
11,185,320 B2 11/2021 Kaiser et al.
11,241,305 B2 2/2022 Denham et al.
11,259,792 B2 3/2022 Denham et al.
11,259,794 B2 3/2022 Stone et al.
11,284,884 B2 3/2022 Denham et al.

(56) References Cited

U.S. PATENT DOCUMENTS 11,311,287 B2 4/2022 Stone et al.
11,317,907 B2 5/2022 Denham et al.
11,376,115 B2 7/2022 Stone et al.
11,446,019 B2 9/2022 Stone et al.
11,471,147 B2 10/2022 Kaiser et al.
11,534,157 B2 12/2022 Norton
11,534,159 B2 12/2022 Denham et al.
11,589,859 B2 2/2023 Kaiser et al.
11,612,391 B2 3/2023 Stone et al.
11,617,572 B2 4/2023 Stone et al.
11,672,527 B2 6/2023 Stone et al.
11,723,648 B2 8/2023 Stone et al.
11,730,464 B2 8/2023 Stone et al.
11,786,236 B2 10/2023 Denham et al.
11,819,205 B2 11/2023 Stone et al.
2001/0002439 A1 5/2001 Bonutti et al.
2001/0010005 A1 7/2001 Kammerer et al.
2001/0014825 A1 8/2001 Burke et al.
2001/0019649 A1 9/2001 Field et al.
2001/0027341 A1 10/2001 Gianotti
2001/0029387 A1 10/2001 Wolf et al.
2001/0037131 A1 11/2001 Schmieding et al.
2001/0037153 A1 11/2001 Charles, Jr. et al.
2001/0041916 A1 11/2001 Bonutti
2001/0041937 A1 11/2001 Rieser et al.
2001/0041938 A1 11/2001 Hein
2001/0044627 A1 11/2001 Justin
2001/0044639 A1 11/2001 Levinson
2001/0047206 A1 11/2001 Sklar et al.
2001/0051815 A1 12/2001 Esplin
2001/0051816 A1 12/2001 Enzerink et al.
2001/0053934 A1 12/2001 Schmieding
2001/0056299 A1 12/2001 Thompson
2002/0001964 A1 1/2002 Choi
2002/0004669 A1 1/2002 Bartlett
2002/0007182 A1 1/2002 Kim
2002/0010513 A1 1/2002 Schmieding
2002/0013607 A1 1/2002 Lemer
2002/0013608 A1 1/2002 Elattrache et al.
2002/0019649 A1 2/2002 Sikora et al.
2002/0029048 A1 3/2002 Miller
2002/0029066 A1 3/2002 Foerster
2002/0032465 A1 3/2002 Lemer
2002/0045902 A1 4/2002 Bonutti
2002/0052628 A1 5/2002 Bowman
2002/0055780 A1 5/2002 Sklar
2002/0058966 A1 5/2002 Tormala et al.
2002/0068254 A1 6/2002 Campbell
2002/0077629 A1 6/2002 Hoffman et al.
2002/0077659 A1 6/2002 Johnson et al.
2002/0082220 A1 6/2002 Hoemann et al.
2002/0091391 A1 7/2002 Cole et al.
2002/0099411 A1 7/2002 Bartlett
2002/0111591 A1 8/2002 Mckinnon et al.
2002/0111653 A1 8/2002 Foerster
2002/0120270 A1 8/2002 Trieu et al.
2002/0120292 A1 8/2002 Morgan
2002/0123752 A1 9/2002 Schultheiss et al.
2002/0128654 A1 9/2002 Steger et al.
2002/0128684 A1 9/2002 Foerster
2002/0129820 A1 9/2002 Ryan et al.
2002/0143336 A1 10/2002 Hearn
2002/0147463 A1 10/2002 Martinek
2002/0156475 A1 10/2002 Lerch et al.
2002/0161401 A1 10/2002 Steiner
2002/0161439 A1 10/2002 Strobel et al.
2002/0165548 A1 11/2002 Jutley
2002/0165611 A1 11/2002 Enzerink et al.
2002/0169452 A1 11/2002 Tormala et al.
2002/0169477 A1 11/2002 Demopulos et al.
2002/0169478 A1 11/2002 Schwartz et al.
2002/0173788 A1 11/2002 Bojarski et al.
2002/0177853 A1 11/2002 Chervitz et al.
2002/0188298 A1 12/2002 Chan
2002/0193830 A1 12/2002 Bonutti
2003/0004545 A1 1/2003 Burkhart et al.
2003/0009235 A1 1/2003 Manrique et al.
2003/0023268 A1 1/2003 Lizardi
2003/0032961 A1 2/2003 Pelo et al.
2003/0033021 A1 2/2003 Plouhar et al.
2003/0033022 A1 2/2003 Plouhar et al.
2003/0036797 A1 2/2003 Malaviya et al.
2003/0036801 A1 2/2003 Schwartz et al.
2003/0050667 A1 3/2003 Grafton et al.
2003/0065361 A1 4/2003 Dreyfuss
2003/0065391 A1 4/2003 Re et al.
2003/0065402 A1 4/2003 Anderson et al.
2003/0078585 A1 4/2003 Johnson et al.
2003/0078603 A1 4/2003 Schaller et al.
2003/0078617 A1 4/2003 Schwartz et al.
2003/0083662 A1 5/2003 Middleton
2003/0083694 A1 5/2003 Archibald, III
2003/0088251 A1 5/2003 Braun et al.
2003/0088272 A1 5/2003 Smith
2003/0093156 A1 5/2003 Metzger et al.
2003/0105477 A1 6/2003 Schwartz et al.
2003/0105489 A1 6/2003 Eichhorn et al.
2003/0114929 A1 6/2003 Knudsen
2003/0120309 A1 6/2003 Colleran et al.
2003/0130670 A1 7/2003 Anderson et al.
2003/0130694 A1 7/2003 Bojarski et al.
2003/0130695 A1 7/2003 Mcdevitt et al.
2003/0135214 A1 7/2003 Fetto
2003/0135239 A1 7/2003 Gabriel et al.
2003/0135265 A1 7/2003 Stinson
2003/0135963 A1 7/2003 Holbrook et al.
2003/0139752 A1 7/2003 Pasricha et al.
2003/0139775 A1 7/2003 Grafton
2003/0149448 A1 8/2003 Foerster et al.
2003/0152522 A1 8/2003 Miller et al.
2003/0153947 A1 8/2003 Koseki
2003/0167072 A1 9/2003 Oberlander
2003/0167090 A1 9/2003 Chervitz et al.
2003/0171811 A1 9/2003 Steiner et al.
2003/0176865 A1 9/2003 Supinski
2003/0176919 A1 9/2003 Schmieding
2003/0176920 A1 9/2003 Sklar et al.
2003/0181925 A1 9/2003 Bain et al.
2003/0187510 A1 10/2003 Hyde
2003/0195528 A1 10/2003 Ritchart
2003/0195564 A1 10/2003 Tran et al.
2003/0195565 A1 10/2003 Bonutti
2003/0208209 A1 11/2003 Gambale et al.
2003/0208210 A1 11/2003 Dreyfuss et al.
2003/0212456 A1 11/2003 Lipchitz et al.
2003/0216809 A1 11/2003 Ferguson
2003/0220646 A1 11/2003 Thelen et al.
2003/0220660 A1 11/2003 Kortenbach et al.
2003/0225459 A1 12/2003 Hammer et al.
2003/0229361 A1 12/2003 Jackson
2003/0229396 A1 12/2003 Andrews
2003/0236555 A1 12/2003 Thornes
2004/0002734 A1 1/2004 Fallin et al.
2004/0006345 A1 1/2004 Vlahos et al.
2004/0006346 A1 1/2004 Holmen et al.
2004/0013380 A1 1/2004 Jimenez
2004/0015171 A1 1/2004 Bojarski et al.
2004/0015172 A1 1/2004 Biedermann et al.
2004/0024456 A1 2/2004 Charles, Jr. et al.
2004/0024457 A1 2/2004 Boyce et al.
2004/0039389 A1 2/2004 Hugh, Jr. et al.
2004/0044351 A1 3/2004 Searle
2004/0044391 A1 3/2004 Porter
2004/0059357 A1 3/2004 Koseki
2004/0073176 A1 4/2004 Utterberg
2004/0087981 A1 5/2004 Berube et al.
2004/0092936 A1 5/2004 Miller et al.
2004/0093031 A1 5/2004 Burkhart et al.
2004/0093032 A1 5/2004 Sinnott et al.
2004/0098051 A1 5/2004 Fallin et al.
2004/0098053 A1 5/2004 Tran
2004/0098099 A1 5/2004 McCullagh et al.
2004/0111117 A1 6/2004 Colleran et al.
2004/0122431 A1 6/2004 Biedermann et al.

(56) References Cited

U.S. PATENT DOCUMENTS

2004/0122454 A1 6/2004 Wang et al.
2004/0122456 A1 6/2004 Saadat et al.
2004/0127907 A1 7/2004 Dakin et al.
2004/0133206 A1 7/2004 Stevens et al.
2004/0133211 A1 7/2004 Raskin et al.
2004/0133238 A1 7/2004 Cerier
2004/0133239 A1 7/2004 Singhatat
2004/0138664 A1 7/2004 Bowman
2004/0138683 A1 7/2004 Shelton et al.
2004/0138704 A1 7/2004 Gambale et al.
2004/0138706 A1 7/2004 Abrams et al.
2004/0138747 A1 7/2004 Kaladelfos
2004/0138755 A1 7/2004 O'connor et al.
2004/0143344 A1 7/2004 Malaviya et al.
2004/0144535 A1 7/2004 Kalman et al.
2004/0147932 A1 7/2004 Burkinshaw et al.
2004/0147958 A1 7/2004 Lam et al.
2004/0148030 A1 7/2004 Ek
2004/0153103 A1 8/2004 Schwartz et al.
2004/0153153 A1 8/2004 Elson et al.
2004/0162579 A1 8/2004 Foerster
2004/0166169 A1 8/2004 Malaviya et al.
2004/0181234 A1 9/2004 Mcdevitt et al.
2004/0182968 A1 9/2004 Gentry
2004/0187314 A1 9/2004 Johnson
2004/0193185 A1 9/2004 Mcbrayer
2004/0199169 A1 10/2004 Koons et al.
2004/0204722 A1 10/2004 Sikora et al.
2004/0220574 A1 11/2004 Pelo et al.
2004/0225183 A1 11/2004 Michlitsch et al.
2004/0225292 A1 11/2004 Sasso et al.
2004/0225305 A1 11/2004 Ewers et al.
2004/0230302 A1 11/2004 May et al.
2004/0236353 A1 11/2004 Bain et al.
2004/0236373 A1 11/2004 William, III
2004/0243139 A1 12/2004 Lewis et al.
2004/0243178 A1 12/2004 Haut et al.
2004/0243180 A1 12/2004 Donnelly et al.
2004/0243235 A1 12/2004 Goh et al.
2004/0249394 A1 12/2004 Morris et al.
2004/0260296 A1 12/2004 Kaiser et al.
2004/0260298 A1 12/2004 Kaiser et al.
2004/0267164 A1 12/2004 Rhodes et al.
2004/0267265 A1 12/2004 Kyle
2004/0267270 A1 12/2004 Jacobs et al.
2004/0267276 A1 12/2004 Camino et al.
2004/0267277 A1 12/2004 Zannis et al.
2004/0267286 A1 12/2004 Gao et al.
2004/0267304 A1 12/2004 Zannis et al.
2004/0267309 A1 12/2004 Garvin
2004/0267317 A1 12/2004 Higgins et al.
2004/0267361 A1 12/2004 Donnelly et al.
2004/0267362 A1 12/2004 Hwang et al.
2005/0004670 A1 1/2005 Gebhardt et al.
2005/0021087 A1 1/2005 Koseki
2005/0021148 A1 1/2005 Gibbs
2005/0027307 A1 2/2005 Schwartz et al.
2005/0033289 A1 2/2005 Warren et al.
2005/0033362 A1 2/2005 Grafton
2005/0033363 A1 2/2005 Bojarski et al.
2005/0038426 A1 2/2005 Chan
2005/0049598 A1 3/2005 West, Jr. et al.
2005/0055027 A1 3/2005 Yeung et al.
2005/0055037 A1 3/2005 Fathauer, Jr.
2005/0064042 A1 3/2005 Vunjak-novakovic et al.
2005/0065521 A1 3/2005 Steger et al.
2005/0065526 A1 3/2005 Drew et al.
2005/0070906 A1 3/2005 Clark et al.
2005/0070928 A1 3/2005 Heino et al.
2005/0074495 A1 4/2005 Schwartz et al.
2005/0076478 A1 4/2005 Miyazaki et al.
2005/0085819 A1 4/2005 Ellis et al.
2005/0090827 A1 4/2005 Gedebou
2005/0090828 A1 4/2005 Alford
2005/0090862 A1 4/2005 Mcdevitt et al.
2005/0096696 A1 5/2005 Forsberg
2005/0096697 A1 5/2005 Forsberg et al.
2005/0096743 A1 5/2005 Schmieding et al.
2005/0101957 A1 5/2005 Buskirk et al.
2005/0107795 A1 5/2005 Morris et al.
2005/0107828 A1 5/2005 Reese
2005/0107882 A1 5/2005 Stone et al.
2005/0119531 A1 6/2005 Sharratt
2005/0119696 A1 6/2005 Walters et al.
2005/0124996 A1 6/2005 Hearn
2005/0125031 A1 6/2005 Pipenhagen et al.
2005/0125036 A1 6/2005 Roby
2005/0125073 A1 6/2005 Orban et al.
2005/0130301 A1 6/2005 Mckay et al.
2005/0131413 A1 6/2005 O'driscoll et al.
2005/0137600 A1 6/2005 Jacobs et al.
2005/0137624 A1 6/2005 Fallman
2005/0143734 A1 6/2005 Cachia et al.
2005/0149033 A1 7/2005 Mcguire et al.
2005/0149118 A1 7/2005 Koyfman et al.
2005/0149119 A1 7/2005 Koyfman et al.
2005/0149122 A1 7/2005 Mcdevitt et al.
2005/0149187 A1 7/2005 Clark et al.
2005/0154471 A1 7/2005 Aram et al.
2005/0159812 A1 7/2005 Dinger, III et al.
2005/0160656 A1 7/2005 Safwat et al.
2005/0165416 A1 7/2005 Bojarski et al.
2005/0165482 A1 7/2005 Goldhahn et al.
2005/0171547 A1 8/2005 Aram
2005/0171603 A1 8/2005 Justin et al.
2005/0171604 A1 8/2005 Michalow
2005/0177237 A1 8/2005 Shappley et al.
2005/0187565 A1 8/2005 Baker et al.
2005/0187577 A1 8/2005 Selvitelli et al.
2005/0187635 A1 8/2005 Metzger
2005/0192581 A1 9/2005 Molz et al.
2005/0192632 A1 9/2005 Geissler et al.
2005/0197711 A1 9/2005 Cachia
2005/0203620 A1 9/2005 Steiner et al.
2005/0209703 A1 9/2005 Fell
2005/0222618 A1 10/2005 Dreyfuss et al.
2005/0222619 A1 10/2005 Dreyfuss et al.
2005/0228448 A1 10/2005 Li
2005/0229433 A1 10/2005 Cachia
2005/0234549 A1 10/2005 Kladakis et al.
2005/0240198 A1 10/2005 Albertson et al.
2005/0251153 A1 11/2005 Sakamoto et al.
2005/0251159 A1 11/2005 Ewers et al.
2005/0251177 A1 11/2005 Saadat et al.
2005/0251207 A1 11/2005 Flores et al.
2005/0251208 A1 11/2005 Elmer et al.
2005/0251209 A1 11/2005 Saadat et al.
2005/0251210 A1 11/2005 Westra et al.
2005/0261642 A1 11/2005 Weston
2005/0267479 A1 12/2005 Morgan et al.
2005/0267533 A1 12/2005 Gertner
2005/0277088 A1 12/2005 Fischer et al.
2005/0277939 A1 12/2005 Miller, III
2005/0277961 A1 12/2005 Stone et al.
2005/0277985 A1 12/2005 Wert et al.
2005/0283040 A1 12/2005 Greenhalgh
2005/0283156 A1 12/2005 Schmieding et al.
2005/0283158 A1 12/2005 West, Jr.
2005/0283192 A1 12/2005 Torrie et al.
2005/0283220 A1 12/2005 Gobran et al.
2005/0288710 A1 12/2005 Fallin et al.
2006/0004364 A1 1/2006 Green et al.
2006/0004410 A1 1/2006 Nobis et al.
2006/0004460 A1 1/2006 Engh et al.
2006/0015103 A1 1/2006 Burke
2006/0015106 A1 1/2006 Lerch et al.
2006/0015107 A1 1/2006 Sklar
2006/0030884 A1 2/2006 Yeung et al.
2006/0030948 A1 2/2006 Manrique et al.
2006/0036265 A1 2/2006 Dant et al.
2006/0052787 A1 3/2006 Re et al.
2006/0052818 A1 3/2006 Drake et al.
2006/0064125 A1 3/2006 Henderson et al.
2006/0064126 A1 3/2006 Fallin et al.

(56) References Cited

U.S. PATENT DOCUMENTS

2006/0069334 A1 3/2006 Moskowitz
2006/0079904 A1 4/2006 Thal
2006/0084943 A1 4/2006 Rosenman et al.
2006/0085000 A1 4/2006 Mohr et al.
2006/0089525 A1 4/2006 Mamo et al.
2006/0089672 A1 4/2006 Martinek
2006/0095130 A1 5/2006 Caborn et al.
2006/0095131 A1 5/2006 Justin et al.
2006/0100627 A1 5/2006 Stone et al.
2006/0100637 A1 5/2006 Rathbun et al.
2006/0106423 A1* 5/2006 Weisel ............... A61B 17/0401 606/232
2006/0111721 A1 5/2006 Puricelli
2006/0116685 A1 6/2006 Urbanski et al.
2006/0121084 A1 6/2006 Borden et al.
2006/0122608 A1 6/2006 Fallin et al.
2006/0122611 A1 6/2006 Morales et al.
2006/0135958 A1 6/2006 Marissen et al.
2006/0149258 A1 7/2006 Sousa
2006/0149266 A1 7/2006 Cordasco
2006/0155287 A1 7/2006 Montgomery et al.
2006/0155328 A1 7/2006 Foerster
2006/0161161 A1 7/2006 Shifrin et al.
2006/0167458 A1 7/2006 Gabele
2006/0167481 A1 7/2006 Baker et al.
2006/0167482 A1 7/2006 Swain et al.
2006/0173492 A1 8/2006 Akerfeldt et al.
2006/0178680 A1 8/2006 Nelson et al.
2006/0178701 A1 8/2006 Schmieding
2006/0178743 A1 8/2006 Carter
2006/0189993 A1 8/2006 Stone
2006/0190041 A1 8/2006 Fallin et al.
2006/0190042 A1 8/2006 Stone et al.
2006/0195101 A1 8/2006 Stevens
2006/0195106 A1 8/2006 Jones et al.
2006/0200235 A1 9/2006 Bianchi et al.
2006/0212055 A1 9/2006 Karabey et al.
2006/0229623 A1 10/2006 Bonutti et al.
2006/0229671 A1 10/2006 Steiner et al.
2006/0229676 A1 10/2006 Doll et al.
2006/0235407 A1 10/2006 Wang et al.
2006/0235413 A1 10/2006 Denham et al.
2006/0241624 A1 10/2006 Kizuka et al.
2006/0241776 A1 10/2006 Brown et al.
2006/0241781 A1 10/2006 Brown et al.
2006/0247642 A1 11/2006 Stone et al.
2006/0253130 A1 11/2006 Wolniewicz
2006/0259048 A1 11/2006 Koseki
2006/0259076 A1 11/2006 Burkhart
2006/0264944 A1 11/2006 Cole
2006/0271192 A1 11/2006 Olsen et al.
2006/0276793 A1 12/2006 Berry
2006/0276809 A1 12/2006 Oliveira
2006/0276818 A1 12/2006 Buser et al.
2006/0276841 A1 12/2006 Barbieri et al.
2006/0276896 A1 12/2006 Fallin et al.
2006/0280768 A1 12/2006 Hwang et al.
2006/0280803 A1 12/2006 Kumar et al.
2006/0282082 A1 12/2006 Fanton et al.
2006/0282083 A1 12/2006 Fanton et al.
2006/0282085 A1 12/2006 Stone
2006/0293709 A1 12/2006 Bojarski et al.
2007/0005068 A1 1/2007 Sklar
2007/0005080 A1 1/2007 Wolniewicz, III et al.
2007/0010857 A1 1/2007 Sugimoto et al.
2007/0016305 A1 1/2007 Chudik
2007/0021779 A1 1/2007 Garvin et al.
2007/0027476 A1 2/2007 Harris et al.
2007/0032800 A1 2/2007 Ortiz et al.
2007/0032823 A1 2/2007 Tegg
2007/0038218 A1 2/2007 Grevious
2007/0043371 A1 2/2007 Teague
2007/0055249 A1 3/2007 Jensen et al.
2007/0055251 A1 3/2007 Huebner et al.
2007/0055255 A1 3/2007 Siegel
2007/0060922 A1 3/2007 Dreyfuss
2007/0067025 A1 3/2007 Schwartz
2007/0071568 A1 3/2007 Dorstewitz
2007/0073307 A1 3/2007 Scribner et al.
2007/0073319 A1 3/2007 Mikkaichi et al.
2007/0073322 A1 3/2007 Mikkaichi et al.
2007/0078435 A1 4/2007 Stone et al.
2007/0078517 A1 4/2007 Engh et al.
2007/0083236 A1 4/2007 Sikora et al.
2007/0088362 A1 4/2007 Bonutti et al.
2007/0093847 A1 4/2007 Scribner et al.
2007/0100350 A1 5/2007 Deffenbaugh et al.
2007/0112384 A1 5/2007 Conlon et al.
2007/0118217 A1 5/2007 Brulez et al.
2007/0123883 A1 5/2007 Ellis et al.
2007/0123984 A1 5/2007 Hodorek
2007/0129809 A1 6/2007 Meridew et al.
2007/0135843 A1 6/2007 Burkhart
2007/0142838 A1 6/2007 Jordan
2007/0156174 A1 7/2007 Kaiser et al.
2007/0162018 A1 7/2007 Jensen et al.
2007/0162120 A1 7/2007 Bouffier
2007/0167926 A1 7/2007 Blott et al.
2007/0167950 A1 7/2007 Tauro et al.
2007/0173948 A1 7/2007 Meridew et al.
2007/0185488 A1 8/2007 Pohjonen et al.
2007/0185532 A1 8/2007 Stone et al.
2007/0185568 A1 8/2007 Schwartz
2007/0191849 A1 8/2007 Elattrache et al.
2007/0191853 A1 8/2007 Stone
2007/0198022 A1 8/2007 Lang et al.
2007/0198036 A1 8/2007 Sklar et al.
2007/0219558 A1 9/2007 Deutsch
2007/0225715 A1 9/2007 Deffenbaugh et al.
2007/0225719 A1 9/2007 Stone et al.
2007/0225763 A1 9/2007 Zwolinski et al.
2007/0225805 A1 9/2007 Schmieding
2007/0233241 A1 10/2007 Graf et al.
2007/0239209 A1 10/2007 Fallman
2007/0239275 A1 10/2007 Willobee
2007/0244565 A1 10/2007 Stchur
2007/0250059 A1 10/2007 Weisshaupt et al.
2007/0250163 A1 10/2007 Cassani
2007/0250175 A1 10/2007 Meridew et al.
2007/0255282 A1 11/2007 Simonton et al.
2007/0260251 A1 11/2007 Weier et al.
2007/0260279 A1 11/2007 Hotter et al.
2007/0265704 A1 11/2007 Mayer et al.
2007/0270856 A1 11/2007 Morales et al.
2007/0270878 A1 11/2007 Leisinger
2007/0276387 A1 11/2007 Morales et al.
2007/0288023 A1 12/2007 Pellegrino et al.
2008/0009904 A1 1/2008 Bourque et al.
2008/0027430 A1 1/2008 Montgomery et al.
2008/0027440 A1 1/2008 Marissen et al.
2008/0027446 A1 1/2008 Stone et al.
2008/0033549 A1 2/2008 Marshall et al.
2008/0046009 A1 2/2008 Albertorio et al.
2008/0051834 A1 2/2008 Mazzocca et al.
2008/0051836 A1 2/2008 Foerster et al.
2008/0058787 A1 3/2008 Gertner
2008/0065114 A1* 3/2008 Stone ................ A61B 17/0401 606/279
2008/0071299 A1 3/2008 Allinniemi et al.
2008/0082101 A1 4/2008 Reisberg
2008/0082127 A1 4/2008 Stone et al.
2008/0082128 A1 4/2008 Stone
2008/0086138 A1 4/2008 Stone et al.
2008/0097430 A1 4/2008 Bernstein et al.
2008/0103528 A1 5/2008 Zirps et al.
2008/0114460 A1 5/2008 Willobee et al.
2008/0119892 A1 5/2008 Brailovski et al.
2008/0132753 A1 6/2008 Goddard
2008/0132932 A1 6/2008 Hoeppner et al.
2008/0132948 A1 6/2008 Surti et al.
2008/0133007 A1 6/2008 Donnelly et al.
2008/0137624 A1 6/2008 Silverstrim et al.
2008/0140092 A1 6/2008 Stone et al.
2008/0140093 A1 6/2008 Stone et al.

(56) References Cited

U.S. PATENT DOCUMENTS

2008/0140128 A1 6/2008 Smisson et al.
2008/0147127 A1 6/2008 Tipirneni et al.
2008/0147187 A1 6/2008 Bollinger et al.
2008/0154260 A1 6/2008 Hoof
2008/0154314 A1 6/2008 Mcdevitt
2008/0161806 A1 7/2008 Donnelly et al.
2008/0161852 A1 7/2008 Kaiser et al.
2008/0161861 A1 7/2008 Huebner
2008/0161864 A1 7/2008 Beck et al.
2008/0166421 A1 7/2008 Buhr et al.
2008/0172097 A1 7/2008 Lerch et al.
2008/0177302 A1 7/2008 Shurnas
2008/0183290 A1 7/2008 Baird et al.
2008/0188933 A1 8/2008 Koob et al.
2008/0188935 A1 8/2008 Saylor et al.
2008/0188936 A1 8/2008 Ball et al.
2008/0208252 A1 8/2008 Holmes
2008/0217263 A1 9/2008 Higgins et al.
2008/0221527 A1 9/2008 Bradley et al.
2008/0221578 A1 9/2008 Zeitani
2008/0228186 A1 9/2008 Gall et al.
2008/0228271 A1 9/2008 Stone et al.
2008/0234730 A1 9/2008 Cotton et al.
2008/0243260 A1 10/2008 Lee et al.
2008/0243261 A1 10/2008 Wyss et al.
2008/0243262 A1 10/2008 Lee
2008/0255613 A1 10/2008 Kaiser et al.
2008/0257363 A1 10/2008 Schoenefeld et al.
2008/0262544 A1 10/2008 Burkhart
2008/0268064 A1 10/2008 Woodell-may
2008/0269674 A1 10/2008 Stone
2008/0275469 A1 11/2008 Fanton et al.
2008/0275477 A1 11/2008 Sterrett et al.
2008/0281428 A1 11/2008 Meyers et al.
2008/0288070 A1 11/2008 Lo
2008/0300611 A1 12/2008 Houser et al.
2008/0312689 A1 12/2008 Denham et al.
2008/0319478 A1 12/2008 Foerster et al.
2009/0018589 A1 1/2009 Smisson, III et al.
2009/0018654 A1 1/2009 Schmieding et al.
2009/0018655 A1 1/2009 Brunelle et al.
2009/0043342 A1 2/2009 Freedland
2009/0054928 A1 2/2009 Denham et al.
2009/0062847 A1 3/2009 Ken
2009/0062854 A1 3/2009 Kaiser et al.
2009/0082790 A1 3/2009 Shad et al.
2009/0082805 A1 3/2009 Kaiser et al.
2009/0084491 A1 4/2009 Uthgenannt et al.
2009/0099598 A1 4/2009 Mcdevitt et al.
2009/0105717 A1 4/2009 Bluechel
2009/0105754 A1 4/2009 Sethi
2009/0118774 A1 5/2009 Miller, III
2009/0118775 A1 5/2009 Burke
2009/0125073 A1 5/2009 Rehm
2009/0138002 A1 5/2009 Fenton
2009/0138054 A1 5/2009 Teague et al.
2009/0156997 A1 6/2009 Trenhaile
2009/0163949 A1 6/2009 Rolnick et al.
2009/0177233 A1 7/2009 Malek
2009/0182335 A1 7/2009 Struhl
2009/0192468 A1 7/2009 Stone
2009/0198277 A1 8/2009 Gordon et al.
2009/0204146 A1 8/2009 Kaiser et al.
2009/0216325 A1 8/2009 May et al.
2009/0228015 A1 9/2009 Ellis
2009/0228042 A1 9/2009 Koogle, Jr. et al.
2009/0234357 A1 9/2009 Morales et al.
2009/0234358 A1 9/2009 Morales et al.
2009/0234451 A1 9/2009 Manderson
2009/0240251 A1 9/2009 Gabele
2009/0240335 A1 9/2009 Arcenio et al.
2009/0241497 A1 10/2009 Imai et al.
2009/0248091 A1 10/2009 Teague et al.
2009/0254089 A1 10/2009 Tipirneni et al.
2009/0265014 A1 10/2009 May et al.
2009/0265015 A1 10/2009 May et al.
2009/0287215 A1 11/2009 Fisher et al.
2009/0299409 A1 12/2009 Coe et al.
2009/0306711 A1 12/2009 Stone et al.
2009/0312776 A1 12/2009 Kaiser et al.
2009/0312793 A1 12/2009 Huxel et al.
2009/0318960 A1 12/2009 Burkhart
2009/0318961 A1 12/2009 Stone et al.
2009/0318965 A1 12/2009 Burkhart
2010/0016891 A1 1/2010 Kennedy et al.
2010/0016899 A1 1/2010 Gelfand
2010/0030321 A1 2/2010 Mach
2010/0042114 A1 2/2010 Schaffhausen et al.
2010/0063540 A1 3/2010 Maiorino
2010/0063541 A1 3/2010 Brunelle et al.
2010/0087857 A1 4/2010 Stone et al.
2010/0094341 A1 4/2010 Raju
2010/0094355 A1 4/2010 Trenhaile
2010/0106254 A1 4/2010 Delsignore
2010/0121348 A1 5/2010 Van Der Burg et al.
2010/0145384 A1 6/2010 Stone et al.
2010/0152752 A1 6/2010 Denove et al.
2010/0191319 A1 7/2010 Lilburn et al.
2010/0191342 A1 7/2010 Byrd et al.
2010/0204700 A1 8/2010 Falahee
2010/0211071 A1 8/2010 Lettmann et al.
2010/0211075 A1 8/2010 Stone
2010/0256677 A1 10/2010 Albertorio et al.
2010/0268273 A1 10/2010 Albertorio et al.
2010/0268275 A1 10/2010 Stone et al.
2010/0270306 A1 10/2010 Shiffer
2010/0274282 A1 10/2010 Olson
2010/0292792 A1 11/2010 Stone et al.
2010/0298872 A1 11/2010 Berndt et al.
2010/0298952 A1 11/2010 Busold et al.
2010/0305698 A1 12/2010 Metzger et al.
2010/0305709 A1 12/2010 Metzger et al.
2010/0305710 A1 12/2010 Metzger
2010/0312245 A1 12/2010 Tipirneni et al.
2010/0312341 A1 12/2010 Kaiser et al.
2010/0324676 A1 12/2010 Albertorio
2010/0331881 A1 12/2010 Hart
2011/0009885 A1 1/2011 Graf et al.
2011/0022083 A1 1/2011 Dimatteo et al.
2011/0026141 A1 2/2011 Barrows
2011/0040387 A1 2/2011 Ries et al.
2011/0046733 A1 2/2011 Eggli
2011/0087225 A1 4/2011 Fritzinger
2011/0087280 A1 4/2011 Albertorio
2011/0087284 A1 4/2011 Stone et al.
2011/0098727 A1 4/2011 Kaiser et al.
2011/0106153 A1 5/2011 Stone et al.
2011/0112537 A1 5/2011 Bernstein et al.
2011/0112538 A1 5/2011 Dell'oca
2011/0124954 A1 5/2011 Ogdahl et al.
2011/0125153 A1 5/2011 Tyber et al.
2011/0160767 A1 6/2011 Stone et al.
2011/0160768 A1 6/2011 Stone et al.
2011/0166608 A1 7/2011 Duggal et al.
2011/0184227 A1 7/2011 Altman et al.
2011/0208239 A1 8/2011 Stone et al.
2011/0208240 A1 8/2011 Stone et al.
2011/0213367 A1 9/2011 Tyber et al.
2011/0213416 A1 9/2011 Kaiser
2011/0218625 A1 9/2011 Berelsman et al.
2011/0224799 A1 9/2011 Stone
2011/0245868 A1 10/2011 Teeslink et al.
2011/0264141 A1 10/2011 Denham et al.
2011/0270278 A1 11/2011 Overes et al.
2011/0270306 A1 11/2011 Denham et al.
2011/0295284 A1 12/2011 Purdue et al.
2011/0319932 A1 12/2011 Avelar et al.
2012/0004669 A1 1/2012 Overes et al.
2012/0024134 A1 2/2012 Dow et al.
2012/0029561 A1 2/2012 Olson
2012/0041485 A1 2/2012 Kaiser et al.
2012/0041486 A1 2/2012 Stone et al.
2012/0041496 A1 2/2012 Walker
2012/0042768 A1 2/2012 Chou et al.

(56) References Cited

U.S. PATENT DOCUMENTS

2012/0046693 A1 2/2012 Denham et al.
2012/0053630 A1 3/2012 Denham et al.
2012/0059417 A1 3/2012 Norton et al.
2012/0059418 A1 3/2012 Denham et al.
2012/0059468 A1 3/2012 Mattern et al.
2012/0060278 A1 3/2012 Mccurdy
2012/0083837 A1 4/2012 Ferragamo et al.
2012/0089193 A1 4/2012 Stone et al.
2012/0095470 A1 4/2012 Kaiser et al.
2012/0109156 A1 5/2012 Overes et al.
2012/0116409 A1 5/2012 Stone
2012/0116450 A1 5/2012 Mcdevitt et al.
2012/0116452 A1 5/2012 Stone et al.
2012/0123447 A1 5/2012 Corrao et al.
2012/0123474 A1 5/2012 Zajac et al.
2012/0123541 A1 5/2012 Albertorio et al.
2012/0130423 A1 5/2012 Sengun et al.
2012/0130492 A1 5/2012 Eggli et al.
2012/0143215 A1 6/2012 Corrao et al.
2012/0150223 A1 6/2012 Manos et al.
2012/0150297 A1 6/2012 Denham et al.
2012/0165864 A1 6/2012 Hernandez et al.
2012/0165866 A1 6/2012 Kaiser et al.
2012/0165867 A1 6/2012 Denham et al.
2012/0165938 A1 6/2012 Denham et al.
2012/0192455 A1 8/2012 Hansen et al.
2012/0197271 A1 8/2012 Astorino et al.
2012/0215257 A1 8/2012 Mcdevitt et al.
2012/0239159 A1 9/2012 Metzger et al.
2012/0245585 A1 9/2012 Kaiser et al.
2012/0265219 A1 10/2012 Rushdy et al.
2012/0265294 A1 10/2012 Nishigishi
2012/0271403 A1 10/2012 Gries
2012/0273085 A1 11/2012 David et al.
2012/0290002 A1 11/2012 Astorino
2012/0290003 A1 11/2012 Dreyfuss
2012/0290004 A1 11/2012 Lombardo et al.
2012/0296427 A1 11/2012 Conner et al.
2012/0310245 A1 12/2012 Hoeppner et al.
2013/0018375 A1 1/2013 Dell'oca
2013/0018416 A1 1/2013 Lombardo et al.
2013/0023928 A1 1/2013 Dreyfuss
2013/0023929 A1 1/2013 Sullivan et al.
2013/0023930 A1 1/2013 Stone et al.
2013/0035698 A1 2/2013 Stone
2013/0035722 A1 2/2013 Mcdevitt et al.
2013/0046341 A1 2/2013 Stone et al.
2013/0060323 A1 3/2013 Mchugo
2013/0090720 A1 4/2013 Mahr et al.
2013/0090731 A1 4/2013 Walker
2013/0103082 A1 4/2013 Kaiser et al.
2013/0110165 A1 5/2013 Burkhart et al.
2013/0110251 A1 5/2013 Metzger et al.
2013/0116730 A1 5/2013 Denham
2013/0123810 A1 5/2013 Brown et al.
2013/0123813 A1 5/2013 Stone et al.
2013/0131722 A1 5/2013 Marchand et al.
2013/0138123 A1 5/2013 Stone et al.
2013/0144337 A1 6/2013 Stone et al.
2013/0144338 A1 6/2013 Stone et al.
2013/0158599 A1 6/2013 Hester et al.
2013/0158601 A1 6/2013 Stone et al.
2013/0172942 A1 7/2013 Lewis et al.
2013/0190818 A1 7/2013 Norton
2013/0190819 A1 7/2013 Norton
2013/0204276 A1 8/2013 Stone et al.
2013/0211452 A1 8/2013 Stone et al.
2013/0231700 A1 9/2013 Gedet et al.
2013/0237997 A1 9/2013 Arai et al.
2013/0245761 A1 9/2013 Conner et al.
2013/0267956 A1 10/2013 Terrill et al.
2013/0274812 A1 10/2013 Dell'oca
2013/0289564 A1 10/2013 Bernstein et al.
2013/0317621 A1 11/2013 Metzger et al.
2013/0331742 A1 12/2013 Aupperle et al.
2013/0331848 A1 12/2013 Kaiser et al.
2014/0005754 A1 1/2014 Finley et al.
2014/0018804 A1 1/2014 Foerster
2014/0046367 A1 2/2014 Stone et al.
2014/0046368 A1 2/2014 Kaiser et al.
2014/0052179 A1 2/2014 Dreyfuss et al.
2014/0058436 A1 2/2014 Rosenbluth et al.
2014/0067081 A1 3/2014 Stone
2014/0081322 A1 3/2014 Sengun et al.
2014/0088655 A1 3/2014 Stone et al.
2014/0094913 A1 4/2014 Berelsman et al.
2014/0128985 A1 5/2014 Sanders et al.
2014/0135835 A1 5/2014 Stone et al.
2014/0163613 A1 6/2014 Stone et al.
2014/0163614 A1 6/2014 Denham et al.
2014/0194927 A1 7/2014 Kaiser et al.
2014/0200583 A1 7/2014 Stone et al.
2014/0257378 A1 9/2014 Norton et al.
2014/0276992 A1 9/2014 Stone et al.
2014/0277447 A1 9/2014 Berelsman et al.
2014/0324101 A1 10/2014 Denham et al.
2014/0330311 A1 11/2014 Denham et al.
2014/0336760 A1 11/2014 Eggli
2014/0350674 A1 11/2014 Stone et al.
2015/0012094 A1 1/2015 Denham et al.
2015/0032216 A1 1/2015 Metzger et al.
2015/0057665 A1 2/2015 Neal et al.
2015/0057757 A1 2/2015 Metzger et al.
2015/0066081 A1 3/2015 Martin
2015/0119890 A1 4/2015 Kaiser et al.
2015/0127051 A1 5/2015 Kaiser et al.
2015/0128792 A1 5/2015 Zachariades et al.
2015/0134000 A1 5/2015 Denham et al.
2015/0143981 A1 5/2015 Dunker
2015/0148888 A1 5/2015 Milner et al.
2015/0173753 A1 6/2015 Spivey et al.
2015/0173887 A1 6/2015 Berelsman et al.
2015/0257750 A1 9/2015 Kaiser et al.
2015/0320026 A1 11/2015 Toddes
2016/0000483 A1 1/2016 Stone
2016/0022261 A1 1/2016 Stone et al.
2016/0038187 A1 2/2016 Mcdonnell
2016/0058436 A1 3/2016 Stone et al.
2016/0058484 A1 3/2016 Mccombs-stearnes et al.
2016/0074049 A1 3/2016 Russell et al.
2016/0081789 A1 3/2016 Denham et al.
2016/0106414 A1 4/2016 Stone et al.
2016/0128684 A1 5/2016 Stone et al.
2016/0183935 A1 6/2016 Stone
2016/0199053 A1 7/2016 Norton et al.
2016/0213369 A1 7/2016 Stone et al.
2016/0242760 A1 8/2016 Kaiser et al.
2017/0014225 A1 1/2017 Denham et al.
2017/0020507 A1 1/2017 Denham et al.
2017/0020569 A1 1/2017 Grant
2017/0035411 A1 2/2017 Kaiser et al.
2017/0049557 A1 2/2017 Denham et al.
2017/0065278 A1 3/2017 Stone
2017/0071593 A1 3/2017 Stone
2017/0071595 A1 3/2017 Stone et al.
2017/0086816 A1 3/2017 Norton
2017/0119382 A1 5/2017 Denham et al.
2017/0128061 A1 5/2017 Stone et al.
2017/0181746 A1 6/2017 Denham et al.
2017/0189011 A1 7/2017 Stone et al.
2017/0189197 A1 7/2017 Werber et al.
2017/0202587 A1 7/2017 Stone et al.
2017/0273686 A1 9/2017 Denham et al.
2017/0311947 A1 11/2017 Kaiser et al.
2017/0319194 A1 11/2017 Mayeski et al.
2017/0319195 A1 11/2017 Denham et al.
2017/0319204 A1 11/2017 Norton et al.
2017/0325808 A1 11/2017 Stone et al.
2017/0333176 A1 11/2017 Stone et al.
2017/0360425 A1 12/2017 Stone et al.
2018/0000477 A1 1/2018 Kaiser et al.
2018/0014864 A1 1/2018 Stone et al.
2018/0020762 A1 1/2018 Jamison
2018/0021036 A1 1/2018 Kaiser et al.

(56) References Cited

U.S. PATENT DOCUMENTS

2018/0021125 A1 1/2018 Berelsman et al.
2018/0042609 A1 2/2018 Denham et al.
2018/0098858 A1 4/2018 Valderrabano et al.
2018/0125476 A1 5/2018 Kaiser et al.
2018/0125477 A1 5/2018 Stone
2018/0153538 A1 6/2018 Kaiser et al.
2018/0153558 A1 6/2018 Bake et al.
2018/0161030 A1 6/2018 Stone et al.
2018/0177501 A1 6/2018 Kaiser et al.
2018/0193015 A1 7/2018 Denham et al.
2018/0221017 A1 8/2018 Stone et al.
2018/0235747 A1 8/2018 Berelsman et al.
2018/0249997 A1 9/2018 Stone et al.
2018/0256153 A1 9/2018 Stone et al.
2019/0083233 A1 3/2019 Denham et al.
2019/0150909 A1 5/2019 Stone et al.
2019/0150923 A1 5/2019 Stone et al.
2019/0231348 A1 8/2019 Stone et al.
2019/0254652 A1 8/2019 Stone et al.
2019/0274681 A1 9/2019 Denham et al.
2019/0282227 A1 9/2019 Norton
2019/0290258 A1 9/2019 Denham et al.
2019/0298345 A1 10/2019 Denham et al.
2019/0328382 A1 10/2019 Stone et al.
2019/0365376 A1 12/2019 Stone et al.
2020/0029955 A1 1/2020 Stone et al.
2020/0085562 A1 3/2020 Stone et al.
2020/0178959 A1 6/2020 Denham et al.
2020/0187932 A1 6/2020 Kaiser et al.
2020/0187933 A1 6/2020 Kaiser et al.
2020/0197002 A1 6/2020 Stone et al.
2020/0297338 A1 9/2020 Stone et al.
2020/0367880 A1 11/2020 Stone et al.
2021/0177397 A1 6/2021 Stone et al.
2021/0228203 A1 7/2021 Denham et al.
2021/0361286 A1 11/2021 Stone et al.
2022/0015757 A1 1/2022 Stone et al.
2022/0054123 A1 2/2022 Kaiser et al.
2022/0096074 A1 3/2022 Denham et al.
2022/0096081 A1 3/2022 Denham et al.
2023/0000484 A1 1/2023 Kaiser et al.
2023/0084732 A1 3/2023 Norton
2023/0146316 A1 5/2023 Stone et al.
2023/0165580 A1 6/2023 Kaiser et al.
2023/0172602 A1 6/2023 Kaiser et al.
2023/0248356 A1 8/2023 Stone et al.
2023/0293165 A1 9/2023 Stone et al.
2023/0389916 A1 12/2023 Denham et al.

FOREIGN PATENT DOCUMENTS

AU 4381268 A 4/1970
AU 5850469 A 1/1971
AU 5963869 A 2/1971
AU 1505470 A 11/1971
AU 2223767 A 5/1973
AU 3615171 A 5/1973
AU 440266 B2 9/1973
AU 5028569 A 9/1973
AU 7110887 A 10/1987
AU 639410 A 11/1989
AU 1713188 A 11/1989
AU 651929 B2 8/1994
AU 3877493 B2 8/1994
BE 1010569 A6 10/1998
CN 1720872 A 1/2006
CN 1777450 A 5/2006
CN 101083954 A 12/2007
CN 101584592 A 11/2009
CN 105208970 A 12/2015
DE 2529669 A1 3/1976
DE 2747312 A1 4/1979
DE 2818254 A1 10/1979
DE 2919009 A1 11/1979
DE 3027138 A1 12/1981
DE 3225620 A1 2/1983
DE 3136083 A1 3/1983
DE 233303 A1 2/1986
DE 4127550 A1 2/1993
DE 4302397 A 7/1993
DE 29621340 U1 4/1998
DE 19841252 A1 3/2000
DE 29922088 U1 4/2000
DE 20207781 U1 8/2002
EP 0019062 A1 11/1980
EP 0108912 A2 5/1984
EP 0129422 A2 12/1984
EP 0129442 A1 12/1984
EP 0172130 A2 2/1986
EP 0241240 A2 10/1987
EP 0241792 A1 10/1987
EP 0260970 A2 3/1988
EP 0270704 A1 6/1988
EP 0282789 A2 9/1988
EP 0315371 A2 5/1989
EP 0317406 A1 5/1989
EP 0340159 A1 11/1989
EP 0346183 A1 12/1989
EP 0349173 A1 1/1990
EP 0374088 A1 6/1990
EP 0409364 A2 1/1991
EP 0415915 A1 3/1991
EP 0440991 A1 8/1991
EP 0441065 A2 8/1991
EP 0447065 A2 9/1991
EP 0451932 A1 10/1991
EP 0464480 A1 1/1992
EP 0490417 A1 6/1992
EP 0497079 A1 8/1992
EP 0502509 A1 9/1992
EP 0502698 A1 9/1992
EP 0520177 A1 12/1992
EP 5201777 A1 12/1992
EP 0546726 A1 6/1993
EP 0552950 A1 7/1993
EP 0574707 A1 12/1993
EP 0582514 A1 2/1994
EP 0591991 A2 4/1994
EP 0598219 A2 5/1994
EP 0611551 A1 8/1994
EP 0627203 A2 12/1994
EP 0651979 A1 5/1995
EP 0669110 A2 8/1995
EP 0686373 A1 12/1995
EP 0702933 A1 3/1996
EP 0775473 A1 5/1997
EP 0913123 A1 5/1999
EP 0913131 A2 5/1999
EP 0995409 A1 4/2000
EP 1013229 A2 6/2000
EP 1093773 A1 4/2001
EP 1093774 A1 4/2001
EP 1555945 A2 7/2005
EP 1741412 A2 1/2007
EP 1864617 A2 12/2007
EP 2238944 A2 10/2010
EP 2544607 A1 1/2013
EP 2709557 A1 3/2014
EP 2895112 A1 7/2015
EP 2934379 A1 10/2015
EP 2434987 B1 6/2016
EP 2775935 B1 5/2017
FR 2622790 A1 5/1989
FR 2634373 A1 1/1990
FR 2655840 A1 6/1991
FR 2663837 A1 1/1992
FR 2682867 A1 4/1993
FR 2687911 A1 9/1993
FR 2688689 A1 9/1993
FR 2704140 A3 10/1994
FR 2717070 A1 9/1995
FR 2723528 A1 2/1996
FR 2734709 A1 12/1996
FR 2744010 A1 8/1997

(56) References Cited

FOREIGN PATENT DOCUMENTS

| | | | |
|---|---|---|---|
| FR | 2745999 | A1 | 9/1997 |
| FR | 2770764 | A1 | 5/1999 |
| GB | 401677 | A | 11/1933 |
| GB | 1413477 | A | 11/1975 |
| GB | 2083751 | A | 3/1982 |
| GB | 2118474 | A | 11/1983 |
| GB | 2129306 | A | 5/1984 |
| GB | 2227175 | A | 7/1990 |
| GB | 2253147 | A | 9/1992 |
| GB | 1485681 | A | 9/1997 |
| GB | 2312376 | A | 10/1997 |
| GB | 2403416 | A | 1/2005 |
| GB | 2454251 | A | 5/2009 |
| JP | 5362911 | U | 5/1978 |
| JP | 5362912 | U | 5/1978 |
| JP | 5374942 | U | 6/1978 |
| JP | 5378230 | U | 6/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | A | 7/1987 |
| JP | 6215964 | U | 10/1987 |
| JP | 62295657 | A | 12/1987 |
| JP | 5269160 | A | 10/1993 |
| JP | 5300917 | A | 11/1993 |
| JP | 751292 | A | 2/1995 |
| JP | 10127672 | A | 5/1998 |
| JP | 10211213 | A | 8/1998 |
| JP | 5362911 | B2 | 12/2013 |
| JP | 5362912 | B2 | 12/2013 |
| JP | 5374942 | B2 | 12/2013 |
| JP | 5378230 | B2 | 12/2013 |
| RU | 2051647 | C1 | 1/1996 |
| RU | 2076667 | C1 | 4/1997 |
| WO | WO-8300615 | A1 | 3/1983 |
| WO | WO-8603666 | A1 | 7/1986 |
| WO | WO-8701270 | A1 | 3/1987 |
| WO | WO-8901767 | A1 | 3/1989 |
| WO | WO-8909030 | A1 | 10/1989 |
| WO | WO-8910096 | A1 | 11/1989 |
| WO | WO-9008510 | A1 | 8/1990 |
| WO | WO-9203980 | A1 | 3/1992 |
| WO | WO-9314705 | A1 | 8/1993 |
| WO | WO-9315694 | A1 | 8/1993 |
| WO | WO-9502373 | A1 | 1/1995 |
| WO | WO-9503003 | A1 | 2/1995 |
| WO | WO-9529637 | A1 | 11/1995 |
| WO | WO-9532670 | A1 | 12/1995 |
| WO | WO-9609797 | A1 | 4/1996 |
| WO | WO-9629029 | A1 | 9/1996 |
| WO | WO-9737603 | A1 | 10/1997 |
| WO | WO-9812991 | A1 | 4/1998 |
| WO | WO-9812992 | A1 | 4/1998 |
| WO | WO-9822047 | A1 | 5/1998 |
| WO | WO-9822048 | A1 | 5/1998 |
| WO | WO-9901084 | A2 | 1/1999 |
| WO | WO-9912480 | A1 | 3/1999 |
| WO | WO-9937219 | A1 | 7/1999 |
| WO | WO-9944544 | A1 | 9/1999 |
| WO | WO-9952472 | A1 | 10/1999 |
| WO | WO-0004159 | A1 | 1/2000 |
| WO | WO-0040159 | A1 | 7/2000 |
| WO | WO-0139671 | A1 | 6/2001 |
| WO | WO-0236020 | A1 | 5/2002 |
| WO | WO-03005914 | A1 | 1/2003 |
| WO | WO-03071962 | A2 | 9/2003 |
| WO | WO-03077772 | A1 | 9/2003 |
| WO | WO-03092551 | A1 | 11/2003 |
| WO | WO-2004091412 | A1 | 10/2004 |
| WO | WO-05104992 | A1 | 11/2005 |
| WO | WO-2005122954 | A1 | 12/2005 |
| WO | WO-2006011786 | A1 | 2/2006 |
| WO | WO-2006023661 | A2 | 3/2006 |
| WO | WO-2006055823 | A2 | 5/2006 |
| WO | WO-2007045460 | A2 | 4/2007 |
| WO | WO-2007103562 | A2 | 9/2007 |
| WO | WO-2007109280 | A2 | 9/2007 |
| WO | WO-2007119057 | A1 | 10/2007 |
| WO | WO-2008002550 | A2 | 1/2008 |
| WO | WO-2008015171 | A1 | 2/2008 |
| WO | WO-2008073588 | A2 | 6/2008 |
| WO | WO-2009012021 | A1 | 1/2009 |
| WO | WO-2009083047 | A1 | 7/2009 |
| WO | WO-2009131820 | A1 | 10/2009 |
| WO | WO-2010138832 | A1 | 12/2010 |
| WO | WO-2011112371 | A1 | 9/2011 |
| WO | WO-2011150238 | A1 | 12/2011 |
| WO | WO-2012134999 | A1 | 10/2012 |
| WO | WO-2012158583 | A1 | 11/2012 |
| WO | WO-2013066974 | A1 | 5/2013 |
| WO | WO-2013074525 | A1 | 5/2013 |
| WO | WO-2014043078 | A1 | 3/2014 |
| WO | WO-2014100109 | A1 | 6/2014 |
| WO | WO-2014151766 | A1 | 9/2014 |

OTHER PUBLICATIONS

"U.S. Appl. No. 16/400,199, Non Final Office Action mailed Feb. 10, 2022", 8 pgs.
"U.S. Appl. No. 16/400,199, Notice of Allowance mailed May 11, 2022", 8 pgs.
"U.S. Appl. No. 16/400,199, Response filed Apr. 13, 2022 to Non Final Office Action mailed Feb. 10, 2022", 11 pgs.
"U.S. Appl. No. 16/428,277, Non Final Office Action mailed May 24, 2022", 7 pgs.
"U.S. Appl. No. 16/428,277, Notice of Allowance mailed Aug. 25, 2022", 9 pgs.
"U.S. Appl. No. 16/428,277, Response filed Apr. 11, 2022 to Restriction Requirement mailed Feb. 11, 2022", 8 pgs.
"U.S. Appl. No. 16/428,277, Response filed Aug. 3, 2022 to Non Final Office Action mailed May 24, 2022", 8 pgs.
"U.S. Appl. No. 16/428,277, Restriction Requirement mailed Feb. 11, 2022", 6 pgs.
"U.S. Appl. No. 16/544,293, Response filed Aug. 15, 2022 to Restriction Requirement mailed Jul. 7, 2022", 7 pgs.
"U.S. Appl. No. 16/544,293, Restriction Requirement mailed Jul. 7, 2022", 6 pgs.
"U.S. Appl. No. 16/593,022, Restriction Requirement mailed Sep. 6, 2022", 6 pgs.
"U.S. Appl. No. 16/690,671, Notice of Allowance mailed Mar. 2, 2022", 7 pgs.
"U.S. Appl. No. 16/690,671, Response filed Feb. 4, 2022 to Non Final Office Action mailed Nov. 15, 2021", 10 pgs.
"U.S. Appl. No. 16/795,181, Examiner Interview Summary mailed Apr. 15, 2022", 2 pgs.
"U.S. Appl. No. 16/795,181, Final Office Action mailed Jun. 7, 2022", 12 pgs.
"U.S. Appl. No. 16/795,181, Non Final Office Action mailed Jan. 24, 2022", 12 pgs.
"U.S. Appl. No. 16/795,181, Notice of Allowance mailed Aug. 25, 2022", 7 pgs.
"U.S. Appl. No. 16/795,181, Response filed Apr. 14, 2022 to Non Final Office Action mailed Jan. 24, 2022", 9 pgs.
"U.S. Appl. No. 16/795,181, Response filed Aug. 3, 2022 to Final Office Action mailed Jun. 7, 2022", 8 pgs.
"U.S. Appl. No. 16/802,228, Notice of Allowance mailed Jun. 15, 2022", 10 pgs.
"U.S. Appl. No. 16/802,248, Non Final Office Action mailed Jun. 17, 2022", 18 pgs.
"U.S. Appl. No. 16/806,611, Restriction Requirement mailed Aug. 26, 22", 6 pgs.
U.S. Appl. No. 18/514,936, filed Nov. 20, 2023, Method and Apparatus for Coupling Soft Tissue to a Bone.
U.S. Appl. No. 18/471,089, filed Sep. 20, 2023, Soft Tissue Repair Device and Associated Methods.
U.S. Appl. No. 18/126,022, filed Mar. 24, 2023, Soft Tissue Repair Device and Associated Methods.

(56) References Cited

OTHER PUBLICATIONS

U.S. Appl. No. 18/531,362, filed Dec. 6, 2023, Method for Tissue Fixation.
U.S. Appl. No. 18/235,540, filed Aug. 18, 2023, Method and Apparatus for Coupling Anatomical Features.
U.S. Appl. No. 18/102,518, filed Jan. 27, 2023, Method and Apparatus for Coupling Soft Tissue to a Bone.
U.S. Appl. No. 18/101,490, filed Jan. 25, 2023, Method and Apparatus for Coupling Soft Tissue to Bone.
U.S. Appl. No. 18/531,396, filed Dec. 6, 2023, Soft Tissue Repair Device and Method.
U.S. Appl. No. 18/531,431, filed Dec. 6, 2023, Method and Apparatus for Forming a Self-Locking Adjustable Loop.
U.S. Appl. No. 18/093,114, filed Jan. 4, 2023, Method and Apparatus for Soft Tissue Fixation.
U.S. Appl. No. 18/134,897, filed Apr. 14, 2023, Method and Apparatus for Soft Tissue Fixation.
U.S. Appl. No. 18/497,342, filed Oct. 30, 2023, Method and Apparatus for Soft Tissue Fixation.
U.S. Appl. No. 17/991,832, filed Nov. 21, 2022, Method for Coupling Soft Tissue to a Bone.
U.S. Appl. No. 11/541,506 U.S. Pat. No. 7,601,165, filed Sep. 29, 2006, Method and Apparatus for Forming a Self-Locking Adjustable Suture Loop.
U.S. Appl. No. 11/784,821 U.S. Pat. No. 9,017,381, filed Apr. 10, 2007, Adjustable Knotless Loops.
U.S. Appl. No. 14/697,140 U.S. Pat. No. 9,861,351, filed Apr. 27, 2015, Adjustable Knotless Loops.
U.S. Appl. No. 15/720,997 U.S. Pat. No. 11,185,320, filed Sep. 29, 2017, Adjustable Knotless Loops.
U.S. Appl. No. 15/903,261 U.S. Pat. No. 10,729,423, filed Feb. 23, 2018, Adjustable Knotless Loops.
U.S. Appl. No. 17/516,664, filed Nov. 1, 2021, Adjustable Knotless Loops.
U.S. Appl. No. 11/347,661 7,749,250, filed Feb. 3, 2006, Soft Tissue Repair Assembly and Associated Method.
U.S. Appl. No. 12/828,977 U.S. Pat. No. 8,409,253, filed Jul. 1, 2010, Soft Tissue Repair Assembly and Associated Method.
U.S. Appl. No. 13/767,401 U.S. Pat. No. 9,414,833, filed Feb. 14, 2013, Soft Tissue Repair Assembly and Associated Method.
U.S. Appl. No. 14/936,831 U.S. Pat. No. 10,441,264, filed Nov. 10, 2015, Soft Tissue Repair Assembly and Associated Method.
U.S. Appl. No. 15/361,917 U.S. Pat. No. 10,702,259, filed Nov. 28, 2016, Soft Tissue Repair Assembly and Associated Method.
U.S. Appl. No. 16/251,342 U.S. Pat. No. 11,116,495, filed Jan. 18, 2019, Soft Tissue Repair Assembly and Associated Method.
U.S. Appl. No. 16/544,293, filed Aug. 19, 2019, Soft Tissue Repair Assembly and Associated Method.
U.S. Appl. No. 11/541,505 U.S. Pat. No. 7,658,751, filed Sep. 29, 2006, Method for Implanting Soft Tissue.
U.S. Appl. No. 12/702,067 U.S. Pat. No. 8,672,968, filed Feb. 8, 2010, Method for Implanting Soft Tissue.
U.S. Appl. No. 14/211,977 U.S. Pat. No. 9,486,211, filed Mar. 14, 2014, Method for Implanting Soft Tissue.
U.S. Appl. No. 15/061,352 U.S. Pat. No. 10,004,493, filed Mar. 4, 2016, Method for Implanting Soft Tissue.
U.S. Appl. No. 15/664,572 U.S. Pat. No. 10,398,430, filed Jul. 31, 2017, Method for Implanting Soft Tissue.
U.S. Appl. No. 16/508,764, filed Jul. 11, 2019, Method for Implanting Soft Tissue.
U.S. Appl. No. 17/492,082, filed Oct. 1, 2021, Method for Implanting Soft Tissue.
U.S. Appl. No. 11/935,681 U.S. Pat. No. 7,905,903, filed Nov. 6, 2007, Method for Tissue Fixation.
U.S. Appl. No. 12/196,398 U.S. Pat. No. 7,959,650, filed Aug. 22, 2008, Adjustable Knotless Loops.
U.S. Appl. No. 13/102,182 U.S. Pat. No. 8,231,654, filed May 6, 2011, Adjustable Knotless Loops.
U.S. Appl. No. 10/984,624 U.S. Pat. No. 7,608,098, filed Nov. 9, 2004, Bone Fixation Device.
U.S. Appl. No. 11/294,694 U.S. Pat. No. 7,914,539, filed Dec. 5, 2005, Tissue Fixation Device.
U.S. Appl. No. 11/408,282, filed Apr. 20, 2006, Soft Tissue Conduit Device.
U.S. Appl. No. 12/419,491 U.S. Pat. No. 8,317,825, filed Apr. 7, 2009, Soft Tissue Conduit Device and Method.
U.S. Appl. No. 11/869,440 U.S. Pat. No. 7,857,830, filed Oct. 9, 2007, Soft Tissue Repair and Conduit Device.
U.S. Appl. No. 12/976,328 U.S. Pat. No. 8,273,106, filed Dec. 22, 2010, Soft Tissue Repair and Conduit Device.
U.S. Appl. No. 12/489,168 U.S. Pat. No. 8,361,113, filed Jun. 22, 2009, Method and Apparatus for Coupling Soft Tissue to a Bone.
U.S. Appl. No. 13/751,846 U.S. Pat. No. 9,492,158, filed Jan. 28, 2013, Method and Apparatus for Coupling Soft Tissue to a Bone.
U.S. Appl. No. 14/983,747 U.S. Pat. No. 10,154,837, filed Dec. 30, 2015, Method and Apparatus for Coupling Soft Tissue to a Bone.
U.S. Appl. No. 15/941,481 U.S. Pat. No. 10,973,507, filed Mar. 30, 2018, Method and Apparatus for Coupling Soft Tissue to a Bone.
U.S. Appl. No. 16/400,199, filed May 1, 2019, Method and Apparatus for Coupling Soft Tissue to a Bone.
U.S. Appl. No. 17/190,686, filed Mar. 3, 2021, Method and Apparatus for Coupling Soft Tissue to a Bone.
U.S. Appl. No. 12/014,399 U.S. Pat. No. 7,909,851, filed Jan. 15, 2008, Soft Tissue Repair Assembly and Associated Method.
U.S. Appl. No. 13/045,691 U.S. Pat. No. 8,292,921, filed Mar. 11, 2011, Soft Tissue Repair Assembly and Associated Method.
U.S. Appl. No. 13/656,821 U.S. Pat. No. 9,173,651, filed Oct. 22, 2012, Soft Tissue Repair Device and Associated Methods.
U.S. Appl. No. 14/876,167 U.S. Pat. No. 10,251,637, filed Oct. 6, 2015, Soft Tissue Repair Device and Associated Methods.
U.S. Appl. No. 15/891,049 U.S. Pat. No. 10,932,770, filed Feb. 7, 2018, Soft Tissue Repair Device and Associated Methods.
U.S. Appl. No. 16/593,022, filed Oct. 4, 2019, Soft Tissue Repair Device and Associated Methods.
U.S. Appl. No. 16/989,386, filed Aug. 10, 2020, Soft Tissue Repair Device and Associated Methods.
U.S. Appl. No. 12/014,340 U.S. Pat. No. 7,905,904, filed Jan. 15, 2008, Soft Tissue Repair Assembly and Associated Method.
U.S. Appl. No. 13/045,689 U.S. Pat. No. 8,337,525, filed Mar. 11, 2011, Soft Tissue Repair Assembly and Associated Method.
U.S. Appl. No. 13/721,970 U.S. Pat. No. 8,632,569, filed Dec. 20, 2012, Soft Tissue Repair Assembly and Associated Method.
U.S. Appl. No. 13/838,755 U.S. Pat. No. 9,510,819, filed Mar. 15, 2013, Soft Tissue Repair Device and Associated Methods.
U.S. Appl. No. 13/833,567 U.S. Pat. No. 9,561,025, filed Mar. 15, 2013, Soft Tissue Repair Device and Associated Methods.
U.S. Appl. No. 14/159,094 U.S. Pat. No. 9,622,736, filed Jan. 20, 2014, Soft Tissue Repair Device and Associated Methods.
U.S. Appl. No. 15/412,676, filed Jan. 23, 2017, Soft Tissue Repair Device and Associated Methods.
U.S. Appl. No. 16/806,611, filed Mar. 2, 2020, Soft Tissue Repair Device and Associated Methods.
U.S. Appl. No. 12/489,181 U.S. Pat. No. 8,298,262, filed Jun. 22, 2009, Method for Tissue Fixation.
U.S. Appl. No. 13/625,413 U.S. Pat. No. 9,402,621, filed Sep. 24, 2012, Method for Tissue Fixation.
U.S. Appl. No. 14/983,108 U.S. Pat. No. 10,321,906, filed Dec. 29, 2015, Method for Tissue Fixation.
U.S. Appl. No. 15/945,425 U.S. Pat. No. 10,987,099, filed Apr. 4, 2018, Method for Tissue Fixation.
U.S. Appl. No. 16/380,742, filed Apr. 10, 2019, Method for Tissue Fixation.
U.S. Appl. No. 10/983,236, filed Nov. 5, 2004, Tissue Repair Assembly.
U.S. Appl. No. 11/347,662, filed Feb. 3, 2006, Tissue Repair Assembly.
U.S. Appl. No. 16/795,181, filed Feb. 19, 2020, Method and Apparatus for Coupling Soft Tissue to a Bone.
U.S. Appl. No. 17/550,074, filed Dec. 14, 2021, Method and Apparatus for Coupling Soft Tissue to a Bone.
U.S. Appl. No. 12/196,410 U.S. Pat. No. 8,118,836, filed Aug. 22, 2008, Method and Apparatus for Coupling Soft Tissue to a Bone.

(56) References Cited

OTHER PUBLICATIONS

U.S. Appl. No. 13/399,125 U.S. Pat. No. 8,840,645, filed Feb. 17, 2012, Method and Apparatus for Coupling Soft Tissue to a Bone.
U.S. Appl. No. 14/492,590 U.S. Pat. No. 9,572,655, filed Sep. 22, 2014, Method and Apparatus for Coupling Soft Tissue to a Bone.
U.S. Appl. No. 14/956,724 U.S. Pat. No. 9,801,708, filed Dec. 2, 2015, Method and Apparatus for Coupling Soft Tissue to a Bone.
U.S. Appl. No. 15/278,777 U.S. Pat. No. 10,092,288, filed Sep. 28, 2016, Method and Apparatus for Coupling Soft Tissue to a Bone.
U.S. Appl. No. 15/455,895 U.S. Pat. No. 10,695,052, filed Mar. 10, 2017, Method and Apparatus for Coupling Soft Tissue to a Bone.
U.S. Appl. No. 15/622,718 U.S. Pat. No. 10,687,803, filed Jun. 14, 2017, Method and Apparatus for Coupling Soft Tissue to a Bone.
U.S. Appl. No. 15/793,216 U.S. Pat. No. 10,729,430, filed Oct. 25, 2017, Method and Apparatus for Coupling Soft Tissue to a Bone.
U.S. Appl. No. 16/420,676, filed May 23, 2019, Method and Apparatus for Coupling Soft Tissue to a Bone.
U.S. Appl. No. 12/196,407 U.S. Pat. No. 8,137,382, filed Aug. 22, 2008, Method and Apparatus for Forming a Self-Locking Adjustable Suture Loop.
U.S. Appl. No. 13/412,116 U.S. Pat. No. 8,771,316, filed Mar. 5, 2012, Method and Apparatus for Coupling Anatomical Features.
U.S. Appl. No. 14/324,688 U.S. Pat. No. 9,498,204, filed Jul. 7, 2014, Method and Apparatus for Coupling Anatomical Features.
U.S. Appl. No. 13/412,127 U.S. Pat. No. 8,721,684, filed Mar. 5, 2012, Method and Apparatus for Coupling Anatomical Features.
U.S. Appl. No. 14/275,548 U.S. Pat. No. 9,510,821, filed May 12, 2014, Method and Apparatus for Coupling Anatomical Features.
U.S. Appl. No. 15/288,183 U.S. Pat. No. 10,398,428, filed Oct. 7, 2016, Method and Apparatus for Coupling Anatomical Features.
U.S. Appl. No. 15/662,572 U.S. Pat. No. 10,716,557, filed Jul. 28, 2017, Method and Apparatus for Coupling Anatomical Features.
U.S. Appl. No. 16/436,023, filed Jun. 10, 2019, Method and Apparatus for Coupling Anatomical Features.
U.S. Appl. No. 17/545,668, filed Dec. 8, 2021, Method and Apparatus for Coupling Anatomical Features.
U.S. Appl. No. 12/196,405 U.S. Pat. No. 8,128,658, filed Aug. 22, 2008, Method and Apparatus for Coupling Soft Tissue to Bone.
U.S. Appl. No. 13/181,729 U.S. Pat. No. 8,551,140, filed Jul. 13, 2011, Method and Apparatus for Coupling Soft Tissue to Bone.
U.S. Appl. No. 13/412,105 U.S. Pat. No. 8,932,331, filed Mar. 5, 2012, Method and Apparatus for Coupling Soft Tissue to Bone.
U.S. Appl. No. 14/594,285 U.S. Pat. No. 9,801,620, filed Jan. 12, 2015, Method and Apparatus for Coupling Soft Tissue to Bone.
U.S. Appl. No. 15/703,727 U.S. Pat. No. 10,603,029, filed Sep. 13, 2017, Method and Apparatus for Coupling Soft Tissue to Bone.
U.S. Appl. No. 16/802,248, filed Feb. 26, 2020, Method and Apparatus for Coupling Soft Tissue to Bone.
U.S. Appl. No. 12/474,802 U.S. Pat. No. 8,088,130, filed May 29, 2009, Method and Apparatus for Coupling Soft Tissue to Bone.
U.S. Appl. No. 13/278,341 U.S. Pat. No. 8,608,777, filed Oct. 21, 2011, Method and Apparatus for Coupling Soft Tissue to Bone.
U.S. Appl. No. 14/107,350 U.S. Pat. No. 9,532,777, filed Dec. 16, 2013, Method and Apparatus for Coupling Soft Tissue to Bone.
U.S. Appl. No. 15/074,553 U.S. Pat. No. 10,004,489, filed Mar. 18, 2016, Method and Apparatus for Coupling Soft Tissue to Bone.
U.S. Appl. No. 15/297,844 U.S. Pat. No. 10,098,629, filed Oct. 19, 2016, Method and Apparatus for Coupling Soft Tissue to Bone.
U.S. Appl. No. 15/865,938 10,542,967, filed Jan. 9, 2018, Method and Apparatus for Coupling Soft Tissue to Bone.
U.S. Appl. No. 15/886,712 U.S. Pat. No. 10,595,851, filed Feb. 1, 2018, Method and Apparatus for Coupling Soft Tissue to Bone.
U.S. Appl. No. 16/802,228, filed Feb. 26, 2020, Method and Apparatus for Coupling Soft Tissue to Bone.
U.S. Appl. No. 12/570,854 U.S. Pat. No. 8,303,604, filed Sep. 30, 2009, Soft Tissue Repair Device and Method.
U.S. Appl. No. 13/645,964 U.S. Pat. No. 9,504,460, filed Oct. 5, 2012, Soft Tissue Repair Device and Method.
U.S. Appl. No. 15/332,590 U.S. Pat. No. 10,265,064, filed Oct. 24, 2016, Soft Tissue Repair Device and Method.
U.S. Appl. No. 16/255,300 U.S. Pat. No. 11,109,857, filed Jan. 23, 2019, Soft Tissue Repair Device and Method.
U.S. Appl. No. 17/392,971, filed Aug. 3, 2021, Soft Tissue Repair Device and Method.
U.S. Appl. No. 12/719,337 U.S. Pat. No. 9,078,644, filed Mar. 8, 2010, Fracture Fixation Device.
U.S. Appl. No. 14/794,309 U.S. Pat. No. 9,833,230, filed Jul. 8, 2015, Fracture Fixation Device.
U.S. Appl. No. 15/060,007 U.S. Pat. No. 10,349,931, filed Mar. 3, 2016, Fracture Fixation Device.
U.S. Appl. No. 15/866,089 U.S. Pat. No. 10,835,232, filed Jan. 9, 2018, Fracture Fixation Device.
U.S. Appl. No. 12/915,962 U.S. Pat. No. 8,562,647, filed Oct. 29, 2010, Method and Apparatus for Securing Soft Tissue to Bone.
U.S. Appl. No. 14/055,172 U.S. Pat. No. 9,724,090, filed Oct. 16, 2013, Method and Apparatus for Attaching Soft Tissue to Bone.
U.S. Appl. No. 15/654,386 U.S. Pat. No. 10,695,045, filed Jul. 19, 2017, Method and Apparatus for Attaching Soft Tissue to Bone.
U.S. Appl. No. 12/938,902 U.S. Pat. No. 8,597,327, filed Nov. 3, 2010, Method and Apparatus for Securing Soft Tissue to Bone.
U.S. Appl. No. 14/094,311 U.S. Pat. No. 9,642,661, filed Dec. 2, 2013, Method and Apparatus for Sternal Closure.
U.S. Appl. No. 15/461,675 U.S. Pat. No. 10,675,073, filed Mar. 17, 2017, Method and Apparatus for Sternal Closure.
U.S. Appl. No. 11/504,882 U.S. Pat. No. 8,998,949, filed Aug. 16, 2006, Soft Tissue Conduit Device.
U.S. Appl. No. 12/029,861 U.S. Pat. No. 8,251,998, filed Feb. 12, 2008, Chondral Defect Repair.
U.S. Appl. No. 13/587,374 U.S. Pat. No. 8,777,956, filed Aug. 16, 2012, Chondral Defect Repair.
U.S. Appl. No. 11/740,035, filed Apr. 25, 2007, Method for Treating Cartilage Defects.
U.S. Appl. No. 11/739,768 U.S. Pat. No. 8,137,354, filed Apr. 25, 2007, Localized Cartilage Defect Therapy.
U.S. Appl. No. 13/350,985 U.S. Pat. No. 9,198,673, filed Jan. 16, 2012, Localized Cartilage Defect Therapy.
U.S. Appl. No. 14/923,506, filed Oct. 27, 2015, Localized Cartilage Defect Therapy.
U.S. Appl. No. 13/111,564 U.S. Pat. No. 8,574,235, filed May 19, 2011, Method for Trochanteric Reattachment.
U.S. Appl. No. 14/071,295 U.S. Pat. No. 9,005,287 filed Nov. 4, 2013, Method for Bone Reattachment.
U.S. Appl. No. 13/288,459 U.S. Pat. No. 9,468,433, filed Nov. 3, 2011, Method and Apparatus for Forming a Self-Locking Adjustable Loop.
U.S. Appl. No. 15/294,994 U.S. Pat. No. 10,517,587, filed Oct. 17, 2016, Method and Apparatus for Forming a Self-Locking Adjustable Loop.
U.S. Appl. No. 16/443,391, filed Jun. 17, 2019, Method and Apparatus for Forming a Self-Locking Adjustable Loop.
U.S. Appl. No. 13/288,463 U.S. Pat. No. 8,936,621, filed Nov. 3, 2011, Method and Apparatus for Forming a Self-Locking Adjustable Loop.
U.S. Appl. No. 14/599,909 U.S. Pat. No. 9,993,241, filed Jan. 19, 2015, Method and Apparatus for Forming a Self-Locking Adjustable Loop.
U.S. Appl. No. 15/917,143 U.S. Pat. No. 11,039,826, filed Mar. 9, 2018, Method and Apparatus for Forming a Self-Locking Adjustable Loop.
U.S. Appl. No. 17/232,672, filed Apr. 16, 2021, Method and Apparatus for Forming a Self-Locking Adjustable Loop.
U.S. Appl. No. 13/720,648 U.S. Pat. No. 9,357,991, filed Dec. 19, 2012, Method and Apparatus for Stitching Tendons.
U.S. Appl. No. 15/166,480 U.S. Pat. No. 10,265,159, filed May 27, 2016, Method and Apparatus for Stitching Tendons.
U.S. Appl. No. 16/160,559, filed Oct. 15, 2018, Method and Apparatus for Stitching Tendons.
U.S. Appl. No. 14/095,639 U.S. Pat. No. 9,918,827, filed Dec. 3, 2013, Scaffold for Spring Ligament Repair.
U.S. Appl. No. 14/095,614 U.S. Pat. No. 9,918,826, filed Dec. 3, 2013, Scaffold for Spring Ligament Repair.
U.S. Appl. No. 15/722,002 U.S. Pat. No. 10,758,221, filed Oct. 2, 2017, Scaffold for Spring Ligament Repair.

(56) References Cited

OTHER PUBLICATIONS

U.S. Appl. No. 13/098,897 U.S. Pat. No. 8,562,645, filed May 2, 2011, Method and Apparatus for Forming a Self-Locking Adjustable Loop.
U.S. Appl. No. 14/055,191 U.S. Pat. No. 9,539,003, filed Oct. 16, 2013, Method and Apparatus for Forming a Self-Locking Adjustable Loop.
U.S. Appl. No. 15/401,768 U.S. Pat. No. 10,610,217, filed Jan. 9, 2017, Method and Apparatus for Forming a Self-Locking Adjustable Loop.
U.S. Appl. No. 15/972,646 U.S. Pat. No. 11,096,684, filed May 7, 2018, Method and Apparatus for Forming a Self-Locking Adjustable Loop.
U.S. Appl. No. 13/098,927 U.S. Pat. No. 8,652,171, filed May 2, 2011, Method and Apparatus for Soft Tissue Fixation.
U.S. Appl. No. 14/182,038 U.S. Pat. No. 9,763,656, filed Feb. 17, 2014, Method and Apparatus for Soft Tissue Fixation.
U.S. Appl. No. 15/682,187 U.S. Pat. No. 10,729,421, filed Aug. 21, 2017, Method and Apparatus for Soft Tissue Fixation.
U.S. Appl. No. 16/895,246, filed Jun. 8, 2020, Method and Apparatus for Soft Tissue Fixation.
U.S. Appl. No. 12/788,978 U.S. Pat. No. 8,801,783, filed May 27, 2010, Prosthetic Ligament System for Knee Joint.
U.S. Appl. No. 14/456,286 U.S. Pat. No. 9,681,940, filed Aug. 11, 2014, Ligament System for Knee Joint.
U.S. Appl. No. 15/626,384 U.S. Pat. No. 10,517,714, filed Jun. 19, 2017, Ligament System for Knee Joint.
U.S. Appl. No. 16/690,671, filed Nov. 21, 2019, Prosthetic Ligament System for Knee Joint.
U.S. Appl. No. 11/386,071 U.S. Pat. No. 8,034,090, filed Mar. 21, 2006, Bone Fixation Device.
U.S. Appl. No. 13/293,825 U.S. Pat. No. 9,149,267, filed Nov. 10, 2011, Method and Apparatus for Coupling Soft Tissue to a Bone.
U.S. Appl. No. 14/854,308 U.S. Pat. No. 10,022,118, filed Sep. 15, 2015, Method and Apparatus for Coupling Soft Tissue to a Bone.
U.S. Appl. No. 13/071,563 U.S. Pat. No. 8,926,613, filed Mar. 25, 2011, Method and Apparatus for Forming a Bone Hole.
U.S. Appl. No. 14/589,101, filed Jan. 5, 2015, Method and Apparatus for Forming a Bone Hole.
U.S. Appl. No. 13/311,936 U.S. Pat. No. 9,408,599, filed Dec. 6, 2011, Method and Apparatus for Coupling Soft Tissue to a Bone.
U.S. Appl. No. 15/231,074, filed Aug. 8, 2016, Method and Apparatus for Coupling Soft Tissue to a Bone.
U.S. Appl. No. 13/757,003 U.S. Pat. No. 9,357,992, filed Feb. 1, 2013, Method for Coupling Soft Tissue to a Bone.
U.S. Appl. No. 13/295,126 U.S. Pat. No. 9,271,713, filed Nov. 14, 2011, Method and Apparatus for Tensioning a Suture.
U.S. Appl. No. 13/281,009 U.S. Pat. No. 9,538,998, filed Oct. 25, 2011, Method and Apparatus for Fracture Fixation.
U.S. Appl. No. 13/269,097 U.S. Pat. No. 8,672,969, filed Oct. 7, 2011, Fracture Fixation Device.
U.S. Appl. No. 14/215,550 U.S. Pat. No. 9,788,876, filed Mar. 17, 2014, Fracture Fixation Device.
U.S. Appl. No. 15/715,731 U.S. Pat. No. 10,743,925, filed Sep. 26, 2017, Fracture Fixation Device.
U.S. Appl. No. 13/757,019 U.S. Pat. No. 9,314,241, filed Feb. 1, 2013, Apparatus for Coupling Soft Tissue to a Bone.
U.S. Appl. No. 15/131,663 U.S. Pat. No. 10,368,856, filed Apr. 18, 2016, Apparatus for Coupling Soft Tissue to a Bone.
U.S. Appl. No. 13/790,982 U.S. Pat. No. 9,370,350, filed Mar. 8, 2013, Apparatus for Coupling Soft Tissue to a Bone.
U.S. Appl. No. 13/790,997 U.S. Pat. No. 9,381,013, filed Mar. 8, 2013, Apparatus for Coupling Soft Tissue to a Bone.
U.S. Appl. No. 15/200,546 U.S. Pat. No. 10,363,028, filed Jul. 1, 2016, Apparatus for Coupling Soft Tissue to a Bone.
U.S. Appl. No. 16/428,277, filed May 31, 2019, Apparatus for Coupling Soft Tissue to a Bone.
U.S. Appl. No. 12/788,973 U.S. Pat. No. 8,500,818, filed May 27, 2010, Knee Prosthesis Assembly With Ligament Link.
U.S. Appl. No. 13/959,145 U.S. Pat. No. 9,414,925, filed Aug. 5, 2013, Method of Implanting a Knee Prosthesis Assembly With a Ligament Link.
U.S. Appl. No. 13/109,672 U.S. Pat. No. 8,968,364, filed May 17, 2011, Method and Apparatus for Fixation of an ACL Graft.
U.S. Appl. No. 14/635,055 U.S. Pat. No. 10,004,588, filed Mar. 2, 2015, Method and Apparatus for Fixation of an ACL Graft.
U.S. Appl. No. 15/956,444 U.S. Pat. No. 11,065,103, filed Apr. 18, 2018, Method and Apparatus for Fixation of an ACL Graft.
U.S. Appl. No. 13/109,667 U.S. Pat. No. 8,771,352, filed May 17, 2011, Method and Apparatus for Tibial Fixation of an ACL Graft.
U.S. Appl. No. 13/889,851 U.S. Pat. No. 9,216,078, filed May 8, 2013, Method and Apparatus for Tibial Fixation of an ACL Graft.
U.S. Appl. No. 14/974,516, filed Dec. 18, 2015, Method and Apparatus for Tibial Fixation of an ACL Graft.
U.S. Appl. No. 13/177,153 U.S. Pat. No. 8,652,172, filed Jul. 6, 2011, Flexible Anchors for Tissue Fixation.
U.S. Appl. No. 14/182,046 U.S. Pat. No. 9,603,591, filed Feb. 17, 2014, Flexible Anchors for Tissue Fixation.
U.S. Appl. No. 12/107,437, filed Apr. 22, 2008, Method and Apparatus for Attaching Soft Tisssue to Bone.
U.S. Appl. No. 12/398,548 U.S. Pat. No. 8,118,868, filed Mar. 5, 2009, Method and Apparatus for Attaching Soft Tissue to Bone.
"AperFix® System Surgical Technique Guide. Single Tunnel Double Bundle.198 ", Cayenne Medical brochure, (Aug. 2008), 8 pgs.
"U.S. Appl. No. 10/984,624, Final Office Action mailed Jan. 5, 2009", 9 pgs.
"U.S. Appl. No. 10/984,624, Non Final Office Action mailed Jul. 10, 2008", 9 pgs.
"U.S. Appl. No. 10/984,624, Notice of Allowance mailed Jun. 12, 2009", 9 pgs.
"U.S. Appl. No. 10/984,624, Response filed Apr. 1, 2009 to Final Office Action mailed Jan. 5, 2009", 16 pgs.
"U.S. Appl. No. 10/984,624, Response filed Apr. 15, 2008 to Restriction Requirement mailed Mar. 24, 2008", 1 pg.
"U.S. Appl. No. 10/984,624, Response filed Oct. 10, 2008 to Non Final Office Action mailed Jul. 10, 2008", 12 pgs.
"U.S. Appl. No. 10/984,624, Restriction Requirement mailed Mar. 24, 2008", 5 pgs.
"U.S. Appl. No. 11/294,694, Final Office Action mailed Sep. 1, 2010", 14 pgs.
"U.S. Appl. No. 11/294,694, Non Final Office Action mailed Mar. 16, 2010", 19 pgs.
"U.S. Appl. No. 11/294,694, Notice of Allowance mailed Nov. 17, 2010", 4 pgs.
"U.S. Appl. No. 11/294,694, Preliminary Amendment filed Jan. 13, 2010", 9 pgs.
"U.S. Appl. No. 11/294,694, Response filed Jun. 16, 2010 to Non Final Office Action mailed Mar. 16, 2010", 16 pgs.
"U.S. Appl. No. 11/294,694, Response filed Nov. 1, 2010 to Final Office Action mailed Sep. 1, 2010", 10 pgs.
"U.S. Appl. No. 11/294,694, Response filed Dec. 22, 2009 to Restriction Requirement mailed Nov. 25, 2009", 1 pg.
"U.S. Appl. No. 11/294,694, Restriction Requirement mailed Nov. 25, 2009", 9 pgs.
"U.S. Appl. No. 11/347,661, Examiner Interview Summary mailed Sep. 11, 2009", 2 pgs.
"U.S. Appl. No. 11/347,661, Final Office Action mailed Mar. 3, 2009", 15 pgs.
"U.S. Appl. No. 11/347,661, Non Final Office Action mailed Aug. 13, 2009", 19 pgs.
"U.S. Appl. No. 11/347,661, Non Final Office Action mailed Aug. 21, 2008", 11 pgs.
"U.S. Appl. No. 11/347,661, Notice of Allowance mailed Feb. 24, 2010", 8 pgs.
"U.S. Appl. No. 11/347,661, Notice of Allowance mailed May 5, 2010", 8 pgs.
"U.S. Appl. No. 11/347,661, Response filed May 29, 2008 to Restriction Requirement mailed Apr. 30, 2008", 1 pg.
"U.S. Appl. No. 11/347,661, Response filed Jun. 3, 2009 to Final Office Action mailed Mar. 3, 2009", 19 pgs.
"U.S. Appl. No. 11/347,661, Response filed Nov. 6, 2009 to Non Final Office Action mailed Aug. 13, 2009", 16 pgs.

(56) References Cited

OTHER PUBLICATIONS

"U.S. Appl. No. 11/347,661, Response filed Nov. 19, 2008 to Non Final Office Action mailed Aug. 21, 2008", 12 pgs.
"U.S. Appl. No. 11/347,661, Restriction Requirement mailed Apr. 30, 2008", 6 pgs.
"U.S. Appl. No. 11/347,662, Examiner Interview Summary mailed Jun. 24, 2010", 3 pgs.
"U.S. Appl. No. 11/347,662, Examiner Interview Summary mailed Nov. 9, 2009", 3 pgs.
"U.S. Appl. No. 11/347,662, Final Office Action mailed Sep. 16, 2009", 13 pgs.
"U.S. Appl. No. 11/347,662, Final Office Action mailed Oct. 26, 2010", 10 pgs.
"U.S. Appl. No. 11/347,662, Non Final Office Action mailed Mar. 9, 2009", 11 pgs.
"U.S. Appl. No. 11/347,662, Non Final Office Action mailed May 21, 2010", 19 pgs.
"U.S. Appl. No. 11/347,662, Non Final Office Action mailed Oct. 28, 2008", 13 pgs.
"U.S. Appl. No. 11/347,662, Response filed Jan. 16, 2009 to Non Final Office Action mailed Oct. 28, 2008", 16 pgs.
"U.S. Appl. No. 11/347,662, Response filed Feb. 12, 2010 to Final Office Action mailed Sep. 16, 2009", 21 pgs.
"U.S. Appl. No. 11/347,662, Response filed Jun. 5, 2009 to Non Final Office Action mailed Mar. 9, 2009", 13 pgs.
"U.S. Appl. No. 11/347,662, Response filed Aug. 20, 2010 to Non Final Office Action mailed May 21, 2010", 13 pgs.
"U.S. Appl. No. 11/386,071, Advisory Action mailed Dec. 23, 2010", 3 pgs.
"U.S. Appl. No. 11/386,071, Examiner Interview Summary mailed Jan. 31, 2011", 3 pgs.
"U.S. Appl. No. 11/386,071, Examiner Interview Summary mailed Jul. 21, 2010", 3 pgs.
"U.S. Appl. No. 11/386,071, Final Office Action mailed Oct. 27, 2010", 10 pgs.
"U.S. Appl. No. 11/386,071, Non Final Office Action mailed May 12, 2010", 13 pgs.
"U.S. Appl. No. 11/386,071, Notice of Allowance mailed Jun. 6, 2011", 6 pgs.
"U.S. Appl. No. 11/386,071, Response filed Jan. 26, 2011 to Advisory Action mailed Dec. 23, 2010", 13 pgs.
"U.S. Appl. No. 11/386,071, Response filed Aug. 12, 2010 to Non Final Office Action mailed May 12, 2010", 14 pgs.
"U.S. Appl. No. 11/386,071, Response filed Dec. 15, 2010 to Final Office Action mailed Oct. 27, 2010", 14 pgs.
"U.S. Appl. No. 11/408,282, Final Office Action mailed Dec. 15, 2008", 8 pgs.
"U.S. Appl. No. 11/408,282, Non Final Office Action mailed May 23, 2008", 12 pgs.
"U.S. Appl. No. 11/408,282, Response filed Aug. 21, 2008 to Non Final Office Action mailed May 23, 2008", 10 pgs.
"U.S. Appl. No. 11/504,882, Examiner Interview Summary mailed Sep. 2, 2010", 3 pgs.
"U.S. Appl. No. 11/504,882, Final Office Action mailed Dec. 21, 2010", 7 pgs.
"U.S. Appl. No. 11/504,882, Non Final Office Action mailed Jun. 19, 2014", 11 pgs.
"U.S. Appl. No. 11/504,882, Non Final Office Action mailed Jun. 23, 2010", 8 pgs.
"U.S. Appl. No. 11/504,882, Non Final Office Action mailed Nov. 13, 2013", 13 pgs.
"U.S. Appl. No. 11/504,882, Notice of Allowance mailed Dec. 1, 2014", 9 pgs.
"U.S. Appl. No. 11/504,882, Response filed Feb. 10, 2014 to Non Final Office Action mailed Nov. 13, 2013", 11 pgs.
"U.S. Appl. No. 11/504,882, Response filed Mar. 18, 2011 to Final Office Action mailed Dec. 21, 2010", 11 pgs.
"U.S. Appl. No. 11/504,882, Response filed Sep. 17, 2014 to Non Final Office Action mailed Jun. 19, 2014", 14 pgs.
"U.S. Appl. No. 11/504,882, Response filed Sep. 23, 2010 to Non Final Office Action mailed Jun. 23, 2010", 12 pgs.
"U.S. Appl. No. 11/504,882, Supplemental Notice of Allowability mailed Mar. 12, 2015", 5 pgs.
"U.S. Appl. No. 11/541,505, Non Final Office Action mailed May 19, 2009", 7 pgs.
"U.S. Appl. No. 11/541,505, Notice of Allowance mailed Sep. 18, 2009", 8 pgs.
"U.S. Appl. No. 11/541,505, Response filed Apr. 9, 2009 to Restriction Requirement mailed Mar. 9, 2009", 1 pg.
"U.S. Appl. No. 11/541,505, Response filed Jun. 18, 2009 to Non Final Office Action mailed May 19, 2009", 5 pgs.
"U.S. Appl. No. 11/541,505, Restriction Requirement mailed Mar. 9, 2009", 9 pgs.
"U.S. Appl. No. 11/541,506, Notice of Allowance mailed Jun. 1, 2009", 10 pgs.
"U.S. Appl. No. 11/541,506, Notice of Allowance mailed Jun. 29, 2009", 8 pgs.
"U.S. Appl. No. 11/541,506, Response filed Apr. 9, 2009 to Restriction Requirement mailed Mar. 9, 2009", 1 pg.
"U.S. Appl. No. 11/541,506, Restriction Requirement mailed Mar. 9, 2009", 6 pgs.
"U.S. Appl. No. 11/739,768, Examiner Interview Summary mailed May 11, 2011", 3 pgs.
"U.S. Appl. No. 11/739,768, Examiner Interview Summary mailed Oct. 4, 2011", 3 pgs.
"U.S. Appl. No. 11/739,768, Final Office Action mailed Aug. 22, 2011", 14 pgs.
"U.S. Appl. No. 11/739,768, Non Final Office Action mailed Mar. 4, 2011", 11 pgs.
"U.S. Appl. No. 11/739,768, Notice of Allowance mailed Nov. 15, 2011", 5 pgs.
"U.S. Appl. No. 11/739,768, Response filed Jun. 6, 2011 to Non Final Office Action mailed Mar. 4, 2011", 15 pgs.
"U.S. Appl. No. 11/739,768, Response filed Oct. 26, 2011 to Final Office Action mailed Aug. 22, 2011", 14 pgs.
"U.S. Appl. No. 11/740,035, Final Office Action mailed Aug. 7, 2008", 9 pgs.
"U.S. Appl. No. 11/740,035, Non Final Office Action mailed Jan. 3, 2008", 9 pgs.
"U.S. Appl. No. 11/740,035, Response filed Apr. 3, 2008 to Non Final Office Action mailed Jan. 3, 2008", 6 pgs.
"U.S. Appl. No. 11/784,821, Corrected Notice of Allowance mailed Dec. 24, 2014", 4 pgs.
"U.S. Appl. No. 11/784,821, Examiner Interview Summary mailed Jun. 26, 2014", 3 pgs.
"U.S. Appl. No. 11/784,821, Examiner Interview Summary mailed Nov. 17, 2009", 3 pgs.
"U.S. Appl. No. 11/784,821, Final Office Action mailed Mar. 10, 2010", 11 pgs.
"U.S. Appl. No. 11/784,821, Non Final Office Action mailed Mar. 28, 2014", 14 pgs.
"U.S. Appl. No. 11/784,821, Non Final Office Action mailed Sep. 4, 2009", 12 pgs.
"U.S. Appl. No. 11/784,821, Notice of Allowance mailed Oct. 21, 2014", 10 pgs.
"U.S. Appl. No. 11/784,821, Response filed Jun. 10, 2010 to Final Office Action mailed Mar. 10, 2010", 20 pgs.
"U.S. Appl. No. 11/784,821, Response filed Jun. 15, 2009 to Restriction Requirement mailed May 13, 2009", 2 pgs.
"U.S. Appl. No. 11/784,821, Response filed Jun. 26, 2014 to Non Final Office Action mailed Mar. 28, 2014", 16 pgs.
"U.S. Appl. No. 11/784,821, Response filed Nov. 23, 2009 to Non Final Office Action mailed Sep. 4, 2009", 17 pgs.
"U.S. Appl. No. 11/784,821, Restriction Requirement mailed May 13, 2009", 6 pgs.
"U.S. Appl. No. 11/869,440, Examiner Interview Summary mailed Mar. 25, 2010", 3 pgs.
"U.S. Appl. No. 11/869,440, Non Final Office Action mailed Mar. 1, 2010", 13 pgs.
"U.S. Appl. No. 11/869,440, Notice of Allowance mailed Aug. 19, 2010", 10 pgs.

(56) References Cited

OTHER PUBLICATIONS

"U.S. Appl. No. 11/869,440, Response filed Jun. 1, 2010 to Non Final Office Action mailed Mar. 1, 2010", 14 pgs.
"U.S. Appl. No. 11/935,681, Examiner Interview Summary mailed Jul. 19, 2010", 3 pgs.
"U.S. Appl. No. 11/935,681, Non Final Office Action mailed May 24, 2010", 12 pgs.
"U.S. Appl. No. 11/935,681, Notice of Allowance mailed Nov. 8, 2010", 10 pgs.
"U.S. Appl. No. 11/935,681, Response filed Apr. 19, 2010 to Restriction Requirement mailed Mar. 17, 2010", 4 pgs.
"U.S. Appl. No. 11/935,681, Response filed Aug. 24, 2010 to Non Final Office Action mailed May 24, 2010", 13 pgs.
"U.S. Appl. No. 11/935,681, Restriction Requirement mailed Mar. 17, 2010", 6 pgs.
"U.S. Appl. No. 12/014,340, Examiner Interview Summary mailed Jun. 22, 2010", 3 pgs.
"U.S. Appl. No. 12/014,340, Non Final Office Action mailed May 25, 2010", 12 pgs.
"U.S. Appl. No. 12/014,340, Notice of Allowance mailed Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement mailed Mar. 25, 2010", 2 pgs.
"U.S. Appl. No. 12/014,340, Response filed Aug. 25, 2010 to Non Final Office Action mailed May 25, 2010", 16 pgs.
"U.S. Appl. No. 12/014,340, Restriction Requirement mailed Mar. 25, 2010", 9 pgs.
"U.S. Appl. No. 12/014,399, Examiner Interview Summary mailed Jun. 23, 2010", 3 pgs.
"U.S. Appl. No. 12/014,399, Non Final Office Action mailed May 26, 2010", 13 pgs.
"U.S. Appl. No. 12/014,399, Notice of Allowance mailed Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement mailed Apr. 6, 2010", 2 pgs.
"U.S. Appl. No. 12/014,399, Response filed Aug. 25, 2010 to Non Final Office Action mailed May 26, 2010", 14 pgs.
"U.S. Appl. No. 12/014,399, Restriction Requirement mailed Apr. 6, 2010", 9 pgs.
"U.S. Appl. No. 12/029,861, Examiner Interview Summary mailed Jan. 27, 2012", 3 pgs.
"U.S. Appl. No. 12/029,861, Final Office Action mailed Dec. 8, 2011", 11 pgs.
"U.S. Appl. No. 12/029,861, Non Final Office Action mailed Jul. 26, 2011", 11 pgs.
"U.S. Appl. No. 12/029,861, Notice of Allowance mailed Apr. 26, 2012", 5 pgs.
"U.S. Appl. No. 12/029,861, Response filed Jan. 26, 2012 to Final Office Action mailed Dec. 8, 2011", 15 pgs.
"U.S. Appl. No. 12/029,861, Response filed May 6, 2011 to Restriction Requirement mailed Apr. 7, 2011", 10 pgs.
"U.S. Appl. No. 12/029,861, Response filed Jun. 23, 2011 to Restriction Requirement mailed May 24, 2011", 1 pgs.
"U.S. Appl. No. 12/029,861, Response filed Oct. 14, 2011 to Non Final Office Action mailed Jul. 26, 2011", 11 pgs.
"U.S. Appl. No. 12/029,861, Restriction Requirement mailed Apr. 7, 2011", 8 pgs.
"U.S. Appl. No. 12/029,861, Restriction Requirement mailed May 24, 2011", 6 pgs.
"U.S. Appl. No. 12/107,437, Examiner Interview Summary mailed May 10, 2010", 4 pgs.
"U.S. Appl. No. 12/107,437, Non Final Office Action mailed Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement mailed Jan. 13, 2010", 1 pgs.
"U.S. Appl. No. 12/107,437, Restriction Requirement mailed Jan. 13, 2010", 7 pgs.
"U.S. Appl. No. 12/196,398, Examiner Interview Summary mailed Nov. 8, 2010", 3 pgs.
"U.S. Appl. No. 12/196,398, Notice of Allowance mailed Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement mailed Sep. 29, 2010", 2 pgs.
"U.S. Appl. No. 12/196,398, Restriction Requirement mailed Sep. 29, 2010", 6 pgs.
"U.S. Appl. No. 12/196,398, Supplemental Notice of Allowability mailed Mar. 9, 2011", 4 pgs.
"U.S. Appl. No. 12/196,398, Supplemental Notice of Allowability mailed Apr. 15, 2011", 4 pgs.
"U.S. Appl. No. 12/196,405, Examiner Interview Summary mailed Jun. 20, 2011", 3 pgs.
"U.S. Appl. No. 12/196,405, Non Final Office Action mailed Apr. 11, 2011", 13 pgs.
"U.S. Appl. No. 12/196,405, Notice of Allowance mailed Oct. 26, 2011", 11 pgs.
"U.S. Appl. No. 12/196,405, Preliminary Amendment filed Nov. 10, 2008", 3 pgs.
"U.S. Appl. No. 12/196,405, Response filed Mar. 16, 2011 to Restriction Requirement mailed Feb. 14, 2011", 1 pgs.
"U.S. Appl. No. 12/196,405, Response filed Jul. 12, 2011 to Non Final Office Action mailed Apr. 11, 2011", 19 pgs.
"U.S. Appl. No. 12/196,405, Restriction Requirement mailed Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary mailed Jul. 14, 2011", 3 pgs.
"U.S. Appl. No. 12/196,407, Non Final Office Action mailed May 4, 2011", 11 pgs.
"U.S. Appl. No. 12/196,407, Notice of Allowance mailed Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement mailed Mar. 22, 2011", 12 pgs.
"U.S. Appl. No. 12/196,407, Response filed Aug. 2, 2011 to Non Final Office Action mailed May 4, 2011", 27 pgs.
"U.S. Appl. No. 12/196,407, Restriction Requirement mailed Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary mailed Jul. 14, 2011", 3 pgs.
"U.S. Appl. No. 12/196,410, Non Final Office Action mailed May 9, 2011", 9 pgs.
"U.S. Appl. No. 12/196,410, Notice of Allowance mailed Oct. 13, 2011", 8 pgs.
"U.S. Appl. No. 12/196,410, Response filed Apr. 20, 2011 to Restriction Requirement mailed Mar. 22, 2011", 13 pgs.
"U.S. Appl. No. 12/196,410, Response filed Aug. 1, 2011 to Non Final Office Action mailed May 9, 2011", 23 pgs.
"U.S. Appl. No. 12/196,410, Restriction Requirement mailed Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary mailed Jul. 12, 2011", 3 pgs.
"U.S. Appl. No. 12/398,548, Non Final Office Action mailed Apr. 12, 2011", 7 pgs.

(56) References Cited

OTHER PUBLICATIONS

"U.S. Appl. No. 12/398,548, Notice of Allowance mailed Oct. 18, 2011", 7 pgs.
"U.S. Appl. No. 12/398,548, Response filed Jul. 12, 2011 to Non Final Office Action mailed Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary mailed May 30, 2012", 3 pgs.
"U.S. Appl. No. 12/419,491, Examiner Interview Summary mailed Nov. 29, 2011", 3 pgs.
"U.S. Appl. No. 12/419,491, Final Office Action mailed Apr. 12, 2012", 12 pgs.
"U.S. Appl. No. 12/419,491, Non Final Office Action mailed Sep. 22, 2011", 12 pgs.
"U.S. Appl. No. 12/419,491, Notice of Allowance mailed Jul. 13, 2012", 10 pgs.
"U.S. Appl. No. 12/419,491, Response filed May 30, 2012 to Final Office Action mailed Apr. 12, 2012", 12 pgs.
"U.S. Appl. No. 12/419,491, Response filed Dec. 9, 2011 to Non Final Office Action mailed Sep. 22, 2011", 17 pgs.
"U.S. Appl. No. 12/474,802, Notice of Allowance mailed Aug. 31, 2011", 13 pgs.
"U.S. Appl. No. 12/474,802, Notice of Allowance mailed Oct. 26, 2011", 4 pgs.
"U.S. Appl. No. 12/474,802, Response filed Mar. 28, 2011 to Restriction Requirement mailed Feb. 24, 2011", 12 pgs.
"U.S. Appl. No. 12/474,802, Restriction Requirement mailed Feb. 24, 2011", 6 pgs.
"U.S. Appl. No. 12/489,168, Examiner Interview Summary mailed Feb. 21, 2012", 3 pgs.
"U.S. Appl. No. 12/489,168, Non Final Office Action mailed Dec. 7, 2011", 10 pgs.
"U.S. Appl. No. 12/489,168, Notice of Allowance mailed Apr. 26, 2012", 8 pgs.
"U.S. Appl. No. 12/489,168, Notice of Allowance mailed Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action mailed Dec. 7, 2011", 15 pgs.
"U.S. Appl. No. 12/489,168, Response filed Nov. 11, 2011 to Restriction Requirement mailed Oct. 20, 2011", 1 pg.
"U.S. Appl. No. 12/489,168, Restriction Requirement mailed Oct. 20, 2011", 8 pgs.
"U.S. Appl. No. 12/489,181, Examiner Interview Summary mailed Feb. 13, 2012", 3 pgs.
"U.S. Appl. No. 12/489,181, Non Final Office Action mailed Jan. 3, 2012", 9 pgs.
"U.S. Appl. No. 12/489,181, Notice of Allowance mailed May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action mailed Jan. 3, 2012", 12 pgs.
"U.S. Appl. No. 12/489,181, Response filed Dec. 5, 2011 to Restriction Requirement mailed Nov. 4, 2011", 1 pg.
"U.S. Appl. No. 12/489,181, Restriction Requirement mailed Nov. 4, 2011", 7 pgs.
"U.S. Appl. No. 12/570,854, Examiner Interview Summary mailed Apr. 16, 2012", 3 pgs.
"U.S. Appl. No. 12/570,854, Non Final Office Action mailed Feb. 10, 2012", 8 pgs.
"U.S. Appl. No. 12/570,854, Notice of Allowance mailed Jun. 29, 2012", 10 pgs.
"U.S. Appl. No. 12/570,854, Notice of Allowance mailed Sep. 19, 2012", 6 pgs.
"U.S. Appl. No. 12/570,854, Response filed May 10, 2012 to Non Final Office Action mailed Feb. 10, 2012", 27 pgs.
"U.S. Appl. No. 12/570,854, Response filed Dec. 20, 2011 to Restriction Requirement mailed Dec. 14, 2011", 1 pg.
"U.S. Appl. No. 12/570,854, Restriction Requirement mailed Dec. 14, 2011", 6 pgs.
"U.S. Appl. No. 12/702,067, Non Final Office Action mailed Mar. 5, 2013", 8 pgs.
"U.S. Appl. No. 12/702,067, Notice of Allowance mailed Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action mailed Mar. 5, 2013", 17 pgs.
"U.S. Appl. No. 12/702,067, Response filed Oct. 2, 2012 to Restriction Requirement mailed Sep. 4, 2012", 1 pg.
"U.S. Appl. No. 12/702,067, Restriction Requirement mailed Sep. 4, 2012", 9 pgs.
"U.S. Appl. No. 12/719,337, Advisory Action mailed Sep. 30, 2014", 4 pgs.
"U.S. Appl. No. 12/719,337, Examiner Interview Summary mailed Apr. 4, 2014", 4 pgs.
"U.S. Appl. No. 12/719,337, Examiner Interview Summary mailed May 14, 2013", 3 pgs.
"U.S. Appl. No. 12/719,337, Examiner Interview Summary mailed Sep. 18, 2014", 3 pgs.
"U.S. Appl. No. 12/719,337, Final Office Action mailed Mar. 12, 2013", 8 pgs.
"U.S. Appl. No. 12/719,337, Final Office Action mailed Jul. 18, 2014", 15 pgs.
"U.S. Appl. No. 12/719,337, Non Final Office Action mailed Jan. 10, 2014", 14 pgs.
"U.S. Appl. No. 12/719,337, Non Final Office Action mailed Sep. 5, 2012", 7 pgs.
"U.S. Appl. No. 12/719,337, Notice of Allowance mailed Mar. 11, 2015", 10 pgs.
"U.S. Appl. No. 12/719,337, Notice of Non-Compliant Amendment mailed May 2, 2014", 3 pgs.
"U.S. Appl. No. 12/719,337, Response filed Apr. 10, 2014 to Non Final Office Action mailed Jan. 10, 2014", 16 pgs.
"U.S. Appl. No. 12/719,337, Response filed May 25, 2012 to Restriction Requirement mailed Apr. 26, 2012", 9 pgs.
"U.S. Appl. No. 12/719,337, Response filed Jun. 5, 2013 to Final Office Action mailed Mar. 12, 2013", 16 pgs.
"U.S. Appl. No. 12/719,337, Response filed Jun. 25, 2014 to Notice of Non-Compliant Amendment mailed May 2, 2014", 10 pgs.
"U.S. Appl. No. 12/719,337, Response filed Sep. 18, 2014 to Final Office Action mailed Jul. 18, 2014", 13 pgs.
"U.S. Appl. No. 12/719,337, Response filed Nov. 28, 2012 to Non Final Office Action mailed Sep. 5, 2012", 14 pgs.
"U.S. Appl. No. 12/719,337, Restriction Requirement mailed Apr. 26, 2012", 8 pgs.
"U.S. Appl. No. 12/788,966, Examiner Interview Summary mailed Jun. 1, 2012", 3 pgs.
"U.S. Appl. No. 12/788,966, Final Office Action mailed May 4, 2012", 16 pgs.
"U.S. Appl. No. 12/788,966, Non Final Office Action mailed Jan. 4, 2012", 12 pgs.
"U.S. Appl. No. 12/788,966, Notice of Allowance mailed Aug. 16, 2012", 10 pgs.
"U.S. Appl. No. 12/788,966, Notice of Allowance mailed Nov. 23, 2012", 2 pgs.
"U.S. Appl. No. 12/788,966, Response filed Apr. 4, 2012 to Non Final Office Action mailed Jan. 4, 2012", 15 pgs.
"U.S. Appl. No. 12/788,966, Response filed Aug. 6, 2012 to Final Office Action mailed May 4, 2012", 12 pgs.
"U.S. Appl. No. 12/788,966, Response filed Dec. 16, 2011 to Restriction Requirement mailed Dec. 7, 2011", 11 pgs.
"U.S. Appl. No. 12/788,966, Restriction Requirement mailed Dec. 7, 2011", 9 pgs.
"U.S. Appl. No. 12/788,973, Advisory Action mailed Jan. 23, 2013", 3 pgs.

(56) References Cited

OTHER PUBLICATIONS

"U.S. Appl. No. 12/788,973, Advisory Action mailed Dec. 27, 2012", 8 pgs.
"U.S. Appl. No. 12/788,973, Final Office Action mailed Sep. 18, 2012", 16 pgs.
"U.S. Appl. No. 12/788,973, Non Final Office Action mailed May 8, 2012", 12 pgs.
"U.S. Appl. No. 12/788,973, Notice of Allowance mailed Mar. 21, 2013", 6 pgs.
"U.S. Appl. No. 12/788,973, Response filed Jan. 16, 2013 to Advisory Action mailed Dec. 27, 2012", 9 pgs.
"U.S. Appl. No. 12/788,973, Response filed Jul. 19, 2012 to Non Final Office Action mailed May 8, 2012", 21 pgs.
"U.S. Appl. No. 12/788,973, Response filed Dec. 16, 2011 to Restriction Requirement mailed Dec. 6, 2011", 11 pgs.
"U.S. Appl. No. 12/788,973, Response filed Dec. 17, 2012 to Final Office Action mailed Sep. 18, 2012", 15 pgs.
"U.S. Appl. No. 12/788,973, Restriction Requirement mailed Dec. 6, 2011", 9 pgs.
"U.S. Appl. No. 12/788,973, Supplemental Notice of Allowance mailed May 24, 2013", 2 pgs.
"U.S. Appl. No. 12/788,978, Advisory Action mailed Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance mailed Apr. 30, 2014", 2 pgs.
"U.S. Appl. No. 12/788,978, Examiner Interview Summary mailed Jan. 28, 2014", 3 pgs.
"U.S. Appl. No. 12/788,978, Examiner Interview Summary mailed Mar. 22, 2013", 3 pgs.
"U.S. Appl. No. 12/788,978, Examiner Interview Summary mailed Sep. 11, 2012", 3 pgs.
"U.S. Appl. No. 12/788,978, Examiner Interview Summary mailed Oct. 29, 2013", 4 pgs.
"U.S. Appl. No. 12/788,978, Examiner Interview Summary mailed Dec. 16, 2013", 3 pgs.
"U.S. Appl. No. 12/788,978, Examiner Interview Summary mailed Dec. 27, 2012", 3 pgs.
"U.S. Appl. No. 12/788,978, Final Office Action mailed Aug. 20, 2013", 17 pgs.
"U.S. Appl. No. 12/788,978, Final Office Action mailed Nov. 2, 2012", 14 pgs.
"U.S. Appl. No. 12/788,978, Non Final Office Action mailed Jan. 11, 2013", 16 pgs.
"U.S. Appl. No. 12/788,978, Non Final Office Action mailed Jul. 13, 2012", 17 pgs.
"U.S. Appl. No. 12/788,978, Notice of Allowance mailed Jan. 24, 2014", 9 pgs.
"U.S. Appl. No. 12/788,978, Notice of Non-Compliant Amendment mailed Jun. 6, 2013", 3 pgs.
"U.S. Appl. No. 12/788,978, Response filed Jan. 2, 2013 to Final Office Action mailed Nov. 2, 2012", 13 pgs.
"U.S. Appl. No. 12/788,978, Response filed Jan. 20, 2014 to Advisory Action mailed Dec. 24, 2013", 4 pgs.
"U.S. Appl. No. 12/788,978, Response filed Apr. 8, 2013 to Non Final Office Action mailed Jan. 11, 2013", 16 pgs.
"U.S. Appl. No. 12/788,978, Response filed May 21, 2012 to Restriction Requirement mailed Apr. 20, 2012", 12 pgs.
"U.S. Appl. No. 12/788,978, Response filed Jul. 3, 2013 to Notice of Non-Compliant Amendment mailed Jun. 6, 2013", 17 pgs.
"U.S. Appl. No. 12/788,978, Response filed Oct. 5, 2012 to Non Final Office Action mailed Jul. 13, 2012", 20 pgs.
"U.S. Appl. No. 12/788,978, Response filed Nov. 20, 2013 to Final Office Action mailed Aug. 20, 2013", 15 pgs.
"U.S. Appl. No. 12/788,978, Restriction Requirement mailed Apr. 20, 2012", 8 pgs.
"U.S. Appl. No. 12/828,977, Examiner Interview Summary mailed Jul. 9, 2012", 3 pgs.
"U.S. Appl. No. 12/828,977, Non Final Office Action mailed May 3, 2012", 9 pgs.
"U.S. Appl. No. 12/828,977, Notice of Allowance mailed Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement mailed Feb. 13, 2012", 9 pgs.
"U.S. Appl. No. 12/828,977, Response filed Jul. 25, 2012 to Non Final Office Action mailed May 3, 2012", 11 pgs.
"U.S. Appl. No. 12/828,977, Restriction Requirement mailed Feb. 13, 2012", 7 pgs.
"U.S. Appl. No. 12/915,962, Examiner Interview Summary mailed Jul. 25, 2012", 3 pgs.
"U.S. Appl. No. 12/915,962, Non Final Office Action mailed May 7, 2012", 11 pgs.
"U.S. Appl. No. 12/915,962, Non Final Office Action mailed Oct. 15, 2012", 9 pgs.
"U.S. Appl. No. 12/915,962, Notice of Allowance mailed Jun. 10, 2013", 12 pgs.
"U.S. Appl. No. 12/915,962, Response filed Jan. 10, 2013 to Non Final Office Action mailed Oct. 15, 2012", 21 pgs.
"U.S. Appl. No. 12/915,962, Response filed Mar. 16, 2012 to Restriction Requirement mailed Feb. 15, 2012", 15 pgs.
"U.S. Appl. No. 12/915,962, Response filed Aug. 7, 2012 to Non Final Office Action mailed May 7, 2012", 26 pgs.
"U.S. Appl. No. 12/915,962, Restriction Requirement mailed Feb. 15, 2012", 8 pgs.
"U.S. Appl. No. 12/938,902, Examiner Interview Summary mailed Dec. 3, 2012", 3 pgs.
"U.S. Appl. No. 12/938,902, Non Final Office Action mailed Sep. 17, 2012", 11 pgs.
"U.S. Appl. No. 12/938,902, Notice of Allowance mailed Jun. 21, 2013", 13 pgs.
"U.S. Appl. No. 12/938,902, Notice of Allowance mailed Oct. 1, 2013", 9 pgs.
"U.S. Appl. No. 12/938,902, Response filed Aug. 6, 2012 to Restriction Requirement mailed Jul. 6, 2012", 14 pgs.
"U.S. Appl. No. 12/938,902, Response filed Dec. 10, 2012 to Non Final Office Action mailed Sep. 17, 2012", 20 pgs.
"U.S. Appl. No. 12/938,902, Restriction Requirement mailed Jul. 6, 2012", 8 pgs.
"U.S. Appl. No. 12/976,328, Examiner Interview Summary mailed Feb. 13, 2012", 3 pgs.
"U.S. Appl. No. 12/976,328, Non Final Office Action mailed Dec. 15, 2011", 13 pgs.
"U.S. Appl. No. 12/976,328, Notice of Allowance mailed Apr. 30, 2012", 9 pgs.
"U.S. Appl. No. 12/976,328, Response filed Mar. 2, 2012 to Non Final Office Action mailed Dec. 15, 2011", 15 pgs.
"U.S. Appl. No. 13/045,689, Examiner Interview Summary mailed May 14, 2012", 3 pgs.
"U.S. Appl. No. 13/045,689, Non Final Office Action mailed Mar. 20, 2012", 11 pgs.
"U.S. Appl. No. 13/045,689, Notice of Allowance mailed Aug. 10, 2012", 10 pgs.
"U.S. Appl. No. 13/045,689, Notice of Allowance mailed Sep. 24, 2012", 7 pgs.
"U.S. Appl. No. 13/045,689, Response filed Jan. 30, 2012 to Restriction Requirement mailed Dec. 29, 2011", 13 pgs.
"U.S. Appl. No. 13/045,689, Response filed Jun. 8, 2012 to Non Final Office Action mailed Mar. 20, 2012", 15 pgs.
"U.S. Appl. No. 13/045,689, Restriction Requirement mailed Dec. 29, 2011", 6 pgs.
"U.S. Appl. No. 13/045,691, Examiner Interview Summary mailed May 14, 2012", 3 pgs.
"U.S. Appl. No. 13/045,691, Non Final Office Action mailed Mar. 20, 2012", 12 pgs.
"U.S. Appl. No. 13/045,691, Notice of Allowance mailed Jun. 19, 2012", 10 pgs.
"U.S. Appl. No. 13/045,691, Response filed Feb. 9, 2012 to Restriction Requirement mailed Jan. 9, 2012", 1 pg.

(56) References Cited

OTHER PUBLICATIONS

"U.S. Appl. No. 13/045,691, Response filed Jun. 8, 2012 to Non Final Office Action mailed Mar. 20, 2012", 17 pgs.
"U.S. Appl. No. 13/045,691, Restriction Requirement mailed Jan. 9, 2012", 6 pgs.
"U.S. Appl. No. 13/071,563, Final Office Action mailed May 23, 2014", 13 pgs.
"U.S. Appl. No. 13/071,563, Non Final Office Action mailed Oct. 23, 2013", 18 pgs.
"U.S. Appl. No. 13/071,563, Notice of Allowance mailed Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action mailed Oct. 23, 2013", 13 pgs.
"U.S. Appl. No. 13/071,563, Response filed Jul. 23, 2014 to Final Office Action mailed May 23, 2014", 14 pgs.
"U.S. Appl. No. 13/071,563, Response filed Sep. 19, 2013 to Restriction Requirement mailed Aug. 19, 2013", 11 pgs.
"U.S. Appl. No. 13/071,563, Restriction Requirement mailed Aug. 19, 2013", 7 pgs.
"U.S. Appl. No. 13/098,897, Examiner Interview Summary mailed Nov. 27, 2012", 3 pgs.
"U.S. Appl. No. 13/098,897, Non Final Office Action mailed Sep. 21, 2012", 9 pgs.
"U.S. Appl. No. 13/098,897, Notice of Allowance mailed Jun. 11, 2013", 13 pgs.
"U.S. Appl. No. 13/098,897, Response filed Aug. 30, 2012 to Restriction Requirement mailed Jul. 30, 2012", 16 pgs.
"U.S. Appl. No. 13/098,897, Response filed Dec. 18, 2012 to Non Final Office Action mailed Sep. 21, 2012", 21 pgs.
"U.S. Appl. No. 13/098,897, Restriction Requirement mailed Jul. 30, 2012", 8 pgs.
"U.S. Appl. No. 13/098,927, Advisory Action mailed Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary mailed Jun. 28, 2013", 3 pgs.
"U.S. Appl. No. 13/098,927, Examiner Interview Summary mailed Sep. 20, 2013", 3 pgs.
"U.S. Appl. No. 13/098,927, Final Office Action mailed May 22, 2013", 10 pgs.
"U.S. Appl. No. 13/098,927, Non Final Office Action mailed Sep. 24, 2012", 12 pgs.
"U.S. Appl. No. 13/098,927, Notice of Allowance mailed Jan. 8, 2014", 5 pgs.
"U.S. Appl. No. 13/098,927, Notice of Allowance mailed Sep. 26, 2013", 14 pgs.
"U.S. Appl. No. 13/098,927, Response filed Jul. 22, 2015 to Final Office Action mailed May 22, 2013", 17 pgs.
"U.S. Appl. No. 13/098,927, Response filed Aug. 27, 2012 to Restriction Requirement mailed Jul. 25, 2012", 14 pgs.
"U.S. Appl. No. 13/098,927, Response filed Dec. 21, 2012 to Non Final Office Action mailed Sep. 24, 2012", 21 pgs.
"U.S. Appl. No. 13/098,927, Restriction Requirement mailed Jul. 25, 2012", 8 pgs.
"U.S. Appl. No. 13/102,182, Notice of Allowance mailed Mar. 22, 2012", 10 pgs.
"U.S. Appl. No. 13/109,667, Advisory Action mailed Feb. 4, 2014", 4 pgs.
"U.S. Appl. No. 13/109,667, Examiner Interview Summary mailed Dec. 20, 2013", 3 pgs.
"U.S. Appl. No. 13/109,667, Final Office Action mailed Oct. 11, 2013", 19 pgs.
"U.S. Appl. No. 13/109,667, Non Final Office Action mailed May 21, 2013", 21 pgs.
"U.S. Appl. No. 13/109,667, Notice of Allowance mailed Feb. 18, 2014", 10 pgs.
"U.S. Appl. No. 13/109,667, Response filed Jan. 13, 2014 to Final Office Action mailed Oct. 11, 2013", 20 pgs.
"U.S. Appl. No. 13/109,667, Response filed May 2, 2013 to Restriction Requirement mailed Apr. 2, 2013", 1 pg.
"U.S. Appl. No. 13/109,667, Response filed Aug. 21, 2013 to Non Final Office Action mailed May 21, 2013", 27 pgs.
"U.S. Appl. No. 13/109,667, Restriction Requirement mailed Apr. 2, 2013", 8 pgs.
"U.S. Appl. No. 13/109,667, Supplemental Notice of Allowability mailed Jun. 12, 2014", 3 pgs.
"U.S. Appl. No. 13/109,667, Supplemental Notice of Allowance mailed May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action mailed May 15, 2014", 10 pgs.
"U.S. Appl. No. 13/109,672, Notice of Allowance mailed Feb. 3, 2015", 2 pgs.
"U.S. Appl. No. 13/109,672, Notice of Allowance mailed Sep. 29, 2014", 9 pgs.
"U.S. Appl. No. 13/109,672, PTO Response to Rule 312 Communication mailed Jan. 27, 2015", 2 pgs.
"U.S. Appl. No. 13/109,672, Response filed Apr. 14, 2014 to Restriction Requirement mailed Feb. 14, 2014", 15 pgs.
"U.S. Appl. No. 13/109,672, Response filed Aug. 15, 2014 to Non Final Office Action mailed May 15, 2014", 20 pgs.
"U.S. Appl. No. 13/109,672, Response filed Nov. 4, 2013 to Restriction Requirement mailed Oct. 2, 2013", 10 pgs.
"U.S. Appl. No. 13/109,672, Restriction Requirement mailed Feb. 14, 2014", 7 pgs.
"U.S. Appl. No. 13/109,672, Restriction Requirement mailed Oct. 2, 2013", 7 pgs.
"U.S. Appl. No. 13/111,564, Corrected Notice of Allowance mailed Oct. 9, 2013", 2 pgs.
"U.S. Appl. No. 13/111,564, Examiner Interview Summary mailed Jun. 18, 2013", 3 pgs.
"U.S. Appl. No. 13/111,564, Non Final Office Action mailed Mar. 18, 2013", 8 pgs.
"U.S. Appl. No. 13/111,564, Notice of Allowance mailed Jun. 28, 2013", 12 pgs.
"U.S. Appl. No. 13/111,564, Response filed Feb. 4, 2013 to Restriction Requirement mailed Jan. 3, 2013", 20 pgs.
"U.S. Appl. No. 13/111,564, Response filed Jun. 18, 2013 to Non Final Office Action mailed Mar. 18, 2013", 25 pgs.
"U.S. Appl. No. 13/111,564, Restriction Requirement mailed Jan. 3, 2013", 5 pgs.
"U.S. Appl. No. 13/177,153, Final Office Action mailed May 28, 2013", 11 pgs.
"U.S. Appl. No. 13/177,153, Non Final Office Action mailed Oct. 2, 2012", 11 pgs.
"U.S. Appl. No. 13/177,153, Notice of Allowance mailed Jan. 7, 2014", 4 pgs.
"U.S. Appl. No. 13/177,153, Notice of Allowance mailed Sep. 17, 2013", 13 pgs.
"U.S. Appl. No. 13/177,153, Response filed Aug. 28, 2013 to Final Office Action mailed May 28, 2013", 19 pgs.
"U.S. Appl. No. 13/177,153, Response filed Sep. 4, 2012 to Restriction Requirement mailed Aug. 2, 2012", 15 pgs.
"U.S. Appl. No. 13/177,153, Response filed Dec. 20, 2012 to Non Final Office Action mailed Oct. 2, 2012", 16 pgs.
"U.S. Appl. No. 13/177,153, Restriction Requirement mailed Aug. 2, 2012", 9 pgs.
"U.S. Appl. No. 13/181,729, Examiner Interview Summary mailed May 9, 2013", 3 pgs.
"U.S. Appl. No. 13/181,729, Final Office Action mailed Mar. 13, 2013", 14 pgs.
"U.S. Appl. No. 13/181,729, Non Final Office Action mailed Oct. 2, 2012", 7 pgs.

(56) References Cited

OTHER PUBLICATIONS

"U.S. Appl. No. 13/181,729, Notice of Allowance mailed May 23, 2013", 9 pgs.
"U.S. Appl. No. 13/181,729, Response filed May 13, 2013 to Final Office Action mailed Mar. 13, 2013", 13 pgs.
"U.S. Appl. No. 13/181,729, Response filed Dec. 20, 2012 to Non Final Office Action mailed Oct. 2, 2012", 15 pgs.
"U.S. Appl. No. 13/269,097, Final Office Action mailed Aug. 8, 2013", 7 pgs.
"U.S. Appl. No. 13/269,097, Non Final Office Action mailed Feb. 12, 2013", 10 pgs.
"U.S. Appl. No. 13/269,097, Notice of Allowance mailed Feb. 3, 2014", 5 pgs.
"U.S. Appl. No. 13/269,097, Notice of Allowance mailed Oct. 21, 2013", 9 pgs.
"U.S. Appl. No. 13/269,097, Response filed May 13, 2013 to Non Final Office Action mailed Feb. 12, 2013", 17 pgs.
"U.S. Appl. No. 13/269,097, Response filed Oct. 8, 2013 to Final Office Action mailed Aug. 8, 2013", 12 pgs.
"U.S. Appl. No. 13/269,097, Response filed Nov. 13, 2012 to Restriction Requirement mailed Oct. 17, 2012", 1 pg.
"U.S. Appl. No. 13/269,097, Restriction Requirement mailed Oct. 17, 2012", 8 pgs.
"U.S. Appl. No. 13/278,341, Notice of Allowance mailed Jun. 18, 2013", 10 pgs.
"U.S. Appl. No. 13/278,341, Response filed Mar. 8, 2013 to Restriction Requirement mailed Feb. 11, 2013", 1 pg.
"U.S. Appl. No. 13/278,341, Restriction Requirement mailed Feb. 11, 2013", 6 pgs.
"U.S. Appl. No. 13/281,009, Corrected Notice of Allowance mailed Nov. 18, 2016", 4 pgs.
"U.S. Appl. No. 13/281,009, Corrected Notice of Allowance mailed Dec. 12, 2016", 2 pgs.
"U.S. Appl. No. 13/281,009, Examiner Interview Summary mailed Nov. 18, 2016", 2 pgs.
"U.S. Appl. No. 13/281,009, Non Final Office Action mailed Jun. 2, 2015", 9 pgs.
"U.S. Appl. No. 13/281,009, Notice of Allowance mailed Feb. 24, 2016", 9 pgs.
"U.S. Appl. No. 13/281,009, Notice of Allowance mailed Jun. 23, 2016", 9 pgs.
"U.S. Appl. No. 13/281,009, Notice of Allowance mailed Oct. 29, 2015", 8 pgs.
"U.S. Appl. No. 13/281,009, Response filed Sep. 2, 2015 to Non Final Office Action mailed Jun. 2, 2015", 13 pgs.
"U.S. Appl. No. 13/281,009, Restriction Requirement mailed Feb. 11, 2015", 6 pgs.
"U.S. Appl. No. 13/288,459, Corrected Notice of Allowance mailed Aug. 3, 2016", 4 pgs.
"U.S. Appl. No. 13/288,459, Corrected Notice of Allowance mailed Sep. 9, 2016", 4 pgs.
"U.S. Appl. No. 13/288,459, Corrected Notice of Allowance mailed Sep. 23, 2016", 4 pgs.
"U.S. Appl. No. 13/288,459, Examiner Interview Summary mailed Feb. 6, 2015", 3 pgs.
"U.S. Appl. No. 13/288,459, Examiner Interview Summary mailed Jan. 11, 2016", 1 pg.
"U.S. Appl. No. 13/288,459, Non Final Office Action mailed Jun. 24, 2015", 10 pgs.
"U.S. Appl. No. 13/288,459, Non Final Office Action mailed Nov. 4, 2014", 15 pgs.
"U.S. Appl. No. 13/288,459, Notice of Allowance mailed Jan. 11, 2016", 13 pgs.
"U.S. Appl. No. 13/288,459, Notice of Allowance mailed May 10, 2016", 7 pgs.
"U.S. Appl. No. 13/288,459, Response filed Mar. 3, 2015 to Non Final Office Action mailed Nov. 4, 2014", 16 pgs.
"U.S. Appl. No. 13/288,459, Response filed Oct. 13, 2014 to Restriction Requirement mailed Aug. 11, 2014", 15 pgs.
"U.S. Appl. No. 13/288,459, Response filed Oct. 23, 2015 to Non Final Office Action mailed Jun. 24, 2015", 14 pgs.
"U.S. Appl. No. 13/288,459, Restriction Requirement mailed Aug. 11, 2014", 9 pgs.
"U.S. Appl. No. 13/288,463, Examiner Interview Summary mailed Jun. 3, 2014", 3 pgs.
"U.S. Appl. No. 13/288,463, Non Final Office Action mailed Feb. 24, 2014", 13 pgs.
"U.S. Appl. No. 13/288,463, Notice of Allowance mailed Aug. 27, 2014", 9 pgs.
"U.S. Appl. No. 13/288,463, Response filed May 27, 2014 to Non Final Office Action mailed Feb. 24, 2014", 15 pgs.
"U.S. Appl. No. 13/288,463, Supplemental Notice of Allowability mailed Dec. 8, 2014", 5 pgs.
"U.S. Appl. No. 13/288,463, Supplemental Notice of Allowability mailed Dec. 19, 2014", 5 pgs.
"U.S. Appl. No. 13/293,825, Notice of Allowability mailed Jun. 22, 2015", 7 pgs.
"U.S. Appl. No. 13/293,825, Notice of Allowance mailed May 19, 2015", 9 pgs.
"U.S. Appl. No. 13/293,825, Response filed Apr. 15, 2015 to Restriction Requirement mailed Feb. 12, 2015", 17 pgs.
"U.S. Appl. No. 13/293,825, Restriction Requirement mailed Feb. 12, 2015", 9 pgs.
"U.S. Appl. No. 13/295,126, Non Final Office Action mailed May 19, 2015", 9 pgs.
"U.S. Appl. No. 13/295,126, Notice of Allowance mailed Oct. 22, 2015", 9 pgs.
"U.S. Appl. No. 13/295,126, Response filed Apr. 13, 2015 to Restriction Requirement mailed Feb. 12, 2015", 1 pgs.
"U.S. Appl. No. 13/295,126, Response filed Aug. 17, 2015 to Non Final Office Action mailed May 19, 2015", 21 pgs.
"U.S. Appl. No. 13/295,126, Restriction Requirement mailed Feb. 12, 2015", 9 pgs.
"U.S. Appl. No. 13/311,936, Examiner Interview Summary mailed Feb. 12, 2015", 2 pgs.
"U.S. Appl. No. 13/311,936, Non Final Office Action mailed Feb. 9, 2015", 13 pgs.
"U.S. Appl. No. 13/311,936, Non Final Office Action mailed Oct. 19, 2015", 8 pgs.
"U.S. Appl. No. 13/311,936, Notice of Allowance mailed Mar. 29, 2016", 8 pgs.
"U.S. Appl. No. 13/311,936, PTO Response to Rule 312 Communication mailed May 10, 2016", 2 pgs.
"U.S. Appl. No. 13/311,936, Response filed Jan. 18, 2016 to Non Final Office Action mailed Oct. 19, 2015", 8 pgs.
"U.S. Appl. No. 13/311,936, Response filed Jun. 9, 2015 to Non Final Office Action mailed Feb. 9, 2015", 12 pgs.
"U.S. Appl. No. 13/311,936, Response filed Oct. 3, 2014 to Restriction Requirement mailed Aug. 5, 2014", 10 pgs.
"U.S. Appl. No. 13/311,936, Restriction Requirement mailed Aug. 5, 2014", 7 pgs.
"U.S. Appl. No. 13/350,985, Final Office Action mailed Apr. 16, 2015", 8 pgs.
"U.S. Appl. No. 13/350,985, Non Final Office Action mailed Dec. 15, 2014", 8 pgs.
"U.S. Appl. No. 13/350,985, Notice of Allowance mailed Jul. 27, 2015", 5 pgs.
"U.S. Appl. No. 13/350,985, Response filed Mar. 13, 2015 to Non Final Office Action mailed Dec. 15, 2014", 10 pgs.
"U.S. Appl. No. 13/350,985, Response filed Jul. 9, 2015 to Final Office Action mailed Apr. 16, 2015", 8 pgs.
"U.S. Appl. No. 13/350,985, Response filed Dec. 2, 2014 to Restriction Requirement mailed Oct. 2, 2014", 9 pgs.
"U.S. Appl. No. 13/350,985, Restriction Requirement mailed Oct. 2, 2014", 6 pgs.
"U.S. Appl. No. 13/399,125, Corrected Notice of Allowance mailed Aug. 28, 2014", 2 pgs.
"U.S. Appl. No. 13/399,125, Examiner Interview Summary mailed May 17, 2013", 3 pgs.
"U.S. Appl. No. 13/399,125, Final Office Action mailed Mar. 20, 2013", 12 pgs.

(56) References Cited

OTHER PUBLICATIONS

"U.S. Appl. No. 13/399,125, Non Final Office Action mailed Oct. 24, 2012", 12 pgs.
"U.S. Appl. No. 13/399,125, Notice of Allowance mailed May 16, 2014", 8 pgs.
"U.S. Appl. No. 13/399,125, Response filed Jan. 10, 2013 to Non Final Office Action mailed Oct. 24, 2012", 15 pgs.
"U.S. Appl. No. 13/399,125, Response filed May 20, 2013 to Final Office Action mailed Mar. 20, 2013", 14 pgs.
"U.S. Appl. No. 13/412,105, Advisory Action mailed Feb. 24, 2014", 3 pgs.
"U.S. Appl. No. 13/412,105, Examiner Interview Summary mailed Feb. 6, 2014", 3 pgs.
"U.S. Appl. No. 13/412,105, Examiner Interview Summary mailed Oct. 11, 2013", 3 pgs.
"U.S. Appl. No. 13/412,105, Final Office Action mailed Dec. 13, 2013", 9 pgs.
"U.S. Appl. No. 13/412,105, Non Final Office Action mailed Jul. 15, 2013", 10 pgs.
"U.S. Appl. No. 13/412,105, Notice of Allowance mailed Aug. 18, 2014", 9 pgs.
"U.S. Appl. No. 13/412,105, Response filed Feb. 10, 2014 to Final Office Action mailed Dec. 13, 2013", 14 pgs.
"U.S. Appl. No. 13/412,105, Response filed Mar. 13, 2014 to Advisory Action mailed Feb. 24, 2014", 19 pgs.
"U.S. Appl. No. 13/412,105, Response filed May 6, 2013 to Restriction Requirement mailed Apr. 5, 2013", 9 pgs.
"U.S. Appl. No. 13/412,105, Response filed Oct. 14, 2013 to Non Final Office Action mailed Jul. 15, 2013", 13 pgs.
"U.S. Appl. No. 13/412,105, Restriction Requirement mailed Apr. 5, 2013", 9 pgs.
"U.S. Appl. No. 13/412,116, Corrected Notice of Allowance mailed Jun. 2, 2014", 2 pgs.
"U.S. Appl. No. 13/412,116, Examiner Interview Summary mailed Dec. 13, 2013", 3 pgs.
"U.S. Appl. No. 13/412,116, Non Final Office Action mailed Sep. 11, 2013", 9 pgs.
"U.S. Appl. No. 13/412,116, Notice of Allowance mailed Feb. 19, 2014", 9 pgs.
"U.S. Appl. No. 13/412,116, Response filed Jul. 3, 2013 to Restriction Requirement mailed Jun. 19, 2013", 1 pg.
"U.S. Appl. No. 13/412,116, Response filed Dec. 11, 2013 to Non Final Office Action mailed Sep. 11, 2013", 11 pgs.
"U.S. Appl. No. 13/412,116, Restriction Requirement mailed Jun. 19, 2013", 9 pgs.
"U.S. Appl. No. 13/412,127, Examiner Interview Summary mailed Nov. 5, 2013", 3 pgs.
"U.S. Appl. No. 13/412,127, Non Final Office Action mailed Aug. 7, 2013", 15 pgs.
"U.S. Appl. No. 13/412,127, Notice of Allowance mailed Dec. 24, 2013", 10 pgs.
"U.S. Appl. No. 13/412,127, Response filed May 23, 2013 to Restriction Requirement mailed Apr. 24, 2013", 2 pgs.
"U.S. Appl. No. 13/412,127, Response filed Nov. 5, 2013 to Non Final Office Action mailed Aug. 7, 2013", 16 pgs.
"U.S. Appl. No. 13/412,127, Restriction Requirement mailed Apr. 24, 2013", 10 pgs.
"U.S. Appl. No. 13/587,374, Final Office Action mailed Nov. 6, 2013", 9 pgs.
"U.S. Appl. No. 13/587,374, Non Final Office Action mailed Jul. 17, 2013", 8 pgs.
"U.S. Appl. No. 13/587,374, Notice of Allowance mailed Feb. 28, 2014", 5 pgs.
"U.S. Appl. No. 13/587,374, Preliminary Amendment filed Jun. 21, 2013", 9 pgs.
"U.S. Appl. No. 13/587,374, Response filed Jan. 24, 2014 to Final Office Action mailed Nov. 6, 2013", 15 pgs.
"U.S. Appl. No. 13/587,374, Response filed Oct. 14, 2013 to Non Final Office Action mailed Jul. 17, 2013", 14 pgs.
"U.S. Appl. No. 13/609,389, 312 Amendment filed Sep. 15, 2014", 4 pgs.
"U.S. Appl. No. 13/609,389, Examiner Interview Summary mailed Feb. 4, 2014", 4 pgs.
"U.S. Appl. No. 13/609,389, Final Office Action mailed May 5, 2014", 14 pgs.
"U.S. Appl. No. 13/609,389, Non Final Office Action mailed Nov. 27, 2013", 12 pgs.
"U.S. Appl. No. 13/609,389, Notice of Allowance mailed Jul. 23, 2014", 5 pgs.
"U.S. Appl. No. 13/609,389, PTO Response to Rule 312 Communication mailed Oct. 16, 2014", 2 pgs.
"U.S. Appl. No. 13/609,389, Response filed Feb. 27, 2014 to Non Final Office Action mailed Nov. 27, 2013", 18 pgs.
"U.S. Appl. No. 13/609,389, Response filed Jul. 10, 2014 to Final Office Action mailed May 5, 2014", 12 pgs.
"U.S. Appl. No. 13/625,413, Final Office Action mailed Oct. 30, 2015", 8 pgs.
"U.S. Appl. No. 13/625,413, Non Final Office Action mailed Jun. 8, 2015", 11 pgs.
"U.S. Appl. No. 13/625,413, Notice of Allowance mailed Apr. 1, 2016", 8 pgs.
"U.S. Appl. No. 13/625,413, Notice of Allowance mailed Dec. 11, 2015", 9 pgs.
"U.S. Appl. No. 13/625,413, Response filed May 11, 2015 to Restriction Requirement mailed Mar. 10, 2015", 1 pg.
"U.S. Appl. No. 13/625,413, Response filed Sep. 8, 2015 to Non Final Office Action mailed Jun. 8, 2015", 16 pgs.
"U.S. Appl. No. 13/625,413, Response filed Dec. 1, 2015 to Final Office Action mailed Oct. 30, 2015", 9 pgs.
"U.S. Appl. No. 13/625,413, Restriction Requirement mailed Mar. 10, 2015", 7 pgs.
"U.S. Appl. No. 13/645,964, Advisory Action mailed Feb. 4, 2016", 2 pgs.
"U.S. Appl. No. 13/645,964, Final Office Action mailed Oct. 6, 2015", 17 pgs.
"U.S. Appl. No. 13/645,964, Non Final Office Action mailed Mar. 15, 2016", 15 pgs.
"U.S. Appl. No. 13/645,964, Non Final Office Action mailed Mar. 17, 2015", 15 pgs.
"U.S. Appl. No. 13/645,964, Notice of Allowance mailed Jul. 21, 2016", 9 pgs.
"U.S. Appl. No. 13/645,964, Response filed Jun. 13, 2016 to Non Final Office Action mailed Mar. 15, 2016", 11 pgs.
"U.S. Appl. No. 13/645,964, Response filed Jul. 17, 2015 to Non Final Office Action mailed Mar. 17, 2015", 17 pgs.
"U.S. Appl. No. 13/645,964, Response filed Dec. 4, 2015 to Final Office Action mailed Oct. 6, 2015", 14 pgs.
"U.S. Appl. No. 13/656,821, Notice of Allowance mailed Jun. 18, 2015", 11 pgs.
"U.S. Appl. No. 13/656,821, Response filed May 11, 2015 to Restriction Requirement mailed Mar. 10, 2015", 1 pg.
"U.S. Appl. No. 13/656,821, Restriction Requirement mailed Mar. 10, 2015", 6 pgs.
"U.S. Appl. No. 13/720,631, Final Office Action mailed Jun. 25, 2014", 10 pgs.
"U.S. Appl. No. 13/720,631, Non Final Office Action mailed Mar. 6, 2014", 7 pgs.
"U.S. Appl. No. 13/720,631, Notice of Allowance mailed Jul. 25, 2014", 5 pgs.
"U.S. Appl. No. 13/720,631, Response filed Jun. 6, 2014 to Non Final Office Action mailed Mar. 6, 2014", 11 pgs.
"U.S. Appl. No. 13/720,631, Response filed Jul. 14, 2014 to Final Office Action mailed Jun. 25, 2014", 6 pgs.
"U.S. Appl. No. 13/720,631, Supplemental Notice of Allowance mailed Sep. 8, 2014", 2 pgs.
"U.S. Appl. No. 13/720,648, Final Office Action mailed Nov. 16, 2015", 7 pgs.
"U.S. Appl. No. 13/720,648, Non Final Office Action mailed Jun. 10, 2015", 11 pgs.
"U.S. Appl. No. 13/720,648, Notice of Allowance mailed Feb. 5, 2016", 11 pgs.

(56) References Cited

OTHER PUBLICATIONS

"U.S. Appl. No. 13/720,648, Response filed Jan. 13, 2016 to Final Office Action mailed Nov. 16, 2015", 9 pgs.
"U.S. Appl. No. 13/720,648, Response filed May 11, 2015 to Restriction Requirement mailed Mar. 10, 2015", 8 pgs.
"U.S. Appl. No. 13/720,648, Response filed Oct. 9, 2015 to Non Final Office Action mailed Jun. 10, 2015", 12 pgs.
"U.S. Appl. No. 13/720,648, Restriction Requirement mailed Mar. 10, 2015", 8 pgs.
"U.S. Appl. No. 13/721,970, Notice of Allowance mailed Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement mailed Apr. 11, 2013", 1 pgs.
"U.S. Appl. No. 13/721,970, Restriction Requirement mailed Apr. 11, 2013", 6 pgs.
"U.S. Appl. No. 13/751,846, Final Office Action mailed Nov. 17, 2015", 9 pgs.
"U.S. Appl. No. 13/751,846, Non Final Office Action mailed Jun. 15, 2015", 10 pgs.
"U.S. Appl. No. 13/751,846, Notice of Allowance mailed Mar. 16, 2016", 11 pgs.
"U.S. Appl. No. 13/751,846, Notice of Allowance mailed Jul. 6, 2016", 9 pgs.
"U.S. Appl. No. 13/751,846, Response filed Feb. 5, 2016 to Final Office Action mailed Nov. 17, 2015", 14 pgs.
"U.S. Appl. No. 13/751,846, Response filed May 11, 2015 to Restriction Requirement mailed Mar. 10, 2015", 15 pgs.
"U.S. Appl. No. 13/751,846, Response filed Oct. 9, 2015 to Non Final Office Action mailed Jun. 15, 2015", 20 pgs.
"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/791,014, Final Office Action mailed Jan. 8, 2016", 11 pgs.
"U.S. Appl. No. 13/791,014, Non Final Office Action mailed Aug. 14, 2015", 9 pgs.
"U.S. Appl. No. 13/791,014, Notice of Allowability mailed Jul. 27, 2017", 2 pgs.
"U.S. Appl. No. 13/791,014, Notice of Allowance mailed Jan. 10, 2017", 15 pgs.
"U.S. Appl. No. 13/791,014, Notice of Allowance mailed Apr. 27, 2017", 8 pgs.
"U.S. Appl. No. 13/791,014, Response filed Jun. 6, 2016 to Final Office Action mailed Jan. 8, 2016", 13 pgs.
"U.S. Appl. No. 13/791,014, Response filed Aug. 3, 2015 to Restriction Requirement mailed May 1, 2015", 9 pgs.
"U.S. Appl. No. 13/791,014, Response filed Nov. 10, 2015 to Non Final Office Action mailed Aug. 14, 2015", 13 pgs.
"U.S. Appl. No. 13/791,014, Restriction Requirement mailed May 1, 2015", 6 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed May 27, 2016", 9 pgs.
"U.S. Appl. No. 13/833,567, Non Final Office Action mailed Oct. 23, 2015", 10 pgs.
"U.S. Appl. No. 13/833,567, Notice of Allowance mailed Sep. 27, 2016", 9 pgs.
"U.S. Appl. No. 13/833,567, Response filed Jan. 22, 2016 to Non Final Office Action mailed Oct. 23, 2015", 11 pgs.
"U.S. Appl. No. 13/833,567, Response filed Apr. 20, 2016 to Final Office Action mailed Mar. 9, 2016", 10 pgs.
"U.S. Appl. No. 13/833,567, Response filed Jun. 25, 2015 to Restriction Requirement mailed Apr. 3, 2015", 10 pgs.
"U.S. Appl. No. 13/833,567, Response filed Aug. 4, 2016 to Non Final Office Action mailed May 27, 2016", 11 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Notice of Allowance mailed Aug. 3, 2016", 8 pgs.
"U.S. Appl. No. 13/838,755, Response filed Apr. 15, 2016 to Final Office Action mailed Feb. 2022, 16", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.

(56) References Cited

OTHER PUBLICATIONS

"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filedJul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Non Final Office Action mailed Sep. 15, 2014", 20 pgs.
"U.S. Appl. No. 13/959,145, Notice of Allowability mailed Jun. 14, 2016", 2 pgs.
"U.S. Appl. No. 13/959,145, Notice of Allowance mailed Apr. 13, 16", 5 pgs.
"U.S. Appl. No. 13/959,145, Response filed Mar. 28, 16 to Final Office Action mailed Jan. 29, 2016", 10 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 13/959,145, Response filed Dec. 15, 2014 to Non Final Office Action mailed Sep. 15, 2014", 21 pgs.
"U.S. Appl. No. 14/055,172, Final Office Action mailed Dec. 22, 2016", 8 pgs.
"U.S. Appl. No. 14/055,172, Non Final Office Action mailed Jul. 14, 2016", 12 pgs.
"U.S. Appl. No. 14/055,172, Notice of Allowance mailed Mar. 29, 2017", 10 pgs.
"U.S. Appl. No. 14/055,172, Response filed Feb. 22, 2017 to Final Office Action mailed Dec. 22, 2016", 11 pgs.
"U.S. Appl. No. 14/055,172, Response filed May 4, 2016 to Restriction Requirement mailed Mar. 4, 2016", 8 pgs.
"U.S. Appl. No. 14/055,172, Response filed Nov. 14, 2016 to Non Final Office Action mailed Jul. 14, 2016", 19 pgs.
"U.S. Appl. No. 14/055,172, Restriction Requirement mailed Mar. 4, 2016", 6 pgs.
"U.S. Appl. No. 14/055,191, Non Final Office Action mailed May 16, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Apr. 29, 2016 to Restriction Requirement mailed Mar. 7, 2016", 8 pgs.
"U.S. Appl. No. 14/055,191, Response filed Aug. 3, 2016 to Non Final Office Action mailed May 16, 2016", 11 pgs.
"U.S. Appl. No. 14/055,191, Restriction Requirement mailed Mar. 7, 2016", 6 pgs.
"U.S. Appl. No. 14/071,295, Non Final Office Action mailed Aug. 15, 2014", 6 pgs.
"U.S. Appl. No. 14/071,295, Notice of Allowance mailed Dec. 10, 2014", 8 pgs.
"U.S. Appl. No. 14/071,295, Response filed Nov. 17, 2014 to Non Final Office Action mailed Aug. 15, 2014", 14 pgs.
"U.S. Appl. No. 14/071,295, Supplemental Notice of Allowability mailed Jan. 26, 2015", 2 pgs.
"U.S. Appl. No. 14/094,311, Corrected Notice of Allowance mailed Mar. 28, 2017", 5 pgs.
"U.S. Appl. No. 14/094,311, Notice of Allowance mailed Aug. 16, 2016", 12 pgs.
"U.S. Appl. No. 14/094,311, Notice of Allowance mailed Dec. 27, 2016", 8 pgs.
"U.S. Appl. No. 14/094,311, Response filed Jul. 26, 2016 to Restriction Requirement mailed Jun. 22, 2016", 10 pgs.
"U.S. Appl. No. 14/094,311, Restriction Requirement mailed Jun. 22, 2016", 6 pgs.
"U.S. Appl. No. 14/095,614, Non Final Office Action mailed Jan. 19, 2017", 9 pgs.
"U.S. Appl. No. 14/095,614, Notice of Allowance mailed May 8, 2017", 8 pgs.
"U.S. Appl. No. 14/095,614, Notice of Allowance mailed Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action mailed Jan. 19, 2017", 14 pgs.
"U.S. Appl. No. 14/095,614, Response filed Sep. 12, 2016 to Restriction Requirement mailed Jul. 11, 2016", 11 pgs.
"U.S. Appl. No. 14/095,614, Restriction Requirement mailed Jul. 11, 2016", 8 pgs.
"U.S. Appl. No. 14/095,639, Non Final Office Action mailed Jan. 18, 2017", 10 pgs.
"U.S. Appl. No. 14/095,639, Notice of Allowance mailed Apr. 13, 2017", 9 pgs.
"U.S. Appl. No. 14/095,639, Notice of Allowance mailed Oct. 30, 2017", 9 pgs.
"U.S. Appl. No. 14/095,639, Response filed Mar. 2, 2017 to Non Final Office Action mailed Jan. 18, 2017", 9 pgs.
"U.S. Appl. No. 14/095,639, Response filed Sep. 12, 2016 to Restriction Requirement mailed Jul. 19, 2016", 7 pgs.
"U.S. Appl. No. 14/095,639, Restriction Requirement mailed Jul. 19, 2016", 8 pgs.
"U.S. Appl. No. 14/107,350, Notice of Allowance mailed Feb. 26, 2016", 11 pgs.
"U.S. Appl. No. 14/107,350, Notice of Allowance mailed Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary mailed Nov. 29, 2016", 1 pg.
"U.S. Appl. No. 14/159,094, Non Final Office Action mailed Jun. 29, 2016", 15 pgs.
"U.S. Appl. No. 14/159,094, Notice of Allowance mailed Nov. 29, 2016", Examiner Interview Summary from Nov. 29, 2016 included, 11 pgs.
"U.S. Appl. No. 14/159,094, Response filed Jun. 3, 2016 to Restriction Requirement mailed Apr. 20, 2016", 9 pgs.
"U.S. Appl. No. 14/159,094, Response filed Sep. 19, 2016 to Non Final Office Action mailed Jun. 29, 2016", 13 pgs.
"U.S. Appl. No. 14/159,094, Restriction Requirement mailed Apr. 20, 2016", 6 pgs.
"U.S. Appl. No. 14/182,038, Advisory Action mailed Mar. 1, 2017", 3 pgs.
"U.S. Appl. No. 14/182,038, Final Office Action mailed Dec. 19, 2016", 8 pgs.
"U.S. Appl. No. 14/182,038, Non Final Office Action mailed Jul. 19, 2016", 10 pgs.
"U.S. Appl. No. 14/182,038, Notice of Allowance mailed May 24, 2017", 9 pgs.
"U.S. Appl. No. 14/182,038, Response filed Feb. 20, 2017 to Final Office Action mailed Dec. 19, 2016", 11 pgs.
"U.S. Appl. No. 14/182,038, Response filed Jun. 27, 2016 to Restriction Requirement mailed Apr. 26, 2016", 8 pgs.
"U.S. Appl. No. 14/182,038, Response filed Oct. 19, 2016 to Non Final Office Action mailed Jul. 19, 2016", 15 pgs.
"U.S. Appl. No. 14/182,038, Restriction Requirement mailed Apr. 26, 2016", 7 pgs.

(56) References Cited

OTHER PUBLICATIONS

"U.S. Appl. No. 14/182,046, Corrected Notice of Allowance mailed Jan. 20, 2017", 6 pgs.
"U.S. Appl. No. 14/182,046, Non Final Office Action mailed Jul. 15, 2016", 9 pgs.
"U.S. Appl. No. 14/182,046, Notice of Allowance mailed Dec. 8, 2016", 7 pgs.
"U.S. Appl. No. 14/182,046, Response filed Jun. 27, 2016 to Restriction Requirement mailed Apr. 26, 2016", 7 pgs.
"U.S. Appl. No. 14/182,046, Response filed Oct. 17, 2016 to Non Final Office Action mailed Jul. 15, 2016", 11 pgs.
"U.S. Appl. No. 14/182,046, Restriction Requirement mailed Apr. 26, 2016", 6 pgs.
"U.S. Appl. No. 14/211,977, Notice of Allowance mailed Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement mailed Mar. 11, 2016", 8 pgs.
"U.S. Appl. No. 14/211,977, Restriction Requirement mailed Mar. 11, 2016", 6 pgs.
"U.S. Appl. No. 14/215,550, Corrected Notice of Allowance mailed Jul. 27, 2017", 2 pgs.
"U.S. Appl. No. 14/215,550, Examiner Interview Summary mailed Mar. 9, 2017", 3 pgs.
"U.S. Appl. No. 14/215,550, Final Office Action mailed Feb. 1, 2017", 11 pgs.
"U.S. Appl. No. 14/215,550, Non Final Office Action mailed Jul. 19, 2016", 12 pgs.
"U.S. Appl. No. 14/215,550, Notice of Allowance mailed Jun. 21, 2017", 8 pgs.
"U.S. Appl. No. 14/215,550, Response filed May 1, 2017 to Final Office Action mailed Feb. 1, 2017", 10 pgs.
"U.S. Appl. No. 14/215,550, Response filed Jun. 22, 2016 to Restriction Requirement mailed Apr. 28, 2016", 7 pgs.
"U.S. Appl. No. 14/215,550, Response filed Dec. 5, 2016 to Non Final Office Action mailed Jul. 19, 2016", 13 pgs.
"U.S. Appl. No. 14/215,550, Restriction Requirement mailed Apr. 28, 2016", 6 pgs.
"U.S. Appl. No. 14/275,548, Examiner Interview Summary mailed May 25, 2016", 3 pgs.
"U.S. Appl. No. 14/275,548, Non Final Office Action mailed Feb. 19, 2016", 14 pgs.
"U.S. Appl. No. 14/275,548, Notice of Allowance mailed Jul. 27, 2016", 7 pgs.
"U.S. Appl. No. 14/275,548, Response filed May 19, 2016 to Non Final Office Action mailed Feb. 19, 2016", 19 pgs.
"U.S. Appl. No. 14/324,688, Corrected Notice of Allowance mailed Sep. 22, 2016", 2 pgs.
"U.S. Appl. No. 14/324,688, Non Final Office Action mailed Jan. 8, 2016", 18 pgs.
"U.S. Appl. No. 14/324,688, Notice of Allowance mailed Jun. 9, 2016", 7 pgs.
"U.S. Appl. No. 14/324,688, Response filed Apr. 8, 2016 to Non Final Office Action mailed Jan. 8, 2016", 15 pgs.
"U.S. Appl. No. 14/456,286, Advisory Action mailed Jun. 21, 2016", 3 pgs.
"U.S. Appl. No. 14/456,286, Final Office Action mailed May 27, 2016", 15 pgs.
"U.S. Appl. No. 14/456,286, Non Final Office Action mailed Oct. 17, 2016", 17 pgs.
"U.S. Appl. No. 14/456,286, Non Final Office Action mailed Dec. 30, 2015", 16 pgs.
"U.S. Appl. No. 14/456,286, Notice of Allowance mailed Feb. 15, 2017", 9 pgs.
"U.S. Appl. No. 14/456,286, Response filed Mar. 30, 2016 to Non Final Office Action mailed Dec. 30, 2015", 15 pgs.
"U.S. Appl. No. 14/456,286, Response filed Jun. 13, 2016 to Final Office Action mailed May 27, 2016", 10 pgs.
"U.S. Appl. No. 14/456,286, Response filed Nov. 16, 2016 to Non Final Office Action mailed Oct. 17, 2016", 9 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/492,590, Notice of Allowance mailed Oct. 5, 2016", 10 pgs.
"U.S. Appl. No. 14/492,590, Response filed Sep. 15, 2016 to Restriction Requirement mailed Jul. 25, 2015", 7 pgs.
"U.S. Appl. No. 14/492,590, Restriction Requirement mailed Jul. 25, 2016", 6 pgs.
"U.S. Appl. No. 14/492,590, Supplemental Response filed Sep. 26, 2016 to Restriction Requirement mailed Jul. 25, 2016", 10 pgs.
"U.S. Appl. No. 14/514,453, Final Office Action mailed Mar. 17, 2016", 17 pgs.
"U.S. Appl. No. 14/514,453, Non Final Office Action mailed Sep. 24, 2015", 11 pgs.
"U.S. Appl. No. 14/514,453, Response filed Dec. 16, 2015 to Non Final Office Action mailed Sep. 24, 2015", 14 pgs.
"U.S. Appl. No. 14/532,333, Response filed Apr. 7, 2016 to Restriction Requirement mailed Feb. 8, 2016", 10 pgs.
"U.S. Appl. No. 14/532,333, Restriction Requirement mailed Feb. 8, 2016", 6 pgs.
"U.S. Appl. No. 14/589,101, Advisory Action mailed Feb. 21, 2017", 5 pgs.
"U.S. Appl. No. 14/589,101, Advisory Action mailed May 22, 2018", 3 pgs.
"U.S. Appl. No. 14/589,101, Examiner Interview Summary mailed Jan. 30, 2017", 3 pgs.
"U.S. Appl. No. 14/589,101, Final Office Action mailed Feb. 22, 2018", 15 pgs.
"U.S. Appl. No. 14/589,101, Final Office Action mailed Oct. 2, 2015", 10 pgs.
"U.S. Appl. No. 14/589,101, Final Office Action mailed Nov. 16, 2016", 12 pgs.
"U.S. Appl. No. 14/589,101, Non Final Office Action mailed Feb. 12, 2015", 10 pgs.
"U.S. Appl. No. 14/589,101, Non Final Office Action mailed May 5, 2016", 14 pgs.
"U.S. Appl. No. 14/589,101, Non Final Office Action mailed Sep. 14, 2017", 13 pgs.
"U.S. Appl. No. 14/589,101, Response filed Jan. 23, 2017 to Final Office Action mailed Nov. 16, 2016", 9 pgs.
"U.S. Appl. No. 14/589,101, Response filed Apr. 10, 2018 to Final Office Action mailed Feb. 22, 2018", 10 pgs.
"U.S. Appl. No. 14/589,101, Response filed Jun. 12, 2015 to Non Final Office Action mailed Feb. 12, 2015", 11 pgs.
"U.S. Appl. No. 14/589,101, Response filed Nov. 13, 2017 to Non Final Office Action mailed Sep. 14, 2017", 10 pgs.
"U.S. Appl. No. 14/589,101, Response filed Dec. 29, 2015 to Final Office Action mailed Oct. 2, 2015", 15 pgs.
"U.S. Appl. No. 14/589,191, Response filed Aug. 5, 2016 to Non Final Office Action mailed May 5, 2016", 16 pgs.
"U.S. Appl. No. 14/594,285, Final Office Action mailed May 22, 2017", 12 pgs.
"U.S. Appl. No. 14/594,285, Non Final Office Action mailed Jan. 11, 2017", 15 pgs.
"U.S. Appl. No. 14/594,285, Notice of Allowance mailed Jun. 27, 2017", 10 pgs.
"U.S. Appl. No. 14/594,285, Response filed Apr. 11, 2017 to Non Final Office Action mailed Jan. 11, 2017", 12 pgs.
"U.S. Appl. No. 14/594,285, Response filed Jun. 14, 2017 to Final Office Action mailed May 22, 2017", 9 pgs.
"U.S. Appl. No. 14/594,285, Response filed Dec. 14, 2016 to Restriction Requirement mailed Nov. 7, 2016", 8 pgs.
"U.S. Appl. No. 14/594,285, Restriction Requirement mailed Nov. 7, 2016", 6 pgs.
"U.S. Appl. No. 14/599,909, Non Final Office Action mailed Jul. 27, 2017", 18 pgs.
"U.S. Appl. No. 14/599,909, Notice of Allowance mailed Feb. 13, 2018", 9 pgs.

(56) References Cited

OTHER PUBLICATIONS

"U.S. Appl. No. 14/599,909, Response filed Sep. 21, 2017 to Non Final Office Action mailed Jul. 27, 2017", 10 pgs.
"U.S. Appl. No. 14/635,055, Non Final Office Action mailed Aug. 28, 2017", 8 pgs.
"U.S. Appl. No. 14/635,055, Notice of Allowance mailed Feb. 28, 2018", 11 pgs.
"U.S. Appl. No. 14/635,055, Response filed Jun. 27, 2017 to Restriction Requirement mailed Apr. 27, 2017", 11 pgs.
"U.S. Appl. No. 14/635,055, Response filed Nov. 28, 2017 to Non Final Office Action mailed Aug. 28, 2017", 13 pgs.
"U.S. Appl. No. 14/635,055, Restriction Requirement mailed Apr. 27, 2017", 7 pgs.
"U.S. Appl. No. 14/697,140, Advisory Action mailed Aug. 11, 2017", 3 pgs.
"U.S. Appl. No. 14/697,140, Final Office Action mailed Jun. 30, 2017", 13 pgs.
"U.S. Appl. No. 14/697,140, Final Office Action mailed Sep. 23, 2016", 10 pgs.
"U.S. Appl. No. 14/697,140, Non Final Office Action mailed Jan. 10, 2017", 12 pgs.
"U.S. Appl. No. 14/697,140, Non Final Office Action mailed Apr. 8, 2016", 8 pgs.
"U.S. Appl. No. 14/697,140, Notice of Allowance mailed Sep. 5, 2017", 7 pgs.
"U.S. Appl. No. 14/697,140, Response filed Mar. 1, 2017 to Non Final Office Action mailed Jan. 10, 2017", 11 pgs.
"U.S. Appl. No. 14/697,140, Response filed Jun. 13, 2016 to Non Final Office Action mailed Apr. 8, 2016", 10 pgs.
"U.S. Appl. No. 14/697,140, Response filed Jul. 27, 2017 to Final Office Action mailed Jun. 30, 2017", 10 pgs.
"U.S. Appl. No. 14/697,140, Response filed Nov. 16, 2016 to Final Office Action mailed Sep. 23, 2016", 13 pgs.
"U.S. Appl. No. 14/794,309, Final Office Action mailed Mar. 20, 2017", 18 pgs.
"U.S. Appl. No. 14/794,309, Non Final Office Action mailed Jun. 20, 2017", 16 pgs.
"U.S. Appl. No. 14/794,309, Non Final Office Action mailed Nov. 22, 2016", 13 pgs.
"U.S. Appl. No. 14/794,309, Notice of Allowance mailed Sep. 18, 2017", 5 pgs.
"U.S. Appl. No. 14/794,309, Preliminary Amendment filed Sep. 22, 2015", 6 pgs.
"U.S. Appl. No. 14/794,309, Response filed Feb. 22, 2017 to Non Final Office Action mailed Nov. 22, 2016", 12 pgs.
"U.S. Appl. No. 14/794,309, Response filed May 22, 2017 to Final Office Action mailed Mar. 20, 2017", 13 pgs.
"U.S. Appl. No. 14/794,309, Response filed Aug. 17, 2017 to Non Final Office Action mailed Jun. 20, 2017", 12 pgs.
"U.S. Appl. No. 14/794,309, Supplemental Preliminary Amendment filed Mar. 3, 1016", 8 pgs.
"U.S. Appl. No. 14/854,308, Notice of Allowance mailed Mar. 16, 2018", 11 pgs.
"U.S. Appl. No. 14/854,308, Response filed Dec. 20, 2017 to Restriction Requirement mailed Oct. 20, 2017", 8 pgs.
"U.S. Appl. No. 14/854,308, Restriction Requirement mailed Oct. 20, 2017", 8 pgs.
"U.S. Appl. No. 14/854,308, Supplemental Preliminary Amendment Filed Aug. 31, 2017", 3 pgs.
"U.S. Appl. No. 14/876,167, Final Office Action mailed Jul. 31, 2018", 8 pgs.
"U.S. Appl. No. 14/876,167, Non Final Office Action mailed Mar. 13, 2018", 8 pgs.
"U.S. Appl. No. 14/876,167, Notice of Allowance mailed Dec. 10, 2018", 8 pgs.
"U.S. Appl. No. 14/876,167, Preliminary Amendment filed Oct. 27, 2015", 8 pgs.
"U.S. Appl. No. 14/876,167, Response filed Jan. 9, 2018 to Restriction Requirement mailed Nov. 22, 2017", 6 pgs.
"U.S. Appl. No. 14/876,167, Response filed Jun. 6, 2018 to Non Final Office Action mailed Mar. 13, 2018", 9 pgs.
"U.S. Appl. No. 14/876,167, Response filed Sep. 28, 2018 to Final Office Action mailed Jul. 31, 2018", 10 pgs.
"U.S. Appl. No. 14/876,167, Restriction Requirement mailed Nov. 22, 2017", 9 pgs.
"U.S. Appl. No. 14/936,831, Advisory Action mailed Jan. 29, 2019", 3 pgs.
"U.S. Appl. No. 14/936,831, Final Office Action mailed Nov. 20, 2018", 8 pgs.
"U.S. Appl. No. 14/936,831, Non Final Office Action mailed May 16, 2018", 11 pgs.
"U.S. Appl. No. 14/936,831, Notice of Allowance mailed Jul. 3, 2019", 8 pgs.
"U.S. Appl. No. 14/936,831, Notice of Non-Compliant Amendment mailed Mar. 14, 2018", 2 pgs.
"U.S. Appl. No. 14/936,831, Preliminary Amendment filed Nov. 11, 2015", 6 pgs.
"U.S. Appl. No. 14/936,831, Response filed Jan. 10, 2018 to Restriction Requirement mailed Nov. 22, 2017", 6 pgs.
"U.S. Appl. No. 14/936,831, Response filed Jan. 21, 2019 to Final Office Action mailed Nov. 20, 2018", 9 pgs.
"U.S. Appl. No. 14/936,831, Response filed Mar. 26, 2018 to Notice of Non-Compliant Amendment mailed Mar. 14, 2018", 6 pgs.
"U.S. Appl. No. 14/936,831, Response filed Aug. 16, 2018 to Non Final Office Action mailed May 16, 2018", 9 pgs.
"U.S. Appl. No. 14/936,831, Restriction Requirement mailed Nov. 22, 2017", 8 pgs.
"U.S. Appl. No. 14/956,724, Examiner Interview Summary mailed Jun. 20, 2017", 3 pgs.
"U.S. Appl. No. 14/956,724, Non Final Office Action mailed Mar. 31, 2017", 17 pgs.
"U.S. Appl. No. 14/956,724, Notice of Allowance mailed Aug. 23, 2017", 9 pgs.
"U.S. Appl. No. 14/956,724, Preliminary Amendment filed Dec. 7, 2015", 8 pgs.
"U.S. Appl. No. 14/956,724, Response filed Jun. 16, 2017 to Non Final Office Action mailed Mar. 31, 2017", 12 pgs.
"U.S. Appl. No. 14/956,724, Supplemental Preliminary Amendment filed Feb. 11, 2016", 7 pgs.
"U.S. Appl. No. 14/956,724, Supplemental Preliminary Amendment filed Oct. 3, 2016", 8 pgs.
"U.S. Appl. No. 14/983,108, Final Office Action mailed Aug. 30, 2018", 9 pgs.
"U.S. Appl. No. 14/983,108, Non Final Office Action mailed Apr. 10, 2018", 7 pgs.
"U.S. Appl. No. 14/983,108, Non Final Office Action mailed Nov. 5, 2018", 8 pgs.
"U.S. Appl. No. 14/983,108, Notice of Allowance mailed Mar. 8, 2019", 8 pgs.
"U.S. Appl. No. 14/983,108, Preliminary Amendment filed Dec. 30, 2015", 7 pgs.
"U.S. Appl. No. 14/983,108, Response filed Jan. 24, 2018 to Restriction Requirement mailed Dec. 4, 2017", 6 pgs.
"U.S. Appl. No. 14/983,108, Response filed Feb. 4, 2019 to Non Final Office Action mailed Nov. 5, 2018", 8 pgs.
"U.S. Appl. No. 14/983,108, Response filed Jun. 13, 2018 to Non Final Office Action mailed Apr. 10, 2018", 10 pgs.
"U.S. Appl. No. 14/983,108, Response filed Oct. 22, 2018 to Final Office Action mailed Aug. 30, 2018", 9 pgs.
"U.S. Appl. No. 14/983,108, Restriction Requirement mailed Dec. 4, 2017", 7 pgs.
"U.S. Appl. No. 14/983,747, Non Final Office Action mailed Apr. 9, 2018", 13 pgs.
"U.S. Appl. No. 14/983,747, Notice of Allowance mailed Sep. 24, 2018", 14 pgs.
"U.S. Appl. No. 14/983,747, Preliminary Amendment filed Jan. 4, 2016", 5 pgs.
"U.S. Appl. No. 14/983,747, Response filed Jan. 24, 2018 to Restriction Requirement mailed Dec. 20, 2017", 5 pgs.
"U.S. Appl. No. 14/983,747, Response filed Jun. 13, 2018 to Non Final Office Action mailed Apr. 9, 2018", 9 pgs.

(56) References Cited

OTHER PUBLICATIONS

"U.S. Appl. No. 14/983,747, Restriction Requirement mailed Dec. 20, 2017", 7 pgs.
"U.S. Appl. No. 14/983,747, Supplemental Response to Restriction Requirement filed Jan. 24, 2018", 5 pgs.
"U.S. Appl. No. 15/060,007, Corrected Notice of Allowability mailed May 1, 2019", 2 pgs.
"U.S. Appl. No. 15/060,007, Final Office Action mailed Jan. 3, 2019", 9 pgs.
"U.S. Appl. No. 15/060,007, Non Final Office Action mailed Nov. 9, 2018", 17 pgs.
"U.S. Appl. No. 15/060,007, Notice of Allowance mailed Mar. 6, 2019", 5 pgs.
"U.S. Appl. No. 15/060,007, Preliminary Amendment filed Mar. 9, 2016", 9 pgs.
"U.S. Appl. No. 15/060,007, Response filed Feb. 15, 2019 to Final Office Action mailed Jan. 3, 2019", 9 pgs.
"U.S. Appl. No. 15/060,007, Response filed Nov. 26, 2018 to Non Final Office Action mailed Nov. 9, 2018", 10 pgs.
"U.S. Appl. No. 15/061,352, Corrected Notice of Allowance mailed Feb. 12, 2018", 2 pgs.
"U.S. Appl. No. 15/061,352, Non Final Office Action mailed Nov. 17, 2017", 6 pgs.
"U.S. Appl. No. 15/061,352, Notice of Allowance mailed Jan. 19, 2018", 10 pgs.
"U.S. Appl. No. 15/061,352, Preliminary Amendment filed Mar. 7, 2016", 8 pgs.
"U.S. Appl. No. 15/061,352, Response filed Dec. 12, 2017 to Non Final Office Action mailed Nov. 17, 2017", 9 pgs.
"U.S. Appl. No. 15/074,553, Corrected Notice of Allowance mailed Feb. 12, 2018", 2 pgs.
"U.S. Appl. No. 15/074,553, Non Final Office Action mailed Nov. 17, 2017", 6 pgs.
"U.S. Appl. No. 15/074,553, Notice of Allowance mailed Jan. 19, 2018", 10 pgs.
"U.S. Appl. No. 15/074,553, Preliminary Amendment filed Mar. 21, 2016", 8 pgs.
"U.S. Appl. No. 15/074,553, Response filed Dec. 12, 2017 to Non Final Office Action mailed Nov. 17, 2017", 8 pgs.
"U.S. Appl. No. 15/131,663, Non Final Office Action mailed Oct. 2, 2018", 7 pgs.
"U.S. Appl. No. 15/131,663, Notice of Allowance mailed Mar. 19, 2019", 8 pgs.
"U.S. Appl. No. 15/131,663, Preliminary Amendment filed Dec. 21, 2016", 6 pgs.
"U.S. Appl. No. 15/131,663, Response Filed Jan. 2, 2019 to Non-Final Office Action Mailed Oct. 2, 2018", 9 pgs.
"U.S. Appl. No. 15/131,663, Response filed Jul. 13, 2018 to Restriction Requirement mailed May 18, 2018", 8 pgs.
"U.S. Appl. No. 15/131,663, Restriction Requirement mailed May 18, 2018", 7 pgs.
"U.S. Appl. No. 15/166,480, Notice of Allowance mailed Sep. 20, 2018", 12 pgs.
"U.S. Appl. No. 15/166,480, Response filed Jul. 18, 2018 to Restriction Requirement mailed May 21, 2018", 6 pgs.
"U.S. Appl. No. 15/166,480, Restriction Requirement mailed May 21, 2018", 6 pgs.
"U.S. Appl. No. 15/166,480, Supplemental Preliminary Amendment filed Jul. 18, 2017", 7 pgs.
"U.S. Appl. No. 15/200,546, Non Final Office Action mailed Oct. 15, 2018", 10 pgs.
"U.S. Appl. No. 15/200,546, Notice of Allowance mailed Mar. 19, 2019", 7 pgs.
"U.S. Appl. No. 15/200,546, Preliminary Amendment filed Dec. 21, 2016", 6 pgs.
"U.S. Appl. No. 15/200,546, Response Filed Jan. 15, 2019 to Non-Final Office Action Mailed Oct. 15, 2018", 10 pgs.
"U.S. Appl. No. 15/200,546, Response Filed Sep. 17, 2018 to Restriction Requirement Mailed Jul. 16, 2018", 8 pgs.
"U.S. Appl. No. 15/200,546, Restriction Requirement mailed Jul. 16, 2018", 6 pgs.
"U.S. Appl. No. 15/278,777, Non Final Office Action mailed Feb. 28, 2018", 14 pgs.
"U.S. Appl. No. 15/278,777, Notice of Allowance mailed Jul. 16, 2018", 8 pgs.
"U.S. Appl. No. 15/278,777, Preliminary Amendment filed Oct. 3, 2016", 7 pgs.
"U.S. Appl. No. 15/278,777, Response filed May 29, 2018 to Non Final Office action mailed Feb. 28, 2018", 11 pgs.
"U.S. Appl. No. 15/288,183, Corrected Notice of Allowability mailed Jun. 21, 2019", 7 pgs.
"U.S. Appl. No. 15/288,183, Non Final Office Action mailed Dec. 10, 2018", 13 pgs.
"U.S. Appl. No. 15/288,183, Notice of Allowance mailed May 9, 2019", 11 pgs.
"U.S. Appl. No. 15/288,183, Preliminary Amendment filed Oct. 31, 2016", 7 pgs.
"U.S. Appl. No. 15/288,183, Response filed Feb. 27, 2019 to Non Final Office Action mailed Dec. 10, 2018", 11 pgs.
"U.S. Appl. No. 15/288,183, Response filed Oct. 25, 2018 to Restriction Requirement mailed Sep. 12, 2018", 7 pgs.
"U.S. Appl. No. 15/288,183, Restriction Requirement mailed Sep. 12, 2018", 6 pgs.
"U.S. Appl. No. 15/288,183, Supplemental Preliminary Amendment filed Jul. 27, 2017", 7 pgs.
"U.S. Appl. No. 15/294,994, Examiner Interview Summary mailed Feb. 26, 2019", 3 pgs.
"U.S. Appl. No. 15/294,994, Final Office Action mailed Jan. 25, 2019", 13 pgs.
"U.S. Appl. No. 15/294,994, Non Final Office Action mailed Aug. 9, 2018", 9 pgs.
"U.S. Appl. No. 15/294,994, Notice of Allowance mailed May 22, 2019", 10 pgs.
"U.S. Appl. No. 15/294,994, Preliminary Amendment filed Jan. 25, 2017", 8 pgs.
"U.S. Appl. No. 15/294,994, Response filed Feb. 27, 2019 to Final Office Action mailed Jan. 25, 2019", 9 pgs.
"U.S. Appl. No. 15/294,994, Response filed Oct. 25, 2018 to Non Final Office Action mailed Aug. 9, 2018", 10 pgs.
"U.S. Appl. No. 15/294,994, Supplemental Preliminary Amendment filed May 31, 2017", 6 pgs.
"U.S. Appl. No. 15/297,844, Notice of Allowance mailed Aug. 30, 2018", 10 pgs.
"U.S. Appl. No. 15/297,844, Preliminary Amendment filed Oct. 20, 2016", 7 pgs.
"U.S. Appl. No. 15/297,844, Supplemental Preliminary Amendment filed Jan. 25, 2018", 6 pgs.
"U.S. Appl. No. 15/332,590, Notice of Allowance mailed Dec. 5, 2018", 13 pgs.
"U.S. Appl. No. 15/332,590, Preliminary Amendment filed Nov. 22, 2016", 5 pgs.
"U.S. Appl. No. 15/361,917, Advisory Action mailed Nov. 19, 2019", 3 pgs.
"U.S. Appl. No. 15/361,917, Final Office Action mailed Sep. 3, 2019", 8 pgs.
"U.S. Appl. No. 15/361,917, Non Final Office Action mailed Apr. 19, 2019", 11 pgs.
"U.S. Appl. No. 15/361,917, Notice of Allowance mailed Mar. 4, 2020", 8 pgs.
"U.S. Appl. No. 15/361,917, Preliminary Amendment filed Nov. 30, 2016", 6 pgs.
"U.S. Appl. No. 15/361,917, Response filed Feb. 14, 2019 to Restriction Requirement mailed Jan. 3, 2019", 6 pgs.
"U.S. Appl. No. 15/361,917, Response filed Jun. 19, 2019 to Non Final Office Action mailed Apr. 19, 2019", 9 pgs.
"U.S. Appl. No. 15/361,917, Response filed Nov. 4, 2019 to Final Office Action mailed Sep. 3, 2019", 8 pgs.
"U.S. Appl. No. 15/361,917, Restriction Requirement mailed Jan. 3, 2019", 6 pgs.
"U.S. Appl. No. 15/401,768, Non Final Office Action mailed Jul. 22, 2019", 10 pgs.

(56) References Cited

OTHER PUBLICATIONS

"U.S. Appl. No. 15/401,768, Notice of Allowance mailed Nov. 20, 2019", 9 pgs.
"U.S. Appl. No. 15/401,768, Preliminary Amendment filed Mar. 23, 2017", 6 pgs.
"U.S. Appl. No. 15/401,768, Response filed May 15, 2019 to Restriction Requirement mailed Mar. 15, 2019", 7 pgs.
"U.S. Appl. No. 15/401,768, Response filed Aug. 28, 2019 to Non Final Office Action mailed Jul. 22, 2019", 10 pgs.
"U.S. Appl. No. 15/401,768, Restriction Requirement mailed Mar. 15, 2019", 6 pgs.
"U.S. Appl. No. 15/401,768, Supplemental Preliminary Amendment filed Jun. 22, 2017", 7 pgs.
"U.S. Appl. No. 15/412,676, Non Final Office Action mailed Jul. 23, 2019", 11 pgs.
"U.S. Appl. No. 15/412,676, Notice of Allowance mailed Dec. 30, 2019", 8 pgs.
"U.S. Appl. No. 15/412,676, Preliminary Amendment filed Jul. 3, 2017", 7 pgs.
"U.S. Appl. No. 15/412,676, Response filed May 15, 2019 to Restriction Requirement mailed Mar. 15, 2019", 7 pgs.
"U.S. Appl. No. 15/412,676, Response filed Oct. 23, 2019 to Non Final Office Action mailed Jul. 23, 2019", 12 pgs.
"U.S. Appl. No. 15/412,676, Restriction Requirement mailed Mar. 15, 2019", 6 pgs.
"U.S. Appl. No. 15/455,895, Examiner Interview Summary mailed Nov. 25, 2019", 3 pgs.
"U.S. Appl. No. 15/455,895, Non Final Office Action mailed Sep. 5, 2019", 11 pgs.
"U.S. Appl. No. 15/455,895, Notice of Allowance mailed Feb. 13, 2020", 7 pgs.
"U.S. Appl. No. 15/455,895, Preliminary Amendment filed Mar. 13, 2017", 6 pgs.
"U.S. Appl. No. 15/455,895, Response filed Jan. 28, 2020 to Non Final Office Action mailed Sep. 5, 2019", 14 pgs.
"U.S. Appl. No. 15/455,895, Supplemental Preliminary Amendment filed May 24, 2019", 6 pgs.
"U.S. Appl. No. 15/461,675, Non Final Office Action mailed Aug. 9, 2019", 10 pgs.
"U.S. Appl. No. 15/461,675, Notice of Allowance mailed Jan. 30, 2020", 7 pgs.
"U.S. Appl. No. 15/461,675, Preliminary Amendment filed Jun. 24, 2017", 6 pgs.
"U.S. Appl. No. 15/461,675, Response filed May 24, 2019 to Restriction Requirement mailed Mar. 26, 2019", 6 pgs.
"U.S. Appl. No. 15/461,675, Response filed Nov. 12, 2019 to Non Final Office Action mailed Aug. 9, 2019", 11 pgs.
"U.S. Appl. No. 15/461,675, Restriction Requirement mailed Mar. 26, 2019", 6 pgs.
"U.S. Appl. No. 15/461,675, Supplemental Preliminary Amendment filed Jun. 28, 2018", 7 pgs.
"U.S. Appl. No. 15/622,718, Examiner Interview Summary mailed Nov. 22, 2019", 3 pgs.
"U.S. Appl. No. 15/622,718, Non Final Office Action mailed Aug. 28, 2019", 14 pgs.
"U.S. Appl. No. 15/622,718, Notice of Allowance mailed Feb. 13, 2020", 8 pgs.
"U.S. Appl. No. 15/622,718, Preliminary Amendment filed Jun. 15, 2017", 7 pgs.
"U.S. Appl. No. 15/622,718, Response filed Jan. 28, 2020 to Non Final Office Action mailed Aug. 28, 2019", 11 pgs.
"U.S. Appl. No. 15/622,718, Response filed Jul. 31, 2019 to Restriction Requirement mailed Jun. 7, 2019", 8 pgs.
"U.S. Appl. No. 15/622,718, Restriction Requirement mailed Jun. 7, 2019", 6 pgs.
"U.S. Appl. No. 15/626,384, Non Final Office Action mailed May 3, 2019", 14 pgs.
"U.S. Appl. No. 15/626,384, Notice of Allowability mailed Oct. 18, 2019", 2 pgs.
"U.S. Appl. No. 15/626,384, Notice of Allowance mailed Aug. 21, 2019", 7 pgs.
"U.S. Appl. No. 15/626,384, Preliminary Amendment filed Aug. 10, 2018", 11 pgs.
"U.S. Appl. No. 15/626,384, Response filed Jul. 31, 2019 to Non-Final Office Action mailed May 3, 2019", 13 pgs.
"U.S. Appl. No. 15/654,386, Non Final Office Action mailed Nov. 7, 2019", 10 pgs.
"U.S. Appl. No. 15/654,386, Notice of Allowance mailed Feb. 20, 2020", 8 pgs.
"U.S. Appl. No. 15/654,386, Preliminary Amendment filed Aug. 30, 2017", 11 pgs.
"U.S. Appl. No. 15/654,386, Response filed Feb. 5, 2020 to Non Final Office Action mailed Nov. 7, 2019", 12 pgs.
"U.S. Appl. No. 15/654,386, Response filed Aug. 23, 2019 to Restriction Requirement mailed Jul. 16, 2019", 9 pgs.
"U.S. Appl. No. 15/654,386, Restriction Requirement mailed Jul. 16, 2019", 6 pgs.
"U.S. Appl. No. 15/659,689, Non Final Office Action mailed Oct. 31, 2018", 13 pgs.
"U.S. Appl. No. 15/659,689, Preliminary Amendment filed Jul. 26, 2017", 7 pgs.
"U.S. Appl. No. 15/662,572, Non Final Office Action mailed Oct. 10, 2019", 14 pgs.
"U.S. Appl. No. 15/662,572, Notice of Allowance mailed Mar. 11, 2020", 9 pgs.
"U.S. Appl. No. 15/662,572, Preliminary Amendment filed Jul. 31, 2017", 7 pgs.
"U.S. Appl. No. 15/662,572, Response filed Jan. 8, 2020 to Non Final Office Action mailed Oct. 10, 2019", 10 pgs.
"U.S. Appl. No. 15/662,572, Response filed Aug. 23, 2019 to Restriction Requirement mailed Jul. 1, 2019", 8 pgs.
"U.S. Appl. No. 15/662,572, Restriction Requirement mailed Jul. 1, 2019", 6 pgs.
"U.S. Appl. No. 15/664,572, Non Final Office Action mailed May 15, 2019", 8 pgs.
"U.S. Appl. No. 15/664,572, Notice of Allowance mailed Jun. 12, 2019", 8 pgs.
"U.S. Appl. No. 15/664,572, Preliminary Amendment filed Aug. 3, 2017", 7 pgs.
"U.S. Appl. No. 15/664,572, Response filed May 17, 2019 to Non Final Office Action mailed May 15, 2019", 9 pgs.
"U.S. Appl. No. 15/682,187, Non Final Office Action mailed Dec. 16, 2019", 10 pgs.
"U.S. Appl. No. 15/682,187, Notice of Allowance mailed Mar. 25, 2020", 9 pgs.
"U.S. Appl. No. 15/682,187, Preliminary Amendment filed Sep. 7, 2017", 6 pgs.
"U.S. Appl. No. 15/682, Response filed Feb. 27, 2020 to Non Final Office Action mailed Dec. 16, 2019", 11 pgs.
"U.S. Appl. No. 15/682,187, Response filed Sep. 18, 2019 to Restriction Requirement mailed Aug. 9, 2019", 7 pgs.
"U.S. Appl. No. 15/682,187, Restriction Requirement mailed Aug. 9, 2019", 6 pgs.
"U.S. Appl. No. 15/703,727, Non Final Office Action mailed Aug. 1, 2019", 11 pgs.
"U.S. Appl. No. 15/703,727, Notice of Allowance mailed Nov. 20, 2019", 7 pgs.
"U.S. Appl. No. 15/703,727, Preliminary Amendment filed Sep. 14, 2017", 7 pgs.
"U.S. Appl. No. 15/703,727, Response filed Nov. 1, 2019 to Non Final Office Action mailed Aug. 1, 2019", 10 pgs.
"U.S. Appl. No. 15/715,731, Non Final Office Action mailed Jan. 21, 2020", 8 pgs.
"U.S. Appl. No. 15/715,731, Notice of Allowance mailed Apr. 8, 2020", 9 pgs.
"U.S. Appl. No. 15/715,731, Preliminary Amendment Filed Sep. 26, 2017", 9 pgs.
"U.S. Appl. No. 15/715,731, Response filed Feb. 27, 2020 to Non Final Office Action mailed Jan. 21, 2020", 12 pgs.
"U.S. Appl. No. 15/715,731, Response Filed Nov. 4, 2019 to Restriction Requirement Mailed Sep. 4, 2019", 9 pgs.

(56) References Cited

OTHER PUBLICATIONS

"U.S. Appl. No. 15/715,731, Restriction Requirement mailed Sep. 4, 2019", 6 pgs.
"U.S. Appl. No. 15/715,731, Supplemental Preliminary Amendment filed Dec. 29, 2017", 8 pgs.
"U.S. Appl. No. 15/720,997, Advisory Action mailed Jun. 15, 2021", 3 pgs.
"U.S. Appl. No. 15/720,997, Advisory Action mailed Oct. 13, 2020", 2 pgs.
"U.S. Appl. No. 15/720,997, Final Office Action mailed Apr. 7, 2021", 9 pgs.
"U.S. Appl. No. 15/720,997, Final Office Action mailed Aug. 4, 2020", 10 pgs.
"U.S. Appl. No. 15/720,997, Non Final Office Action mailed Jan. 6, 2020", 10 pgs.
"U.S. Appl. No. 15/720,997, Non Final Office Action mailed Jul. 16, 2019", 11 pgs.
"U.S. Appl. No. 15/720,997, Non Final Office Action mailed Nov. 23, 2020", 7 pgs.
"U.S. Appl. No. 15/720,997, Notice of Allowance mailed Jul. 29, 2021", 7 pgs.
"U.S. Appl. No. 15/720,997, Preliminary Amendment filed Oct. 2, 2017", 6 pgs.
"U.S. Appl. No. 15/720,997, Response filed Jan. 25, 2021 to Non Final Office Action mailed Nov. 23, 2020", 9 pgs.
"U.S. Appl. No. 15/720,997, Response filed Mar. 27, 2020 to Non Final Office Action mailed Jan. 6, 2020", 10 pgs.
"U.S. Appl. No. 15/720,997, Response filed Jun. 2, 2021 to Final Office Action mailed Apr. 7, 2021", 9 pgs.
"U.S. Appl. No. 15/720,997, Response filed Jul. 7, 2021 to Advisory Action mailed Jun. 15, 2021", 6 pgs.
"U.S. Appl. No. 15/720,997, Response filed Sep. 30, 2020 to Final Office Action mailed Aug. 4, 2020", 11 pgs.
"U.S. Appl. No. 15/720,997, Response filed Oct. 3, 2019 to Non-Final Office Action mailed Jul. 16, 2019", 9 pgs.
"U.S. Appl. No. 15/722,002, Non Final Office Action mailed Feb. 4, 2020", 8 pgs.
"U.S. Appl. No. 15/722,002, Notice of Allowance mailed Apr. 8, 2020", 7 pgs.
"U.S. Appl. No. 15/722,002, Preliminary Amendment filed Jun. 29, 2018", 5 pgs.
"U.S. Appl. No. 15/722,002, Response filed Mar. 5, 2020 to Non Final Office Action mailed Feb. 4, 2020", 7 pgs.
"U.S. Appl. No. 15/722,002, Response filed Nov. 14, 2019 to Restriction Requirement mailed Sep. 17, 2019", 6 pgs.
"U.S. Appl. No. 15/722,002, Restriction Requirement mailed Sep. 17, 2019", 6 pgs.
"U.S. Appl. No. 15/793,216, Examiner Interview Summary mailed Nov. 4, 2019", 4 pgs.
"U.S. Appl. No. 15/793,216, Non Final Office Action mailed Aug. 1, 2019", 21 pgs.
"U.S. Appl. No. 15/793,216, Notice of Allowance mailed Mar. 23, 2020", 7 pgs.
"U.S. Appl. No. 15/793,216, Preliminary Amendment filed Oct. 26, 2017", 8 pgs.
"U.S. Appl. No. 15/793,216, Response filed Jan. 28, 2020 to Non Final Office Action mailed Aug. 1, 2019", 13 pgs.
"U.S. Appl. No. 15/865,938, Notice of Allowance mailed Sep. 17, 2019", 11 pgs.
"U.S. Appl. No. 15/865,938, Preliminary Amendment filed Jan. 10, 2018", 7 pgs.
"U.S. Appl. No. 15/866,089, Corrected Notice of Allowability mailed Aug. 27, 2020", 2 pgs.
"U.S. Appl. No. 15/866,089, Final Office Action mailed Mar. 25, 2020", 15 pgs.
"U.S. Appl. No. 15/866,089, Non Final Office Action mailed Dec. 4, 2019", 16 pgs.
"U.S. Appl. No. 15/866,089, Notice of Allowance mailed Jul. 15, 2020", 5 pgs.
"U.S. Appl. No. 15/866,089, Preliminary Amendment filed Jan. 10, 2018", 10 pgs.
"U.S. Appl. No. 15/866,089, Response filed Feb. 27, 2020 to Non Final Office Action mailed Dec. 4, 2019", 10 pgs.
"U.S. Appl. No. 15/866,089, Response filed Jun. 18, 2020 to Final Office Action mailed Mar. 25, 2020", 11 pgs.
"U.S. Appl. No. 15/886,712, Non Final Office Action mailed Sep. 27, 2019", 8 pgs.
"U.S. Appl. No. 15/886,712, Notice of Allowance mailed Nov. 14, 2019", 7 pgs.
"U.S. Appl. No. 15/886,712, Preliminary Amendment filed Feb. 2, 2018", 8 pgs.
"U.S. Appl. No. 15/886,712, Response filed Oct. 18, 2019 to Non Final Office Action mailed Sep. 27, 2019", 9 pgs.
"U.S. Appl. No. 15/891,049, Examiner Interview Summary mailed Aug. 10, 2020", 3 pgs.
"U.S. Appl. No. 15/891,049, Examiner Interview Summary mailed Dec. 4, 2020", 2 pgs.
"U.S. Appl. No. 15/891,049, Final Office Action mailed Nov. 10, 2020", 10 pgs.
"U.S. Appl. No. 15/891,049, Non Final Office Action mailed Jul. 14, 2020", 16 pgs.
"U.S. Appl. No. 15/891,049, Notice of Allowance mailed Dec. 22, 2020", 8 pgs.
"U.S. Appl. No. 15/891,049, Preliminary Amendment filed Feb. 8, 2018", 6 pgs.
"U.S. Appl. No. 15/891,049, Response filed May 29, 2020 to Restriction Requirement mailed May 5, 2020", 9 pgs.
"U.S. Appl. No. 15/891,049, Response filed Aug. 17, 2020 to Non Final Office Action mailed Jul. 14, 2020", 18 pgs.
"U.S. Appl. No. 15/891,049, Response filed Dec. 1, 2020 to Final Office Action mailed Nov. 10, 2020", 12 pgs.
"U.S. Appl. No. 15/891,049, Restriction Requirement mailed May 5, 2020", 6 pgs.
"U.S. Appl. No. 15/891,049, Supplemental Preliminary Amendment filed Dec. 20, 2019", 8 pgs.
"U.S. Appl. No. 15/903,261, Notice of Allowance mailed Mar. 26, 2020", 9 pgs.
"U.S. Appl. No. 15/903,261, Preliminary Amendment filed Feb. 28, 2018", 6 pgs.
"U.S. Appl. No. 15/917,143, Non Final Office Action mailed Aug. 7, 2020", 6 pgs.
"U.S. Appl. No. 15/917,143, Notice of Allowance mailed Feb. 24, 2021", 8 pgs.
"U.S. Appl. No. 15/917,143, Preliminary Amendment filed Mar. 14, 2018", 7 pgs.
"U.S. Appl. No. 15/917,143, Response filed Jun. 17, 2020 to Restriction Requirement mailed May 5, 2020", 8 pgs.
"U.S. Appl. No. 15/917,143, Response filed Oct. 29, 2020 to Non Final Office Action mailed Aug. 7, 2020", 11 pgs.
"U.S. Appl. No. 15/917,143, Restriction Requirement mailed May 5, 2020", 6 pgs.
"U.S. Appl. No. 15/941,481, Non Final Office Action mailed Aug. 14, 2020", 21 pgs.
"U.S. Appl. No. 15/941,481, Notice of Allowance mailed Dec. 3, 2020", 8 pgs.
"U.S. Appl. No. 15/941,481, Preliminary Amendment filed Mar. 30, 2018", 7 pgs.
"U.S. Appl. No. 15/941,481, Response filed Jun. 24, 2020 to Restriction Requirement mailed May 19, 2020", 8 pgs.
"U.S. Appl. No. 15/941,481, Response filed Nov. 16, 2020 to Non Final Office Action mailed Aug. 14, 2020", 15 pgs.
"U.S. Appl. No. 15/941,481, Restriction Requirement mailed May 19, 2020", 7 pgs.
"U.S. Appl. No. 15/945,425, Non Final Office Action mailed Aug. 25, 2020", 11 pgs.
"U.S. Appl. No. 15/945,425, Notice of Allowance mailed Dec. 24, 2020", 8 pgs.
"U.S. Appl. No. 15/945,425, Preliminary Amendment filed Apr. 5, 2018", 8 pgs.
"U.S. Appl. No. 15/945,425, Response filed Jun. 24, 2020 to Restriction Requirement mailed May 19, 2020", 7 pgs.

(56) References Cited

OTHER PUBLICATIONS

"U.S. Appl. No. 15/945,425, Response filed Nov. 23, 2020 to Non Final Office Action mailed Aug. 25, 2020", 10 pgs.
"U.S. Appl. No. 15/945,425, Restriction Requirement mailed May 19, 2020", 7 pgs.
"U.S. Appl. No. 15/945,425, Supplemental Preliminary Amendment filed May 10, 2018", 6 pgs.
"U.S. Appl. No. 15/956,444, Non Final Office Action mailed Dec. 7, 2020", 7 pgs.
"U.S. Appl. No. 15/956,444, Notice of Allowance mailed Mar. 11, 2021", 8 pgs.
"U.S. Appl. No. 15/956,444, Preliminary Amendment filed Apr. 19, 2018", 7 pgs.
"U.S. Appl. No. 15/956,444, PTO Response to Rule 312 Communication mailed Jun. 8, 2021", 2 pgs.
"U.S. Appl. No. 15/956,444, Response filed Feb. 23, 2021 to Non Final Office Action mailed Dec. 7, 2020", 11 pgs.
"U.S. Appl. No. 15/956,444, Response filed Sep. 14, 2020 to Restriction Requirement mailed Jul. 14, 2020", 8 pgs.
"U.S. Appl. No. 15/956,444, Restriction Requirement mailed Jul. 14, 2020", 7 pgs.
"U.S. Appl. No. 15/972,646, Non Final Office Action mailed Dec. 7, 2020", 11 pgs.
"U.S. Appl. No. 15/972,646, Notice of Allowance mailed Apr. 21, 2021", 8 pgs.
"U.S. Appl. No. 15/972,646, Preliminary Amendment filed May 9, 2018", 6 pgs.
"U.S. Appl. No. 15/972,646, Response filed Feb. 22, 2021 to Non Final Office Action mailed Dec. 7, 2020", 13 pgs.
"U.S. Appl. No. 15/972,646, Response filed Sep. 2020 to Restriction Requirement mailed Jul. 27, 2020", 7 pgs.
"U.S. Appl. No. 15/972,646, Restriction Requirement mailed Jul. 27, 2020", 6 pgs.
"U.S. Appl. No. 16/160,559, 312 Amendment filed Dec. 9, 2021", 7 pgs.
"U.S. Appl. No. 16/160,559, Non Final Office Action mailed May 14, 2021", 12 pgs.
"U.S. Appl. No. 16/160,559, Notice of Allowance mailed Sep. 16, 2021", 14 pgs.
"U.S. Appl. No. 16/160,559, Preliminary Amendment filed Oct. 17, 2018", 6 pgs.
"U.S. Appl. No. 16/160,559, PTO Response to Rule 312 Communication mailed Dec. 24, 2021", 2 pgs.
"U.S. Appl. No. 16/160,559, Response filed Mar. 2, 21 to Restriction Requirement mailed Jan. 27, 2021", 7 pgs.
"U.S. Appl. No. 16/160,559, Response filed Aug. 11, 2021 to Non Final Office Action mailed May 14, 2021", 10 pgs.
"U.S. Appl. No. 16/160,559, Restriction Requirement mailed Jan. 27, 2021", 6 pgs.
"U.S. Appl. No. 16/251,342, Notice of Allowance mailed Jul. 26, 2021", 8 pgs.
"U.S. Appl. No. 16/251,342, Preliminary Amendment filed Jan. 21, 2019", 6 pgs.
"U.S. Appl. No. 16/251,342, Response filed May 3, 2021 to Restriction Requirement mailed Apr. 30, 2021", 8 pgs.
"U.S. Appl. No. 16/251,342, Restriction Requirement mailed Apr. 30, 2021", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/255,300, Notice of Allowance mailed Jul. 19, 2021", 10 pgs.
"U.S. Appl. No. 16/255,300, Preliminary Amendment filed Jan. 24, 2019", 6 pgs.
"U.S. Appl. No. 16/380,742, Notice of Allowance mailed Jan. 3, 2022", 13 pgs.
"U.S. Appl. No. 16/380,742, Preliminary Amendment filed Apr. 12, 2019", 6 pgs.
"U.S. Appl. No. 16/380,742, Response filed Oct. 20, 2021 to Restriction Requirement mailed Aug. 20, 2021", 6 pgs.
"U.S. Appl. No. 16/380,742, Restriction Requirement mailed Aug. 20, 2021", 7 pgs.
"U.S. Appl. No. 16/380,742, Supplemental Preliminary Amendment filed Mar. 1, 2021", 5 pgs.
"U.S. Appl. No. 16/400,199, Preliminary Amendment filed May 7, 2019", 7 pgs.
"U.S. Appl. No. 16/400,199, Response filed Nov. 15, 2021 to Restriction Requirement mailed Oct. 1, 2021", 8 pgs.
"U.S. Appl. No. 16/400,199, Restriction Requirement mailed Oct. 1, 2021", 7 pgs.
"U.S. Appl. No. 16/420,676, Non Final Office Action mailed Jul. 20, 2021", 11 pgs.
"U.S. Appl. No. 16/420,676, Notice of Allowance mailed Nov. 15, 2021", 9 pgs.
"U.S. Appl. No. 16/420,676, Preliminary Amendment filed Jun. 3, 2019", 5 pgs.
"U.S. Appl. No. 16/420,676, Response filed Oct. 20, 2021 to Non Final Office Action mailed Jul. 20, 2021", 14 pgs.
"U.S. Appl. No. 16/428,277, Preliminary Amendment filed Jun. 3, 2019", 5 pgs.
"U.S. Appl. No. 16/436,023, Examiner Interview Summary mailed Aug. 23, 2021", 2 pgs.
"U.S. Appl. No. 16/436,023, Non Final Office Action mailed May 19, 2021", 18 pgs.
"U.S. Appl. No. 16/436,023, Notice of Allowance mailed Oct. 27, 2021", 8 pgs.
"U.S. Appl. No. 16/436,023, Preliminary Amendment filed Jun. 12, 2019", 6 pgs.
"U.S. Appl. No. 16/436,023, Response filed Aug. 19, 2021 to Non Final Office actio mailed May 19, 2021", 9 pgs.
"U.S. Appl. No. 16/443,391, Non Final Office Action mailed Aug. 31, 2021", 11 pgs.
"U.S. Appl. No. 16/443,391, Notice of Allowance mailed Jan. 7, 2022", 5 pgs.
"U.S. Appl. No. 16/443,391, Preliminary Amendment filed Jun. 19, 2019", 6 pgs.
"U.S. Appl. No. 16/443,391, Response filed Nov. 15, 2021 to Non Final Office Action mailed Aug. 31, 2021", 9 pgs.
"U.S. Appl. No. 16/508,764, Notice of Allowance mailed Oct. 20, 2021", 10 pgs.
"U.S. Appl. No. 16/508,764, Preliminary Amendment filed Jul. 12, 2019", 7 pgs.
"U.S. Appl. No. 16/508,764, Supplemental Amendment filed Sep. 30, 2021", 6 pgs.
"U.S. Appl. No. 16/544,293, Preliminary Amendment filed Aug. 21, 2019", 7 pgs.
"U.S. Appl. No. 16/544,293, Supplemental Preliminary Amendment filed Oct. 28, 2020", 6 pgs.
"U.S. Appl. No. 16/593,022, Preliminary Amendment filed Oct. 30, 2019", 8 pgs.
"U.S. Appl. No. 16/593,022, Supplemental Preliminary Amendment filed Oct. 21, 2020", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Non Final Office Action mailed Nov. 15, 2021", 8 pgs.
"U.S. Appl. No. 16/690,671, Preliminary Amendment filed Dec. 11, 2019", 7 pgs.
"U.S. Appl. No. 16/795,181, Preliminary Amendment filed Feb. 20, 2020", 6 pgs.
"U.S. Appl. No. 16/802,228, Preliminary Amendment filed Mar. 4, 2020", 7 pgs.
"U.S. Appl. No. 16/802,248, Preliminary Amendment filed Mar. 5, 2020", 8 pgs.
"U.S. Appl. No. 16/806,611, Preliminary Amendment filed Mar. 4, 2020", 7 pgs.

(56) References Cited

OTHER PUBLICATIONS

"U.S. Appl. No. 16/895,246, Preliminary Amendment filed Jun. 9, 2020", 6 pgs.
"U.S. Appl. No. 16/989,386, Supplemental Preliminary Amendment filed Oct. 21, 2020", 8 pgs.
"U.S. Appl. No. 17/190,686, Preliminary Amendment filed Mar. 10, 2021", 7 pgs.
"U.S. Appl. No. 17/392,971, Preliminary Amendment filed Aug. 18, 2021", 9 pgs.
"U.S. Appl. No. 17/492,082, Preliminary Amendment filed Oct. 25, 2021", 6 pgs.
"U.S. Appl. No. 17/516,664, Preliminary Amendment filed Nov. 10, 2021", 6 pgs.
"U.S. Appl. No. 17/545,668, Preliminary Amendment filed Dec. 9, 2021", 5 pgs.
"U.S. Appl. No. 17/550,074, Preliminary Amendment filed Dec. 15, 2021", 5 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report mailed Dec. 11, 2017", 2 pgs.
"Australian Application Serial No. 2014236885, Response filed Feb. 14, 2018 to First Examination Report mailed Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Bio-Intrafix (TCP/PLA) & Intrafix, Tibial Soft Tissue Fasteners", DePuy Mitek, ((date unknown)), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.
"Canadian Application Serial No. 2906596, Office Action mailed Feb. 26, 2018", 3 pgs.
"Chinese Application Serial No. 201480027708.4, Office Action mailed Feb. 14, 2017", (W/ English Translation), 18 pgs.
"Chinese Application Serial No. 201480027708.4, Office Action mailed May 26, 2016", W/ English Translation, 15 pgs.
"Chinese Application Serial No. 201480027708.4, Office Action mailed Aug. 18, 2017", (W/ English Translation), 8 pgs.
"Chinese Application Serial No. 201480027708.4, Response filed May 2, 2017 to Office Action mailed Feb. 14, 2017", (W/ English Translation), 17 pgs.
"Chinese Application Serial No. 201480027708.4, Response filed Oct. 10, 2016 to Office Action mailed May 26, 2016", (W/ English Translation of Claims), 14 pgs.
"Chinese Application Serial No. 201480027708.4, Response filed Oct. 31, 2017 to Office Action mailed Aug. 18, 2017", (W/ English Claims), 7 pgs.
"Declaration of John White regarding PSCD and Customized Device and Exhibits 1-5".
"Do your next distal tendon repair with . . . The Lubbers Technique", Teno Fix® brochure, Ortheon® Medical, (2003), 2 pgs.
"European Application No. 16168202.6, Extended European Search Report mailed Aug. 16, 2017", 11 pgs.
"European Application No. 16168202.6, Response filed Nov. 3, 2017 to Extended European Search Report mailed Aug. 16, 2017", 9 pgs.
"European Application Serial No. 10727548.9, Examination Notification Art. 94(3) mailed Sep. 18, 2014", 6 pgs.
"European Application Serial No. 10727548.9, Office Action mailed Jan. 11, 2016", 6 pgs.
"European Application Serial No. 10727548.9, Office Action mailed Jan. 19, 2012", 2 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Examination Notification Art. 94(3) mailed Feb. 4, 2014", 3 pgs.
"European Application Serial No. 11707316.3, Examination Notification Art. 94(3) mailed Dec. 17, 2014", 5 pgs.
"European Application Serial No. 11707316.3, Office Action mailed Nov. 10, 2015", 6 pgs.
"European Application Serial No. 11707316.3, Response filed Jun. 5, 2014 to Examination Notification Art. 94(3) mailed Feb. 4, 2014", 7 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Office Action mailed Jan. 3, 2014", 2 pgs.
"European Application Serial No. 12721676.0, Preliminary Amendment filed Nov. 19, 2013", 9 pgs.
"European Application Serial No. 12721676.0, Response filed Apr. 11, 2016 to Communication pursuant to Article 94(3) EPC mailed Sep. 30, 2015", 38 pgs.
"European Application Serial No. 12721676.0, Response filed Jul. 10, 2014 to Office Action mailed Jan. 3, 2014", 2 pgs.
"European Application Serial No. 12791902.5, Examination Notification Art. 94(3) mailed Aug. 14, 2015", 4 pgs.
"European Application Serial No. 12791902.5, Office Action mailed Jul. 15, 2014", 2 pgs.
"European Application Serial No. 12791902.5, Response filed Feb. 23, 2016 to Examination Notification Art. 94(3) mailed Aug. 14, 2015", 12 pgs.
"European Application Serial No. 12806211.4, Examination Notification Art. 94(3) mailed Aug. 13, 2015", 5 pgs.
"European Application Serial No. 12806211.4, Office Action mailed Jul. 18, 2014", 2 pgs.
"European Application Serial No. 12806211.4, Response filed Feb. 23, 2016 to Communication Pursuant to Article 94(3) EPC mailed Aug. 13, 2015", 11 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Communication Pursuant to Article 94(3) EPC mailed Jul. 13, 2020", 4 pgs.
"European Application Serial No. 14716173.1, Office Action mailed Nov. 5, 2015", 2 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 14716173.1, Response filed Sep. 25, 17 to Office Action mailed Mar. 14, 2017", 12pgs.
"European Application Serial No. 16168202.6, Communication Pursuant to Article 94(3) EPC mailed Apr. 25, 2018", 5 pgs.
"European Application Serial No. 16168202.6, Communication pursuant to Article 94(3) EPC mailed Dec. 11, 2018", 6 pgs.
"European Application Serial No. 16168202.6, Partial European Search Report mailed May 9, 2017", 12 pgs.
"European Application Serial No. 16168202.6, Response filed Sep. 5, 2018 to Communication Pursuant to Article 94(3) EPC mailed Apr. 25, 2018", 13 pgs.
"European Application Serial No. 17169003.5, Extended European Search Report mailed May 11, 2018", 8 pgs.
"European Application Serial No. 17169003.5, Response Filed Dec. 19, 2018 to Extended European Search Report mailed May 11, 2018", 22 pgs.
"European Application Serial No. 12806211.4, Communication Pursuant to Article 94(3) EPC mailed Jun. 23, 2016", 4 pgs.
"EZ Loc Femoral Fixation Device", copyright 2005 Arthrotek, Inc, (2005), 8 pgs.
"Information of Polydioxanone", Dolphin Sutures, [Online] Retrieved from the internet: <https://www.dolphinsutures.com/resoucres/information-on-polydioxanone>, (2018), 2 pgs.
"International Application Serial No. PCT/US2009/039580, International Preliminary Report on Patentability mailed Nov. 4, 2010", 9 pgs.

(56) References Cited

OTHER PUBLICATIONS

"International Application Serial No. PCT/US2009/039580, International Search Report mailed Jul. 30, 2009", 4 pgs.
"International Application Serial No. PCT/US2009/039580, Written Opinion mailed Jul. 30, 2009", 7 pgs.
"International Application Serial No. PCT/US2010/036602, International Preliminary Report on Patentability mailed Dec. 8, 2011", 9 pgs.
"International Application Serial No. PCT/US2010/036602, International Search Report mailed Nov. 8, 2010", 6 pgs.
"International Application Serial No. PCT/US2010/036602, Written Opinion mailed Nov. 8, 2010", 7 pgs.
"International Application Serial No. PCT/US2011/026349, International Preliminary Report on Patentability mailed Sep. 20, 2012", 11 pgs.
"International Application Serial No. PCT/US2011/026349, International Search Report mailed Jul. 28, 2011", 6 pgs.
"International Application Serial No. PCT/US2011/026349, Invitation to Pay Additional Fees mailed Jun. 9, 2011", 5 pgs.
"International Application Serial No. PCT/US2011/026349, Written Opinion mailed Jul. 28, 2011", 9 pgs.
"International Application Serial No. PCT/US2011/038188, International Preliminary Report on Patentability mailed Dec. 6, 2012", 14 pgs.
"International Application Serial No. PCT/US2011/038188, International Search Report mailed Oct. 14, 2011", 6 pgs.
"International Application Serial No. PCT/US2011/038188, Invitation to Pay Additional Fees mailed Aug. 5, 2011", 5 pgs.
"International Application Serial No. PCT/US2011/038188, Written Opinion mailed Oct. 14, 2011", 12 pgs.
"International Application Serial No. PCT/US2012/030294, International Preliminary Report on Patentability mailed Oct. 10, 2013", 9 pgs.
"International Application Serial No. PCT/US2012/030294, International Search Report mailed May 23, 2012", 6 pgs.
"International Application Serial No. PCT/US2012/030294, Written Opinion mailed May 23, 2012", 7 pgs.
"International Application Serial No. PCT/US2012/037703, International Preliminary Report on Patentability mailed Nov. 28, 2013", 10 pgs.
"International Application Serial No. PCT/US2012/037703, International Search Report mailed Sep. 21, 2012", 6 pgs.
"International Application Serial No. PCT/US2012/037703, Invitation to Pay Additional Fees mailed Jul. 19, 2012", 7 pgs.
"International Application Serial No. PCT/US2012/037703, Written Opinion mailed Sep. 21, 2012", 8 pgs.
"International Application Serial No. PCT/US2012/062738, International Preliminary Report on Patentability mailed May 15, 2014", 9 pgs.
"International Application Serial No. PCT/US2012/062738, International Search Report mailed Mar. 6, 2013", 6 pgs.
"International Application Serial No. PCT/US2012/062738, Written Opinion mailed Mar. 6, 2013", 7 pgs.
"International Application Serial No. PCT/US2012/064832, International Preliminary Report on Patentability mailed May 30, 2014", 9 pgs.
"International Application Serial No. PCT/US2012/064832, International Search Report mailed Feb. 6, 2013", 3 pgs.
"International Application Serial No. PCT/US2012/064832, Written Opinion mailed Feb. 6, 2013", 7 pgs.
"International Application Serial No. PCT/US2013/058921, International Preliminary Report on Patentability mailed Mar. 26, 2015", 9 pgs.
"International Application Serial No. PCT/US2013/058921, International Search Report mailed Oct. 21, 2013", 5 pgs.
"International Application Serial No. PCT/US2013/058921, Written Opinion mailed Oct. 21, 2013", 6 pgs.
"International Application Serial No. PCT/US2013/075989, International Preliminary Report on Patentability mailed Jul. 2, 2015", 10 pgs.
"International Application Serial No. PCT/US2013/075989, International Search Report mailed Mar. 6, 2014", 4 pgs.
"International Application Serial No. PCT/US2013/075989, Written Opinion mailed Mar. 6, 2014", 7 pgs.
"International Application Serial No. PCT/US2014/026413, International Preliminary Report on Patentability mailed Sep. 24, 2015", 10 pgs.
"International Application Serial No. PCT/US2014/026413, International Search Report mailed Jun. 6, 2014", 5 pgs.
"International Application Serial No. PCT/US2014/026413, Written Opinion mailed Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.
"Make your next tendon repair an open-and-shut case. The Teno Fix® Tendon Repair System", Teno Fix® brochure, Ortheon® Medical, (2003), 2 pgs.
"Mallory-Head Modular Calcar Revision System", Biomet Orthopedics, Inc., (2006), 20 pgs.
"Next Generation in Knee Ligament Reconstruction & Repair Technology", Suture Tensioner w/Tensiometer, Arthrex®, Inc. catalog, (2009).
"PANALOK Anchor with PDS II and ETHIBOND Suture", Mitek Products ETHICON, (1997), 2 pgs.
"Rapid Sternal Closure", KLS Martin L.P., [Online] retrieved from the internet: U.S. Appl. No. 13/645,964 , (2006).
"Rotator Cuff Fixation", Acufex Fastenator System: Shoulder Arthroscopy; H-2-H-22, 22 pgs.
"SE Graft Tensioning System Surgical Technique", Linvatec Corporation copyright 2003, (2004), 12 pgs.
"SportMesh™ Soft Tissue Reinforcment, Made from . . . Artelon® optimal tissue repair", Biomet® Sports Medicine, Inc., (2007), 8 pgs.
"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.

(56) References Cited

OTHER PUBLICATIONS

Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Fromm, Stuart M.D. E, "", Rapidloc, Meniscal Repair System, Mitek Products, Ethicon, (2001), 6 pgs.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, MD, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D, "Acl Reconstruction with Acufex Director Drill Guide and Endobutton CL Fixation System", Smith & Nephew: Knee Series, Technique Guide, (2005), 12 pgs.
Saxena, Pankaj, et al., "Use of Double Wires in Sternal Closure, A Useful Technique", Texas Heart® Institute. Journal List> Tex Heart Inst J > v.33(4), (2006).
Smith, et al., "Endoscopic Meniscal Repair Using the T-Fix", (1996), 16 pgs.
Smith, et al., "Fast-Fix", Meniscal Repair System;, (2001), 3 pgs.
Steadman, et al., "Microfracture: Surgical Technique and Rehabilitation to Treat Chondral Defects", Clinical Orthopaedics and Related Research 391, (2001), S362-S369.
Thomas, Roseberg D, "Technique for ACL Reconstruction with Acufex Director Drill Guide and Endobutton CL", Smith & Nephew, Technique Guide, (1999), 18 pgs.
Weiler, A, et al., "Biodegradierbare Interferenzschrauben in der Kreuzbandchirurgie", Opjournal 14, (1998), 278-284.
Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.
"U.S. Appl. No. 16/428,277, Corrected Notice of Allowability mailed Sep. 16, 2022", 6 pgs.
"U.S. Appl. No. 16/544,293, Corrected Notice of Allowability mailed Mar. 17, 2023", 7 pgs.
"U.S. Appl. No. 16/544,293, Non Final Office Action mailed Sep. 21, 2022", 14 pgs.
"U.S. Appl. No. 16/544,293, Notice of Allowance mailed Mar. 8, 2023", 11 pgs.
"U.S. Appl. No. 16/544,293, Response filed Nov. 28, 2022 to Non-Final Office Action mailed Sep. 21, 2022", 10 pgs.
"U.S. Appl. No. 16/593,022, Response filed Sep. 9, 2022 to Restriction Requirement mailed Sep. 6, 2022", 8 pgs.
"U.S. Appl. No. 16/593,022, Response filed Nov. 4, 2022 to Restriction Requirement mailed Oct. 31, 2022", 8 pgs.
"U.S. Appl. No. 16/593,022, Restriction Requirement mailed Oct. 31, 2022", 6 pgs.
"U.S. Appl. No. 16/593,022, Supplemental Amendment filed Nov. 7, 2022 to Restriction Requirement mailed Oct. 31, 2022", 9 pgs.
"U.S. Appl. No. 16/802,248, Notice of Allowance mailed Oct. 28, 2022", 9 pgs.
"U.S. Appl. No. 16/802,248, Response filed Sep. 14, 2022 to Non Final Office Action mailed Jun. 17, 2022", 12 pgs.
"U.S. Appl. No. 16/806,611, Notice of Allowance mailed Feb. 15, 2023", 10 pgs.
"U.S. Appl. No. 16/806,611, Response filed Sep. 9, 2022 to Restriction Requirement mailed Aug. 26, 2022", 9 pgs.
"U.S. Appl. No. 16/806,611, Response filed Nov. 7, 2022 to Restriction Requirement mailed Nov. 1, 2022", 9 pgs.
"U.S. Appl. No. 16/806,611, Restriction Requirement mailed Nov. 1, 2022", 6 pgs.
"U.S. Appl. No. 16/895,246, Non Final Office Action mailed Dec. 13, 2022", 8 pgs.
"U.S. Appl. No. 16/895,246, Notice of Allowance mailed Apr. 5, 2023", 13 pgs.
"U.S. Appl. No. 16/895,246, Response filed Jan. 11, 2023 to Non Final Office Action mailed Dec. 13, 2022", 8 pgs.
"U.S. Appl. No. 16/895,246, Response filed Sep. 28, 2022 to Restriction Requirement mailed Sep. 9, 2022", 7 pgs.
"U.S. Appl. No. 16/895,246, Restriction Requirement mailed Sep. 9, 2022", 6 pgs.
"U.S. Appl. No. 16/987,001, Notice of Allowance mailed Feb. 17, 2023", 15 pgs.
"U.S. Appl. No. 16/989,386, Non Final Office Action mailed Mar. 15, 2023", 13 pgs.
"U.S. Appl. No. 16/989,386, Notice of Allowance mailed Jul. 26, 2023", 9 pgs.
"U.S. Appl. No. 16/989,386, PTO Response to Rule 312 Communication mailed Oct. 19, 2023", 2 pgs.
"U.S. Appl. No. 16/989,386, Response filed May 19, 2023 to Non Final Office Action mailed Mar. 15, 2023", 11 pgs.
"U.S. Appl. No. 16/989,386, Response filed Dec. 5, 2022 to Restriction Requirement mailed Nov. 14, 2022", 9 pgs.
"U.S. Appl. No. 16/989,386, Restriction Requirement mailed Nov. 14, 2022", 6 pgs.
"U.S. Appl. No. 17/190,686, Notice of Allowance mailed Oct. 5, 2023", 8 pgs.
"U.S. Appl. No. 17/190,686, Restriction Requirement mailed Jun. 6, 2023", 7 pgs.
"U.S. Appl. No. 17/190,686, Supplemental Amendment filed Apr. 12, 2023", 9 pgs.
"U.S. Appl. No. 17/232,672, Preliminary Amendment filed Apr. 19, 2021", 5 pgs.
"U.S. Appl. No. 17/492,082, Notice of Allowance mailed Apr. 17, 2023", 8 pgs.
"U.S. Appl. No. 17/545,668, Notice of Allowance mailed Jun. 22, 2023", 7 pgs.
"U.S. Appl. No. 17/940,022, Preliminary Amendment filed Sep. 26, 2022", 6 pgs.
"U.S. Appl. No. 17/991,832, Preliminary Amendment filed Dec. 14, 2022", 6 pgs.
"U.S. Appl. No. 17/190,686, Response filed Aug. 3, 2023 to Restriction Requirement mailed Jun. 6, 2023", 9 pgs.
"U.S. Appl. No. 18/093,114, Supplemental Amendment filed Jan. 11, 2023", 6 pgs.
"U.S. Appl. No. 18/101,490, Supplemental Preliminary Amendment filed Jan. 26, 2023", 7 pgs.
"U.S. Appl. No. 18/102,518, Preliminary Amendment filed Jan. 30, 2023", 6 pgs.

(56) References Cited

OTHER PUBLICATIONS

"U.S. Appl. No. 18/126,022, Preliminary Amendment filed Apr. 28, 2023", 6 pgs.
"U.S. Appl. No. 18/134,897, Supplemental Amendment filed Nov. 1, 2023", 8 pgs.
"U.S. Appl. No. 18/134,897, Supplemental Preliminary Amendment filed Apr. 17, 2023", 6 pgs.
"U.S. Appl. No. 18/235,540, Supplemental Preliminary Amendment filed Aug. 30, 2023", 5 pgs.
"U.S. Appl. No. 18/471,089, Supplemental Preliminary Amendment filed Sep. 21, 2023", 7 pgs.
"U.S. Appl. No. 18/497,342, Supplemental Amendment filed Nov. 1, 2023", 7 pgs.
"U.S. Appl. No. 18/514,936, Preliminary Amendment filed Nov. 20, 2023", 4 pgs.
"U.S. Appl. No. 18/514,936, Supplemental Amendment filed Nov. 22, 2023", 6 pgs.

* cited by examiner

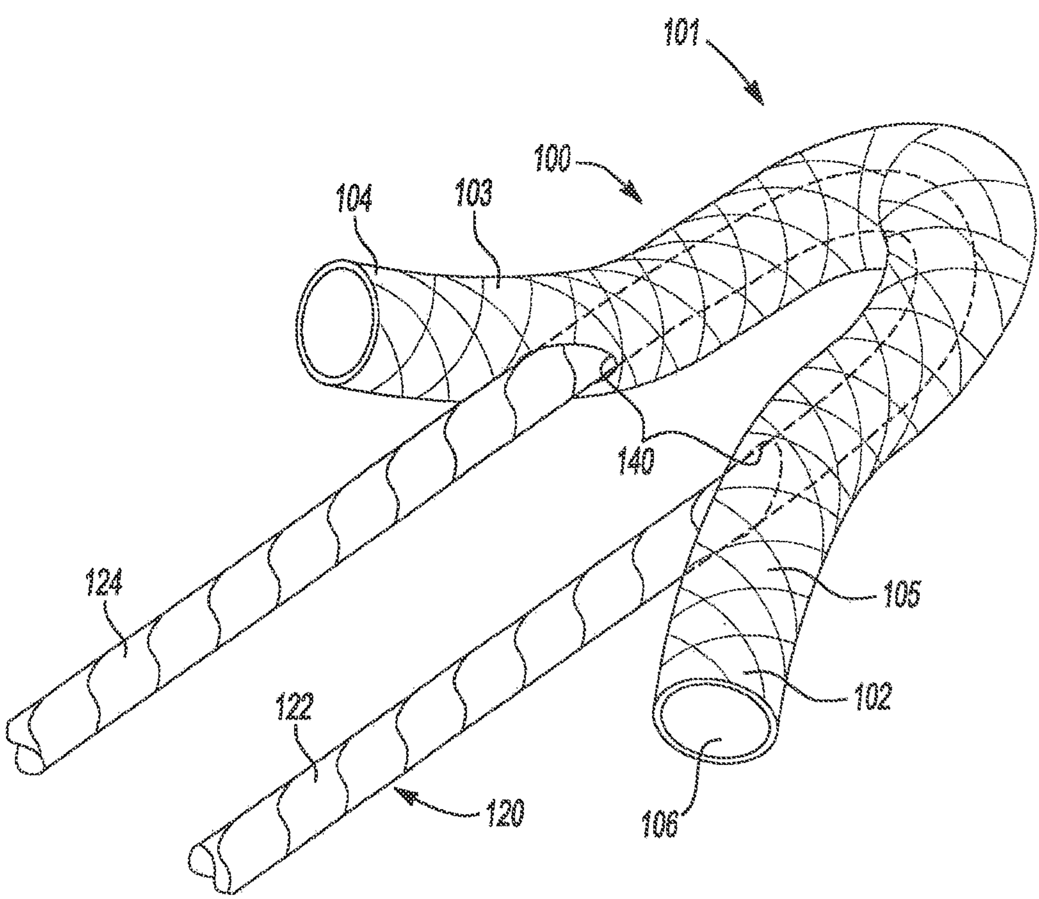
IFig-1C 100
100
100
100
128
120
130
124
122

A
A'
218
212
120
214
210
200, 200a
100

212
120
218
200, 200b
216
A
A'
210
202
100

124
122
120
128
210
100
A
A'
218
200, 200c
202

100
210
206
A
A'
212
200, 200d
120
204
202

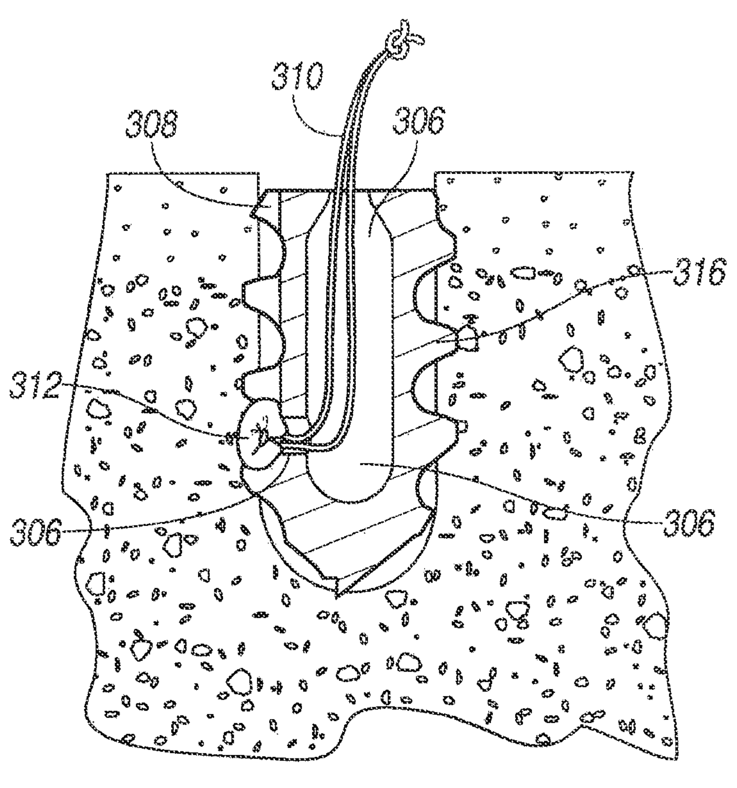
FIG. 13
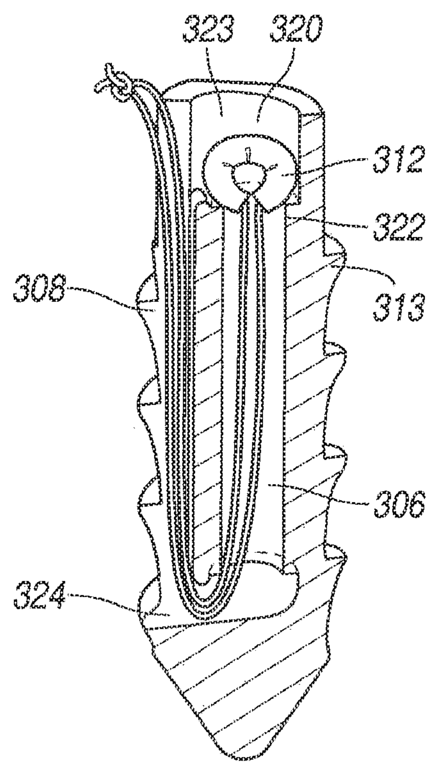
FIG. 14
FIG. 15

METHOD FOR TISSUE FIXATION

CROSS-REFERENCE TO RELATED APPLICATIONS

This application is a continuation of U.S. patent application Ser. No. 16/380,742 filed Apr. 10, 2019, now U.S. Pat. No. 11,311,287 issued on Apr. 26, 2022, which is a continuation of U.S. patent application Ser. No. 15/945,425 filed Apr. 4, 2018, now U.S. Pat. No. 10,987,099 issued on Apr. 27, 2021, which is a continuation of U.S. patent application Ser. No. 14/983,108 filed Dec. 29, 2015, now U.S. Pat. No. 10,321,906 issued on Jun. 18, 2019, which is a continuation of U.S. patent application Ser. No. 13/625,413 filed Sep. 24, 2012, now U.S. Pat. No. 9,402,621 issued on Aug. 2, 2016, which is a divisional of U.S. patent application Ser. No. 12/489,181 filed Jun. 22, 2009, now U.S. Pat. No. 8,298,262 issued on Oct. 30, 2012, which is a continuation-in-part application of: (1.) U.S. patent application Ser. No. 12/474,802 filed on May 29, 2009, now U.S. Pat. No. 8,088,130 issued on Jan. 3, 2012, (2.) U.S. patent application Ser. No. 12/014,399 filed on Jan. 15, 2008, now U.S. Pat. No. 7,909,851 issued on Mar. 22, 2011, (3.) U.S. patent application Ser. No. 12/014,340 filed on Jan. 15, 2008, now U.S. Pat. No. 7,905,904 issued on Mar. 15, 2011, (4.) U.S. patent application Ser. No. 11/935,681 filed on Nov. 6, 2007, now U.S. Pat. No. 7,905,903 issued on Mar. 15, 2011.

U.S. patent application Ser. No. 13/625,413 filed Sep. 24, 2012, now U.S. Pat. No. 9,402,621 issued on August 2. 2016, is also a divisional of U.S. patent application Ser. No. 13/412,116 filed on Mar. 5, 2012, now U.S. Pat. No. 8,771,316 issued on Jul. 8, 2014, which is a continuation-in-part of: (1.) U.S. patent application Ser. No. 12/196,405 filed on Aug. 22, 2008, now U.S. Pat. No. 8,128,658 issued on Mar. 6, 2012, (2.) U.S. patent application Ser. No. 12/196,407 filed on Aug. 22, 2008, now U.S. Pat. No. 8,137,382 issued on Mar. 20, 2012, and (3.) U.S. patent application Ser. No. 12/196,410 filed on Aug. 22, 2008, now U.S. Pat. No. 8,118,836 issued on Feb. 21, 2012.

The disclosures of the above applications are incorporated herein by reference.

INTRODUCTION

Trauma or disease in soft tissue, such as cartilage, ligament, or muscle can cause tears or detachment from bone or other defects that can be repaired by reattaching or securing the soft tissue to the bone. Various devices and methods are known for attaching and securing soft tissue to bone.

The present teachings provide a versatile tissue fixation method that can be used with various bone anchors or other implantable fixation members to attach soft tissue to bone or any tissue to other tissue.

SUMMARY

The present teachings provide a method for securing a strand to at least one fixation member for a surgical procedure, wherein the fixation member includes an aperture therethrough. The method includes passing a strand having first and second ends through a flexible sleeve, passing the sleeve through the aperture of the fixation member in a first direction, tensioning the strand, and moving the sleeve in a second direction different than the first direction to secure the sleeve to the fixation member without tying the strand on the fixation member.

The present teachings provide a method for securing a strand to a plurality of anchors for a surgical procedure. The method includes inserting a plurality of anchors into the bone, passing a flexible strand having first and second ends through a plurality of flexible sleeves serially coupled on the strand, passing each sleeve in a first configuration into and through an aperture of a corresponding anchor in a first direction, deforming each sleeve to a second configuration, and tying a single knot at the first and second ends of the strand.

The present teachings provide a method for securing a strand to a plurality of bone anchors for a surgical procedure. The method includes passing a flexible strand slidably through a plurality of flexible sleeves, forming a single slipknot on a portion of the strand outside all the sleeves, the slipknot the defining a closed loop, knotlessly securing each sleeve into a corresponding bone anchor, and reducing a length of the loop.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1C is a perspective view of another connector device according to the present teachings;

FIGS. 10A-15 represent various suture constructions coupled to a hollow fixation element;

FIGS. 19A-20 represent an alternate fastener and suture construction;

DESCRIPTION OF VARIOUS ASPECTS

The following description is merely exemplary in nature and is in no way intended to limit the scope of the present teachings, applications, or uses. The present teachings can be used for various orthopedic applications including coupling bone to bone, bone to soft tissue, soft tissue repair, and generally attaching soft tissue to bone, or attaching suture or other anchors to bone, or any other tissue repair procedure. The present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic, blood vessels, annulus of spine or other procedures.

Figure 1:
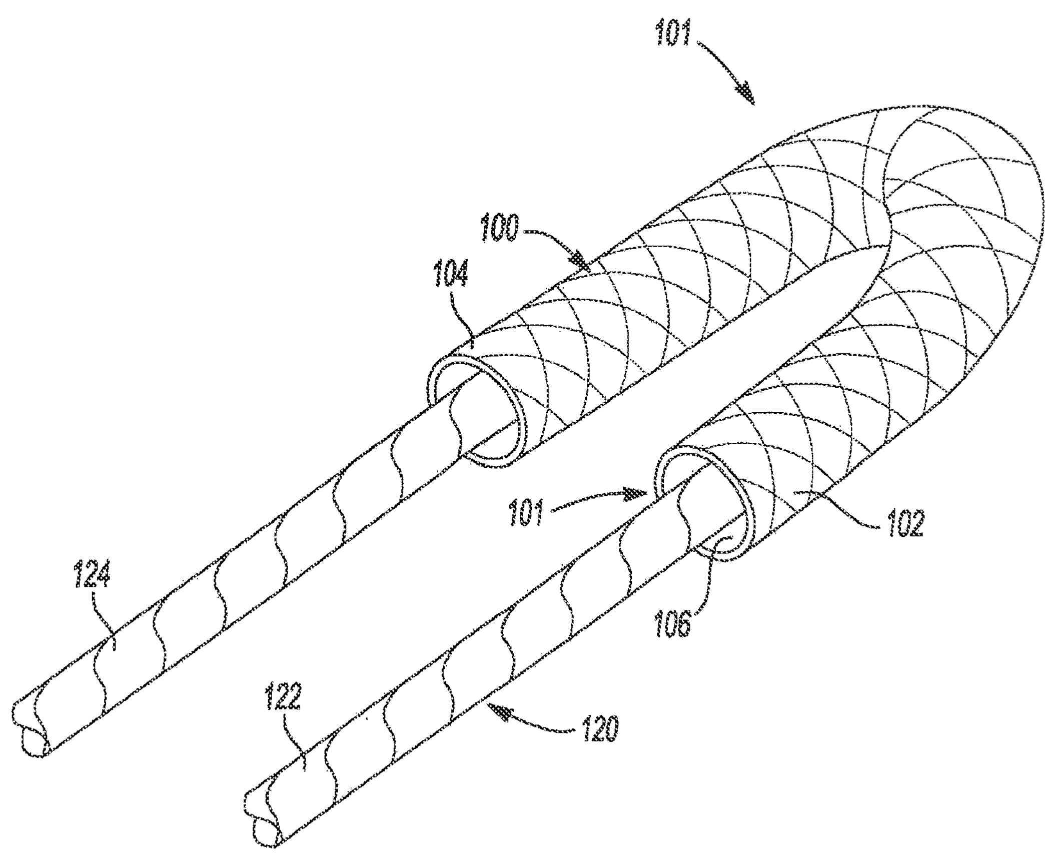
FIG. 1 is a perspective view of a connector device according to the present teachings.

Referring to FIG. 1, an exemplary connector device 101 that can be used for attaching soft tissue to bone is illustrated. The connector device 101 can include a flexible tubular sleeve or tube 100 having an inner bore 106 that extends between first and second open ends 102, 104. The sleeve 100 can be made of resorbable or non-resorbable materials, including braided suture, sponges and sponge-like, perforated materials, woven/braided from biocompatible materials or fibers, such as, for example, polymer, polyester, polyethylene, cotton, silk, or other natural or synthetic materials. The sleeve 100 can be made of suture material braided from thin filaments into a form that does not include a core filament. The sleeve 100 can have a generally flaccid shape that can be manipulated in different configurations like a piece of string or shoelace, for example. Accordingly, the sleeve 100 can be bent, folded or otherwise manipulated or deformed into various configurations, such as a bent or U-shape configuration shown in FIGS. 1, 1A and 1B, or a substantially straight configuration shown in FIG. 4, or a deformed or bunched-up, puckered configuration, such as the ball-like configuration shown in FIG. 3, or the bell-like shaped shown in FIG. 3A, as discussed below.

Figure 1A:
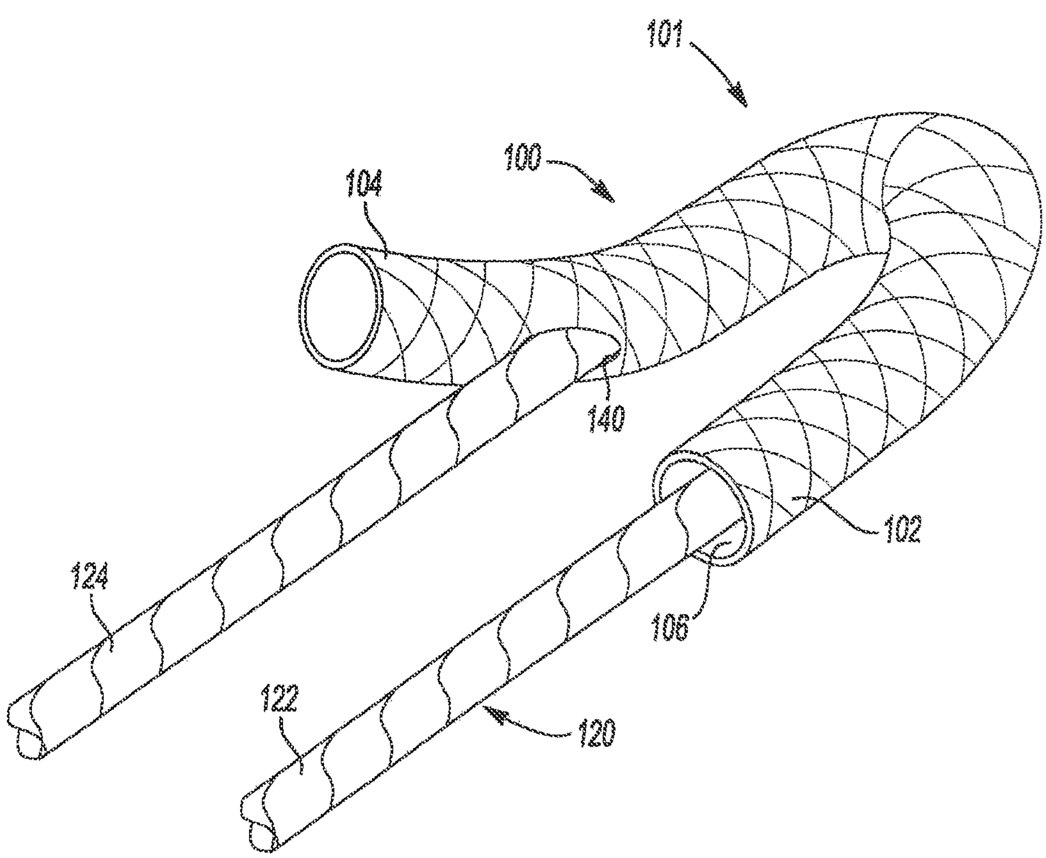
FIG. 1A is a perspective view of a connector device according to the present teachings.
Figure 1B:
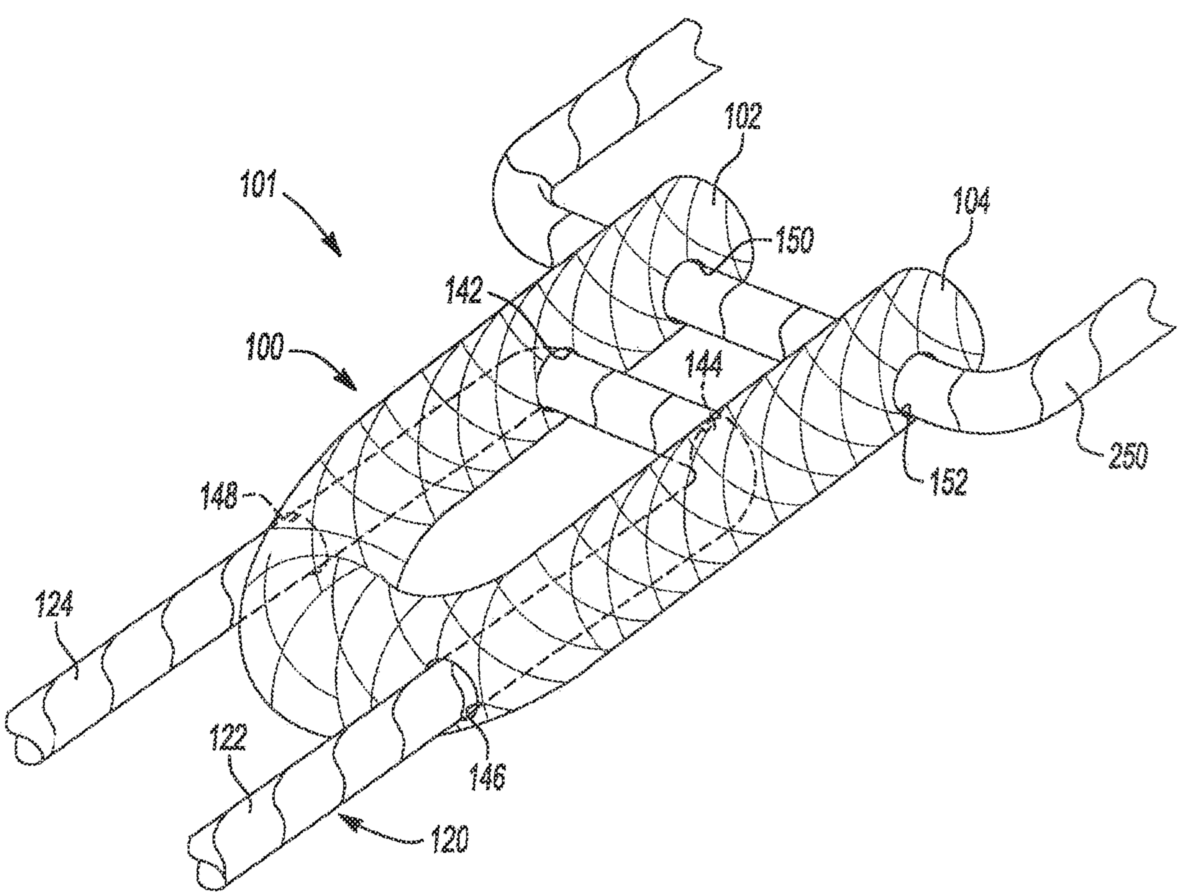
FIG. 1B is a perspective view of another connector device according to the present teachings.

Referring to FIGS. 1, 1A, 1B, and 1C the connector device 101 can also include an elongated flexible strand 120 having first and second ends 122, 124. The strand 120 can pass axially through the bore 106 of the sleeve 100, such that the first and second strand ends 122, 124 exit the corresponding first and second ends 102, 104 of the sleeve 100, as illustrated in FIG. 1. In one aspect, the strand 120 can exit the bore 106 through at least one opening 140 of the sleeve 100 intermediate the first and second ends 102, 104 of the sleeve, as shown in FIG. 1A. In another aspect, the strand 120 can exit the bore 106 through two openings 140 of the sleeve 100 intermediate the first and second ends 102, 104 of the sleeve 100, as shown in FIG. 1C. First and second end portions or sleeve legs 103, 105, are defined between each end 104, 102 and the corresponding opening 140. In another aspect, the strand 120 can pass through openings 142, 144, 146, 148, such that an intermediate portion of the strand 120 is outside the bore 106, as shown in FIG. 1B.

The strand 120 can also be made of materials similar to the sleeve 100, such as braided filaments or fibers of biocompatible material, including natural and synthetic fibers, such as cotton, silk, polymer, polyester, polyethylene, thin wire, suture, and other materials. The strand 120 can also be in the form of a flat tubular suture or a braided suture with or without a core. The connector device 101 with the sleeve 100 and strand 120 are implantable in soft tissue or bone.

Figures 2, 2A:
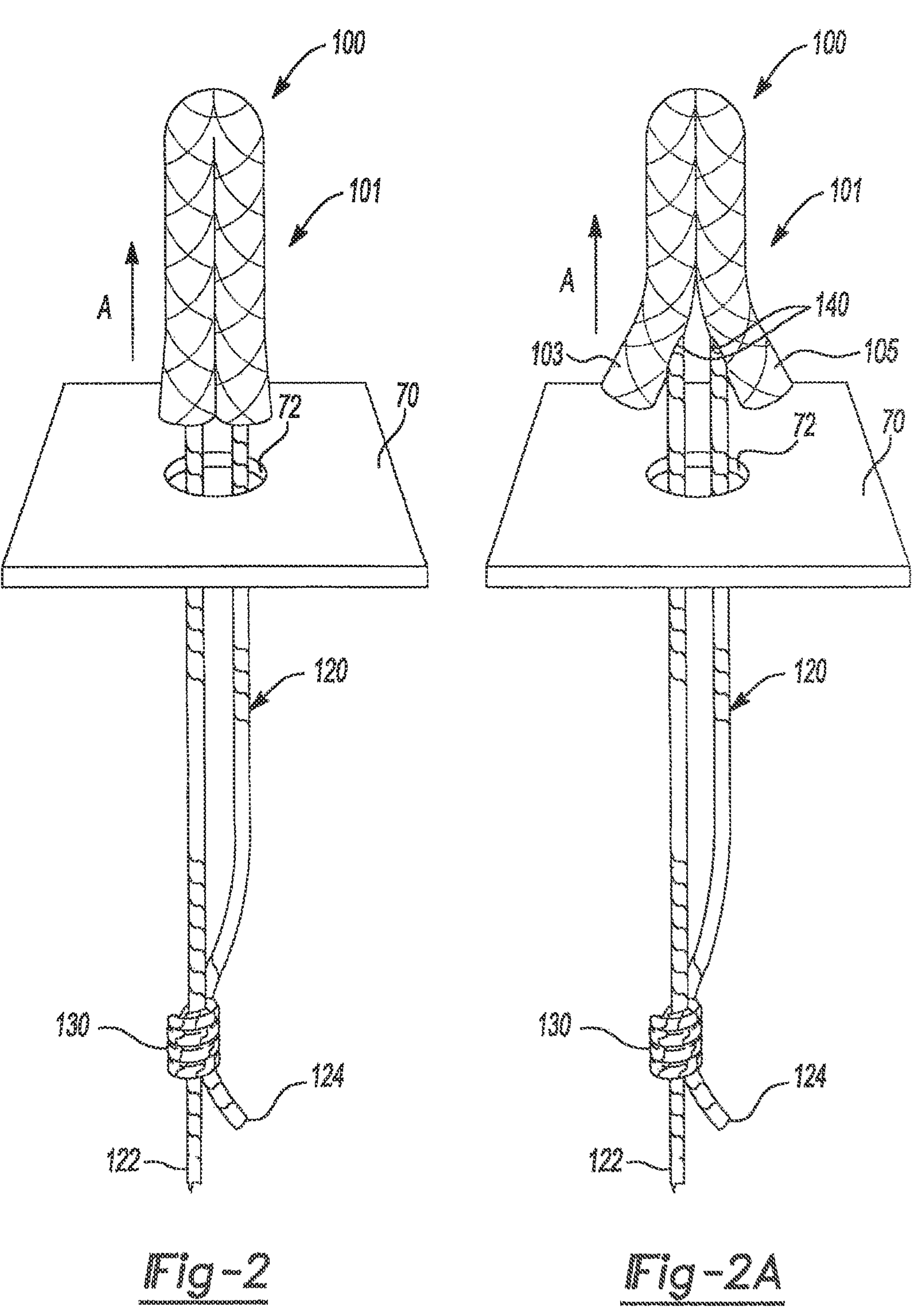
FIG. 2 is a perspective view of the connector device of FIG. 1, shown prior to engagement with a representative aperture.
FIG. 2A is a perspective view of the connector device of FIG. 1C, shown prior to engagement with a representative aperture.

Referring to FIGS. 1-3A, a general procedure for using the connector device 101 is illustrated. The sleeve 100 with the strand 120 therethrough can be folded and pushed through on orifice 72 or other aperture defined through a support 70 in the direction of arrow "A", as shown in FIGS. 2 and 2A. The strand ends of 122, 124 can be connected with a knot 130, such as slipknot, forming a strand loop 128 passing through the bore 106 of the sleeve 100.

Figures 3, 3A:
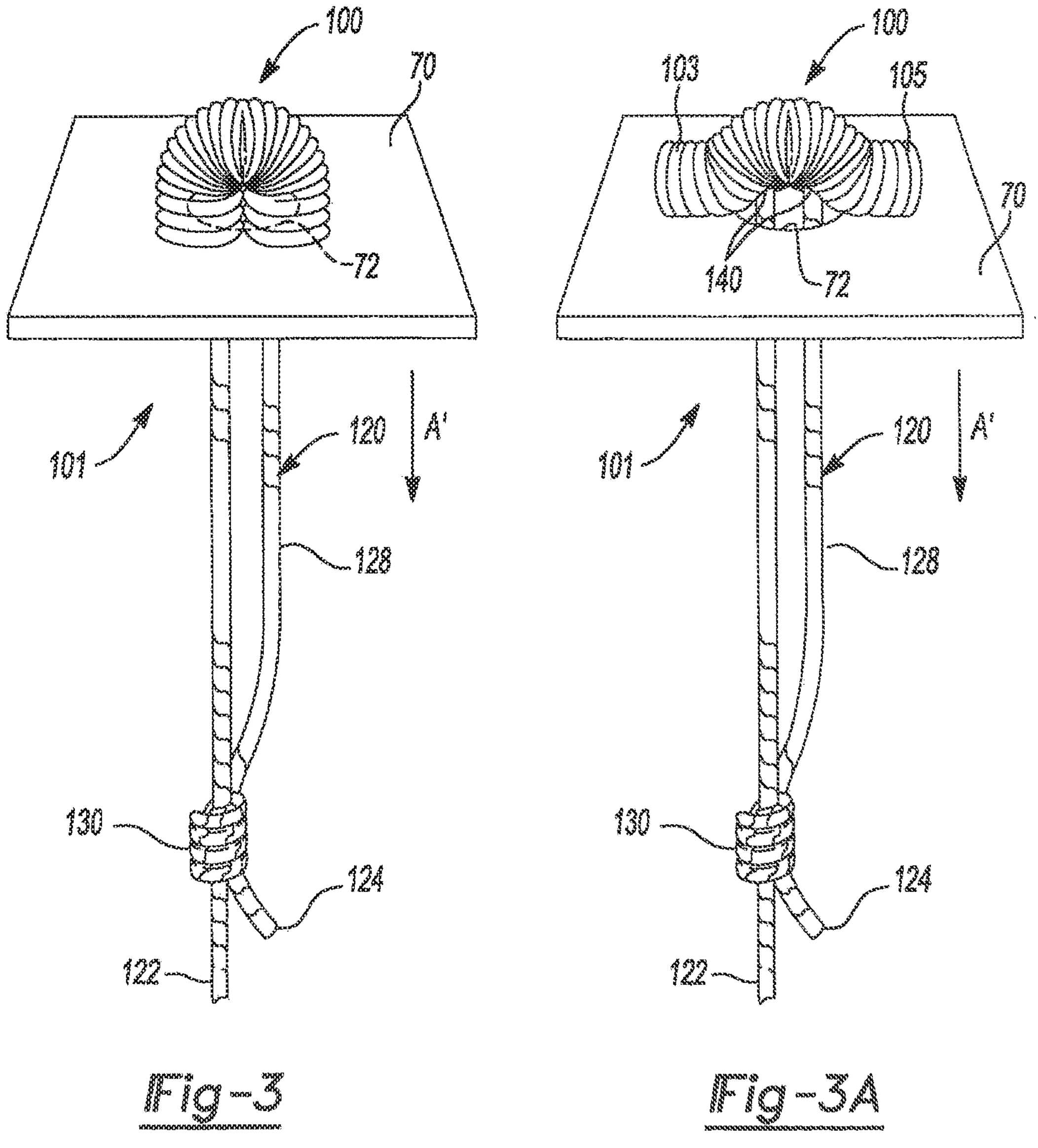
FIG. 3 is a perspective view of the connector device of FIG. 1, shown in engagement with a representative aperture.
FIG. 3A is a perspective view of the connector device of FIG. 1C, shown in engagement with a representative aperture.

Referring to FIGS. 2 and 3, pulling on one of the strand ends 122, 124, shortens the length of the strand loop 128 and the tension causes the sleeve 100 to change configuration, bunching up from a folded and/or flaccid configuration to a bunched-up, ball-like configuration that cannot pass through the orifice 72, such that the strand 120 can be secured on the support 70. In this configuration, the strand ends 122, 124 and the sleeve 100 remain on opposite sides of the orifice 72.

Similarly, and referring to FIGS. 2A and 3A, pulling on one of the strand ends 122, 124, shortens the length of the strand loop 128 and the tension causes the sleeve 100 to change configuration, bunching up from a folded and/or flaccid configuration to a bunched-up bell-like shape with the legs 103, 105 extended outward and pressed against the support 70. In this configuration, the sleeve 100 cannot pass through the orifice 72 in the direction of the arrow A'. The strand ends 122, 124 and the sleeve 100 remain on opposite sides of the orifice 72, and the legs 103, 105 provide additional resistance for securing the strand 120 to the support 70.

The orifice 72 can be of any shape, including any regular or irregular closed curves or polygons, or combination thereof, including circular elliptical, oval, triangular, tetragonal, hexagonal, lobed, or other shapes. The shape and size of the orifice 72 is such that the sleeve 100 in its bent shape deforms sufficiently to slide through the orifice 72 when introduced along one direction A. Once the sleeve 100 passes through and out of the orifice 72 and returns to its undeformed flaccid configuration, the sleeve 100 will bunch up against the orifice 72 when directed or pulled in the opposite direction A', as the ends 102, 104 of the sleeve 100, or the sleeve legs 103, 105, and/or deformed shape are caught against the support 70. It is noted that the strand 120 can still slide relative to the sleeve 100 and the orifice 72, therefore the orifice 72 can act effectively as an anchor eyelet.

The support 70 can be soft tissue, bone, implant, anchor or other threaded or unthreaded implantable fixation member such as those illustrated in FIGS. 5-8 at 200. The fixation members are generically referenced with numeral 200 or specifically with reference numerals 200*a*-200*d*. The connector device 101 and the fixation member 200 can form an implantable fixation assembly that can be used for securing soft tissue to bone, as further discussed below in connection with FIG. 9.

It will be appreciated that the connector device 101 can be used as a versatile suture lock that is easy to use, avoids knot-tying, and saves time during the surgical procedure. Further, as the flexible strand 120 is held against the support 70, the flexible strand 120 is prevented from pulling through without being knot-tied to the support 70. It is estimated that the flexible strand 120 can withstand a pulling force greater than that in a knot tied in the same-sized strand.

Any of the connector devices 101 illustrated in FIGS. 1, 1A, 1B, 1C, or combinations thereof, can be used with a fixation member 200 for fastening any type of ligaments, grafts or sutures, and can be used, for example, for rotator cuff repair for the shoulder, for acromioclavicular (AC) joint reconstruction, for tibial graft fixation, for ACL reconstruction, and generally for fastening tendons or grafts and sutures to tissue, including soft tissue and bone. In many of such shoulder repair procedures, a tendon is secured to the bone with many suture anchors requiring repeated knot-tying. Such knot-tying is cumbersome and time consuming during an arthroscopic procedure, as it is generally performed through an insertion cannula that is used to deliver the suture anchor. As discussed below, the connector device 101 illustrated in FIGS. 4 and 9 can be used to secure multiple suture anchors or other fixation members 200 without individual knots for each fixation member 200, and with only one final knot 130 for the entire series of fixation members 200 outside the cannula. Moreover, the knot 130 that forms the single loop 128 of the flexible strand 120 can be pre-tied.

Figure 4:
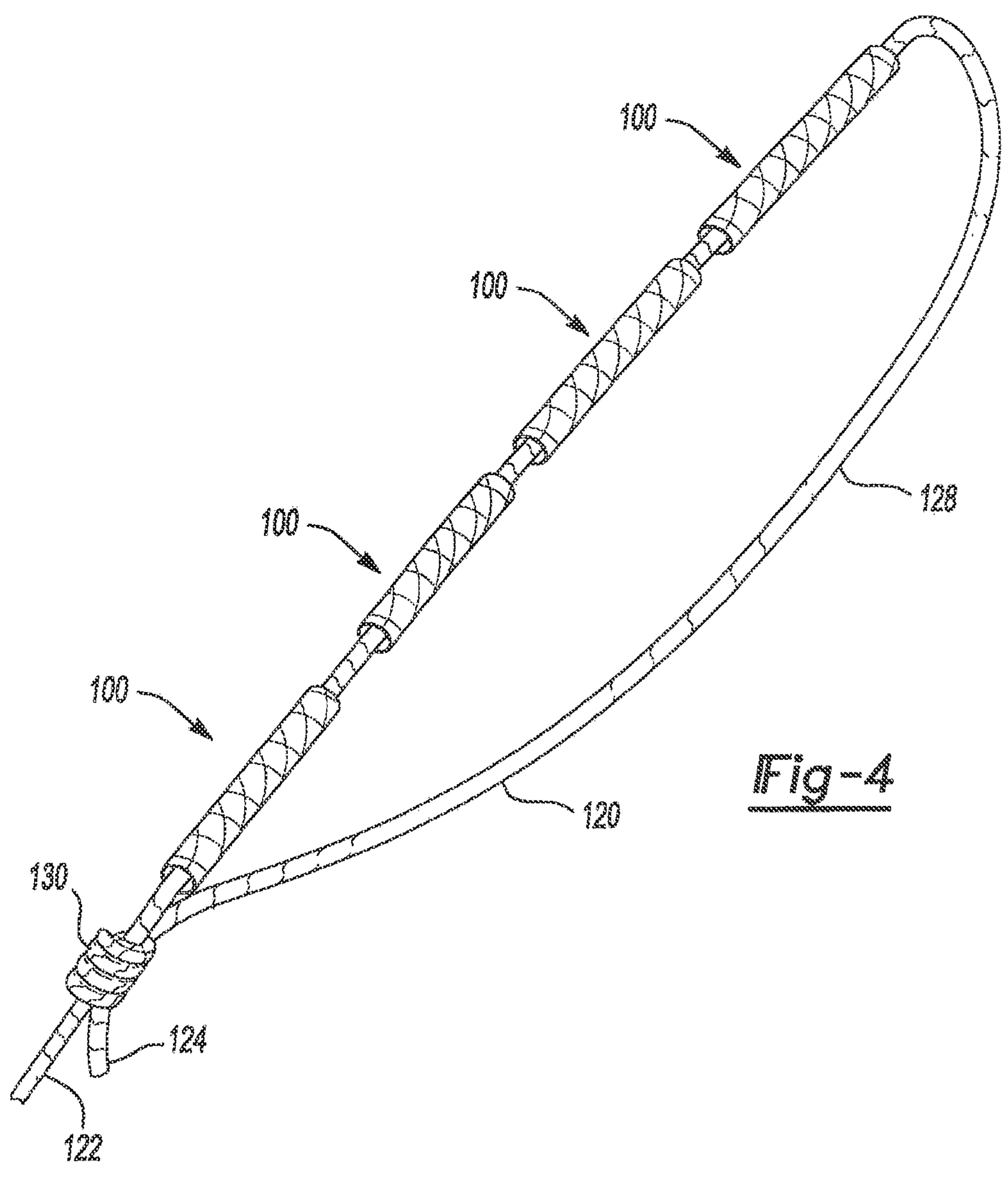
FIG. 4 is a perspective view of a series of interconnected connector devices according to the present teachings.
Figures 5, 6, 7, 8:
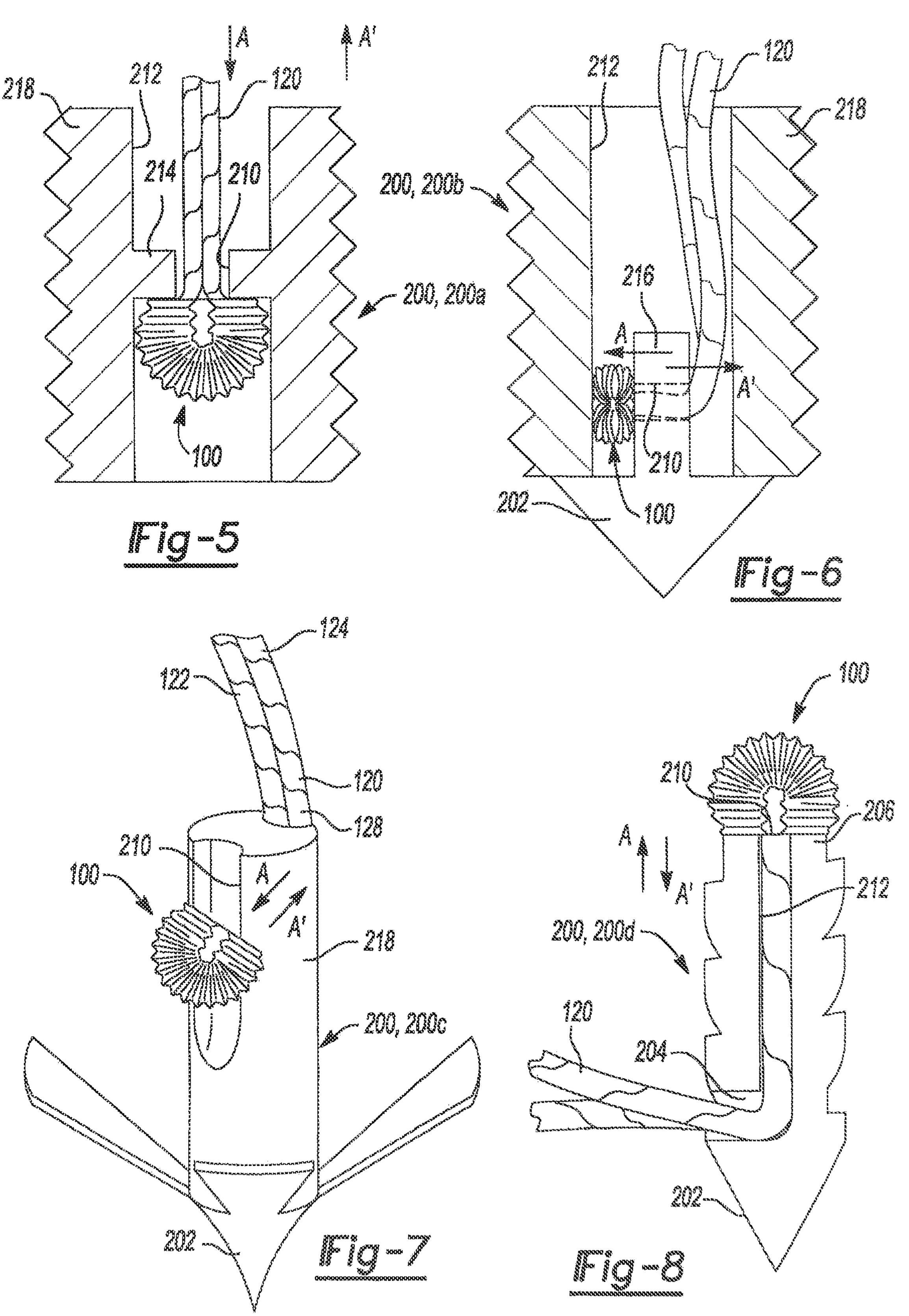
FIG. 5 is a side view of the connector device of FIG. 1, shown with a first anchor.
FIG. 6 is a side view of the connector device of FIG. 1, shown with a second anchor.
FIG. 7 is a side view of the connector device of FIG. 1, shown with a third anchor.
FIG. 8 is a side view of the connector device of FIG. 1, shown with a fourth anchor.
Figure 9:
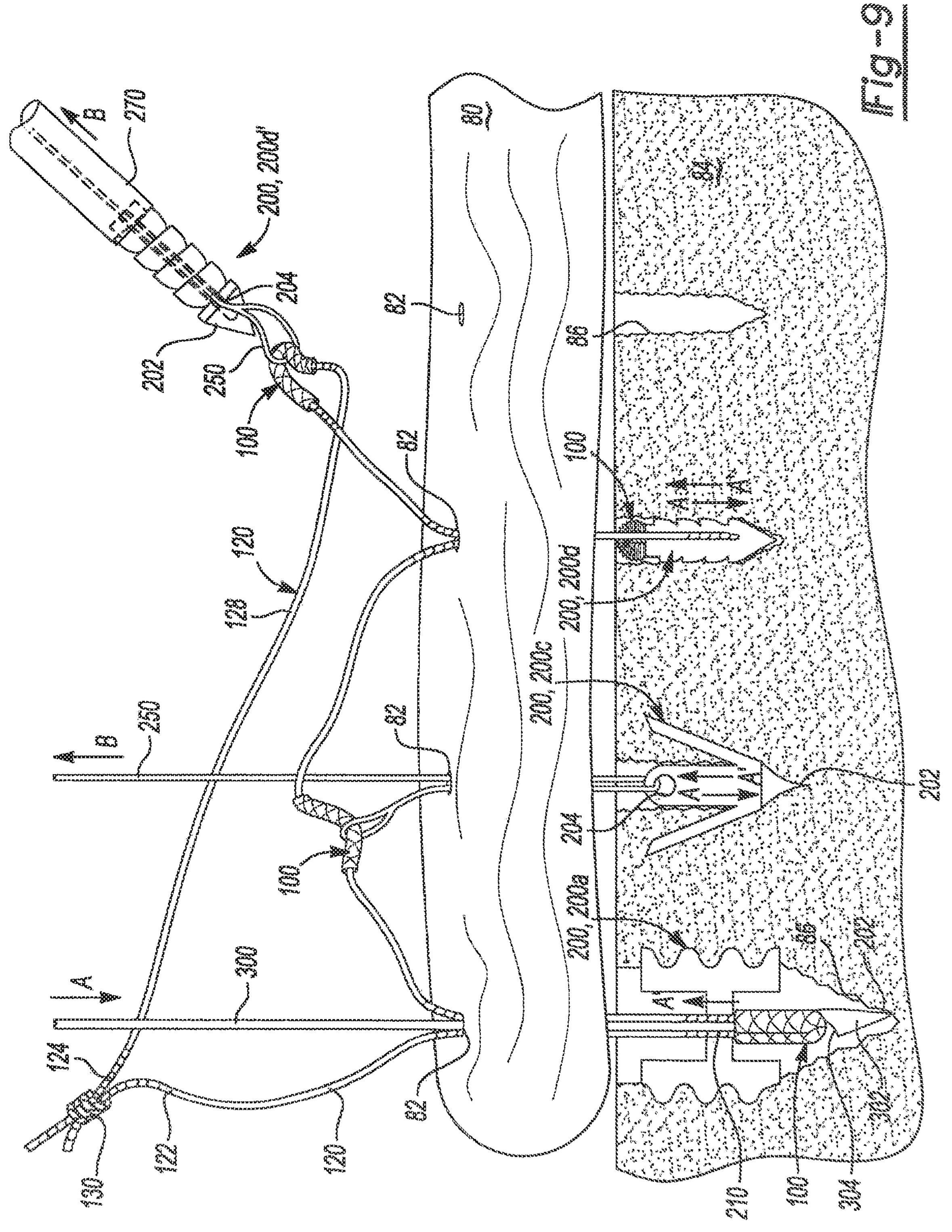
FIG. 9 is an exemplary method of using a series of interconnected connector devices for securing soft tissues to bone.
Figures 10A, 10B:
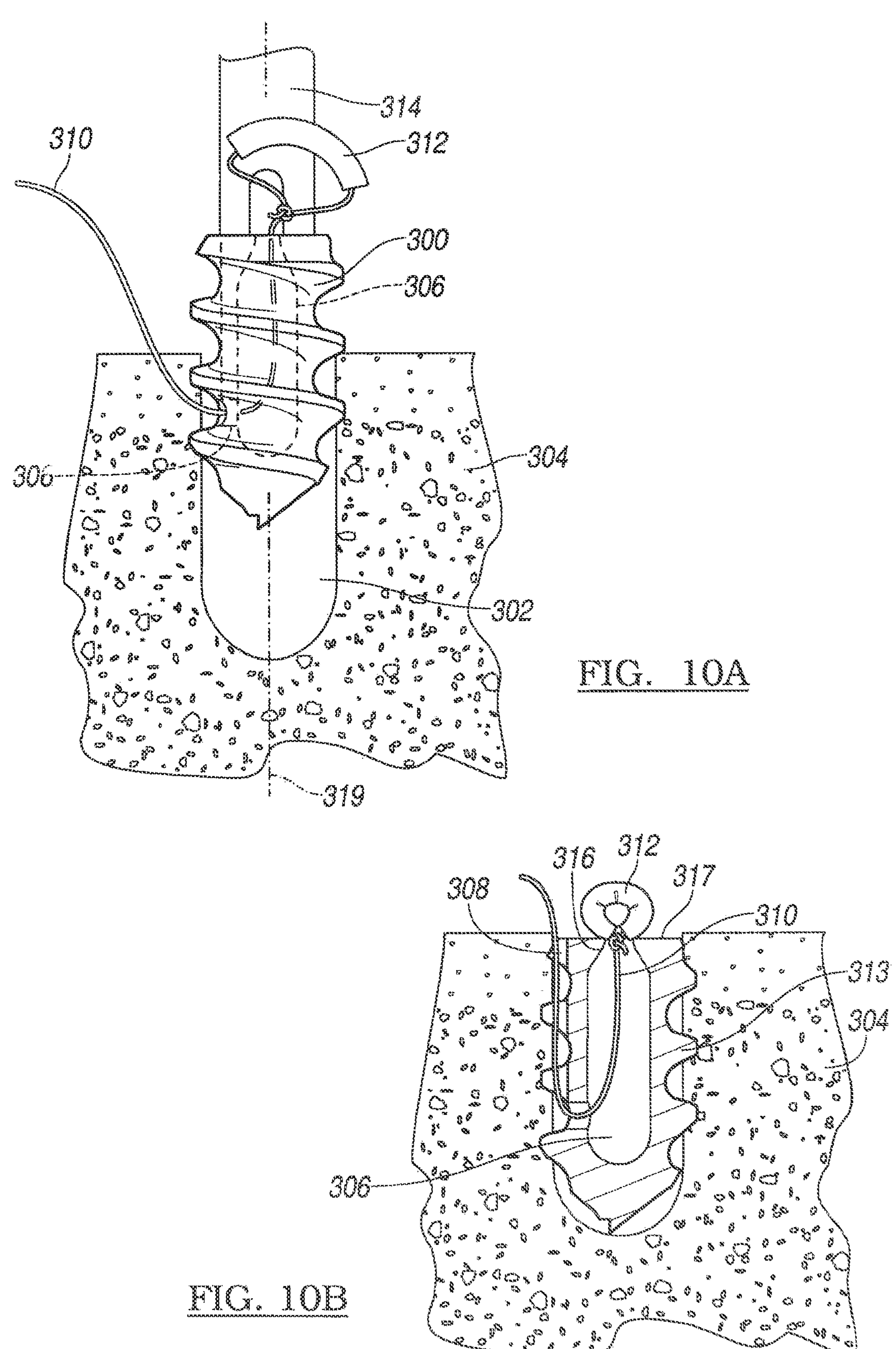
Figure 11A:
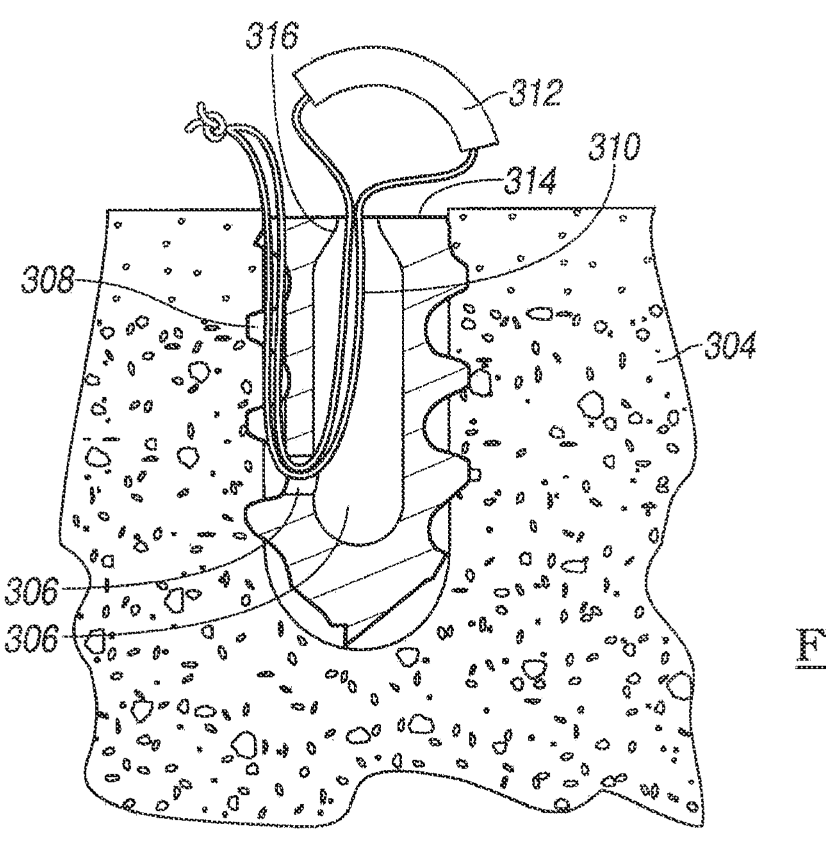
Figure 11B:
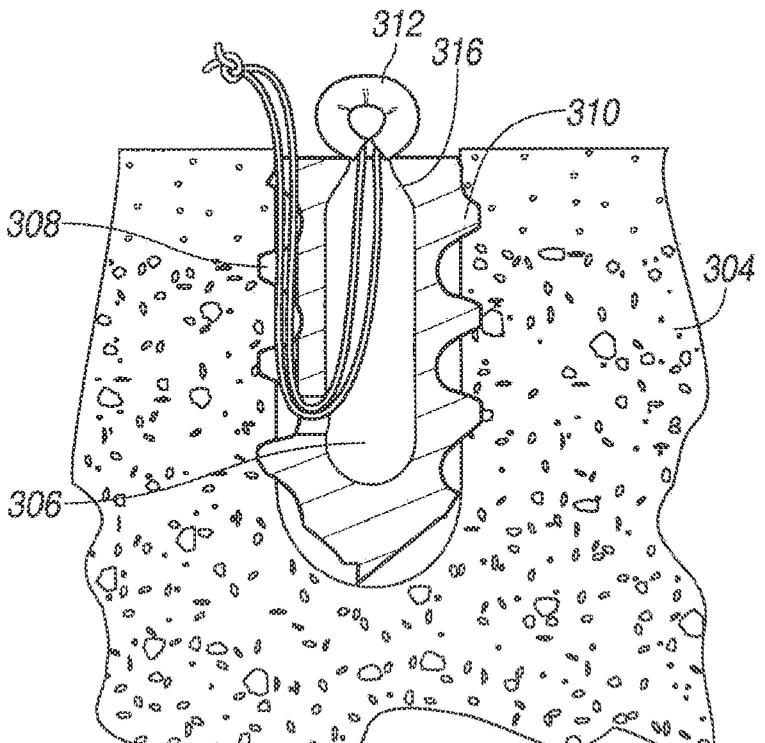
Figure 12A:
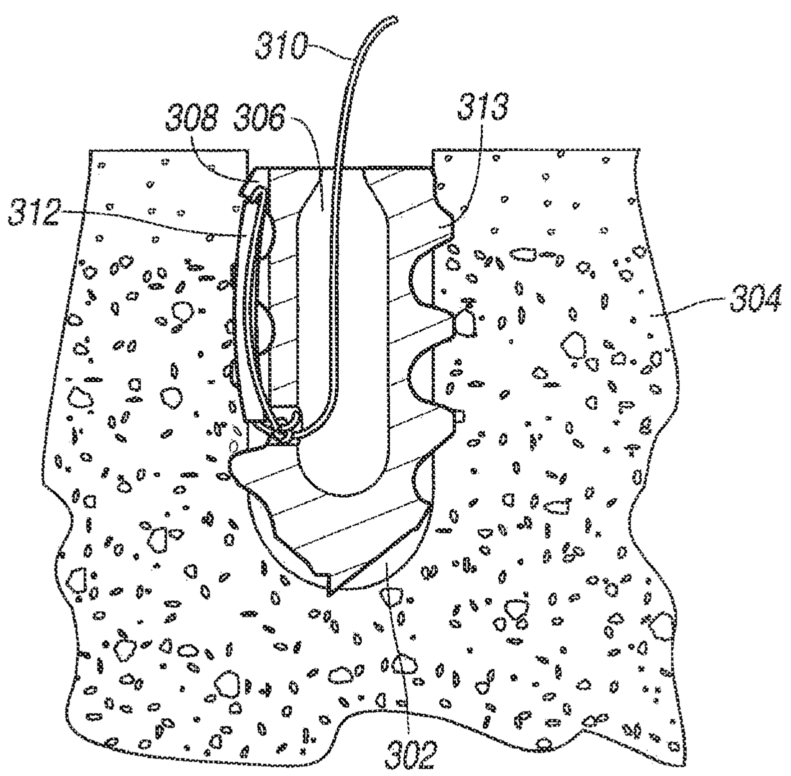
Figure 12B:
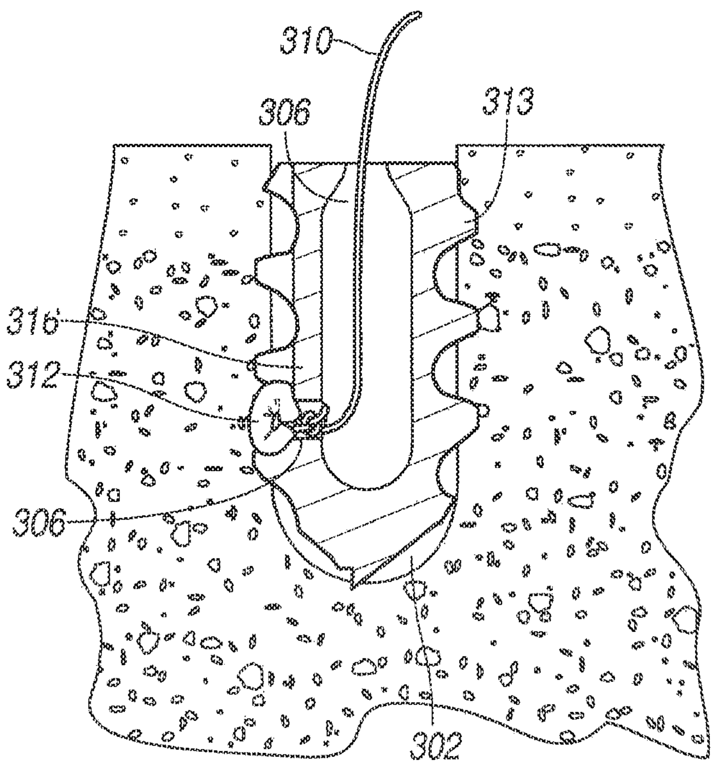
Figure 16A:
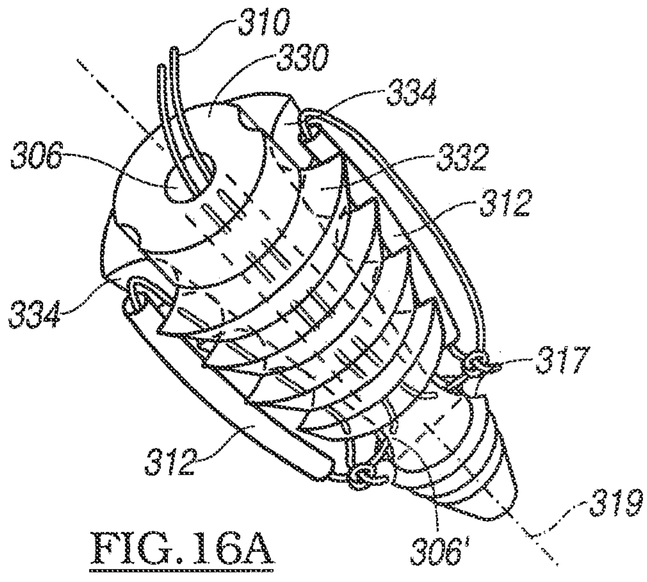
FIGS. 16A-18C represent alternate fasteners and suture constructions according to the teachings of one embodiment.
Figure 16B:
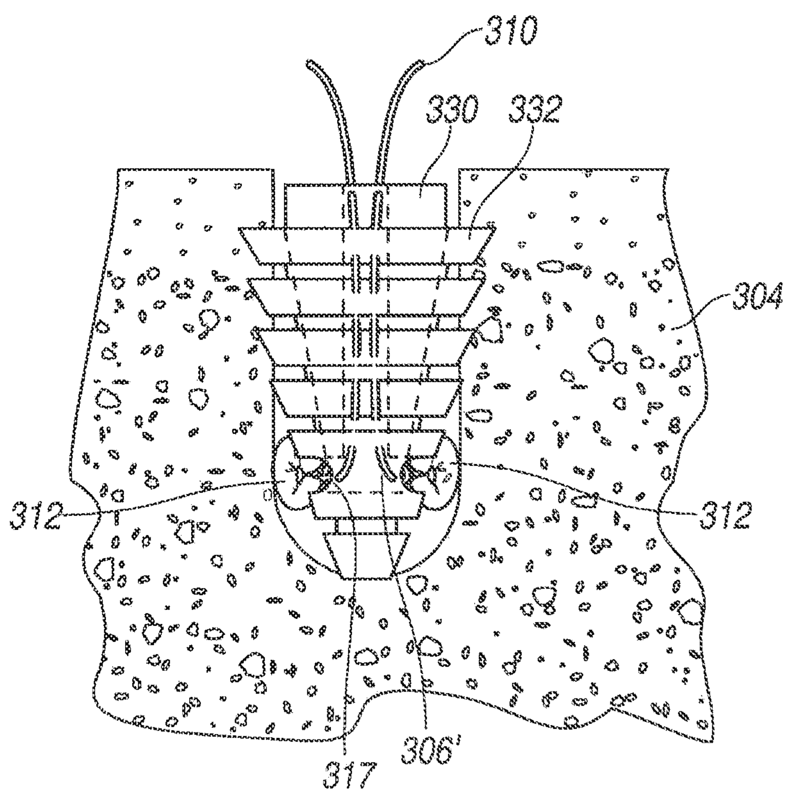
Figure 17:
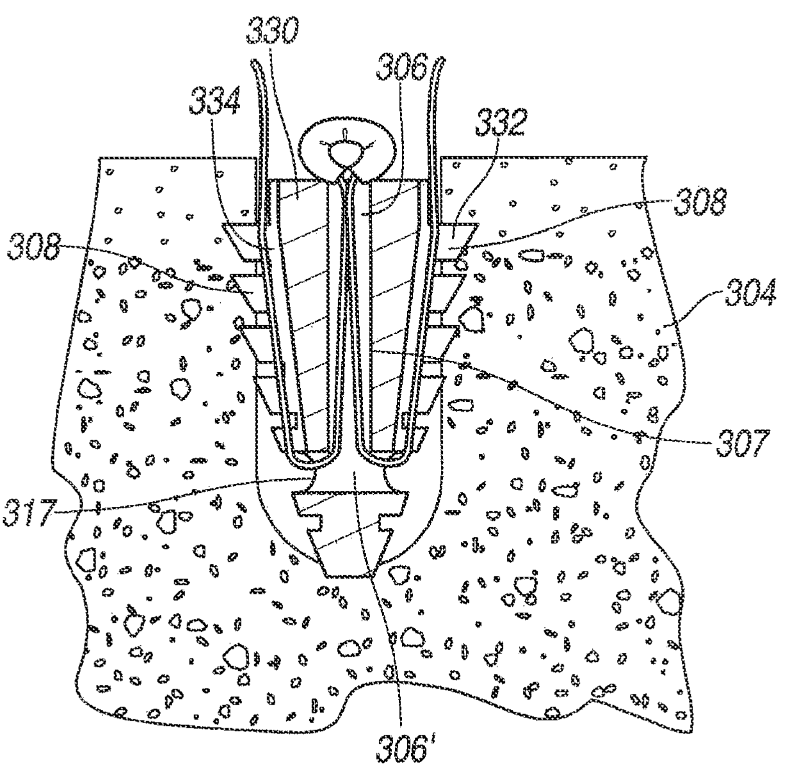
Figure 18A:
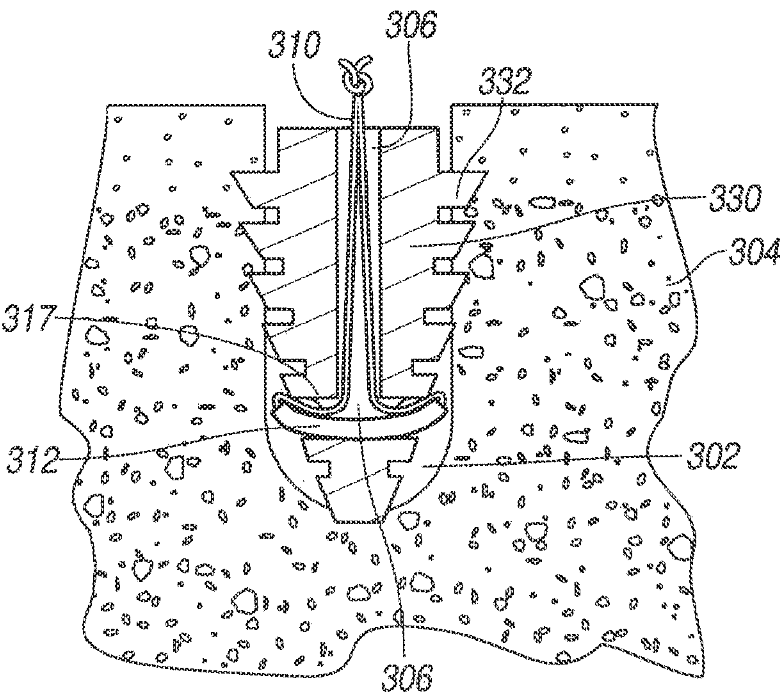
Figure 18B:
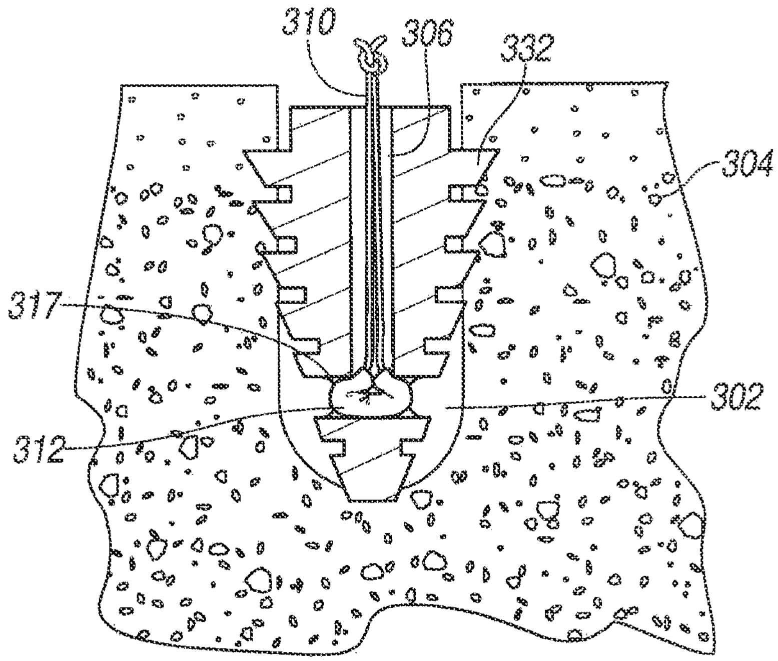
Figure 18C:
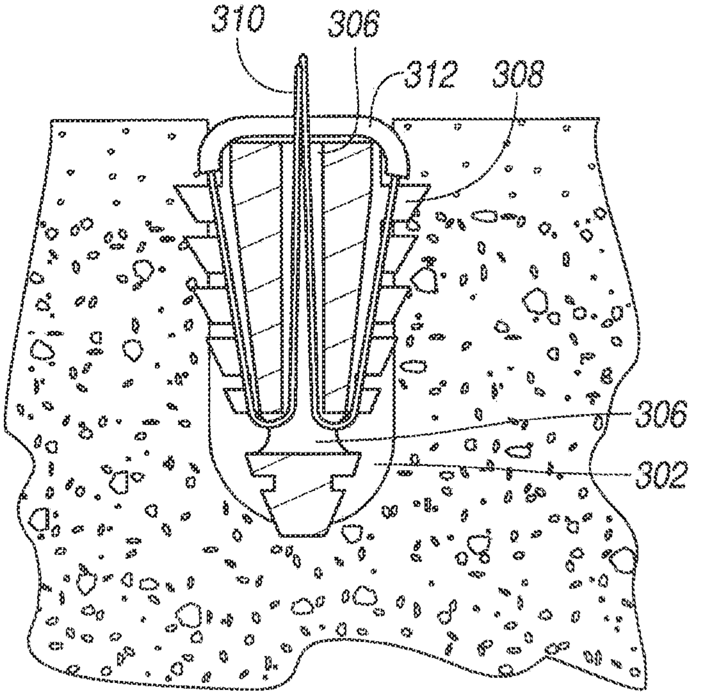

Referring to FIG. 5, the fixation member 200 can be in the form of an externally threaded open-ended tubular member 200*a* and can include a body 218 having an open-ended longitudinal bore 212 interrupted by a cross-wall 214. The wall 214 defines a through-slot or other aperture 210 substantially coaxial with the bore 212. The sleeve 100 can pass through the aperture 210 in a folded configuration in the direction of arrow A, while the strand ends 122, 124 of the strand 120 remaining outside the fixation member 200. The sleeve 100 can be held against the wall 214 in a bunched-up (ball or bell-like) configuration when pulled by the strand 120 in the direction A'. In the same manner, a plurality of sleeves 100 strung together in a single loop 128 of a single strand 120, as shown in FIG. 4, can be secured to a corresponding plurality of fixation members 200, without requiring individual knots, as shown in FIG. 9 and discussed below. Using a plurality of sleeves 100 in a single loop 128 allows a fast and efficient procedure of creating a suture mat for attaching soft tissue 80 to bone 84 in multiple locations without having to tie knots arthroscopically through a cannula for each individual fixation member 200.

Referring to FIG. 6, the fixation member 200 can be an implant in the form of a tubular anchor 200*b* having a body 218 and include a longitudinal bore 212 closed at one end with a pointed anchoring tip 202. The anchoring tip 202 can be integrally or removably coupled to the body 218. The anchoring tip 202 can include a longitudinal extension 216 received in the bore 212. The extension 216 can define an aperture 210 substantially parallel with the bore 212. The sleeve 100 can be passed through the aperture 210 in the direction of arrow A, such that the strand 120 passes through the aperture 210, through the bore 212 and exits the fixation member 200. The sleeve 100 can be held between a wall of the bore 212 and the extension 216 in a bunched-up (ball or bell-like) configuration after the strand 120 is pulled away from the fixation member 200 in another direction, such as the direction of arrow A'. It should be appreciated that the directions A and A' need not be opposite. Pulling in any direction A' that will cause the strand 120 to tension can suffice. Although FIGS. 5 and 6 illustrate examples of an aperture 210 that is respectively coaxially or perpendicularly oriented relative to the bore 212 of the fixation member 200, it will be appreciated that the aperture 210 is not limited to these orientations. The fixation member 200*b* can also be used in a single loop 128 with multiple similar or different fixation members 200 for attaching soft tissue 80 to bone 84 in multiple locations, as illustrated in FIG. 9.

Referring to FIG. 7, the fixation member 200 can be an implant in the form of harpoon-type anchor 200*c* having a pointed anchoring tip 202. The fixation member 200 can include a central body 218 defining an aperture 210. The sleeve 100 can be passed through the aperture 210 in the direction of arrow A. The strand 120 can form a loop 128 passing through the aperture 210 in the direction of arrow A. The strand ends 122, 124 can be pulled away from the fixation member 200 in the direction of arrow A', such that the sleeve 100 is held against the body 218 in a bunched-up (ball or bell-like) configuration. The fixation member 200*c* can also be used in a single loop 128 with multiple similar or different fixation members 200 for attaching soft tissue 80 to bone 84 in multiple locations, as illustrated in FIG. 9.

Referring to FIG. 8, the fixation member 200 can be an implant in the form of an externally threaded suture anchor 200*d* having a body 218 with an anchoring tip 202 and including a longitudinal bore 212 extending from a proximal end 206 to a distal eyelet 204. The sleeve 100 can be passed through the eyelet 204, the bore 212 and the aperture 210 defined at proximal end 206 of the bore 212 in the direction of arrow A. The strand 120 can form a loop 128 passing through the bore 212 and exiting the eyelet 204. The strand ends 122, 124 can be pulled away from the fixation member 200 in the direction of arrow A', such that the sleeve 200 can be secured against the proximal end 206 in a bunched-up (ball or bell-like) configuration. The fixation member 200*d* can also be used in a single loop 128 with multiple similar or different fixation members 200 for attaching soft tissue 80 to bone 84 in multiple locations, as illustrated in FIG. 9.

The connector device 101 can be pushed through the aperture in the fixation member 200 using an inserter, such as the inserter 300 shown in FIG. 9 and the inserter described and shown in FIGS. 8A-9B and 13-15 of the cross-referenced patent application Ser. No. 11/347,661 filed on Feb. 3, 2006, although other inserters can also be used. The sleeves 100 of the connector device 101 can be coupled to corresponding fixation members 200, either before or after the fixation members 200 are secured in the bone 84.

Referring to FIGS. 4 and 9, a series of sleeves 100 can be strung along a single loop or chain 128 of the strand 120 without other knots except a single slipknot 130 coupling the strand ends 122, 1224. Each sleeve 100 can be inserted in a corresponding prepared bone bore 84 or in a corresponding fixation member 200 to attach soft tissue 80 to a bone 84. It will be appreciated that identical or different fixation members 200, such as, for example, fixation members 200*a*-200*d*, can be used for securing the corresponding sleeves 100, and one or more fixation members 200 can be omitted, such that the sleeve 100 is secured directly in a bone bore 86 without using a fixation member 200. Some exemplary options are illustrated in a single illustration in FIG. 9.

It will be appreciated that the sleeve 100 can be inserted or secured to the fixation member 200 either before or after the fixation member 200 has been implanted into the bone 84. For example, the sleeve 100 can be secured to the fixation member 200 prior to bone implantation, either manually or by using an inserter, such as the inserter 300 that includes a tip 302 and a hook 304 in which the sleeve can be supported in a folded, U-shape configuration with the strand 120 therethrough. Alternatively, and as illustrated in FIG. 9 in connection with the fixation member 200*a*, the fixation member 200*a* can first be implanted into bone 84. The tip 302 of the inserter 300 with the sleeve 100 thereon can be pushed through the aperture 210 of the fixation member 200*a* in the direction of arrow A.

Referring to FIG. 9 and in connection with the exemplary fixation member 200*c*, another method of securing the sleeve 100 to the fixation member 200*c*, after the fixation member 200*c* is implanted, is illustrated. Specifically, an auxiliary flexible member or string 250 in the form of a monofilament made of polyethylene, polyester, silk, or other biocompatible fiber or thin string-like material can be looped around the sleeve 100 and passed through the aperture 210 of the fixation member 200*c*. Pulling the auxiliary member 250 in the direction of arrow "B" causes the sleeve 100 and portion of the strand 120 to pass through the aperture 210 in a folded configuration. The auxiliary member 250 can be then pulled out and completely removed from the sleeve 100 and fixation member 200*c*. The sleeve 100 can be secured to the fixation member 200*c* in a bunched-up (ball or bell-like) configuration by pulling on the ends 122, 124 of the strand loop 128 to shorten the loop 128, as described above. In another aspect, the auxiliary flexible member 250 can be looped through openings 150, 152 of the sleeve 100, as shown in FIG. 1B.

With continued reference to FIG. 9, fixation member 200*d* is shown implanted in bone bore 86 with the sleeve 100 shown in a bunched-up (ball or bell-like) configuration. Another fixation member 200*d'* is illustrated before implantation into the bone bore 86. The fixation member 200*d'* can be coupled to a cannulated or other fixation-member inserter 270 for insertion through an incision or other opening 82 in soft tissue 80 and into a bone bore 86. The opening 82 can be pre-formed with another surgical instrument or by the pointed tip 202 of the fixation member 200*d'* as it is pushed through the soft tissue 80. Similarly, the bone bore 86 can be pre-formed, or created by the threaded fixation member 200*d'* as it is threadably inserted into the bone 84. An auxiliary member 250 can be used to manipulate the sleeve 100 and secure the sleeve 100 into the fixation member 200*d'*, as described above in connection with fixation member 200*c*. The auxiliary member 250 can be looped around the sleeve 100 and passed through the eyelet 204 into the bore 212 and out of the aperture 210 at the proximal end 206. The sleeve 100 can be pulled through the eyelet 204, the bore 212 and aperture 210 by pulling the auxiliary member 250 in the direction of the arrow B either before or after implantation of the fixation member 200*d'* into the bone 84.

After all the sleeves 100 have been secured to the corresponding fixation members 200, the single loop 128 is tightened by pulling one of the strand ends 122, 124 relative to slipknot 130. In this manner, tissue to tissue attachment in multiple locations without the need of individual knots for each location is conveniently performed, thus avoiding the need of tying individual knots through cannulas for each fixation member 200. The procedure can be used for any tissue to tissue attachment, including, but not limited to, various arthroscopic procedures, such as, for example, rotator cuff repair, acromioclavicular reconstruction, and other procedures for which multiple anchor fixation can be beneficial. The procedure can be performed efficiently by simply passing by pulling or pushing the connector device 101 through an aperture or eyelet of the anchor or other fixation member 200 in one direction and then tensioning or pulling the strand 120 of the connector device 101 in the another direction for a knotless attachment of the strand 120 to the fixation member 200. The pull-out strength of the attachment can be a function of the strand size, but greater than using a mere strand with a knot.

Generally, and described above, the connector device 101 including one or more sleeves 100 can be to secure a strand 120, such as a suture to soft tissue 80 or bone, and to attach soft tissue to bone. Any of the connector devices 101 illustrated in FIGS. 1, 1A, 1B and 1C, can be used with or without a fixation member 200 and with or without an inserter 300 and with or without an auxiliary member 250 for manipulation the sleeve 100, although only the connector 101 of FIG. 1 is shown in the exemplary illustrations of FIGS. 4-9. Accordingly, a fixation assembly kit can be provided that includes, for example, a plurality of sleeves 100, a cartridge of continuous stand 120 or separate pieces of strand 120, a cartridge or separate pieces of auxiliary member material, one or more inserters, various fixation members 200, and one or more fixation member inserters 270. The sleeves 100 and strand 120 can be provided preloaded on one or more inserters 300. When a fixation member 200 is used, the fixation member 200 can be provided preloaded on a fixation member inserter 270. The connector device 101 allows tissue to tissue attachment in multiple locations without the need of individual knots for each location. After multiple-location attachment is performed, the single loop 128 is tightened by pulling one of the strand ends 122, 124 relative to slipknot 130.

With general reference to FIGS. 10A-15, shown is a fastener 300 which is coupled to a bore 302 defined within a bone 304. The fastener 300 defines a suture accepting aperture 306 and a suture accepting channel 308. In this regard, the suture accepting channel 308 is defined on an exterior surface of the fastener 300 and can intersect the aperture 306. Coupled to the fastener 300 is a suture construction 310 as previously described.

The fastener 300 has an exterior surface having a bone engaging flange 313. This bone engaging flange 313 can be a helical thread which circumscribes a central axis 319 defining the fastener 300. The suture construction 310 is fed in a first direction through the suture accepting aperture 306. Optionally, defined adjacent a suture bearing surface 317 of the fastener 300, is a portion of the suture accepting aperture having a restricted diameter 316. As will be described further below, the restricted diameter 316 and bearing surface 317 are configured to engage first and second ends of the flexible sleeve 312 to facilitate the collapsing or change in cross-section of the flexible sleeve 312 when the flexible sleeve 312 is pulled in a second direction. This allows the locking engagement of the suture construction 310 to the fastener 300.

Shown in FIGS. 10A-11B are fasteners 300 engaged within the bore 302 in bone 304. Shown are sutures 310 fed through the suture accepting aperture 306 and then through the channel 308 which is defined in the exterior surface of the fastener 300 and/or within the bone engaging flange 313. As shown in FIGS. 12A-15, the flexible sleeve can be positioned within the suture accepting channel 308 prior to the insertion of the fastener 300 within the bore 302 defined in the bone 304. Upon application of tension to the single or multiple suture strands 310, the suture can be translated in the second direction through the aperture 306 having a restricted diameter 316 to cause engagement of and subsequent collapsing of the flexible sleeve 312. This collapsed sleeve 312 has a second cross-section which allows for the interference of the threads within the bore 302 defined in the bone 304, thus restricting the rotation of the fastener 300 within the bore 302. Further, the collapsing of the tube 312 allows for the fixing of the suture 310 to the fastener 300.

As best seen in FIGS. 14 and 15, the suture accepting aperture 306 can have various profiles. In this regard, the suture accepting aperture 306 can have a first portion having a first diameter 320 and a second portion 322 having a second diameter smaller than the first portion. This first portion 320 can define a chamber 323 which functions to accept the collapsed flexible sleeve. Additionally, the channel 308 can be sized so as to allow the collapse of the flexible sleeve 312 in a manner which would not restrict the rotation of the fastener 300 within the bore 302 defined within the bone. Drive surfaces can additionally be formed within the chamber 323.

With general reference to FIGS. 16A-18C, shown are an alternate fastener 330 which is used to couple suture 310 to a bone 304. The fastener 330 has a central suture accepting aperture 306 which is generally defined along a central axis 319 of the fastener 330. Additionally, defined generally perpendicular to the center line of the fastener is a second suture accepting aperture 306'. The fastener 330 has a plurality of bone engaging flanges 332 which are radially disposed about the central axis 319. The bone engaging flanges 332 can be formed generally perpendicular to the central axis 319.

As best seen in FIGS. 16B-18B, the fastener 330 can have a generally conical shape to facilitate the insertion of the fastener 330 within the bore 302. This conical shape can also be defined on the exterior surface of the bone engaging flanges 332. Defined within the bone engaging flanges 332 or an exterior surface of the fastener 330 can be a pair of suture or flexible sleeve accepting channels 334. Prior to insertion of the fastener 330 into the bore 302, either of the suture and/or a non-compressed flexible sleeve 312 can be positioned within the channels 334.

The fastener 330 can be liner or rotatably inserted into the bore 302. After insertion of the fastener 330 within the bore 302, tension is applied to one or more of the suture strands 310 to cause the movement of the flexible sleeve 312 in a first direction. This causes the flexible sleeve 312 to engage a bearing surface 317 of the fastener 330. The engagement of the flexible sleeve 312 with the bearing surface 317 causes the collapse of the flexible sleeve as been previously described. This functions to lock the suture 310 to fastener 330 and to increase retention forces between the fastener 330 and the bore 302.

Figures 19A, 19B, 19C, 20:
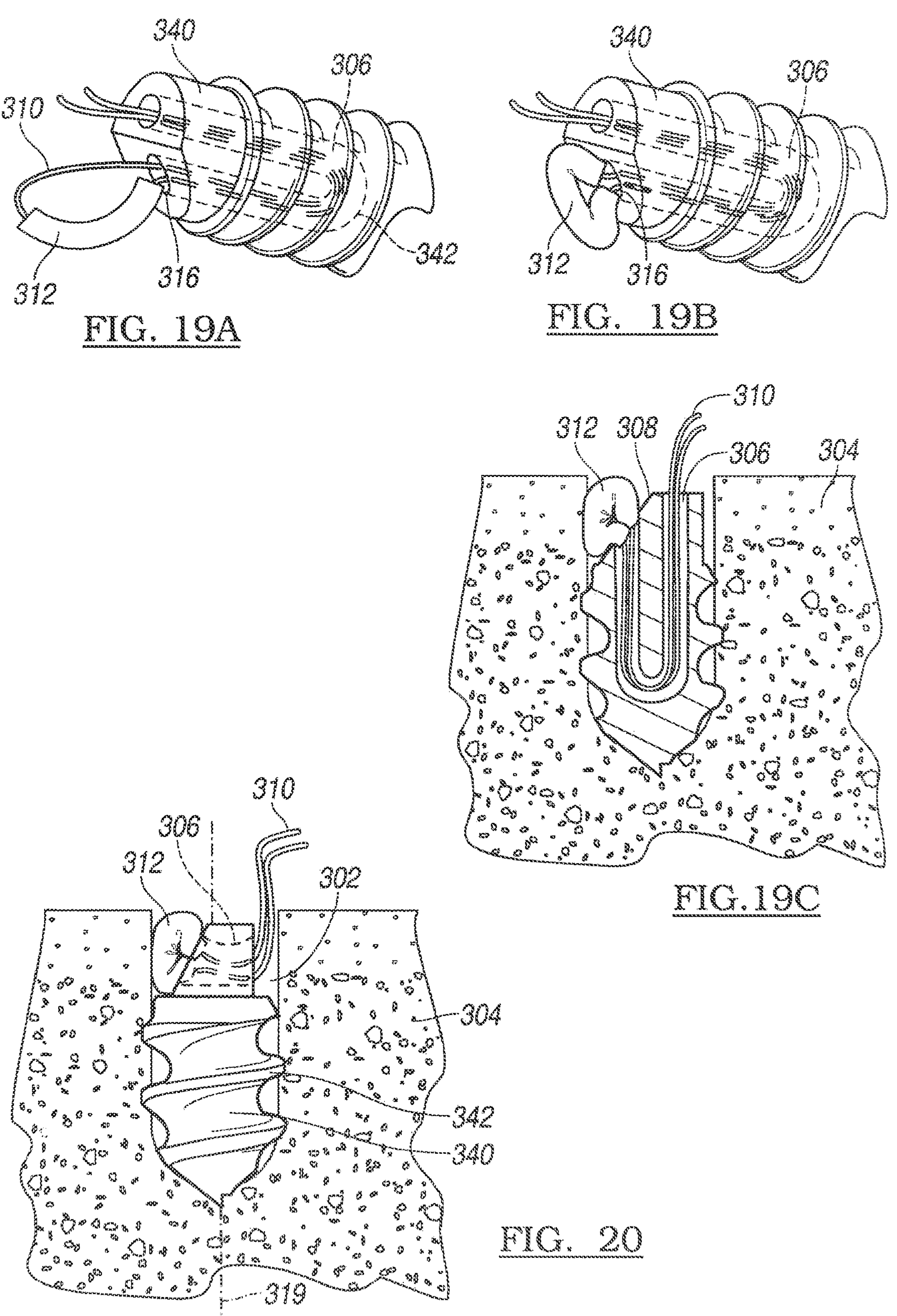
Figure 21:
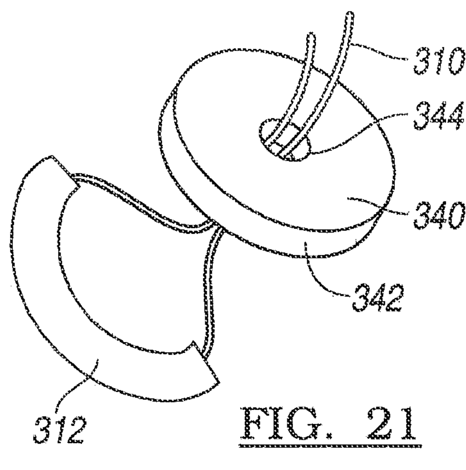
FIGS. 21-24 represent an alternate fastener and suture construction according to the present teachings.
Figure 22:
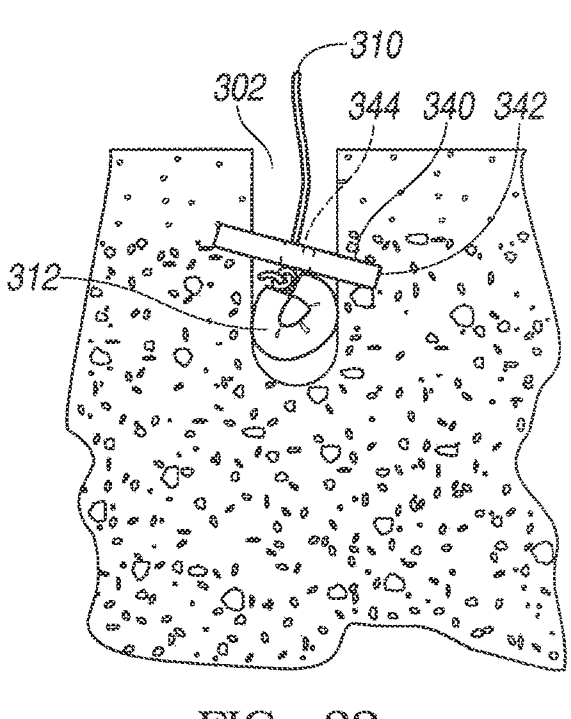
Figure 23:
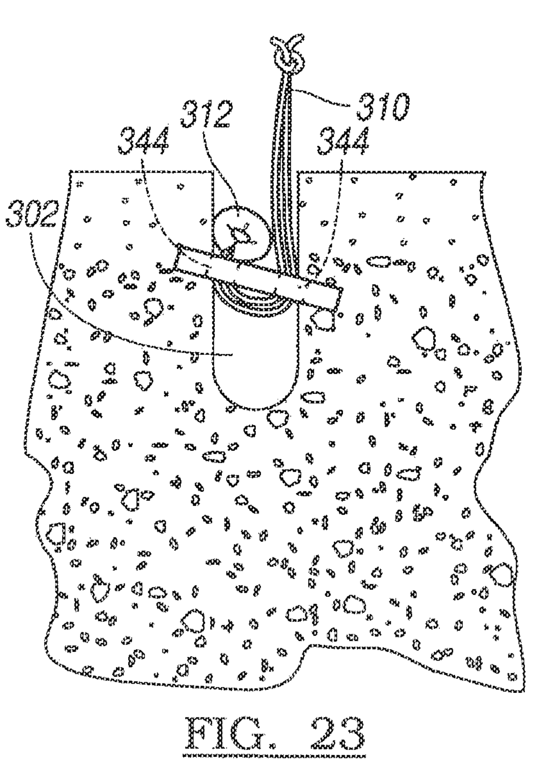
Figure 24:
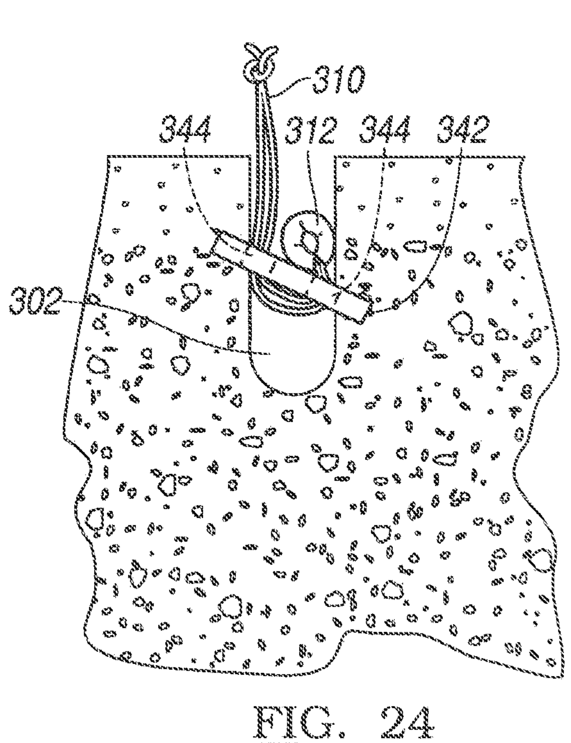

FIGS. 19A-20 represent an alternate fastener 340 coupled to a suture 310. The fastener 340 has a suture accepting bore 306 defined therein. This bore 306 can have portions which are parallel to and/or perpendicular to a central axis 319 defining the fastener body. The exterior of the fastener defines a channel or cutout 308 which functions to accept the collapsible sleeve 312 threaded onto the suture 310. This cutout 308 can be accessible through the bore 302 once the fastener 340 is inserted.

FIGS. 19C and 20 depict cross-sectional and side views of the fastener 340 inserted within a bore 302 defined within bone 304. Once tension is applied to the collapsible sleeve 312 and suture 310, the sleeve 312 is pulled into a pocket defined by the channel or cutout 308. This collapsible sleeve 312 can bear upon an interior surface of the bore 302 as well as the channel or cutout 308 to lock a suture 310 to the fastener 340, as well as aid in the fixation of construct in bone. Also shown are bone engaging flanges 342 which couple the fastener to bone 304.

As seen in FIGS. 21-24, an alternate anchor 340 is positioned within an aperture 302. The anchor 340 is rotated within the aperture 302 to engage the bone. Application of tension to an end or ends of the suture 310 can cause the anchor 340 to rotate and engage the bone. The alternate suture anchor 340 is coupled to a suture 310 and a collapsible sleeve 312. Optionally, the anchor 340 can take the form a generally flat cylinder or tube having a bone engaging surface 342 and a suture accepting bore 344 therethrough. While shown as a disk, it is envisioned the anchor 340 can have an elongated profile.

Application of tension to an end or ends of the suture construction 310 can cause the anchor 340 to rotate and engage the bone and to cause the collapse of the flexible sleeve 312. This fixably couples the suture 310 to the anchor 340 as well as the bone 304.

Figures 25A, 25B:
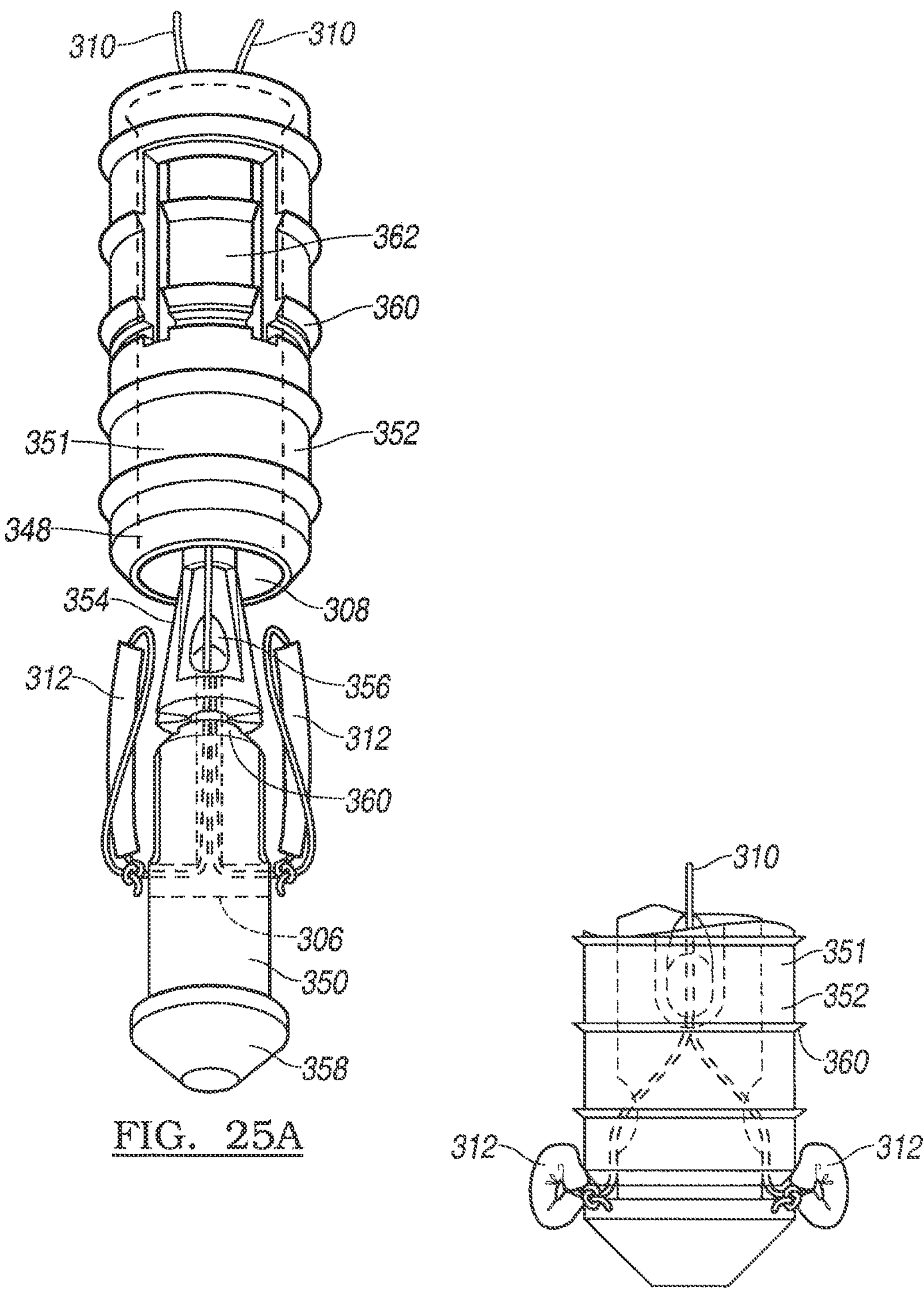
FIGS. 25A and 25B represent two-part fasteners and suture construction.

FIGS. 25A and 25B represent a fastener 348 having first and second portions 350, 352. Additionally shown is an insertion tool 354 which is used to facilitate the first and second fastener portions 350, 352 into an aperture 302 defined within a bone 304. The first portion of the fastener 348 has a head 358 which can have a generally conical shape. Additionally, the head 358 can have a bearing surface which functions, to constrain the movement of the suture construction 310 and/or the collapsible flexible tube 312.

The second fastener portion 352 has an interior portion 308 which can facilitate the acceptance of the flexible sleeve 312. Defined on an outer surface of the second portion 352 can be a plurality of bone engaging flanges 360. Optionally, the second portion can have an expandable member 362 which facilitates the engagement of the flanges 360 into the bone 304 upon the coupling of the first and second portions 350, 352. For installation, a central tool 354 has a pair of apertures with suture ends 310 threaded therethrough. The suture 310 can have a pair of flexible sleeves 312 being mounted thereon. These flexible sleeves 312 are optionally threaded through the suture accepting bore 306 defined within the first portion 350 of the two portion fastener 348.

FIG. 25B represents an assembled two component fastener 348 shown in FIG. 25A. In this regard, the first portion 350 is disposed within the central aperture 351 in the second portion fastener 352. As can be seen, the suture 310 is disposed between the first and second portions 350, 352. Application of tension to the suture 310 causes the collapse of the flexible sleeve 312 and associated locking of the suture construction 310 to the fastener 348.

Figures 26A, 26B, 26C:
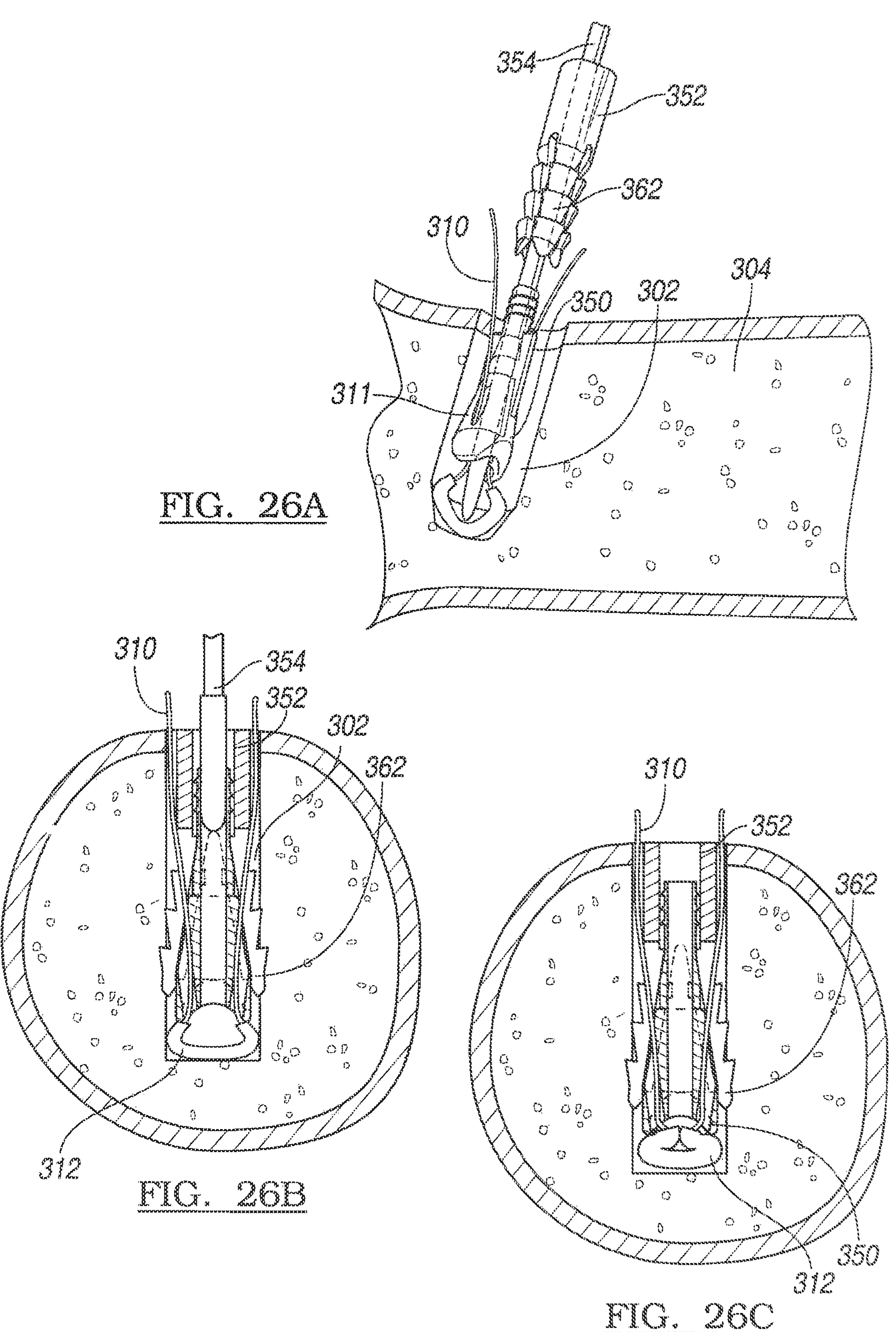
FIGS. 26A-26C represent the insertion of the fastener shown in FIGS. 25A and 25B.

With general reference to FIGS. 26A-27, shown is the insertion of a two-part fastener 348 according to the present teachings. Shown is the first portion 350 having a tapered smooth exterior surface, and a second fastener portion 352 having a plurality of movable bone engaging flanges 362. A pair of apertures 306 defined within the first fastener 350 accept the suture 310 and flexible sleeve 312.

As best shown in FIGS. 26B and 26C, the first and second portions of the fastener 350, 352 are fed over an insertion tool 354. Disposed on the first portion 350 of the fastener 348 is a suture 310 having the flexible sleeve 312 threaded thereon. Threaded through an optional pair of apertures 311 within the first fastener portion 350 is a pair of ends of the suture 310. These ends are then threaded through a central bore or a slot defined in the second fastener portion 352.

After the insertion of the fastener 348 into a bore 302 defined within the bone 304, the second fastener portion 302 is coupled to the first fastener portion 305. This coupling optionally causes an expansion of the bone engaging flanges 362. Tension can be applied to the ends of the suture 310 to cause the compression of the flexible member 312. This collapsing of the flexible member can then lock the suture 310 to the first and/or second portions of the fastener 350, 352.

The foregoing discussion discloses and describes merely exemplary arrangements. One skilled in the art will readily recognize from such discussion, and from the accompanying drawings and claims, that various changes, modifications and variations can be made therein without departing from the spirit and scope of the present teachings as defined in the following claims. For example, multiple fixation members can be inserted in bone and can be coupled to suture anchors as described. The suture anchors can be coupled to the anchors before or after the anchors are coupled to the bone.

What is claimed is:

1. A method of anchoring a flexible strand to bone, the method comprising:

locating an anchor and an auxiliary strand coupled to the anchor in a first bone hole with a first end of the auxiliary strand and a second end of the auxiliary strand extending away from the anchor outside the first bone hole, wherein the auxiliary strand being coupled to the anchor includes the auxiliary strand extending through a passage in the anchor inside the first bone hole; and pulling on the second end of the auxiliary strand, after said locating, so as to pull the first end of the auxiliary strand completely through the passage in the anchor and thereby pull a portion of a flexible strand that is coupled to the first end of the auxiliary strand completely through the passage, wherein, prior to said pulling, the flexible strand is already anchored in a second bone hole that is spaced apart from the first bone hole, wherein said locating leaves the first end of the auxiliary strand extending out of the anchor through a first exterior opening in the anchor and the second end of the auxiliary strand extending out of the anchor through a second exterior opening in the anchor such that said pulling on the second end of the auxiliary strand pulls the first end of the auxiliary strand and the portion of the flexible strand that is coupled to the first end of the auxiliary strand into the anchor through the first exterior opening, along said passage, and back out of the anchor through the second exterior opening.

2. The method of claim 1 further comprising tensioning the flexible strand after said pulling.

3. The method of claim 2, wherein said tensioning of the flexible strand applies tension to a soft tissue positioned over the bone.

4. The method of claim 3, wherein the soft tissue comprises a rotator cuff.

5. The method of claim 1, wherein the passage is generally U-shaped in the anchor during said pulling.

6. The method of claim 1, wherein said pulling brings the portion of the flexible strand outside the first bone hole.

7. The method of claim 6, wherein the first exterior opening and the second exterior opening are both situated opposite a leading end of the anchor as the anchor is delivered into the first bone hole during said locating.

8. A method of anchoring a flexible strand to bone, the method comprising:

locating an anchor in a first bone hole with an auxiliary strand extending through a passage in the anchor inside the first bone hole; and pulling on a second end of the auxiliary strand outside the first bone hole, after said locating, so as to pull a looped first end of the auxiliary strand into the passage in the anchor and thereby pull a portion of a flexible strand that is coupled to the looped first end of the auxiliary strand into the passage, wherein, prior to said pulling, the flexible strand is already anchored in a second bone hole that is spaced apart from the first bone hole, wherein said pulling is effective to pull the looped first end of the auxiliary strand and the portion of the flexible strand that is coupled to the looped first end of the auxiliary strand completely through the passage.

9. The method of claim 8, wherein said pulling brings the portion of the flexible strand outside the first bone hole.

10. The method of claim 9, wherein, after being pulled completely through the passage, the portion of the flexible strand extends out of the anchor through a first exterior opening in the anchor, the first exterior opening being situated opposite a leading end of the anchor as the anchor is delivered into the first bone hole during said locating.

11. The method of claim 8 further comprising tensioning the flexible strand after said pulling.

12. The method of claim 11, wherein said tensioning of the flexible strand applies tension to a soft tissue positioned over the bone.

13. The method of claim 12, wherein the soft tissue comprises a rotator cuff.

14. The method of claim 8, wherein the passage is generally U-shaped in the anchor during said pulling.

15. The method of claim 8, wherein said locating leaves the looped first end of the auxiliary strand extending out of the anchor through a first exterior opening in the anchor and the second end of the auxiliary strand extending out of the anchor through a second exterior opening in the anchor, and wherein said pulling on the second end of the auxiliary strand pulls the looped first end of the auxiliary strand and the portion of the flexible strand that is coupled to the looped first end of the auxiliary strand into the anchor through the first exterior opening, along said passage, and back out of the anchor through the second exterior opening.

16. The method of claim 15, wherein the first exterior opening and the second exterior opening are both situated opposite a leading end of the anchor as the anchor is delivered into the first bone hole during said locating.

17. A method of anchoring a flexible strand to bone, the method comprising:

locating an anchor in a first bone hole with an auxiliary strand extending through a passage in the anchor inside the first bone hole, wherein said locating leaves a first end of the auxiliary strand and a second end of the auxiliary strand outside the first bone hole; and pulling on the second end of the auxiliary strand, after said locating, so as to pull the first end of the auxiliary strand completely through the passage in the anchor and thereby pull a portion of a flexible strand that is coupled to the first end of the auxiliary strand completely through the passage, wherein, prior to said pulling the flexible strand is already anchored in a second bone hole that is spaced apart from the first bone hole, wherein the passage is generally U-shaped in the anchor during said pulling.

18. The method of claim 17 further comprising tensioning the flexible strand after said pulling so as to apply tension to a soft tissue positioned over the bone.

19. The method of claim 17, wherein the passage extends through the anchor between a first exterior opening in the anchor and a second exterior opening in the anchor which are both situated opposite a leading end of the anchor as the anchor is delivered into the first bone hole during said locating.

20. The method of claim 19, wherein said locating leaves the first end of the auxiliary strand extending out of the anchor through the first exterior opening in the anchor and the second end of the auxiliary strand extending out of the anchor through the second exterior opening in the anchor such that said pulling on the second end of the auxiliary strand pulls the first end of the auxiliary strand and the portion of the flexible strand that is coupled to the first end of the auxiliary strand into the anchor through the first exterior opening, along said passage, and back out of the anchor through the second exterior opening.

* * * * *